United States Patent
Sanabria et al.

(10) Patent No.: US 11,958,915 B2
(45) Date of Patent: Apr. 16, 2024

(54) METHODS FOR TREATMENT AND DIAGNOSIS OF NON-ALCOHOLIC STEATOHEPATITIS AND/OR HEPATOCELLULAR CARCINOMA

(71) Applicant: Marshall University Research Corporation, Huntington, WV (US)

(72) Inventors: Juan Sanabria, Huntington, WV (US); Sandrine Pierre, Huntington, WV (US); Moumita Banerjee, Huntington, WV (US); Zijian Xie, Huntington, WV (US); Joseph Shapiro, Huntington, WV (US)

(73) Assignee: MARSHALL UNIVERSITY RESEARCH CORPORATION, Huntington, WV (US)

( * ) Notice: Subject to any disclaimer, the term of this patent is extended or adjusted under 35 U.S.C. 154(b) by 245 days.

(21) Appl. No.: 17/223,881

(22) Filed: Apr. 6, 2021

(65) Prior Publication Data

US 2021/0309698 A1 Oct. 7, 2021

Related U.S. Application Data

(60) Provisional application No. 63/005,867, filed on Apr. 6, 2020.

(51) Int. Cl.
| | |
|---|---|
| *C07K 7/08* | (2006.01) |
| *A61K 38/00* | (2006.01) |
| *C12Q 1/6886* | (2018.01) |
| *G01N 33/574* | (2006.01) |
| *G01N 33/68* | (2006.01) |

(52) U.S. Cl.
CPC .............. *C07K 7/08* (2013.01); *C12Q 1/6886* (2013.01); *G01N 33/57438* (2013.01); *G01N 33/6848* (2013.01); *A61K 38/00* (2013.01); *C07K 2319/10* (2013.01); *G01N 2333/4703* (2013.01); *G01N 2800/52* (2013.01)

(58) Field of Classification Search
CPC .... C07K 7/08; C07K 2319/10; C12Q 1/6886; G01N 33/57438; G01N 33/6848; G01N 2333/4703; G01N 2800/52; A61K 38/00
See application file for complete search history.

(56) References Cited

U.S. PATENT DOCUMENTS 9,226,952 B2 * 1/2016 Xie ......................... C12N 9/14

FOREIGN PATENT DOCUMENTS

WO WO201071767 * 6/2010 ........... A61K 39/395

OTHER PUBLICATIONS

Yang et al. A global view of hepatocellular carcinoma: trends, risk, prevention and management. Nat Rev Gastroneterol Hepatol, Oct. 2019, vol. 16, No. 10, pp. 589-604. (Year: 2019).*
Zhao et al. Elevated Src expression associated with hepatocelluar carcinoma metastasis in northern Chinese patients. Oncology Letters, Vo. 10, pp. 3026-3034. (Year: 2015).*
Abbas, R., et al. Polyethylene Glycol Modified-Albumin Enhances the Cold Preservation Properties of University of Wisconsin Solution in Rat Liver and a Hepatocyte Cell Line, Journal of Surgical Research 2010;164, 95-104.
Aini, W, et al. Accelerated telomere reduction and hepatocyte senescence in tolerated human liver allografts. Transpl Immunol. 2014;31(2):55-9.
Andres Ibarra, R, et al. Disturbances in the glutathione/ophthalmate redox buffer system in the woodchuck model of hepatitis virus-induced hepatocellular carcinoma. HPB Surg. 2011;2011:789323.
Cai, T., et al. Regulation of caveolin-1 membrane trafficking by the Na/K-ATPase. J Cell Biol. 2008; 182(6):1153-69.
Gall, W.E., et al. alpha-Hydroxybutyrate is an early biomarker of insulin resistance and glucose intolerance in a hondiabetic population. PLoS One. 2010;5(5):e10883.
Grek, C.L., et al. Causes and consequences of cysteine S-glutathionylation. J Biol Chem. 2013;288(37):26497-504.
Barra, R., et al. Metabolomic Analysis of Liver Tissue from the VX2 Rabbit Model of Secondary Liver Tumors. HPB Surg. 2014;2014:310372.
Karagozian, R., et al. Obesity-associated mechanisms of hepatocarcinogenesis. Metabolism. 2014;63(5):607-17.
Kombu, R.S., et al. Dynamics of glutathione and ophthalmate traced with 2H-enriched body water in rats and humans. Am J Physiol Endocrinol Metab. 2009;297(1):E260-9.
Lade, A., et al. Contributions of metabolic dysregulation and inflammation to nonalcoholic steatohepatitis, hepatic fibrosis, and cancer. Curr Opin Oncol. 2014;26(1):100-7.
Li, Z., et al. Naktide, a Na/K-ATPase-derived Peptide Src Inhibitor, Antagonizes Ouabain-activated Signal Transduction in Cultured Cells. J Biol Chem. 2009;284(31):21066-76.
Li, Z., et al. Na/K-ATPase mimetic pNaKtide peptide inhibits the growth of human cancer cells. J Biol Chem. 2011;286 (37):32394-403.
Liang, M., et al. Functional characterization of Src-interacting Na/K-ATPase using RNA interference assay. J Biol Chem. 2006;281(28):19709-19.

(Continued)

*Primary Examiner* — Marcela M Cordero Garcia
(74) *Attorney, Agent, or Firm* — Stites & Harbison, PLLC; Terry L. Wright

(57) ABSTRACT

Methods for treating non-alcoholic steatohepatitis and/or hepatocellular carcinoma include administering a polypeptide antagonist of a Na/K ATPase/Src receptor complex to a subject in need thereof. Methods and assays for diagnosis or prognosis of non-alcoholic steatohepatitis and/or hepatocellular carcinoma in a subject are also provided and include the steps of providing a biological sample from the subject, determining an expression level or activity in the sample of at least one biomarker selected from Caveolin-1, Survivin, and SMAC; and comparing the expression level or activity of the at least one biomarker in the sample, if present, to a control expression level or activity of the at least one biomarker. Prophylaxis or treatment of the non-alcoholic steatohepatitis and/or hepatocellular carcinoma in a subject can then be initiated based on the expression level or activity of Caveolin-1, Survivin, and SMAC in the sample.

7 Claims, 84 Drawing Sheets

Specification includes a Sequence Listing.

(56) References Cited

OTHER PUBLICATIONS

Liu, C.C., et al. Oxidative inhibition of the vascular Na+-K+ pump via NADPH oxidase-dependent beta1-subunit glutathionylation: implications for angiotensin II-induced vascular dysfunction. Free Radic Biol Med. 2013;65:563-72.

Petrushanko, I.Y., et al. S-glutathionylation of the Na, K-ATPase Catalytic Alpha Subunit Is a Determinant of the Enzyme Redox Sensitivity. J Biol Chem. 2012;287(38):32195-205.

Hirsova, P., et al. Vismodegib suppresses TRAIL-mediated liver injury in a mouse model of nonalcoholic steatohepatitis. PLOS One. 2013;8(7):e70599.

Aravinthan, A., et al. Gene polymorphisms of cellular senescence marker p21 and disease progression in non-alcohol-related fatty liver disease. Cell Cycle 2014;13:9;1489-1494.

Marshall University Medical Center, Health Sciences Center 32nd Annual Research Day at Marshall University, Mar. 6, 2020, Oral and Poster Presentation, abstracts at pp. 54, 59, and 101.

* cited by examiner

Log10 NMC vs HFD+Exercise

Hep 3B

0μm  30μm  100μm

SNU475

0μm  30μm  100μm

NASH in the Mouse (24weeks)

NASH-HCC in the Mouse (24 Weeks)

NASH-HCC in the Mouse (28 Weeks)

NASH related HCC in the Human

NASH-HCC in the Mouse (24 Weeks)

Caveolin-1 (24 Weeks HCC)

NASH-HCC in the Mouse (28 Weeks)

Caveolin-1 (28 Weeks HCC)

Survivin expression in α1-NKA Knockdown (siRNA) cells in Two HCC Human Cell Lines

* p<0.05
**p<0.01

```
                        SEQUENCE LISTING

<160> NUMBER OF SEQ ID NOS: 5

<210> SEQ ID NO 1
<211> LENGTH: 20
<212> TYPE: PRT
<213> ORGANISM: Homo sapiens

<400> SEQUENCE: 1

Ser Ala Thr Trp Leu Ala Leu Ser Arg Ile Ala Gly Leu Cys Asn Arg
1               5                   10                  15

Ala Val Phe Gln
            20

<210> SEQ ID NO 2
<211> LENGTH: 13
<212> TYPE: PRT
<213> ORGANISM: Human immunodeficiency virus

<400> SEQUENCE: 2

Gly Arg Lys Lys Arg Arg Gln Arg Arg Arg Pro Pro Gln
1               5                   10

<210> SEQ ID NO 3
<211> LENGTH: 16
<212> TYPE: PRT
<213> ORGANISM: Drosophila melanogaster

<400> SEQUENCE: 3

Arg Gln Ile Lys Ile Trp Phe Gln Asn Arg Arg Met Lys Trp Lys Lys
1               5                   10                  15

<210> SEQ ID NO 4
<211> LENGTH: 8
<212> TYPE: PRT
<213> ORGANISM: Homo sapiens

<400> SEQUENCE: 4

Lys Lys Gly Lys Lys Gly Lys Lys
1               5

<210> SEQ ID NO 5
<211> LENGTH: 33
<212> TYPE: PRT
<213> ORGANISM: Artificial Sequence
<220> FEATURE:
<223> OTHER INFORMATION: TAT NaKtide Fusion Polypeptide

<400> SEQUENCE: 5

Gly Arg Lys Lys Arg Arg Gln Arg Arg Arg Pro Pro Gln Ser Ala Thr
1               5                   10                  15

Trp Leu Ala Leu Ser Arg Ile Ala Gly Leu Cys Asn Arg Ala Val Phe
            20                  25                  30

Gln
```

METHODS FOR TREATMENT AND DIAGNOSIS OF NON-ALCOHOLIC STEATOHEPATITIS AND/OR HEPATOCELLULAR CARCINOMA

RELATED APPLICATIONS

This application claims priority from U.S. Provisional Application Ser. No. 63/005,867, filed Apr. 6, 2020, the entire disclosure of which is incorporated herein by this reference.

TECHNICAL FIELD

The presently-disclosed subject matter generally relates to methods for treatment and diagnosis of non-alcoholic steatohepatitis and/or hepatocellular carcinoma. In particular, certain embodiments of the presently-disclosed subject matter relate to methods for treatment and diagnosis of non-alcoholic steatohepatitis and/or hepatocellular carcinoma via disruptions or detection of alterations in Na/K-ATPase-mediated signaling.

BACKGROUND

Global incidence and prevalence of chronic liver disease and its sequela, end stage liver disease (ESLD) and hepatocellular carcinoma (HCC) are increasing as a consequence of both viral hepatitis and a continuous spread of the metabolic disturbances related to the obesity epidemic. Global viral hepatitis (GVH) has increased from 0.89 million (1990) to 1.45 million (2013), and in 2013 viral hepatitis was the seventh leading cause of deaths worldwide. Nevertheless, it is expected that GVH deaths will decrease as a result of both hepatitis A virus/hepatitis B virus (HAV/HBV) vaccination and to the development of highly successful antiviral therapies towards hepatitis C virus (HCV). In contrast, it is estimated that by the year 2030, 2.2 billion people around the world will be overweight, and 1.1 billion will be obese. The metabolic syndrome (obesity, HTN, and diabetes) is the most significant risk factor for Non-Alcoholic SteatoHepatitis (NASH), and 36.1% of adult men and 32.4% of adult women had metabolic syndrome in 2010 at an estimated medical cost as high as $209.7 billion. Furthermore, Hepatocellular Carcinoma (HCC) has been reported more often in non-cirrhotic livers in the background of NASH.

The incidence of HCC and its related mortality is increasing, becoming the 3rd cause and fastest growing cause of cancer related mortality worldwide, the 7th in the US, and the 2nd cause in the Appalachian population, mainly from the metabolic cellular disturbances promoted by the epidemic of obesity and a paucity of markers for its early detection. With fewer treatment options and a 70% recurrence rate, HCC has become a major and steadily increasing global health challenge. The majority (>80%) of obese subjects (BMI>30) have non-alcoholic fatty liver disease (NAFLD) and it could progress to non-alcoholic steatohepatitis (NASH), the most common cause nowadays of cirrhosis and HCC. To date, however, the only maneuvers shown to consistently achieve a reduction of NASH progression are weight loss and exercise. Accordingly, additional methods for treating and diagnosing NASH and HCC would be both highly desirable and beneficial.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

The presently-disclosed subject matter generally includes methods for treatment and diagnosis of non-alcoholic steatohepatitis and/or hepatocellular carcinoma via disruptions or detection of alterations in Na/K-ATPase-mediated signaling. In some embodiments, a method for treating non-alcoholic steatohepatitis and/or hepatocellular carcinoma is provided that comprises administering a polypeptide antagonist of a Na/K ATPase/Src receptor complex to a subject in need thereof. In some embodiments, the polypeptide antagonist comprises the sequence of SEQ ID NO: 1, or a functional fragment, and/or functional variant thereof. In some embodiments, the polypeptide antagonist further includes a cell penetrating polypeptide having an amino acid sequence selected from the group consisting of SEQ ID NOS: 2-4. In some embodiments, the polypeptide antagonist comprises the sequence of SEQ ID NO: 5, or a functional fragment, and/or functional variant thereof.

With respect to the administration of a polypeptide antagonist in accordance with the presently-disclosed subject matter, in some embodiments, the administering step includes oral administration, transdermal administration, administration by inhalation, nasal administration, topical administration, intraaural administration, rectal administration, intravenous administration, intramuscular administration, subcutaneous administration, intravitreous administration, subconjunctival administration, intracameral administration, intraocular administration or combinations thereof. In some embodiments, the subject that is administered the polypeptide antagonist is human. In some embodiments, administering the polypeptide antagonist increases a level of expression or activity of SMAC in the subject, and/or administering the polypeptide antagonist reduces a level of expression or activity of Caveolin-1 or Survivin in the subject.

Further provided, in some embodiments, are methods for diagnosis or prognosis of non-alcoholic steatohepatitis and/or hepatocellular carcinoma in a subject. In some embodiments, a method for diagnosis or prognosis of non-alcoholic steatohepatitis and/or hepatocellular carcinoma in a subject is provided that comprises the steps of: (a) providing a biological sample from the subject; (b) determining an expression level or activity in the sample of at least one biomarker selected from Caveolin-1, Survivin, and SMAC; and (c) comparing the expression level or activity of the at least one biomarker in the sample, if present, to a control expression level or activity of the at least one biomarker. The subject is then diagnosed as having non-alcoholic steatohepatitis and/or hepatocellular carcinoma or a risk thereof if there is a measurable difference in the expression level or activity of the at least one biomarker in the sample as compared to the control level. In some embodiments, the biological sample comprises blood, plasma, serum, or a tumor biopsy. In some embodiments, the subject being diagnosed is human, such as, in certain embodiments, a human subject that has non-alcoholic steatohepatitis and/or hepatocellular carcinoma.

In implementing the diagnostic and prognostic methods, in some embodiments, determining the expression level or activity in the sample of the at least one biomarker comprises determining the expression level or activity in the sample of the at least one biomarker using mass spectrometry (MS) analysis, immunoassay analysis, or both. In some embodiments, treatment can be selected or modified for the non-alcoholic steatohepatitis and/or hepatocellular carcinoma based on the determined expression level or activity of the at least one biomarker.

With respect to the biomarkers used for the diagnosis and prognosis of non-alcoholic steatohepatitis and/or hepatocellular carcinoma in the subject, in some embodiments, the at least one biomarker is Caveolin-1 and/or Survivin, and there is an increase in the expression level or activity of Caveolin-1 and/or Survivin as compared to the control sample. In some embodiments, the at least one biomarker is SMAC, and there is a decrease in the expression level or activity of SMAC as compared to the control sample.

Still further provided, in some embodiments, are methods for determining whether to initiate or continue prophylaxis or treatment of a non-alcoholic steatohepatitis and/or hepatocellular carcinoma in a subject. In some embodiments, a method for determining whether to initiate or continue prophylaxis or treatment of a non-alcoholic steatohepatitis and/or hepatocellular carcinoma in a subject is provided comprising the steps of: (a) providing a series of biological samples over a time period from the subject; (b) analyzing the series of biological samples to determine an expression level or activity in each of the biological samples of at least one biomarker selected from Caveolin-1, Survivin, and SMAC; and (c) comparing any measurable change in the expression level or activity of the at least one biomarker in each of the biological samples to thereby determine whether to initiate or continue the prophylaxis or therapy of the non-alcoholic steatohepatitis and/or hepatocellular carcinoma. In some embodiments, such methods further comprise determining whether to initiate or continue prophylaxis or therapy of the non-alcoholic steatohepatitis and/or hepatocellular carcinoma based on the expression level or activity of Caveolin-1, Survivin, and SMAC in the sample.

In yet further embodiments, assays for assessing non-alcoholic steatohepatitis and/or hepatocellular carcinoma are provided. In some embodiments, an assay for assessing non-alcoholic steatohepatitis and/or hepatocellular carcinoma in a subject, comprises: applying an agent capable of detecting an expression level or activity of Caveolin-1, Survivin, and SMAC in a biological sample obtained from a subject; and determining the expression level or activity of Caveolin-1, Survivin, and SMAC in the biological sample.

Further features and advantages of the present invention will become evident to those of ordinary skill in the art after a study of the description, figures, and non-limiting examples in this document.

BRIEF DESCRIPTION OF THE SEQUENCE LISTING

Figure 1A:
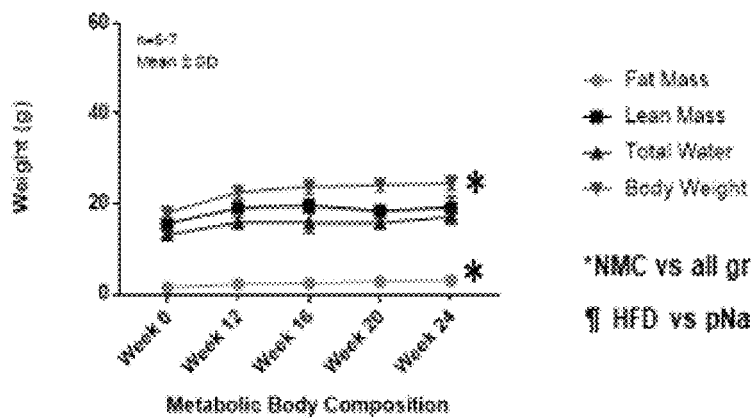
FIGS. 1A-1B are graphs showing Metabolic Body Composition in the Murine model of NASH by MM, where animals were exposed to normal mouse chow (NMC), or high fat diet+fructose (HFD), where interventions included pNaKtide dissolved in normal saline (NS), or a standardized exercise protocol, where rodents exposed to HFD significantly increased their total body weight (TBW) mainly due to an expansion of their fat mass compartment when compared to the NMC group (in FIG. 1A, $p<0.05$, ANOVA), and where although animals in the intervention groups (pNaKtide and exercise, in FIG. 1B) did not lose weight, they have a trend to maintain their body weight without any further gain on their fat compartment.
Figure 1A:
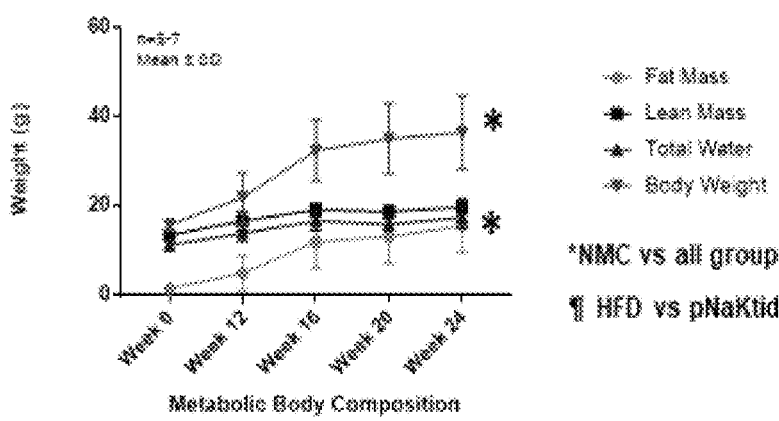
Figure 1A:
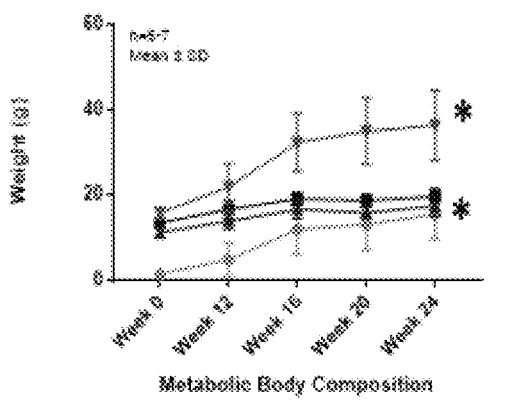

SEQ ID NO: 1 is an amino acid sequence of an embodiment of a polypeptide in accordance with the presently-disclosed subject matter (NaKtide);
SEQ ID NO: 2 is an amino acid sequence encoding a TAT cell penetrating peptide;
SEQ ID NO: 3 is an amino acid sequence encoding a penetratin (AP) cell penetrating peptide; and
SEQ ID NO: 4 is an amino acid sequence encoding the N-terminal poly-lysine domain of the α1 subunit of Na/K-ATPase (A1N); and
SEQ ID NO: 5 is another amino acid sequence of an embodiment of a polypeptide in accordance with the presently-disclosed subject matte (pNaKtide).

DESCRIPTION OF EXEMPLARY EMBODIMENTS

The details of one or more embodiments of the presently-disclosed subject matter are set forth in this document.

Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

In certain instances, nucleotides and polypeptides disclosed herein are included in publicly-available databases, such as GENBANK® and SWISSPROT. Information including sequences and other information related to such nucleotides and polypeptides included in such publicly-available databases are expressly incorporated by reference. Unless otherwise indicated or apparent the references to such publicly-available databases are references to the most recent version of the database as of the filing date of this Application.

The present application can "comprise" (open ended), "consist of" (closed ended), or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

The presently-disclosed subject matter is based, at least in part, on the discovery that a newly synthesized 33-amino peptide may hold advantage not only in the prevention, but in the treatment of NASH and its sequelae, ESLD and HCC by exercising a blocking effect on Src phosphorylation at the α1-subunit of the Na/K-ATPase (NKA). Accordingly, in some embodiments of the presently-disclosed subject matter, methods for the treatment of non-alcoholic steatohepatitis and/or hepatocellular carcinoma are provided that include administering to a subject in need thereof an agent (e.g., a polypeptide) that treats non-alcoholic steatohepatitis and/or hepatocellular carcinoma by inhibiting or reducing the receptor and signaling function of the Na/K-ATPase and Src complex. In some embodiments, the agent inhibits or reduces such function by acting as an antagonist of the Na/K-ATPase and Src complex. In some embodiments of the presently-disclosed subject matter, the therapeutic methods make use of a polypeptide to treat non-alcoholic steatohepatitis and/or hepatocellular carcinoma, where the polypeptide inhibits the receptor function of the Na/K-ATPase and Src complex and acts an antagonist for the receptor function of the Na/K-ATPase and Src complex.

The terms "polypeptide," "protein," and "peptide" are used interchangeably herein to refer to a polymer of amino acids regardless of its size or function. The terms "protein," "polypeptide," and "peptide" are used interchangeably herein to also refer to a gene product, homologs, orthologs, paralogs, fragments, any protease derived peptide (fragment), and other equivalents, variants, and analogs of a polymer of amino acids.

In some embodiments, the polypeptides are comprised of the sequence of SEQ ID NO: 1 (SATWLALSRIAGLCN-RAVFQ; NaKtide), or fragments, and/or variants thereof. The terms "polypeptide fragment" or "fragment" when used in reference to such a polypeptide, refers to a polypeptide in which amino acid residues are deleted as compared to the reference polypeptide itself, but where the remaining amino acid sequence is usually identical to the corresponding positions in the reference polypeptide. Such deletions may occur at the amino-terminus of the reference polypeptide, the carboxy-terminus of the reference polypeptide, or both. Polypeptide fragments can also be inclusive of "functional fragments," in which case the fragment retains some or all of the activity of the reference polypeptide.

The term "variant," as used herein, refers to an amino acid sequence that is different from the reference polypeptide by one or more amino acids. In some embodiments, a variant polypeptide may differ from a reference polypeptide by one or more amino acid substitutions. For example, a NaKtide polypeptide variant can differ from the NaKtide polypeptide of SEQ ID NO: 1 by one or more amino acid substitutions, i.e., mutations. In this regard, polypeptide variants comprising combinations of two or more mutations can respectively be referred to as double mutants, triple mutants, and so forth. It will be recognized that certain mutations can result in a notable change in function of a polypeptide, while other mutations will result in little to no notable change in function of the polypeptide. Such polypeptide variants can also be inclusive of "functional variants," in which case the variant retains some or all of the activity of the reference polypeptide.

In some embodiments, the present polypeptides include polypeptides that share at least 75% homology with the NaKtide polypeptide of SEQ ID NO: 1. In some embodiments, the polypeptides share at least 85% homology with the NaKtide polypeptide of SEQ ID NO: 1. In some embodiments, the polypeptides share at least 90% homology with the NaKtide polypeptide of SEQ ID NO: 1. In some embodiments, the polypeptides share at least 95% homology with the NaKtide polypeptide of SEQ ID NO: 1.

"Percent identity," or "percent homology" when used herein to describe to an amino acid sequence or a nucleic acid sequence, relative to a reference sequence, can be determined using the formula described by Karlin and Altschul (Proc. Natl. Acad. Sci. USA 87: 2264-2268, 1990, modified as in Proc. Natl. Acad. Sci. USA 90:5873-5877, 1993). Such a formula is incorporated into the basic local alignment search tool (BLAST) programs of Altschul et al. (J. Mol. Biol. 215: 403-410, 1990). [BLAST nucleotide searches are performed with the NBLAST program, score+ 100, word length=12, to obtain nucleotide sequences homologous to a nucleic acid molecule of the invention. BLAST protein searches are performed with the XBLAST program, score=50, word length=3, to obtain amino acid sequences homologous to a reference polypeptide (e.g., SEQ ID NO: X). To obtain gapped alignments for comparison purposes, Gapped BLAST is utilized as described in Altschul, et al. (Nucleic Acids Res. 25: 3389-3402, 1997). When utilizing BLAST and Gapped BLAST programs, the default parameters of the respective programs (e.g., XBLAST and NBLAST) are used. In this regard, reference is made to the most recent version of the programs that are available as of Jul. 19, 2012.

Embodiments of the present polypeptides can further comprise one or more leader sequences, and, in some embodiments the leader sequences include, but are not limited to, cell penetrating peptides (CPPs). The term "cell penetrating peptide" (CPP) is used herein to generally refer to short peptides that can or that assist in facilitating the transport of molecular cargo across plasma membranes found in a cell. In some instances, the molecular cargo includes another polypeptide, such as the polypeptides described herein. Of course, the cell penetrating peptides can be conjugated to the molecular cargo (e.g., polypeptide) via any number of means, including covalent bonds and/or non-covalent bonds. In a number of instances, however, such cell penetrating peptides will often include a relatively high concentration of positively-charged amino acids, such as lysine and arginine, and will have a sequence that contains an alternating pattern of charged (polar) and non-charged amino acids.

In some embodiments of the presently-disclosed subject matter, an exemplary leader sequence or cell-penetrating peptide can include the trans-activating transcriptional activator (TAT) cell penetrating peptide, which is represented by the sequence of SEQ ID NO: 2 (GRKKRRQRRRPPQ). Another exemplary leader sequence includes penetratin (AP), which is represented by the sequence of SEQ ID NO: 3 (RQIKIWFQNRRMKWKK). Yet another exemplary leader sequence includes an amino acid sequence encoding the N-terminal poly-lysine domain of the α1 subunit of Na/K-ATPase (A1N), which is represented by the sequence of SEQ ID NO: 4 (KKGKKGKK). Those of ordinary skill will appreciate though that other leader sequences, including other cell penetrating peptides, can also be used in conjunction with the presently-disclosed polypeptides. In some embodiments, a polypeptide including a leader sequence, such as a cell penetrating peptide, attached to the NaKtide sequence of SEQ ID NO: 1 is referred to herein as a pNaKtide (e.g., SEQ ID NO: 5; GRKKRRQRRRPPQSATWLALSRIAGLCNRAVFQ, which includes the TAT cell penetrating peptide of SEQ ID NO: 2 fused to the NaKtide sequence of SEQ ID NO: 1).

The terms "treatment" or "treating," as used herein, refer to the medical management of a subject with the intent to cure, ameliorate, or stabilize a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; treatment directed to minimizing or partially inhibiting the development of the associated disease, pathological condition, or disorder; and supportive treatment, that is, treatment employed to supplement another therapy directed toward the improvement of the associated disease, pathological condition, or disorder.

The terms "reducing," "reduction," "inhibiting," "inhibition" and grammatical variations thereof do not necessarily refer to the ability to completely inactivate all target biological activity in all cases. Rather, the skilled artisan will understand that those terms refer to decreasing biological activity of a target, such as can occur when a ligand binds a site of the target, a protein in a biochemical pathway of the target is blocked, a non-native complexes with a target, or the like. Such decrease in biological activity can be determined relative to a control, wherein the control can be representative of an environment in which an inhibitor is not administered. For example, in some embodiments, a decrease in activity relative to a control can be about a 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% decrease. In some embodiments, the increases and/or decreases described herein can be in reference to a control subject having non-alcoholic steatohepatitis and/or hepatocellular carcinoma and that has not been treated with one of the presently-disclosed polypeptides. In other embodiments, the increases and/or decreases described herein can be in reference to a baseline obtained in a subject that is in need of treatment, but has not yet began a particular therapeutic regimen. In some embodiments, administration of the polypeptide antagonist in accordance with the presently-disclosed subject matter reduces or treats one or more of the underlying causes and/or symptoms of non-alcoholic steatohepatitis and/or hepatocellular carcinoma. For example, in some embodiments, administering the polypeptide antagonist increases a level of expression or activity of SMAC in the subject. In other embodiments, administering the polypeptide antagonist reduces a level of expression or activity of Caveolin-1 or Survivin in the subject. Measurement of such foregoing reductions can be performed using routine procedures known to those of ordinary skill in the art, such as those described in further detail herein below.

For administration of a therapeutic composition as disclosed herein (e.g., a polypeptide of SEQ ID NO: 5), conventional methods of extrapolating human dosage based on doses administered to a murine animal model can be carried out using the conversion factor for converting the mouse dosage to human dosage: Dose Human per kg=Dose Mouse per kg/12 (Freireich, et al., (1966) Cancer Chemother Rep. 50: 219-244). Drug doses can also be given in milligrams per square meter of body surface area because this method rather than body weight achieves a good correlation to certain metabolic and excretionary functions. Moreover, body surface area can be used as a common denominator for drug dosage in adults and children as well as in different animal species as described by Freireich, et al. (Freireich et al., (1966) Cancer Chemother Rep. 50:219-244). Briefly, to express a mg/kg dose in any given species as the equivalent mg/sq m dose, multiply the dose by the appropriate km factor. In an adult human, 100 mg/kg is equivalent to 100 mg/kg×37 kg/sq m=3700 mg/m$^2$.

Suitable methods for administering a therapeutic composition in accordance with the methods of the presently-disclosed subject matter include, but are not limited to, systemic administration, parenteral administration (including intravascular, intramuscular, and/or intraarterial administration), oral delivery, buccal delivery, rectal delivery, subcutaneous administration, intraperitoneal administration, inhalation, intratracheal installation, surgical implantation, transdermal delivery, local injection, intranasal delivery, and hyper-velocity injection/bombardment. Where applicable, continuous infusion can enhance drug accumulation at a target site (see, e.g., U.S. Pat. No. 6,180,082). In some embodiments, the administration of the composition is via oral administration, transdermal administration, administration by inhalation, nasal administration, topical administration, intraaural administration, rectal administration, intravenous administration, intramuscular administration, subcutaneous administration, intravitreous administration, subconjunctival administration, intracameral administration, intraocular administration or combinations thereof.

Regardless of the route of administration, the compositions of the presently-disclosed subject matter are typically administered in amount effective to achieve the desired response. As such, the term "effective amount" is used herein to refer to an amount of the therapeutic composition (e.g., a polypeptide of SEQ ID NO: 5 and a pharmaceutically vehicle, carrier, or excipient) sufficient to produce a measurable biological response (e.g., a decrease in non-alcoholic steatohepatitis and/or hepatocellular carcinoma). Actual dosage levels of active ingredients in a therapeutic composition of the present invention can be varied so as to administer an amount of the active compound(s) that is effective to achieve the desired therapeutic response for a particular subject and/or application. Of course, the effective amount in any particular case will depend upon a variety of factors including the activity of the therapeutic composition, formulation, the route of administration, combination with other drugs or treatments, severity of the condition being treated, and the physical condition and prior medical history of the subject being treated. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

For additional guidance regarding formulation and dose, see U.S. Pat. Nos. 5,326,902; 5,234,933; PCT International Publication No. WO 93/25521; Berkow et al., (1997) The Merck Manual of Medical Information, Home ed. Merck Research Laboratories, Whitehouse Station, N.J.; Goodman et al., (1996) Goodman & Gilman's the Pharmacological Basis of Therapeutics, 9th ed. McGraw-Hill Health Professions Division, New York; Ebadi, (1998) CRC Desk Reference of Clinical Pharmacology. CRC Press, Boca Raton, Fla.; Katzung, (2001) Basic & Clinical Pharmacology, 8th ed. Lange Medical Books/McGraw-Hill Medical Pub. Division, New York; Remington et al., (1975) Remington's Pharmaceutical Sciences, 15th ed. Mack Pub. Co., Easton, Pa.; and Speight et al., (1997) Avery's Drug Treatment: A Guide to the Properties, Choice, Therapeutic Use and Economic Value of Drugs in Disease Management, 4th ed. Adis International, Auckland/Philadelphia; Duch et al., (1998) Toxicol. Lett. 100-101:255-263.

Further provided, in some embodiments of the presently-disclosed subject matter, are methods and systems for diagnosis and prognosis of non-alcoholic steatohepatitis and/or hepatocellular carcinoma that make use of at least one biomarker. In some embodiments, the at least one biomarker used to diagnose non-alcoholic steatohepatitis and/or hepatocellular carcinoma is selected from Caveolin-1, Survivin, SMAC, and combinations thereof.

The exemplary human biomarkers described herein are not intended to limit the present subject matter to human polypeptide biomarkers or mRNA biomarkers only. Rather, the present subject matter encompasses biomarkers across animal species that are associated with non-alcoholic steatohepatitis and/or hepatocellular carcinoma.

A "biomarker" is a molecule useful as an indicator of a biologic state in a subject. With reference to the present subject matter, the biomarkers disclosed herein can be polypeptides that exhibit a change in expression level or activity, which can be correlated with the risk of developing, the presence of, or the progression of non-alcoholic steatohepatitis and/or hepatocellular carcinoma in a subject. In addition, the biomarkers disclosed herein are inclusive of messenger RNAs (mRNAs) encoding the biomarker polypeptides, as measurement of a change in expression of an mRNA can be correlated with changes in expression of the polypeptide encoded by the mRNA. As such, determining an amount of a biomarker in a biological sample is inclusive of determining an amount of a polypeptide biomarker and/or an amount of an mRNA encoding the polypeptide biomarker either by direct or indirect (e.g., by measure of a complementary DNA (cDNA) synthesized from the mRNA) measure of the mRNA.

In some embodiments of the presently-disclosed subject matter, a method for diagnosing non-alcoholic steatohepatitis and/or hepatocellular carcinoma in a subject is provided that includes the steps of: providing a biological sample from the subject; determining an expression level or activity in the sample of at least one biomarker selected from Caveolin-1, Survivin, SMAC, and/or combinations thereof; and comparing the expression level or activity of the at least one biomarker in the sample, if present, to a control expression level or activity of the at least one biomarker. In some embodiments, the subject is then diagnosed as having non-alcoholic steatohepatitis and/or hepatocellular carcinoma or a risk thereof if there is a measurable difference in the expression level or activity of the at least one biomarker in the sample as compared to the control level.

The terms "diagnosing" and "diagnosis" as used herein refer to methods by which the skilled artisan can estimate and even determine whether or not a subject is suffering from a given disease or condition. The skilled artisan often makes a diagnosis on the basis of one or more diagnostic indicators, such as for example a marker, the amount (including presence or absence) of which is indicative of the presence, severity, or absence of the condition.

Along with diagnosis, clinical disease prognosis is also an area of great concern and interest. It is important to know the stage and rapidity of advancement of the non-alcoholic steatohepatitis and/or hepatocellular carcinoma in order to plan the most effective therapy. If a more accurate prognosis can be made, appropriate therapy, and in some instances less severe therapy for the patient can be chosen. Measurement of biomarker levels disclosed herein can be useful in order to categorize subjects according to advancement of non-alcoholic steatohepatitis and/or hepatocellular carcinoma who will benefit from particular therapies and differentiate from other subjects where alternative or additional therapies can be more appropriate.

As such, "making a diagnosis" or "diagnosing", as used herein, is further inclusive of determining a prognosis, which can provide for predicting a clinical outcome (with or without medical treatment), selecting an appropriate treatment (or whether treatment would be effective), or monitoring a current treatment and potentially changing the treatment, based on the measure of diagnostic biomarker levels disclosed herein.

The phrase "determining a prognosis" as used herein refers to methods by which the skilled artisan can predict the course or outcome of a condition in a subject. The term "prognosis" does not refer to the ability to predict the course or outcome of a condition with 100% accuracy, or even that a given course or outcome is predictably more or less likely to occur based on the presence, absence or levels of test biomarkers. Instead, the skilled artisan will understand that the term "prognosis" refers to an increased probability that a certain course or outcome will occur; that is, that a course or outcome is more likely to occur in a subject exhibiting a given condition, when compared to those individuals not exhibiting the condition. For example, in individuals not exhibiting the condition (e.g., not expressing the biomarker or expressing it at a reduced level), the chance of a given outcome may be about 3%. In certain embodiments, a prognosis is about a 5% chance of a given outcome, about a 7% chance, about a 10% chance, about a 12% chance, about a 15% chance, about a 20% chance, about a 25% chance, about a 30% chance, about a 40% chance, about a 50% chance, about a 60% chance, about a 75% chance, about a 90% chance, or about a 95% chance.

The skilled artisan will understand that associating a prognostic indicator with a predisposition to an adverse outcome is a statistical analysis. For example, a biomarker level (e.g., quantity of expression in a sample) of greater than a control level in some embodiments can signal that a subject is more likely to suffer from or experience non-alcoholic steatohepatitis and/or hepatocellular carcinoma than subjects with a level less than or equal to the control level, as determined by a level of statistical significance. Additionally, a change in marker concentration from baseline levels can be reflective of subject prognosis, and the degree of change in marker level can be related to the severity of adverse events. Statistical significance is often determined by comparing two or more populations, and determining a confidence interval and/or a p value. See, e.g., Dowdy and Wearden, Statistics for Research, John Wiley & Sons, New York, 1983, incorporated herein by reference in its entirety. Preferred confidence intervals of the present subject matter are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

In other embodiments, a threshold degree of change in the level of a prognostic or diagnostic biomarker can be established, and the degree of change in the level of the indicator in a biological sample can simply be compared to the threshold degree of change in the level. A preferred threshold change in the level for markers of the presently disclosed subject matter is about 5%, about 10%, about 15%, about 20%, about 25%, about 30%, about 50%, about 75%, about 100%, and about 150%. In yet other embodiments, a "nomogram" can be established, by which a level of a prognostic or diagnostic indicator can be directly related to an associated disposition towards a given outcome. The skilled artisan is acquainted with the use of such nomograms to relate two numeric values with the understanding that the uncertainty in this measurement is the same as the uncertainty in the marker concentration because individual sample measurements are referenced, not population averages.

In some embodiments of the presently-disclosed subject matter, multiple determination of one or more diagnostic or prognostic biomarkers can be made, and a temporal change in the biomarker can be used to monitor the progression of disease and/or efficacy of appropriate therapies directed against the disease. In such an embodiment for example, one might expect to see a decrease or an increase in the biomarker(s) over time during the course of effective therapy. Thus, the presently disclosed subject matter provides in some embodiments a method for determining treatment efficacy and/or progression of non-alcoholic steatohepatitis and/or hepatocellular carcinoma in a subject. In some embodiments, the method comprises determining an amount of at least one biomarker associated with non-alcoholic steatohepatitis and/or hepatocellular carcinoma, such as for example at least one biomarker selected from Caveolin-1, Survivin, and SMAC, in biological samples collected from the subject at a plurality of different time points and comparing the amounts of the at least one biomarker in the samples collected at different time points. For example, a first time point can be selected prior to initiation of a treatment and a second time point can be selected at some time after initiation of the treatment. One or more biomarker levels can be measured in each of the samples taken from different time points and qualitative and/or quantitative differences noted. A change in the amounts of the biomarker levels from the first and second samples can be correlated with determining treatment efficacy and/or progression of the disease in the subject.

The terms "correlated" and "correlating," as used herein in reference to the use of diagnostic and prognostic biomarkers, refers to comparing the presence or quantity of the biomarker in a subject to its presence or quantity in subjects known to suffer from, or known to be at risk of, a given condition (e.g., non-alcoholic steatohepatitis and/or hepatocellular carcinoma); or in subjects known to be free of a given condition, i.e. "normal individuals." For example, a biomarker level in a biological sample can be compared to a level known to be associated with a specific type of non-alcoholic steatohepatitis and/or hepatocellular carcinoma. The sample's biomarker level is said to have been correlated with a diagnosis; that is, the skilled artisan can use the biomarker level to determine whether the subject suffers from or is experiencing a specific type of non-alcoholic steatohepatitis and/or hepatocellular carcinoma, and respond accordingly. Alternatively, the sample's biomarker level can be compared to a control marker level known to be associated with a good outcome (e.g., the absence of non-alcoholic steatohepatitis and/or hepatocellular carcinoma), such as an average level found in a population of normal subjects.

In certain embodiments, a diagnostic or prognostic biomarker is correlated to a condition or disease by merely its presence or absence. In other embodiments, a threshold level of a diagnostic or prognostic biomarker can be established, and the level of the indicator in a subject sample can simply be compared to the threshold level.

As noted, in some embodiments, multiple determination of one or more diagnostic or prognostic biomarkers can be made, and a temporal change in the marker can be used to determine a diagnosis or prognosis. For example, a diagnostic marker can be determined at an initial time, and again at a second time. In such embodiments, an increase in the marker from the initial time to the second time can be diagnostic of a particular type of non-alcoholic steatohepatitis and/or hepatocellular carcinoma, or a given prognosis. Likewise, a decrease in the marker from the initial time to the second time can be indicative of a particular type of non-alcoholic steatohepatitis and/or hepatocellular carcinoma, or a given prognosis. Furthermore, in some embodiments, the degree of change of one or more markers can be related to the severity of non-alcoholic steatohepatitis and/or hepatocellular carcinoma and future adverse events.

The skilled artisan will also understand that, while in certain embodiments comparative measurements can be made of the same diagnostic marker at multiple time points, one can also measure a given marker at one time point, and a second marker at a second time point, and a comparison of these markers can provide diagnostic information.

With regard to the step of providing a biological sample from the subject, the term "biological sample" as used herein refers to any body fluid or tissue potentially comprising the one or more biomarkers described for use herein. In some embodiments, for example, the biological sample can be a blood sample, a serum sample, a plasma sample, or subfractions thereof. In some embodiments, the biological sample comprises a tumor biopsy.

Turning now to the step of identifying an expression level or activity of one or more markers in the biological sample, various methods known to those skilled in the art can be used to identify the one or more markers in the provided biological sample. In some embodiments, determining the amount of biomarkers in samples comprises using a RNA measuring assay to measure mRNA encoding biomarker polypeptides in the sample and/or using a protein measuring assay to measure amounts of biomarker polypeptides in the sample.

In certain embodiments, the amounts of biomarkers can be determined by probing for mRNA of the biomarker in the sample using any RNA identification assay known to those skilled in the art. Briefly, RNA can be extracted from the sample, amplified, converted to cDNA, labeled, and allowed to hybridize with probes of a known sequence, such as known RNA hybridization probes (selective for mRNAs encoding biomarker polypeptides) immobilized on a substrate, e.g., array, or microarray, or quantitated by real time PCR (e.g., quantitative real-time PCR, such as available from Bio-Rad Laboratories, Hercules, Calif., U.S.A.). Because the probes to which the nucleic acid molecules of the sample are bound are known, the molecules in the sample can be identified. In this regard, DNA probes for one or more biomarkers can be immobilized on a substrate and provided for use in practicing a method in accordance with the present subject matter.

In some embodiments, determining the amount of biomarkers in samples comprises the use of mass spectrometry and/or immunoassay devices and methods to measure polypeptides in samples, although other methods are well known to those skilled in the art as well. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety. Immunoassay devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, can be employed to determine the presence or amount of analytes without the need for a labeled molecule. See, e.g., U.S. Pat. Nos. 5,631,171; and 5,955,377, each of which is hereby incorporated by reference in its entirety.

Thus, in certain embodiments of the presently-disclosed subject matter, the marker peptides are analyzed using an immunoassay. The presence or amount of a marker (e.g., Caveolin-1, Survivin, or SMAC) can be determined using antibodies or fragments thereof specific for each marker and detecting specific binding. For example, in some embodiments, the antibody specifically binds Survivin, which is inclusive of antibodies that bind the full-length peptide or a fragment thereof. In some embodiments, the antibody is a monoclonal antibody, such as an anti-Survivin monoclonal antibody. In other embodiments, the antibody is a polyclonal antibody.

Any suitable immunoassay can be utilized, for example, enzyme-linked immunoassays (ELISA), radioimmunoassays (RIAs), competitive binding assays, and the like. Specific immunological binding of the antibody to the marker can be detected directly or indirectly. Direct labels include fluorescent or luminescent tags, metals, dyes, radionuclides, and the like, attached to the antibody. Indirect labels include various enzymes well known in the art, such as alkaline phosphatase, horseradish peroxidase and the like.

The use of immobilized antibodies or fragments thereof specific for the markers is also contemplated by the presently-disclosed subject matter. The antibodies can be immobilized onto a variety of solid supports, such as magnetic or chromatographic matrix particles, the surface of an assay plate (such as microtiter wells), pieces of a solid substrate material (such as plastic, nylon, paper), and the like. An assay strip can be prepared by coating the antibody or a plurality of antibodies in an array on a solid support. This strip can then be dipped into the test biological sample and then processed quickly through washes and detection steps to generate a measurable signal, such as for example a colored spot.

In some embodiments, mass spectrometry (MS) analysis can be used alone or in combination with other methods (e.g., immunoassays) to determine the presence and/or quantity of the one or more biomarkers of interest in a biological sample. In some embodiments, the MS analysis comprises matrix-assisted laser desorption/ionization (MALDI) time-of-flight (TOF) MS analysis, such as for example direct-spot MALDI-TOF or liquid chromatography MALDI-TOF mass spectrometry analysis. In some embodiments, the MS analysis comprises electrospray ionization (ESI) MS, such as for example liquid chromatography (LC) ESI-MS. Mass analysis can be accomplished using commercially-available spectrometers, such as for example triple quadrupole mass spectrometers. Methods for utilizing MS analysis, including MALDI-TOF MS and ESI-MS, to detect the presence and quantity of biomarker peptides in biological samples are known in the art. See for example U.S. Pat. Nos. 6,925,389; 6,989,100; and 6,890,763 for further guidance, each of which is incorporated herein by this reference.

With further respect to the measurement of the biomarkers described herein, in some embodiments, the Caveolin-1, Survivin, or SMAC biomarker is detected in the sample using a method selected from the group consisting of ELISA, Luminex, FACs, Western blot, dot blot, immunoprecipitation, immunohistochemistry, immunocytochemistry, immunofluorescence, immunodetection methods, optical spectroscopy, radioimmunoassay, mass spectrometry, HPLC, qPCR, RT-qPCR, multiplex qPCR, SAGE, RNA-seq, microarray analysis, FISH, MassARRAY technique, and combinations thereof.

Although certain embodiments of the methods only call for a qualitative assessment of the presence or absence of the one or more markers in the biological sample, other embodiments of the method call for a quantitative assessment of the amount of each of the one or more markers in the biological sample. Such quantitative assessments can be made, for example, using one of the above mentioned methods, as will be understood by those skilled in the art.

In certain embodiments of the method, a subject is identified having non-alcoholic steatohepatitis and/or hepatocellular carcinoma upon identifying the one or more biomarkers in a biological sample obtained from the subject. In other embodiments of the method, the identification of one or more of such markers in a biological sample obtained from the subject results in the subject being identified as having a risk of non-alcoholic steatohepatitis and/or hepatocellular carcinoma.

In certain embodiments of the method, it can be desirable to include a control sample that is analyzed concurrently with the biological sample, such that the results obtained from the biological sample can be compared to the results obtained from the control sample. Additionally, it is contemplated that standard curves can be provided, with which assay results for the biological sample can be compared. Such standard curves present levels of biomarkers as a function of assay units, i.e., fluorescent signal intensity, if a fluorescent signal is used. Using samples taken from multiple donors, standard curves can be provided for control levels of the one or more markers in normal tissue.

The analysis of markers can be carried out separately or simultaneously with additional markers within one test sample. For example, several markers can be combined into one test for efficient processing of a multiple samples and for potentially providing greater diagnostic and/or prognostic accuracy. In addition, one skilled in the art would recognize the value of testing multiple samples (for example, at successive time points) from the same subject. Such testing of serial samples can allow the identification of changes in marker levels over time. Increases or decreases in marker levels, as well as the absence of change in marker levels, can provide useful information about the disease status that includes, but is not limited to, identifying the approximate time from onset of the event, the presence and amount of salvageable tissue, the appropriateness of drug therapies, the effectiveness of various therapies, and identification of the subject's outcome, including risk of future events.

The analysis of markers can be carried out in a variety of physical formats as well. For example, the use of microtiter plates or automation can be used to facilitate the processing of large numbers of test samples. Alternatively, single sample formats could be developed to facilitate immediate treatment and diagnosis in a timely fashion, for example, in ambulatory transport or emergency room settings.

As mentioned above, depending on the embodiment of the method, identification of the one or more markers can be a qualitative determination of the presence or absence of the markers, or it can be a quantitative determination of the concentration of the markers. In this regard, in some embodiments, the step of identifying the subject as having non-alcoholic steatohepatitis and/or hepatocellular carcinoma or a risk thereof requires that certain threshold measurements are made, i.e., the levels of the one or more markers in the biological sample exceed control level. In certain embodiments of the method, the control level is any detectable level of the marker. In other embodiments of the method where a control sample is tested concurrently with the biological sample, the control level is the level of detection in the control sample. In other embodiments of the method, the control level is based upon and/or identified by a standard curve. In other embodiments of the method, the control level is a specifically identified concentration, or concentration range. As such, the control level can be chosen, within acceptable limits that will be apparent to those skilled in the art, based in part on the embodiment of the method being practiced and the desired specificity, etc.

In some embodiments of the presently-disclosed subject matter, a system, kit, or assay for diagnosing non-alcoholic steatohepatitis and/or hepatocellular carcinoma in a subject is provided, or a system, kit, or assay for determining whether to initiate or continue prophylaxis or treatment of non-alcoholic steatohepatitis and/or hepatocellular carcinoma in a subject is provided. Such systems, kits, or assays can be provided, for example, as commercial kits that can be used to test a biological sample, or series of biological samples, from a subject. The system can also include certain samples for use as controls. The system can further include one or more standard curves providing levels of markers as a function of assay units.

In some embodiments, a system for the analysis of biomarkers is provided that comprises antibodies having specificity for one or more markers associated with non-alcoholic steatohepatitis and/or hepatocellular carcinoma. Such a system can comprise devices and reagents for the analysis of at least one test sample. The system can further comprise instructions for using the system and conducting the analysis. Optionally the systems can contain one or more reagents or devices for converting a marker level to a diagnosis or prognosis of the subject.

The present methods can be performed on a wide variety of subjects. Indeed, the term "subject" as used herein is not particularly limited. The term "subject" is inclusive of vertebrates, such as mammals, and the term "subject" can include human and veterinary subjects. Thus, the subject of the herein disclosed methods can be a human, non-human primate, horse, pig, rabbit, dog, sheep, goat, cow, cat, guinea pig, rodent, or the like. The term does not denote a particular age or sex. Thus, adult and newborn subjects, as well as fetuses, whether male or female, are intended to be covered.

The practice of the presently-disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Oligonucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

The presently-disclosed subject matter is further illustrated by the following specific but non-limiting examples.

EXAMPLES

Materials and Methods for Examples 1-5

Figure 8:
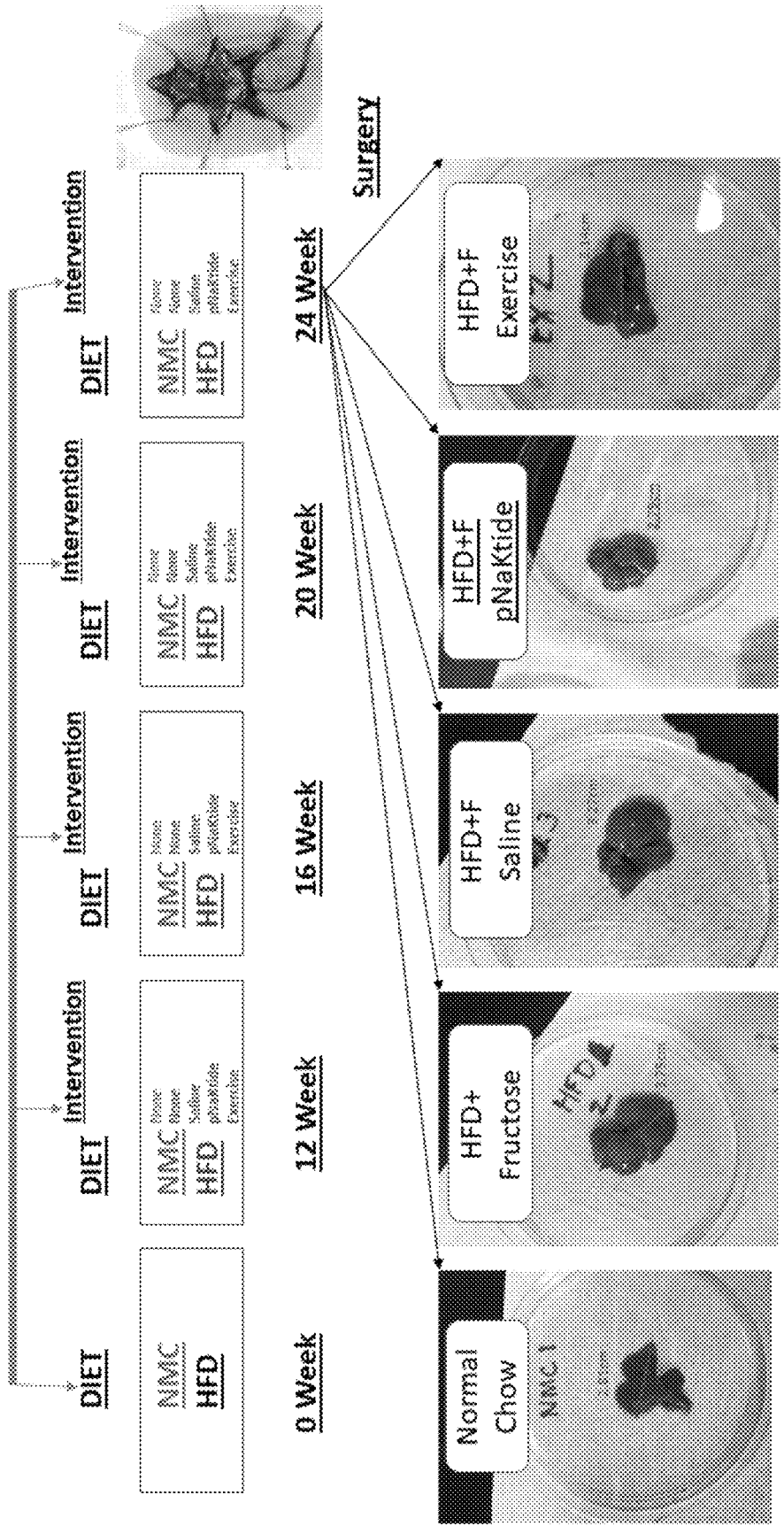
FIG. 8 is a schematic diagram showing the experimental design and animal flow for the metabolic assessment of the Murine diet-induced NASH Model, where rodents were exposed to normal mouse chow (NMC), high fat diet+fructose (HFD), and pNaKtide, or exercise, where diet regimens started at 0 W to 24 W, while interventions started at 12 W to 24 W and, sampling was performed at weeks 0, 12, 16, 20, and 24, where HDF saline and pNaKtide groups share a similar vehicle (1 ml of NS0.9% IP/week), where animals were operated at weeks 0, 12, 16, 20, and 24, and where livers were removed after the blood sample was obtained.

Animal Model & Experimental Design. Seven week old female C57BL/6J mice from Jackson Laboratory (Farmington, Conn.) were housed following a 12 h:12 h light-dark cycle under a temperature and humidity-controlled environment. After quarantine, rodents were exposed ad libitum to standard mouse chow (NMC, Bio-Serv, NJ) or Western diet consistent in high-fat diet complemented with 55% fructose-in-water (HFD, Bio-Serv, NJ). It was observed that rodents exposed to HFD for 12 weeks gain weight and developed fatty livers with NASH and progressive fibrosis. After 12 weeks, rodents were categorized into groups of NMC and HFD±intervention (pNaKtide or exercise). Control and intervention groups were maintained for another 12 weeks when the study was concluded (FIG. 8). Animals (n=7 per group) were divided into 1) NMC, 2) HFD, 3) HFD plus normal saline-HFD saline group (100 µl of NS0.9%, IP once a week), 4) HFD plus pNaKtide, pNaKtide group (25 mg/kg TBW dissolved in 100 µl of NS0.9%, IP once a week), and 5) HFD plus exercise (30 minutes standardized protocol on an endless rotating wheel motivated by electroshock, five times/week), Exercise group. Animal care followed the guidelines of the Marshall University IACUC under approved protocols.

Metabolic Body Composition. Metabolic body composition was assessed by EchoMRI-100H Body Composition Analyzer (Houston, Tex.) a week before animals were sacrificed. Records of total body weight (TBW), body water compartment, lean body mass, and body fat compartments were saved in GraphPad V7.04 (Loyola, CA, licensed to Marshall University).

Surgical Procedure. Surgical procedures were scheduled for weeks 0, 12, 16, 20, and 24 for each study group. On the assigned day, mice were sedated/euthanized by pentobarbital (5 mg/kg TBW, IP). At laparotomy and under magnification, blood was drawn from the IVC, followed by liver excision. Livers were washed with NS0.9% at room temperature, pictured and sharply divided before being snap-frozen in liquid nitrogen and stored at −80° C. for later use, or fixed at 4° C. (10% formaldehyde, FIGS. 9A-9C). Before anesthetic inductions (30 minutes), animals were administered octanoate by IP injection (10 mg/100 µl 0.9% NS pH adjusted at room temperature).

In prior studies, a clinical test was used that measures the capacity of the liver to oxidize fatty acids to ketone bodies as a surrogate of liver mitochondrial β-lipid oxidation. Unlike long-chain fatty acids, octanoate is water-soluble at physiological pH and is not incorporated into lipids. Also, since the entry of octanoate into liver mitochondria does not involve the carnitine system, keto-genesis from octanoate is not inhibited by dietary or intravenous carbohydrates. Thus, after the IP administration of octanoate, a wave of octanoate reaches the liver via the portal vein. There, octanoate is either oxidized to ketone bodies or is carried to the systemic circulation. The capacity of the liver to oxidize octanoate is reflected by the concentration of octanoate and the production of ketone bodies in peripheral blood within the hour following IP administration. It was predicted the plasma concentration ratio [octanoate]/[ketone bodies] will be low in healthy animals, and high in rodents with NASH.

Gene Expression, Protein Activity, and Protein Glutathionylation. Proteins gene expression involved in cellular metabolism (mTOR1, FOX01, SIRT7), cell senescence (Tp53), and cellular replication (GrB2, Src) were evaluated by Western blot. The effect on lipid metabolism by diet±interventions was assessed by the expression of the Peroxisome Proliferator-Activated Receptors (PPARs) and its transcriptional coactivator PGC-1α using RT-PCR methods. The Na/K-ATPase activity was determined as described below. NAK subunits were immuno-precipitated, and their degree of glutathionylation was quantitated following published protocols validated in our laboratory.

Morphological Assessment. The NAFLD score calculated liver fat content; liver fibrosis was measured by the fibrosis score and senescence/apoptotic activities were performed by counting positive cells on special staining's (SA-3-gal activity and TUNEL), respectively on digitally recorded images at 40× magnification from the label but blinded liver slides saved using ImageJ1.51u software.

Statistical Analysis. Parametric data was examined with analyses of variance (ANOVA). Individual group means were compared by t-test employing the Holm-Sidak correction for multiple comparisons. Non-parametric data was analyzed with Kruskal-Wallis and individual groups compared by chi square ($\chi^2$), using the Holm-Sidak correction for multiple comparisons. Principal Component Analysis (PCA) was also conducted to investigate and visualize the pattern of metabolite differences among groups. All analyses were carried out using the R-language and environment, a platform from the R project for statistical modeling, computing, and graphics.

Metabolomics: Plasma Treatment and Mass Spectrometry. Materials and reagents, as well as plasma treatment and specific MS/MS methods to measure glutathione sp. and non-target metabolites (n=81) were as described below.

Materials and Reagents. General chemicals, as well as glutathione (GSH) and glutathione disulfide (GS:SG) were from Sigma-Aldrich (St. Louis, Mo.). Homo-glutathione was from Chem-Impex International (Wood Dale, Ill.). Ophthalmic acid was from Bachem (Torrance, Calif.).

Acetonitrile was procured from Fisher Scientific (Pittsburgh, Pa.). Octanoate was purchased from Sigma (Milwaukee, Wis.).

Plasma Treatment. Heparinized blood, collected in glass tubes, was cooled by gentle repeated inversions in an ice water slurry for 1 min and centrifuged (3,000 g) at 4° C. for 10 min. To prevent its oxidation, GSH was immediately converted to a stable thioether by treating 100 µl of blood with 100 µl of 50 mM iodoacetate in 10 mM ammonium bicarbonate, pH=10, adjusted with concentrated ammonia hydroxide. After the buffy layer and the red blood cell pellet were removed, aliquots of plasma were treated with 50 µl of iodoacetate buffer (vol:vol, 1:1), collected in pre-labeled micro-tubes and quick-frozen to be stored at −80° C. until analysis.

Liquid Chromatography-Mass Spectrometry (LC-MS) for Glutathione Sp. Reduced and oxidized glutathione (GSH and GSSG) and OA in plasma were analyzed using methods validated previously with minor modifications. In brief, plasma samples were first treated with iodoacetate to derivatize GSH as GS-carboxymethyl, then GSSG in plasma was converted to GS-cyanomethyl using iodoacetonitrile after dithiothreitol reduction. The internal standard homo-glutathione was spiked at the beginning of the process. OA determination was done separately by protein precipitation. All calibration curves consisted of two blanks and seven calibration points. The curve ranges were as follows: GSH, 0.78-200 µM; GSSG, 0.157-400 µM; ophthalmate, 0.156-20 µM. A weighting factor of $1/x2$ was applied over the calibration curves. The resulting peak area ratios of analyte/internal standard were plotted against the concentrations. Electrospray-ionization mass spectrometry of thioethers was performed on a Thermo Scientific TSQ Quantum Ultra mass spectrometer (Thermo Fisher Scientific, Waltham, Mass.), equipped with a heated electrospray ion source (HESI-II), coupled to an Agilent 1200 HPLC. The chromatography was done with a reversed-phase C18 column (Synergi 4µ Hydro-RP, 50×2.0 mm, Phenomenex). The compounds of interest were separated from mouse plasma endogenous components using 1% acetonitrile containing 0.1% formic acid at 0.1 ml/min isocratic. The mass spectrometry was operated under positive ionization mode with the ion spray voltage at 4000V. The ion transfer tube temperature was maintained at 400° C., and the vaporizer temperature was 40° C. The gas setting for sheath, aux, and ion sweep were 50, 2, and 0 arb, respectively. Argon gas pressure was 1.5 mTorr used as the collision gas in Q2. The collision energy was 15V for monitored transitions. Peak width for Q1 and Q3 was set at 0.7FWHM. Xcalibur software (version2.1.0, Thermo) was used for data registration. The area under the curve of the spectra was recorded and captured on a database for concentration calculations and data analyses.

Liquid Chromatography-Mass Spectrometry (LC-MS) for Non-Targeted Metabolon. Solvent extraction from thaw samples was performed with MAA (methanol:acetonitrile: acetone; 1:1:1) and internal standards were reconstituted with methanol:$H_2O$; 2:98. LC-MS analyses were performed on a 1290 Infinity Binary LC system from Agilent used for chromatographic separation in conjunction with a Waters Acquity UPLC HSS T3 1.8 µm 2.1×100 mm column in connection with a Water Acquity UPLC HSS T# 1.8 µm pre-column. The column temperature was set up at 55° C. at a flow rate of 0.45 ml/min with time intervals for system equilibration (7 min) and data acquisition (27 min) for a total run time of 34 min. Mobile phase-A was 0.1% formic acid in the water, and mobile phase-B was 0.1% formic acid in methanol. For elution, mobile phase-A and B were initially held at 98%:2% for 20 min. Then, from 20.1 min, the mobile phase was brought to 25%-A: 75%-B and held there for 2 min. Then, from 22.1 min, the eluent was brought to 2%-A and held there until 30 min. Finally, from 30.1 to 37 min, the eluent was bought back for re-equilibration to 98%-A. Positive and Negative mass spectra curves were acquired in scan mode with a mass range of 50 to 1000 m/z. Inline calibration was performed using debrisoquine sulfate (m/z 176.1182) and HP-0921 from Agilent (m/z 922.0098) in the positive mode, and 4-NBA (m/z 166.0146) and HP-0921 from Agilent (m/z 966.0007 formate adduct) in the negative mode. Mass spectrometer was set up as follows: gas temperature of the ion source at 325° C. with drying gas flow at 10 l/ml; the nebulizer pressure was 45 psi with a sheath gas at 400° C., a sheath flow of 12 l/ml and capillary voltage of 4000V, fragmentor voltage at 140V, and skimmer voltage at 65V. Raw data were deconvoluted with the National Institute of Standards and Technology (NIST) Automated Mass Spectral Deconvolution and Identification Software (AMDIS). After spectral analysis and data processing of 800 signals, 94 signals could be identified in 89% of all samples. Identified signals were confirmed by our metabolomic library and the Fiehn library (Agilent Technologies Inc, Santa Clara, Calif.). For further quantification, the data was exported to the University of Michigan Core Metabolomic Server. The concentration of each metabolite was expressed as its relative peak area (divided by the area of the corresponding internal standard in the same chromatogram). Some small compounds, although they were specifically targeted, were not found or identified with certainty in the present model. They included glycerol, pyruvate, and aceto-acetone. All 94 identified metabolites were included in the statistical analyses.

Statistical Analyses of Non-Targeted Metabolites. Statistical modeling was performed using a linear mixed-effect model of analysis of variance (mixed two-way ANOVA), fitted univariately to each variable (single metabolite concentration). For statistical inference, empirical Bayes methods and posterior estimators derived from them (moderated F-, t-, and B statistics) were used that have proven to result in higher statistical power and to be useful for ranking variables in terms of evidence for differential expression. Information was borrowed by constraining the within-block correlations to be equal between variables and using empirical Bayes methods to moderate the standard deviations between them. These methods are particularly appropriate when only a few samples are available, as is always the case in high throughput datasets. Besides, the transformed $\log^{10}$ data was interrogated by comparing the RFD group to the NMC group and the intervention groups (pNaKtide and exercise) to generated heat maps using the R software V5.1 (licensed to Marshall University). Each metabolite from each animal in each group was compared at weeks 0, 12, 16, 20, and 24, followed by comparisons among groups of each metabolite/animal to construct visual metabolomics signatures displayed in a color array.

Gene Expression, Protein Activity, and Protein Glutathionylation. Proteins gene expression involved in cellular metabolism (mTOR1, FOX01, SIRT7), cell senescence (Tp53, Src), and cellular replication (GrB2, Src) were evaluated by Western blot. 80 µg of homogenized liver tissue were prepared to be loaded on nitrocellulose membranes, which were subsequently exposed to protein-specific monoclonal antibody and developed according to protocols for the FluorChem M System (San Jose, Calif.). In addition, WB was used to detect the presence/absence of pNaKtide in liver tissue in treated/non-treated animal groups and to quantitate the expression of the α1-subunit of the Na/K-ATPase. A polyclonal rabbit antibody against pNaKtide was developed internally. Polyclonal rabbit antibody against the α1-subunit was purchased from Millipore Sigma. The integrated density of the bands in the spectra was measured using ImageJ1.51u software, and spectra/data was saved on laboratory books and GraphPad Prism software, respectively (Loyola, CA, V7.04 licensed to Marshall University). For the Src expression, phosphorylated (pSrc) and complete (cSrc) varieties were run on liver samples, and integrated densities were measured. The ratio pSrc/pSrc+cSrc was displayed.

Real-Time Poly-Chain Reaction (RT-PCR). The effect on lipid metabolism by diet+interventions was assessed by the expression of the Peroxisome Proliferator-Activated Receptors (PPARs) and its transcriptional coactivator PGC-1α using RT-PCR methods. Expression of glyceraldehyde-3-phosphate-dehydrogenase (GAPDH) was run as a housekeeping gene. Total RNA was extracted from flash-frozen liver tissue using RNeasy Protect Mini kit (QIAGEN, MD) according to the manufacturer's instructions. Total RNA (1ag) was transcribed into cDNA using SuperScript 1.11 (Invitrogen, CA) reverse transcription reagents. A quantitative real-time polymerase chain reaction analyzed total RNA. RT-PCR was performed using LightCycler 480 SYBR Green I Master (Roche Life Science) reagents on a Roche LightCycler 480 Instrument II (Roche Life Science, Indianapolis, Ind.). Specific primers for PPRγ, PGC1α, and GAPDH were used. Each reaction was performed in triplicate, and all experimental samples were normalized-using GAPDH as an internal control. The comparative threshold cycle (Ct) method was used to calculate the fold amplification as specified by the manufacturer. Total RNA was analyzed as well to assess the expression of the α1-subunit of the Na/K-ATPase.

Na/K-ATPase Activity Assay. The Na/K-ATPase activity was determined as previously described. Briefly, 100 mg of wet weight liver tissue was minced and homogenized in 2 ml of buffer solution (0.25M sucrose, 1.25 mM EGTA, and 10 mM Tris-HCl, pH 7.0) in Glass-cold high-speed homogenizer at 2° C. to yield a 1:2 dilution; after filtration through a gauze, further dilutions of the homogenates (1:4 and 1:8) was made by adding homogenizing buffer. Diluted samples were warmed to 37° C. for 5 min followed by the mixing of diluted sample with reactive medium (vol:vol, 1:9) for a final concentrations of ATP (5.0 mM), $Mg^{++}$ (5.0 mM), $Na^+$ (120 mM), $K^+$ (12.5 mM), Tris (25.0 mM), (137.5 mM) and azide (5.0 mM) at a pH=7.40 and constant T=37° C. The reaction was terminated by adding cold TCA at 5 min of reaction time. The released inorganic phosphate (Pt) was detected by the use of BioMol Green reagent (Enzo Life Sciences, NY) at room temperature. Samples, controls, and standard phosphate solutions were incubated with BioMol green for 25 min in the dark, followed by optical density read at 620 nm. For each run, a standard curve was generated to calculate Pi in μmoles/hr/mg protein. The protein content was determined by the Lowry method, and estimates of Na/K-ATPase activity for a negative control parallel run (10 mM of Ouabain added to sample) were performed.

Glutathionylation of the α1-NKA by Immunoprecipitation. NAK subunits were immuno-precipitated, and their degree of glutathionylation was quantitated following published protocols validated in our laboratory. Na/K-ATPase al subunit was immuno-precipitated using the NaK-ATPase α-1 antibody (06-520, Millipore). In brief, 50 mg of mouse liver was homogenized in ice-cold homogenization buffer with protease inhibitor (250 mM D-Mannitol, 30 mM L-histidine, 5 mM EGTA, 0.1% Deoxycholate, adjusted to a pH of 6.8 with Tris-base). From each sample, 1600 μg of total protein (for a protein concentration of 2 μg/μl) was incubated in lysis buffer (100 mM NaCl, 20 mM Tris-base, 10 mM NaF, 1 mM PMSF, 1 mg/ml C12E8, pH=7.4) for 2 hour at 4° C. with end-over-end rotation. After incubation, samples were centrifuged at 13,200 rpm×15 min, and the supernatant was collected. Then, 400 m of total protein from each sample was incubated in lysis buffer (protein concentration of 1 μg/μl) with α-1-NaK-ATPase antibody (1:1000), over-night at 4° C. with end-over-end rotation. After incubation, 100 μl of protein G agarose beads (16-266, Millipore) were added to the lysate and incubated for 3 h at 4° C. with end-over-end rotation. The beads were then sedimented by spinning down at 13,200 rpm×1 min and washed three times with cold lysis buffer. Sample loading dye (Invitrogen™ 4X Bolt™ LDS Sample Buffer) was added, and the mixture was heated to 56° C. for 30 min. The supernatant was used for immunoblotting. For SDS-PAGE, equal amounts of protein were loaded into each lane of a 10% gel. Proteins were electro-blotted onto a nitrocellulose membrane (Amersham Protran, GE Healthcare), blocked for 1 hr at room temperature in TBST-buffer (10 mM Tris-Base, 0.9% NaCl, 0.1% Tween-20 pH=7.4) containing 4% skimmed milk powder. To detect glutathionylation of NaK-ATPase α-1 subunit, the membranes were probed with mouse monoclonal anti-GSH primary antibody 1:1000 (101-A, clone D8, Virogen) after overnight incubation (4° C.) and detected with respective secondary antibody (m-IgGkBP-HRP: SC-516102, Santa Cruz; 1:1000). Finally, the total α-1 expression was detected by the primary sub-unit antibody (1:4000), and respective secondary antibodies (IgG HRP conjugated at 1:6000, SC-516102, Santa Cruz). Samples to be compared were loaded on the same gel. Relative protein concentrations were quantified by ImageJ1.51u software (Loyola, CA, V7.04 licensed to Marshall University) using background subtraction.

Morphological Assessment. The morphological assessment was conducted as follows:

Liver Fat Content Assessment. The NAFLD activity score (NAS) was used on digitally recorded images at 40× magnification from the labelled but blinded liver slides stained with H&E. Five pictures from each animal in each group were graded for individual criteria, and the aggregated scores were saved for data analysis. Criteria used for the NAS include macro-vesicular steatosis, micro-vesicular steatosis, inflammatory cell infiltrate, and cellular hypertrophy. Steatosis was graded whether the fat vacuoles displaced the nucleus (macro) or not (micro) as 0=<5%, 1=5-33%, 2=34-66%, and 3=>66%. Inflammatory-foci was defined as an aggregate of more than 5 inflammatory cells as a cluster and it was scored as 0 (<0.5 foci), 1 (0.5-1.0 foci), 2 (1.0-2.0 foci), and 3 (>2.0 foci). Hepatocellular hypertrophy was defined as cellular enlargement more than 1.5 times the normal hepatocyte diameter. The number of cells and their size were determined using ImageJ1.51u software (NIH, MD).

Liver Collagen Deposition Assessment. Masson's Trichrome staining was performed following a standardized protocol to assess fibrosis development. Stained liver slides were graded for fibrosis using the following scale: 0: None; 1: Enlarged, fibrotic portal tracts; 2: peri-portal or portal-portal septa, but intact architecture; 3: Fibrosis with architectural distortion, but no evident cirrhosis; 4: probable or definitive cirrhosis with bridging fibrosis. Five pictures from each animal in each group were graded for individual criteria, and the aggregated scores were saved for data analyses. Digitally recorded images at ×40 magnification from labeled but blinded liver slides were evaluated, and scores were recorded for data comparison.

Liver Cell Senescence Activity Assessment. The SA-β-gal activity was detected using the Senescence Associated 13-Galactosidase Staining kit (Cell signaling Technology #9860, MA) on fresh, snap frozen in liquid nitrogen liver tissue embedded in OCT. Briefly, 6 μm liver sections were fixed in kit fixative solution for 2 min at room temperature, then washed in PBS twice. Slides were stained overnight in SA-β-gal staining solution at 37° C. and pH5.5. In the morning, slides were rinsed with PBS×2, counter-stained with Nuclear Fast Red solution for 3-5 min to have a final PBS wash. Sections were dehydrated using an increasing concentration of alcohol, cleared in xylene, and mounted with permount. Five pictures from each animal in each group were graded for individual criteria, and the aggregated scores were saved for data analyses. The percentage of cells with SA-β-gal activity (blue-stained/over total counted cells) was evaluated on the same day. Digitally recorded images at ×40 magnification from labeled but blinded liver slides were saved using ImageJ1.51u software.

Liver Cell Apoptosis Activity Assessment. Apoptosis activity was detected by the terminal deoxynucleotidyl transferase (TdT)-mediated dUTP nick end labeling (TUNEL) method on digital records from blinded liver slides (Click-iT Plus TUNEL assay kit, Invitrogen by Thermo Fisher Scientific, MA). Five pictures from each animal in each group were graded for individual criteria, and the aggregated scores were saved for data analyses. Images ×40 magnification were analyzed using ImageJ1.51u software, and data was generated by comparing the percentage of positive counted cells on DAPI/GFP superimposed images. A Faculty Pathologist supervised morphological assessment of all liver slides at Marshall University.

Example 1—Metabolic Body Composition

Figure 1B:
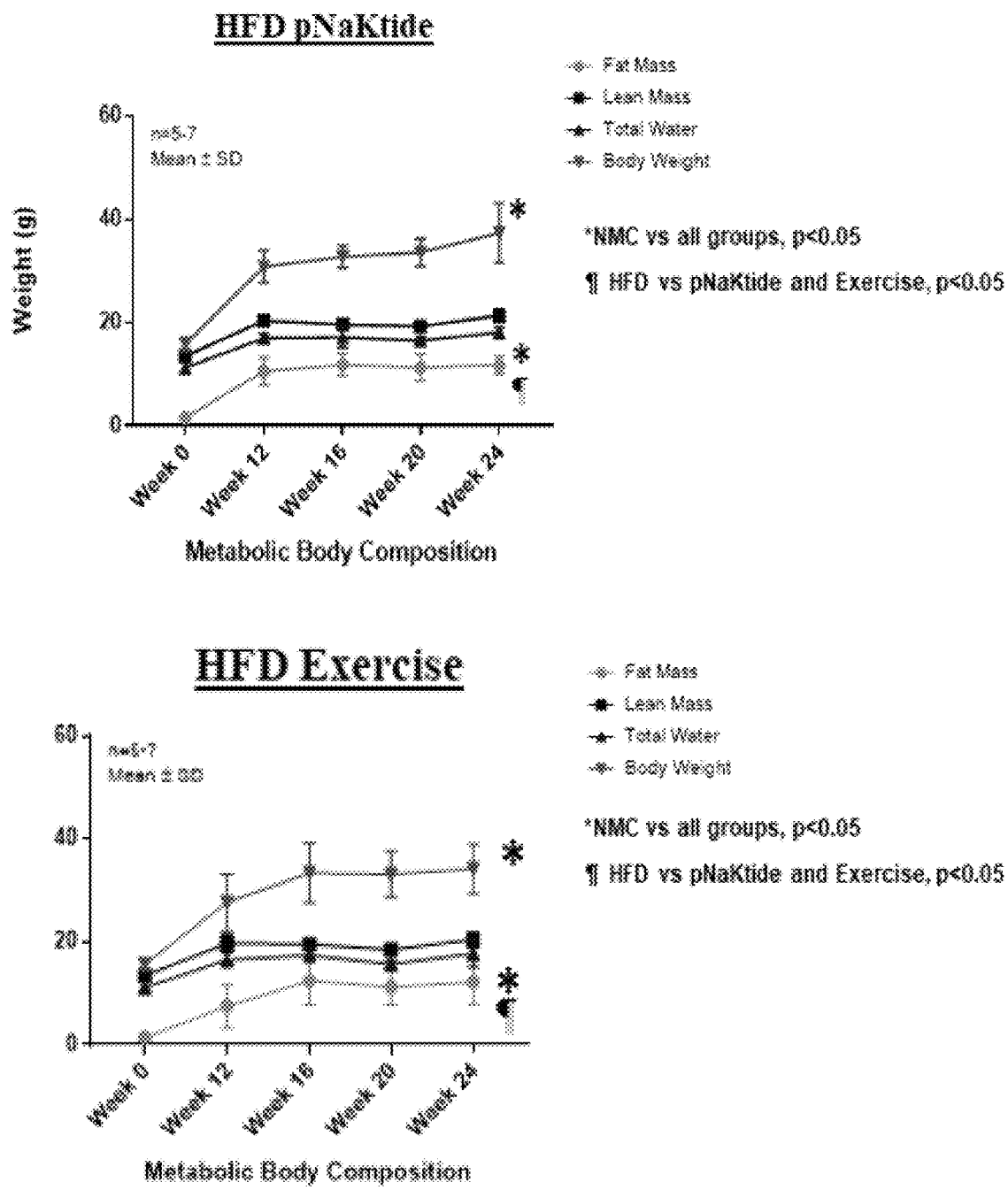
Figure 1C:
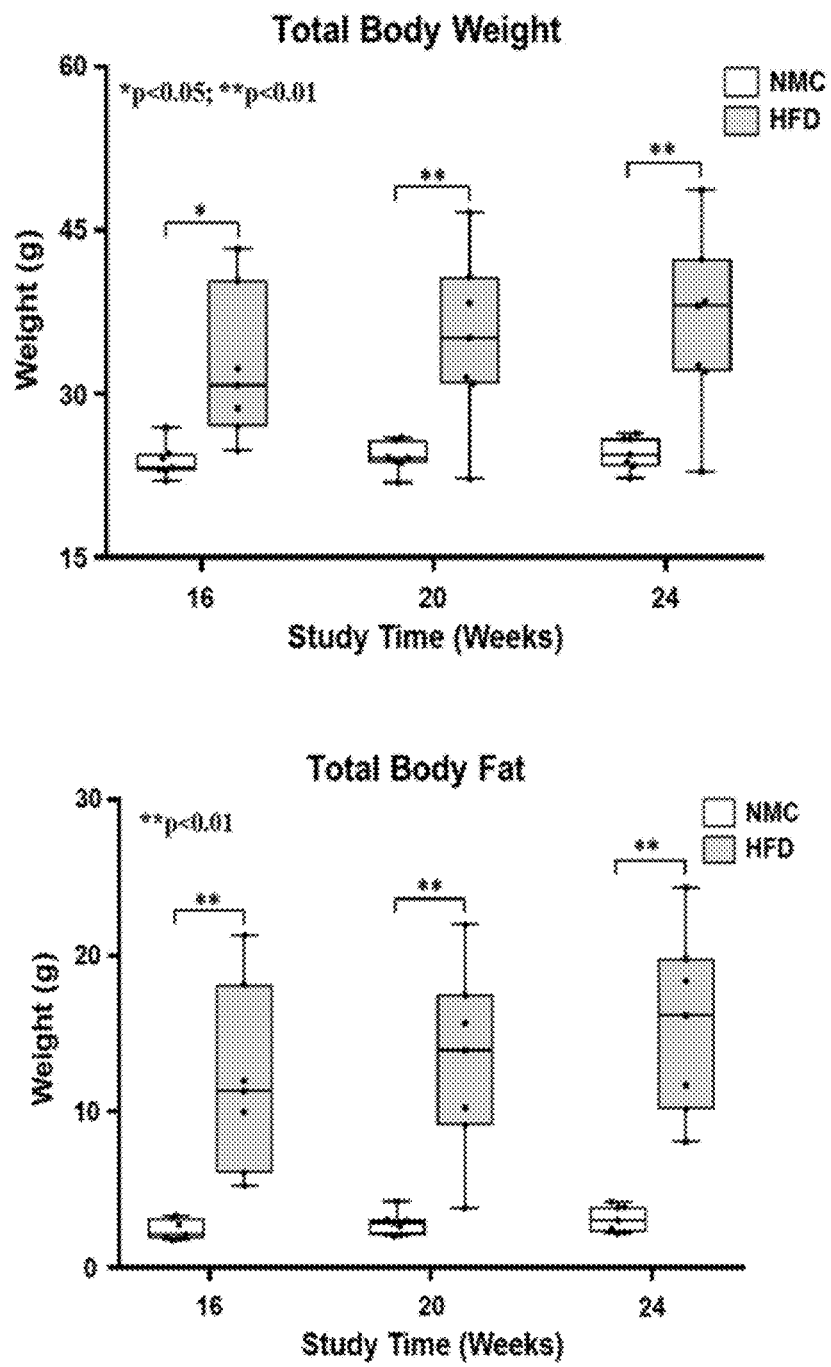
FIG. 1C includes graphs showing metabolic body composition the murine model of NASH without showing the pNaKtide intervention, where animals (n=5-7) were exposed to NMC or HFD, and where, again, the rodents exposed increased their total body weight (TBW) mainly due to expansion of their fat mass compartment when compared to the NMC group (displayed as plots of M±SEM, $p<0.05$, by ANOVA followed by t-test).
Figure 1D:
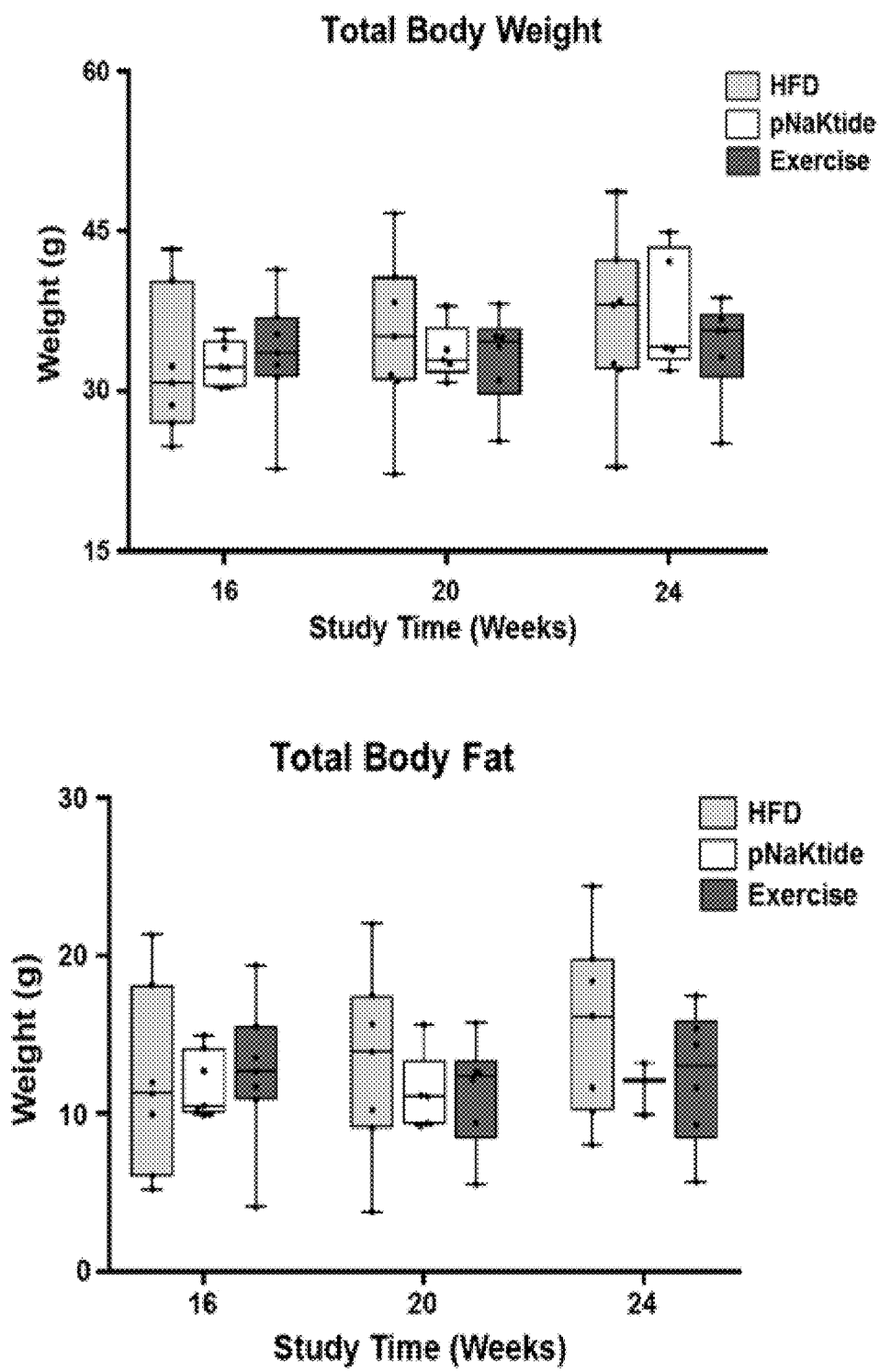
FIG. 1D includes graphs showing metabolic body composition the murine model of NASH with the pNaKtide intervention, where animals (n=5-7) were exposed to HFD and, again, the rodents exposed increased their total body weight (TBW) mainly due to expansion of their fat mass with similar values among all groups (displayed as plots of M±SEM, $p>0.05$, by ANOVA).

Total body weight (TBW) from murine on HFD was significantly higher due to an expansion of their fat mass compartment when compared to the NMC & interventions groups (pNaKtide & Exercise) (FIG. 1A, $p<0.05$, ANOVA; FIGS. 1C-1D). Even though rodents from the pNaKtide and Exercise groups were maintained on HFD, their weight was stable without further weight gain and stabilization of their fat compartment during the study period (FIG. 1B; FIG. 1D).

Example 2—Oxi-Redox Status & Glutathione Species

Figure 2A:
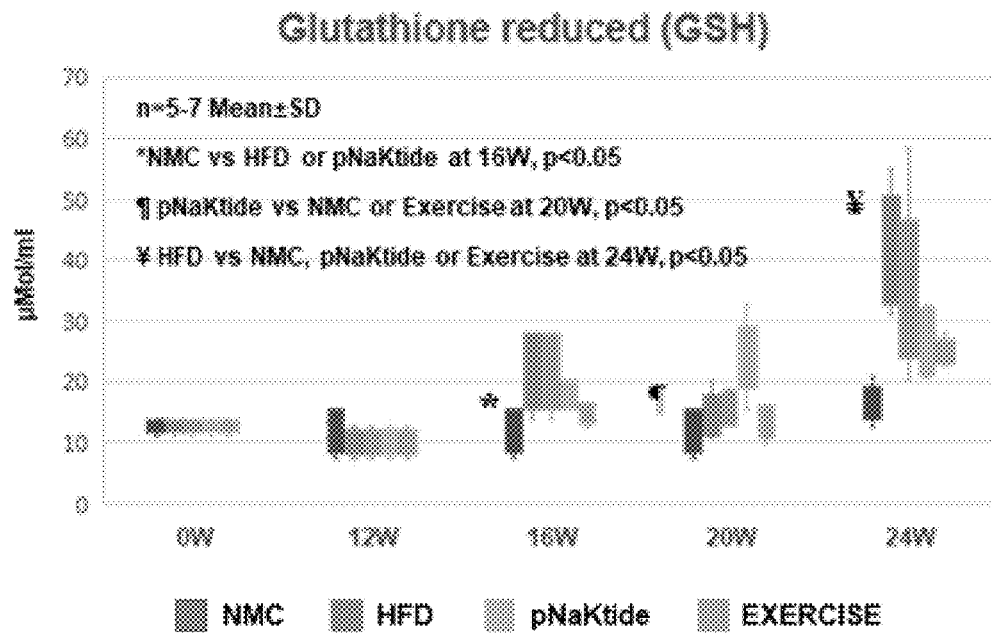
FIGS. 2A-2D are graphs showing cell oxi-redox assessment in plasma from rodents with NASH, where there was a significant difference in the Glutathione sp. (glutathione reduced (GSH, FIG. 2A), glutathione oxidized (GS:SG, FIG. 2B), and ophthalmate (OA, FIG. 2C)) among groups (displayed as plots of Mean±SD, $p<0.05$, ANOVA), where animals in the HFD group had a significantly higher concentration of GSH, GS:SG, and OA when compared to the NMC at week 16 (in FIG. 2A to FIG. 2C, $p<0.05$, t-test), where, in addition, the HFD group had a significantly higher concentration of GS:SG than the NMC and the intervention groups at week 24 ($p<0.05$, t-test). The GSH and glutathione ratio (GSG/GS:SG) was significantly higher in the pNaKtide group when compared to any other group at week 20 (in FIG. 2A and FIG. 2D, respectively, $p<0.05$, t-test).
Figure 2B:
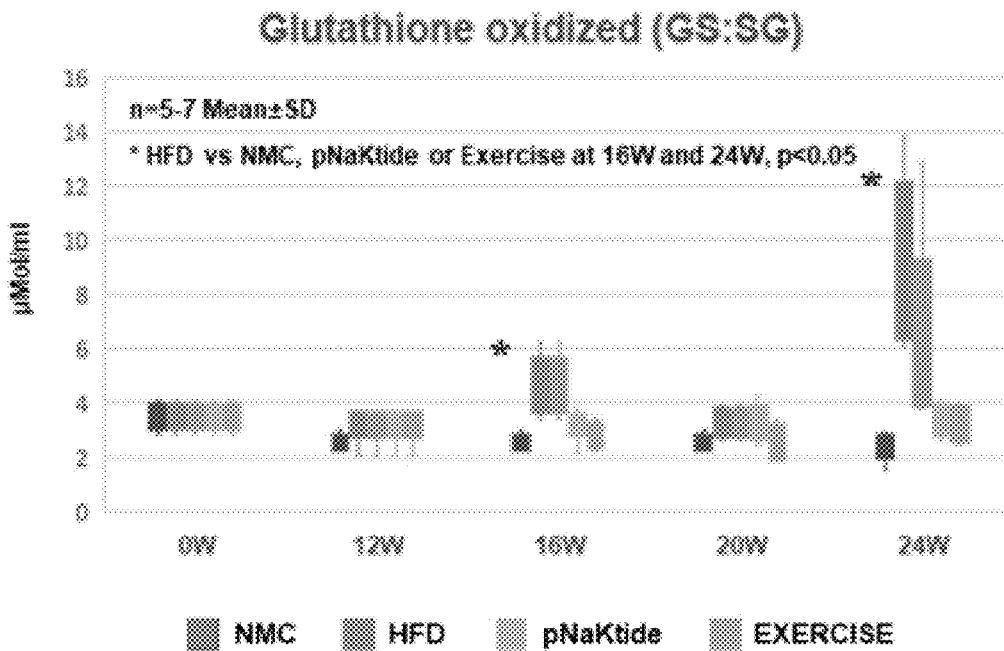
Figure 2C:
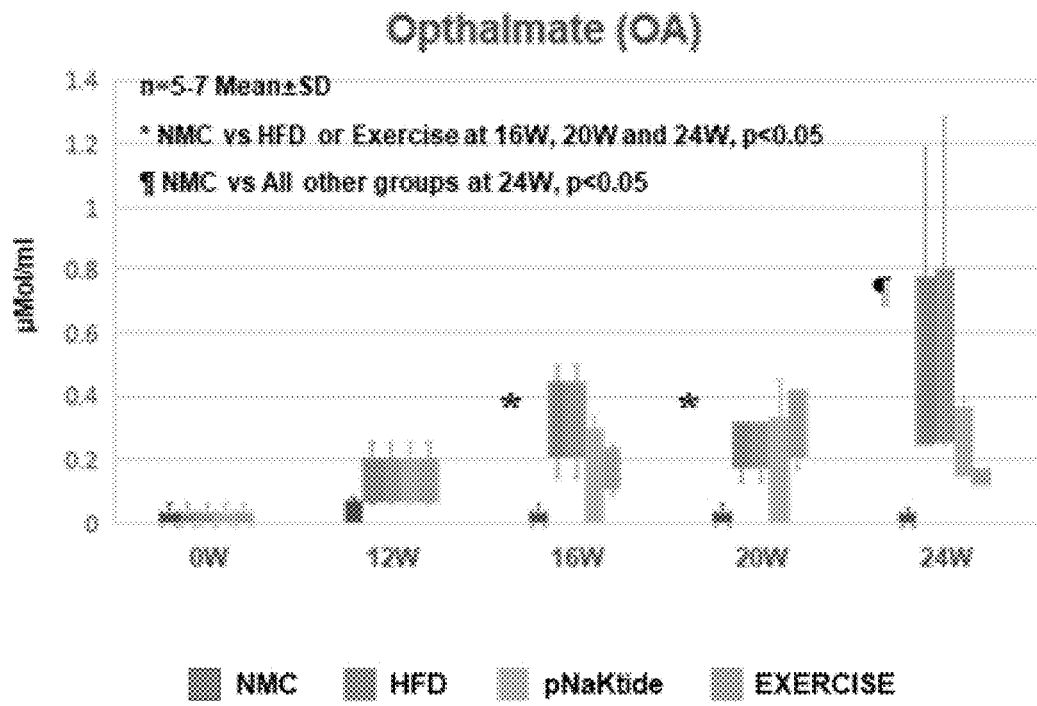
Figure 2D:
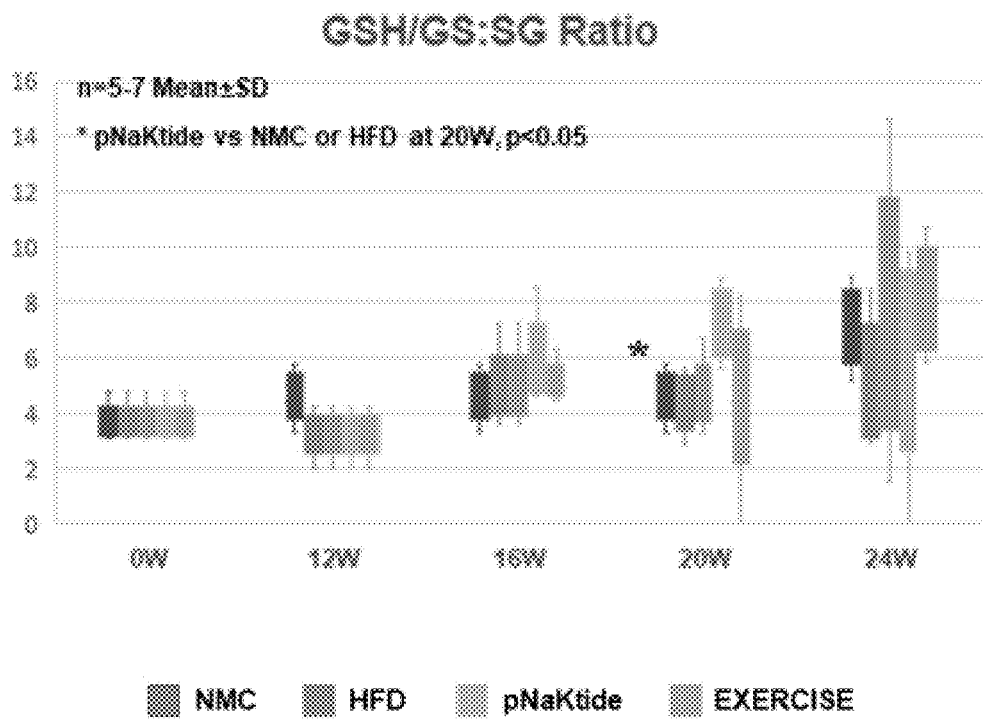
Figure 2E:
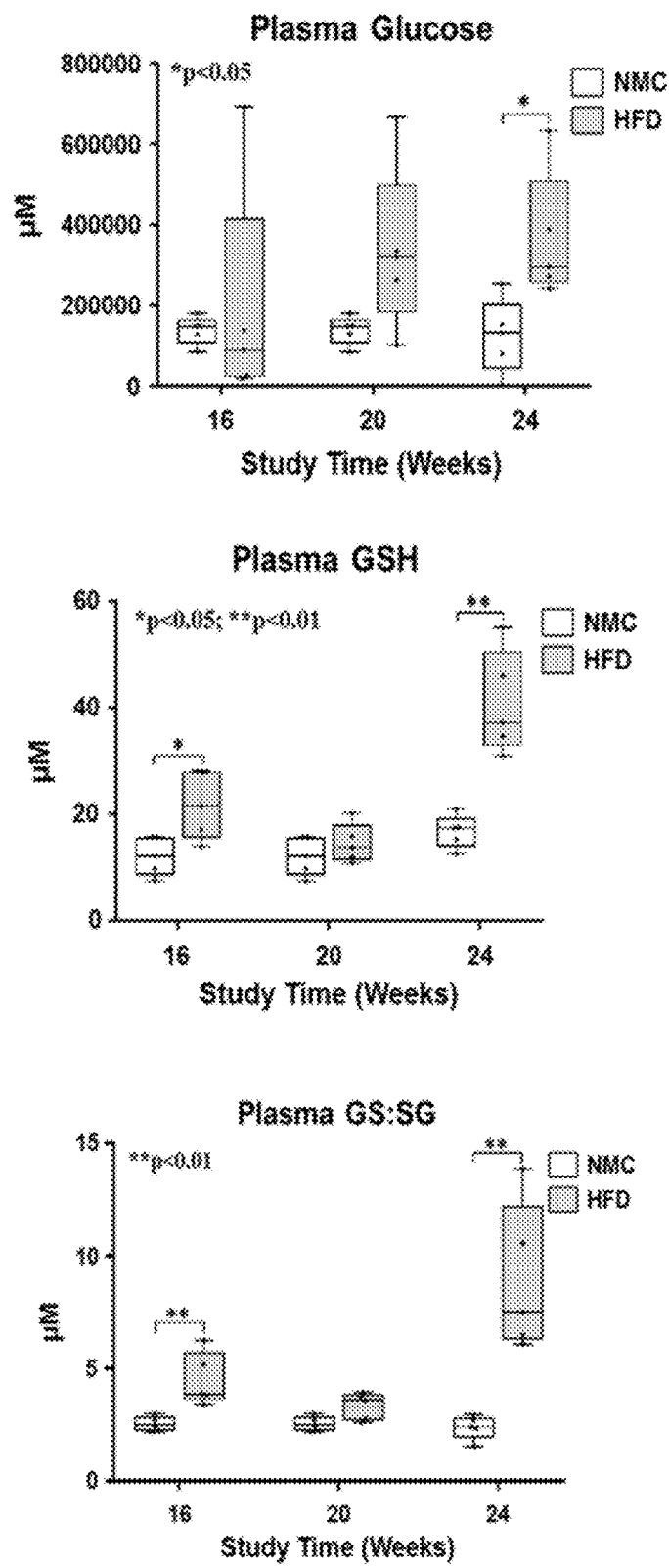
FIG. 2E includes further graphs showing glucose and glutathione sp. concentrations in plasma without pNaKtide intervention, where glucose concentration from the NMC group was significantly different when compared to the HFD group by week 24 ($p<0.05$), where there was a significant difference in the Glutathione sp. (glutathione reduced GSH, and glutathione oxidized GS:SG) among groups ($p<0.01$, by ANOVA), and where animals in the HFD group had a significantly higher concentration of GSH and GS:SG when compared to the NMC at week 24 ($p<0.01$).
Figure 2F:
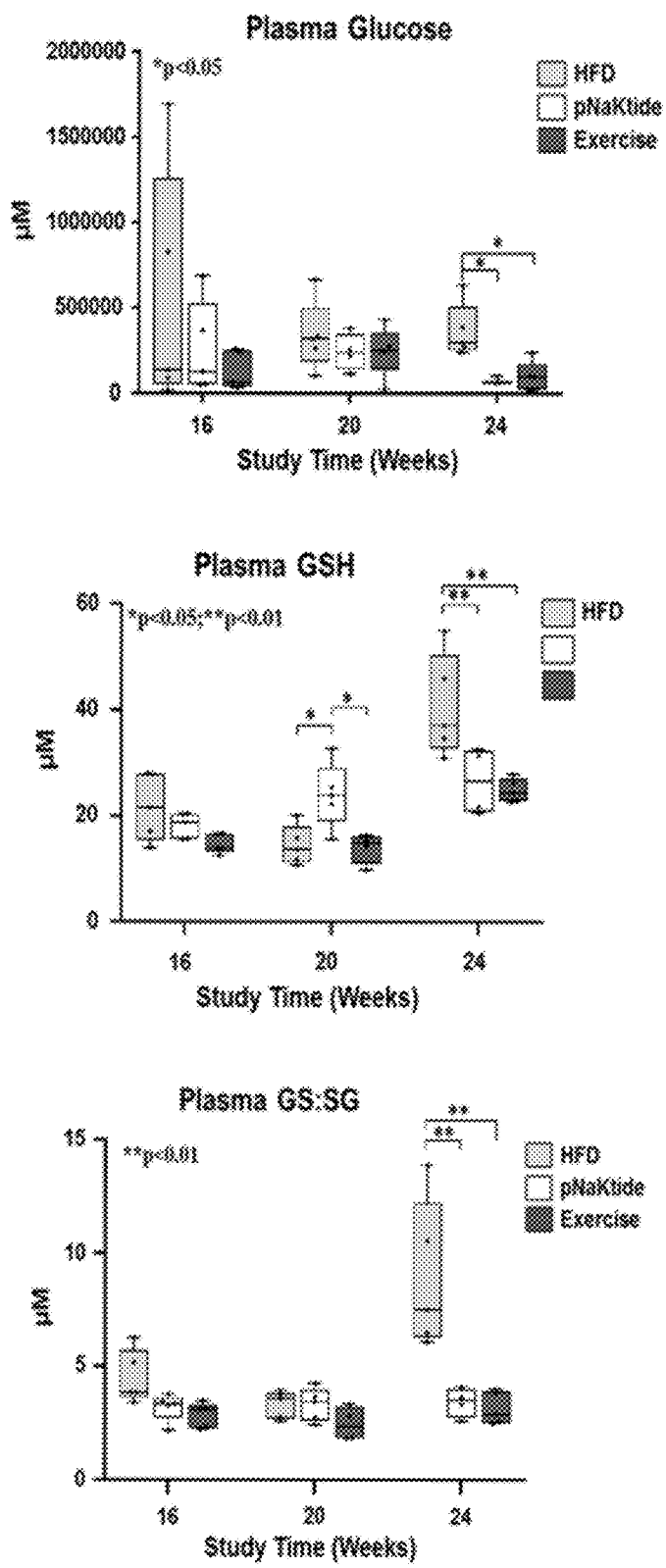
FIG. 2F includes further graphs showing glucose and glutathione sp. concentrations in plasma with pNaKtide intervention, where glucose concentration from the HFD group was significantly different when compared to the pNaKtide or exercise groups by week 24 ($p<0.05$ by ANOVA, followed by t-test), where there was a significant difference in the Glutathione sp. (glutathione reduced GSH, and glutathione oxidized GS:SG) among groups ($p<0.01$), and where animals in the HFD group had a significantly higher concentration of GSH and GS:SG when compared to the pNaKtide and Exercise groups at week 24.

There was a significant difference in the Glutathione sp. (glutathione reduced (GSH), glutathione oxidized (GS:SG), and ophthalmic acid (OA)) among groups ($p<0.05$, ANOVA). The HFD group had a significantly higher concentration of GSH, GS:SG, and OA when compared to the NMC at weeks 16 and 24 (FIG. 2A). Also, the HFD group had a significantly higher concentration of GSH, GS:SG, and OA than the intervention groups at week 24 (FIGS. 2A-2C, $p<0.05$, t-test). Nevertheless, the concentration of glutathione sp. was not significantly different in the pNaKtide group when compared to animals exposed to NMC ($p>0.05$, t-test). The glutathione ratio (GSH/GS:SG) was significantly higher in the pNaKtide group when compared to any other group at week 20 (FIG. 2D, $p<0.05$, t-test).). As shown in FIG. 2E, glucose concentration from the NMC group was significantly different when compared to the HFD group by week 24 ($p<0.05$), there was a significant difference in the Glutathione sp. (glutathione reduced GSH, and glutathione oxidized GS:SG) among groups ($p<0.01$, by ANOVA), and the animals in the HFD group had a significantly higher concentration of GSH and GS:SG when compared to the NMC at week 24 ($p<0.01$). As shown in FIG. 2F, glucose concentration from the HFD group was significantly different when compared to the pNaKtide or exercise groups by week 24 ($p<0.05$ by ANOVA, followed by t-test), there was a significant difference in the Glutathione sp. (glutathione reduced$^{GSH}$ and glutathione oxidized GS:SG) among groups ($p<0.01$), and the animals in the HFD group had a significantly higher concentration of GSH and GS:SG when compared to the pNaKtide and Exercise groups at week 24.

Example 3—ß-Lipid Oxidation, Insulin Resistance and Metabolic Prints

Figure 3A:
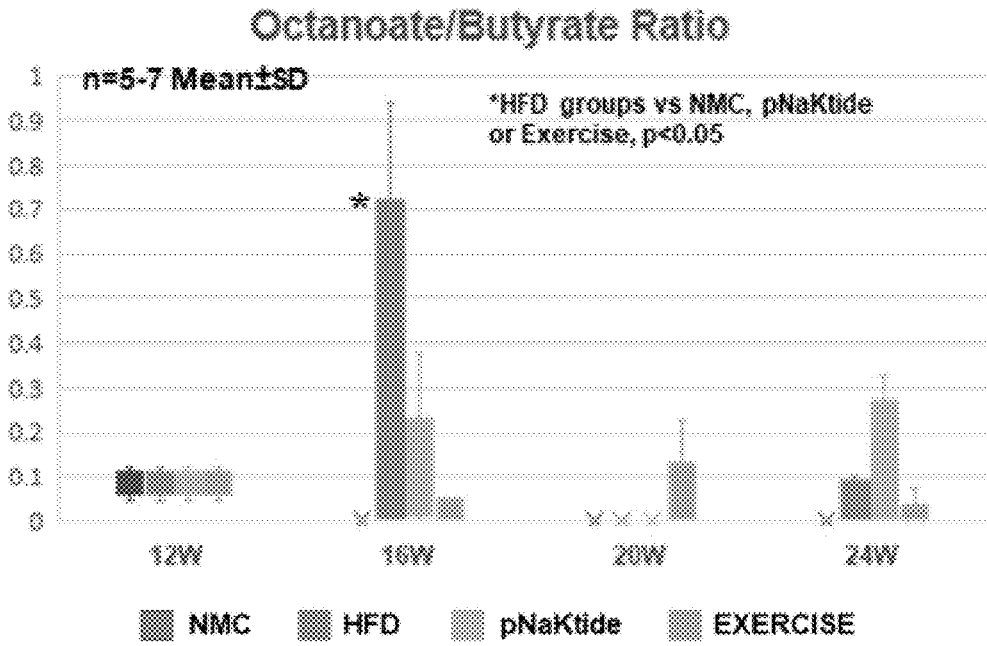
FIGS. 3A-3D include graphs and images showing β-lipid oxidation assessment and metabolic gene expression profile in the rodent with NASH, where (FIG. 3A) the octanoate/butyrate concentrations ratio in plasma differed significantly among groups (displayed as plots of M±SD, $p<0.05$ by ANOVA) and the HFD groups had a significant increase in the ratio when compared to NMC or intervention groups at week 16, where (FIG. 3B) a significant difference in mTOR1 and Sirt7 expression was observed among groups at week 16 (p<0.05, ANOVA) and while mTOR1 was downregulated in the HFD group, SIRT7 was downregulated in all groups but animals on NMC, where (FIG. 3C) PPRγ had a significant peak at week 16 in the pNaKtide group when compared NMC and HFD groups (p<0.05, t-test), where although a peak was observed on PPRγ in the exercise group, it did not reach significance when compared to the HFD and NMC groups, and where (FIG. 3D) GC1α were significantly different n the pNaKtide and exercise groups when compared to the HFD and NMC groups with a peak at 16 weeks (p<0.05, t-test) and a second peak was noted at week 24 in the Exercise group.
Figure 3B:
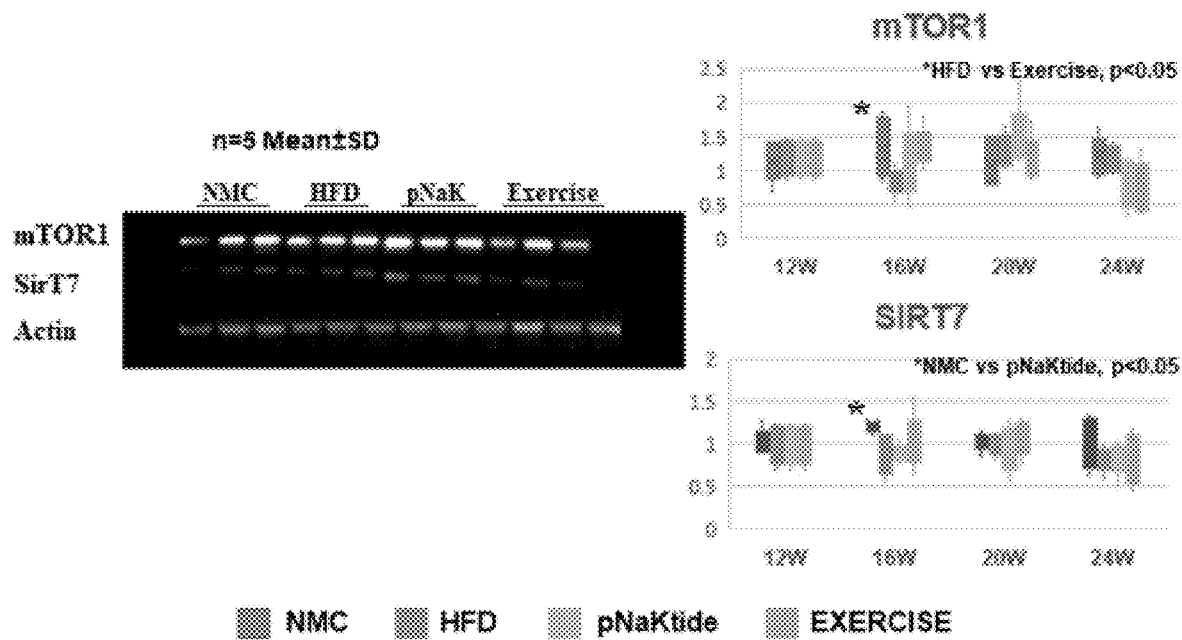
Figure 3C:
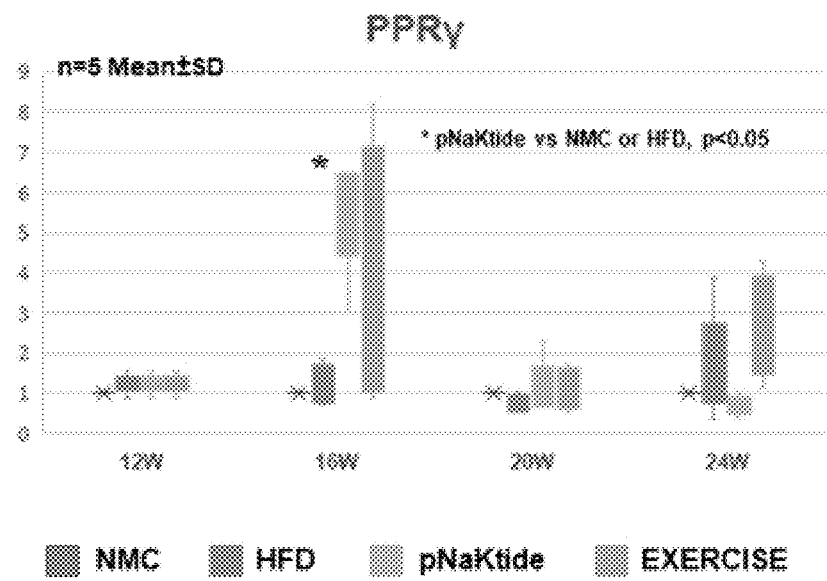
Figure 3D:
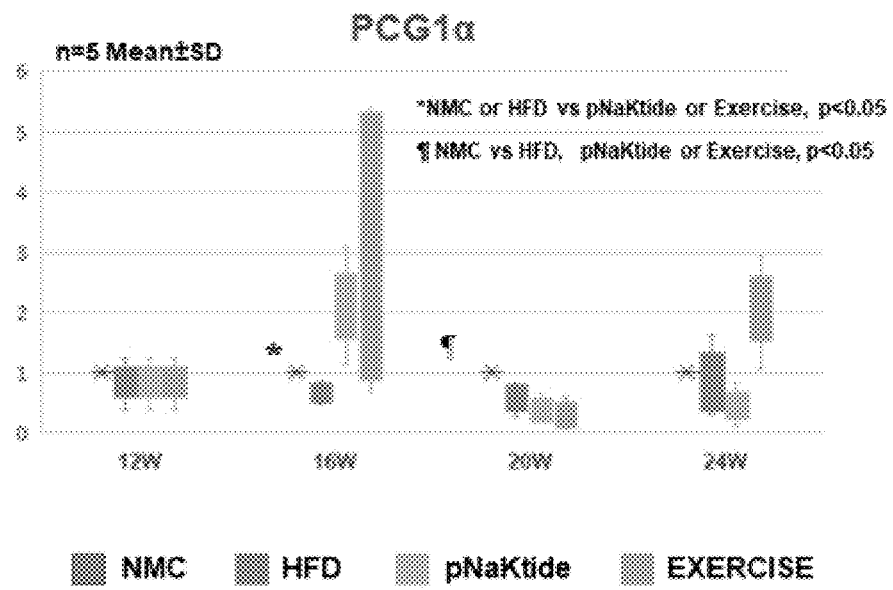

Octanoate/butyrate concentration ratios were interrogated as a surrogate of mitochondrial β-lipid oxidation, while blood glucose levels served as a marker of insulin resistance. The octanoate/butyrate ratio was significantly higher in the HFD groups when compared to the NMC and the intervention groups at week 16 (FIG. 3A, $p<0.05$, ANOVA). Interestingly, mTOR1 and Sirt7 expression were significantly downregulated in the HFD group in the same period (week 16, FIG. 3B, $p<0.05$, t-test). Additionally, the expression of the Peroxisome Proliferator-Activated Receptor-γ (PPAR γ), and its transcriptional coactivator PGC-1α was significantly increased in the pNaKtide group when compared to the NMC and the HFD group (FIGS. 3C-3D, $p<0.05$, ANOVA). The transcription of PPARγ peaked in the pNaKtide group at 16 W to return to similar levels when compared to the other groups by week 20. Similar behavior was observed for the PCG1α expression with a peak at week 16 in the pNaKtide and exercise groups, which returned to comparable levels of the NMC group by week 24. Furthermore, there was a significant down-regulation in the expression of PCG1α in animals exposed to HFD at week 20 when compared to NMC ($p<0.05$, t-test).

Figure 4A:
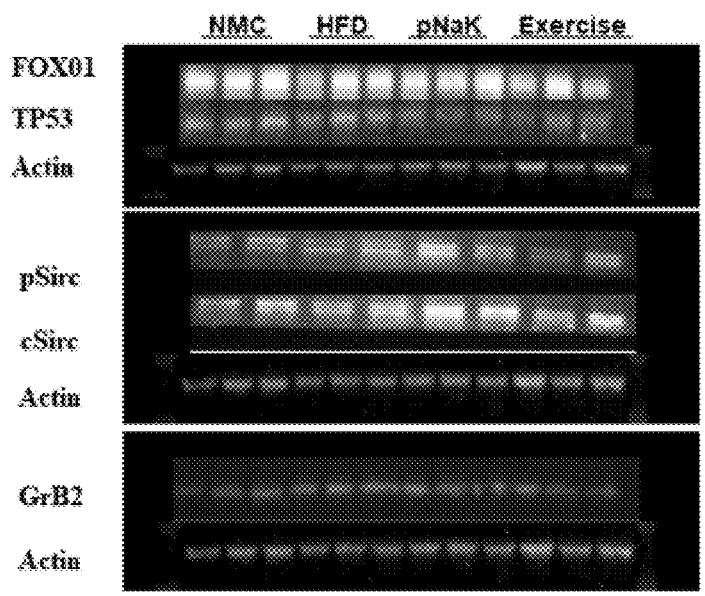
FIGS. 4A-4E include images and graphs showing insulin resistant status and carbohydrate gene expression assessment in rodents with NASH, where glucose concentration from the NMC groups was significantly different when compared to the HFD groups (p<0.05, ANOVA) but did not reach significance when compared to the intervention groups pNaKtide and exercise (displayed in FIG. 4A as plots of M±SD), where FOX01 expression was significantly upregulated in the intervention groups when compared to the NMC & HFD groups at week 24, while Tp53 expression was significantly downregulated in the HFD and pNaKtide groups when compared to the NMC group at week 16 (FIG. 4C), where phosphorylated Src protein expression (pSrc) was found to be significantly upregulated in the HFD group when compared to other groups (in FIG. 4D, p<0.05, ANOVA), and where, furthermore, Grb2 expression was significantly downregulated in the pNaKtide group when compared to NMC & HFD groups at week 20 (in FIG. 4E, p<0.05, ANOVA followed by t-test).
Figure 4A:
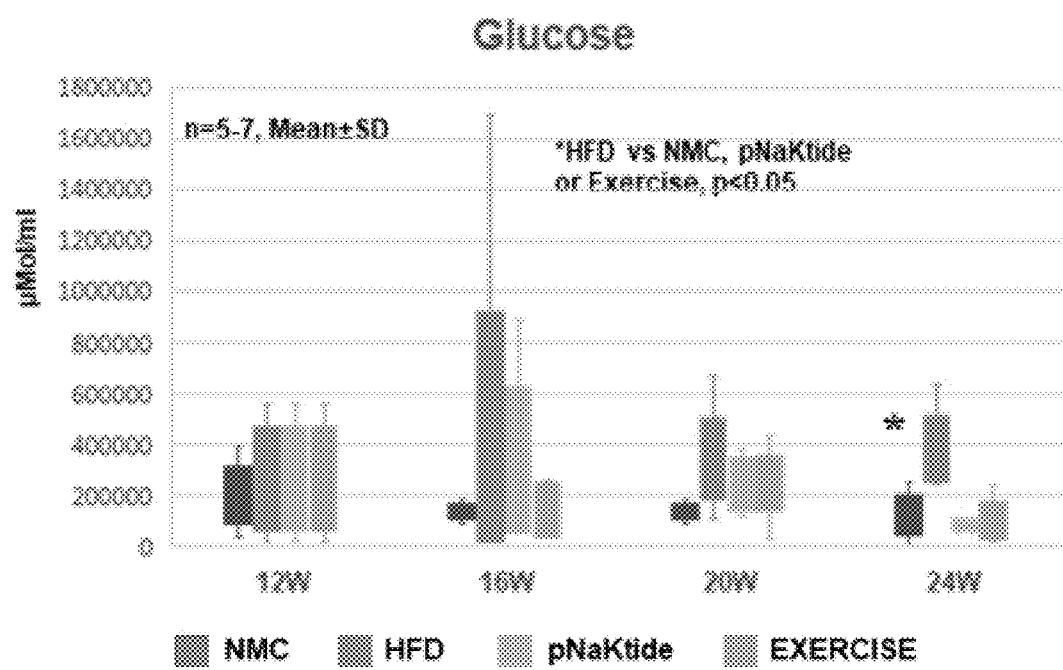
Figure 4B:
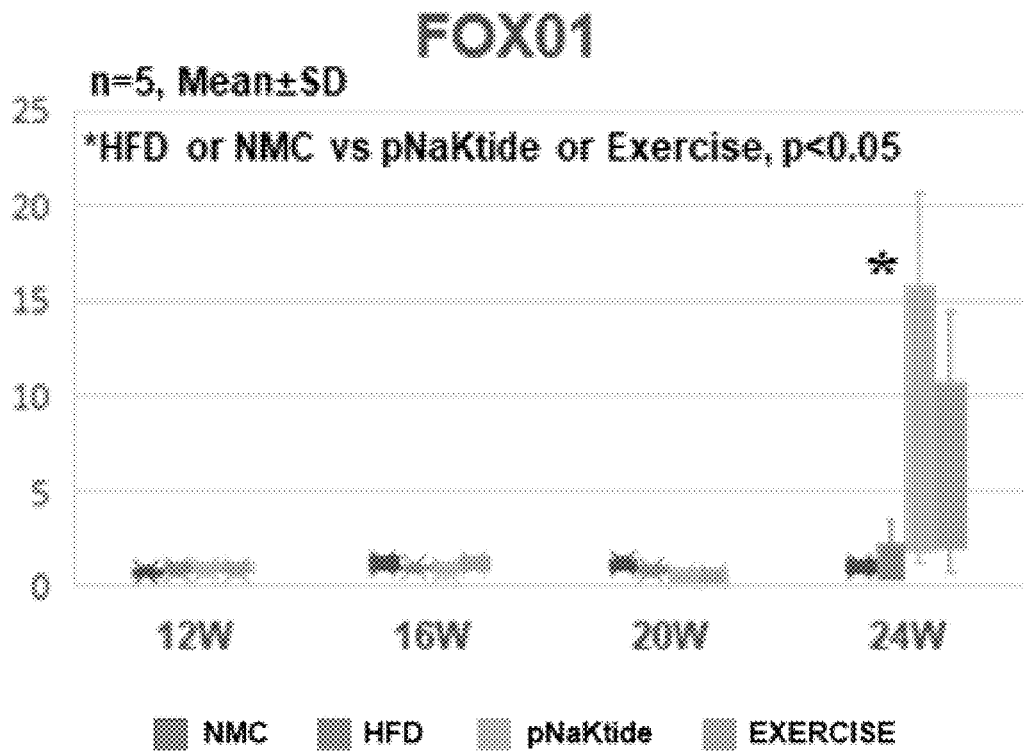
Figure 4C:
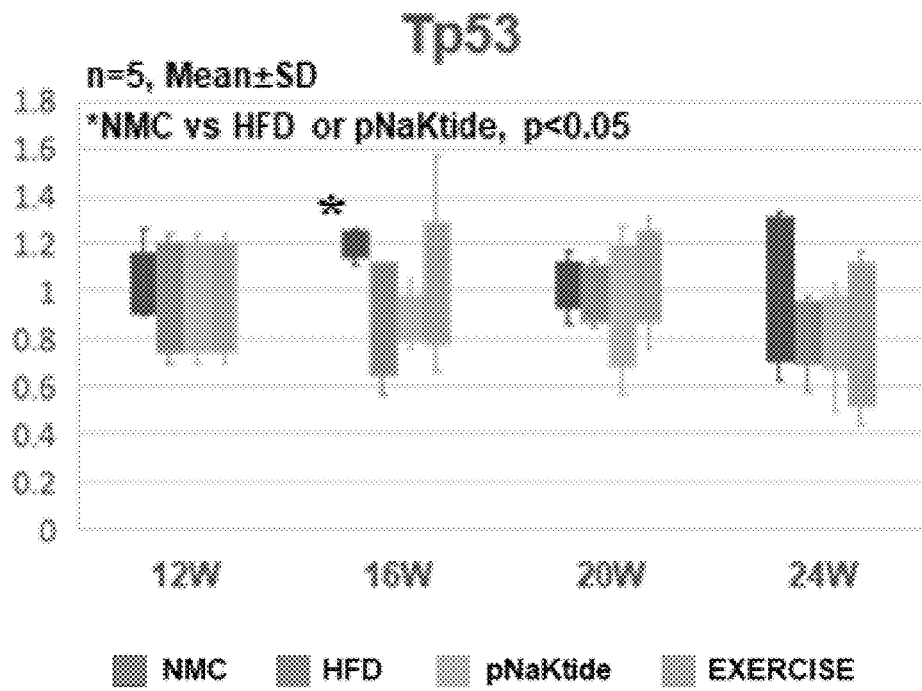
Figure 4D:
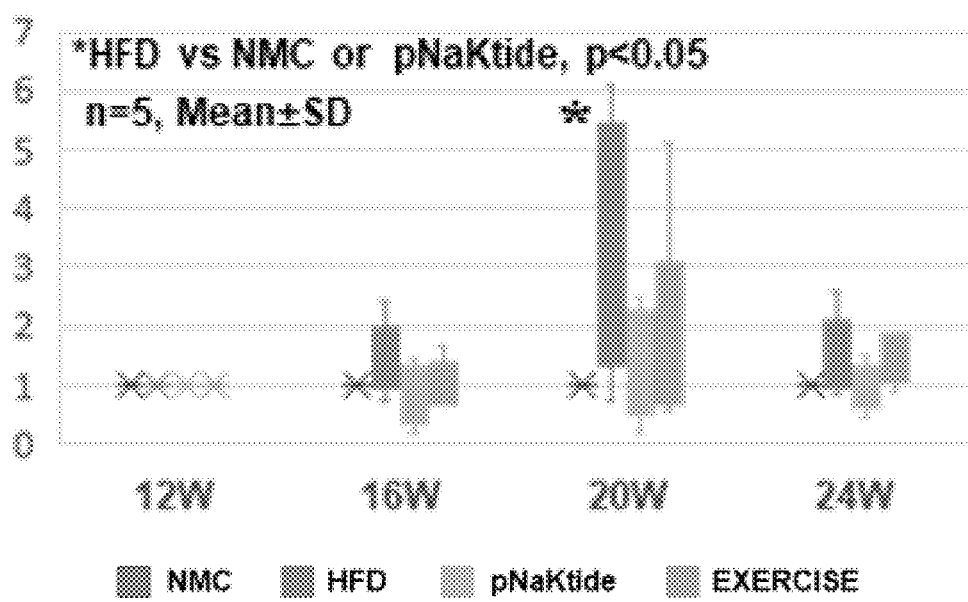
Figure 4E:
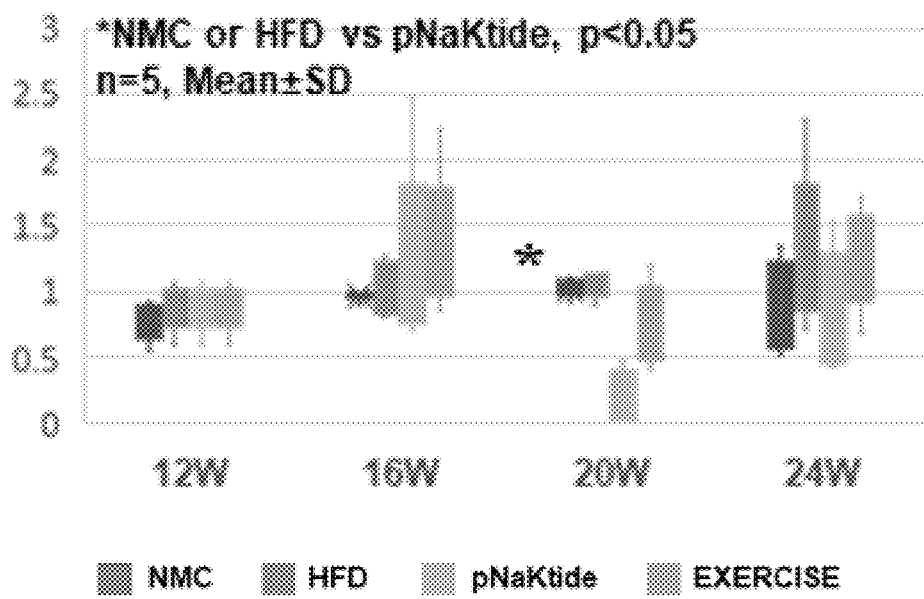

Glucose concentration (BS) in animals from the NMC groups was significantly different when compared to the HFD groups ($p<0.05$, ANOVA), but did not reach significance when compared to the intervention (pNaKtide and Exercise) groups (displayed in FIG. 4A as plots of M±SD). The HFD groups maintained a higher concentration of BS after week 16, while the intervention groups resolved such glucose intolerance by weeks 20 and 24. FOX01 and TP53 expression were significantly different among groups (FIGS. 4B-4C, respectively, $p<0.05$, ANOVA). FOX01 expression was significantly upregulated in the intervention groups when compared to the NMC & HFD groups at week 24. In contrast, TP53 expression was significantly downregulated in the HFD and pNaKtide groups when compared to the NMC group at week 16. Src protein expression displayed as the ratio of the phosphorylated over total Src (pSrc/pSrc+CSrc) was significantly different among groups (FIG. 4D, $p<0.05$, ANOVA). Src phosphorylation peaked in the HFD groups at week 20, with paucity on pSrc peak in the pNaKtide and Exercise groups ($p<0.05$, t-test). Furthermore, GrB2 expression was significantly downregulated in the pNaKtide group when compared to NMC & HFD groups at week 20 (FIG. 4E, $p<0.05$, ANOVA followed by t-test).

Metabolic prints HFD differed from NMC & intervention groups (pNaKtide and Exercise) by principal component analyses ($p<0.05$, PCA). Metabolite prints separated experimental groups by diet (HFD vs. NMC) and by intervention (HFD with NO intervention vs. HFD WITH intervention)

Figure 5A:
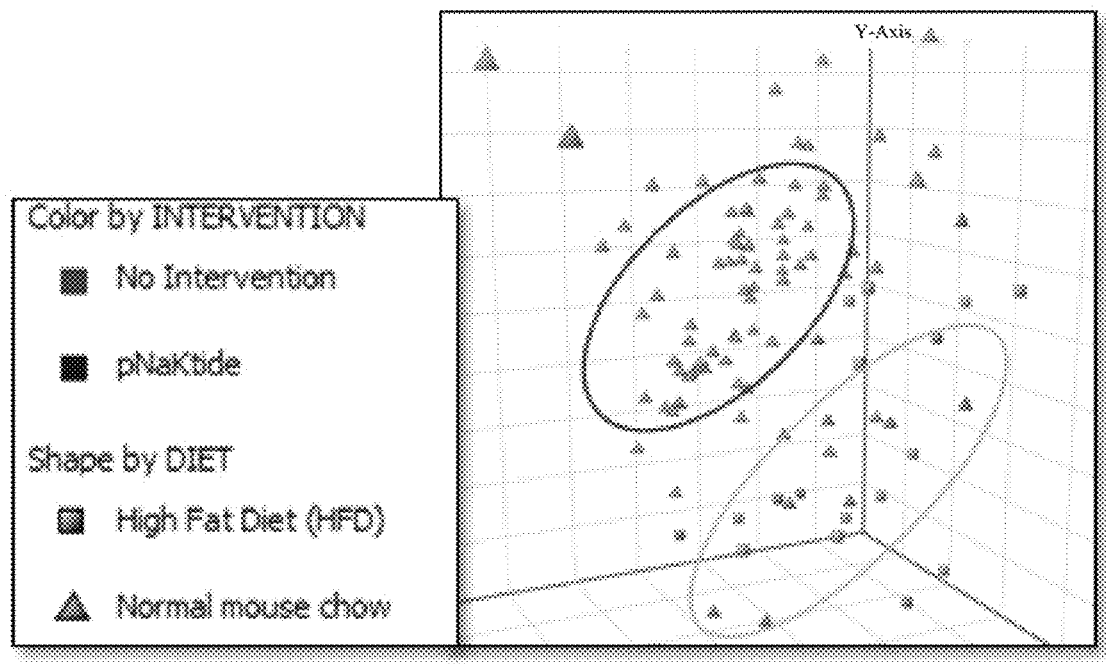
FIGS. 5A-5E include graphs showing metabolic prints and Heat Map signatures on treated plasma from diet-induced NASH in the rodent, where rodents were exposed to normal mouse chow (NMC) or high fat diet+fructose (HFD), where interventions include pNaKtide, and exercise, where HFD groups were discriminated from NMC and intervention groups (pNaKtide & exercise) by their metabolic prints at week 24 (in FIGS. 5A-5B, p<0.05, PCA), where metabolites prints separated experimental groups by diet HFD vs NMC and by intervention no intervention vs pNaKtide or exercise, where, furthermore, metabolite data was $Log^{10}$ transformed, and R-lab software was directed to compare and display as a visual array NMC vs HFD groups (FIG. 5C, Log 10_Ratio-HFD_CTL), NMC vs pNaKtide groups (FIG. 5D, Log 10_RatioP_CTL), and Exercise vs NMC groups (FIG. 5E, Log 10_RatioE_CTL), and where there is a significant difference in the metabolic print among groups (p<0.01, PCA).
Figure 5B:
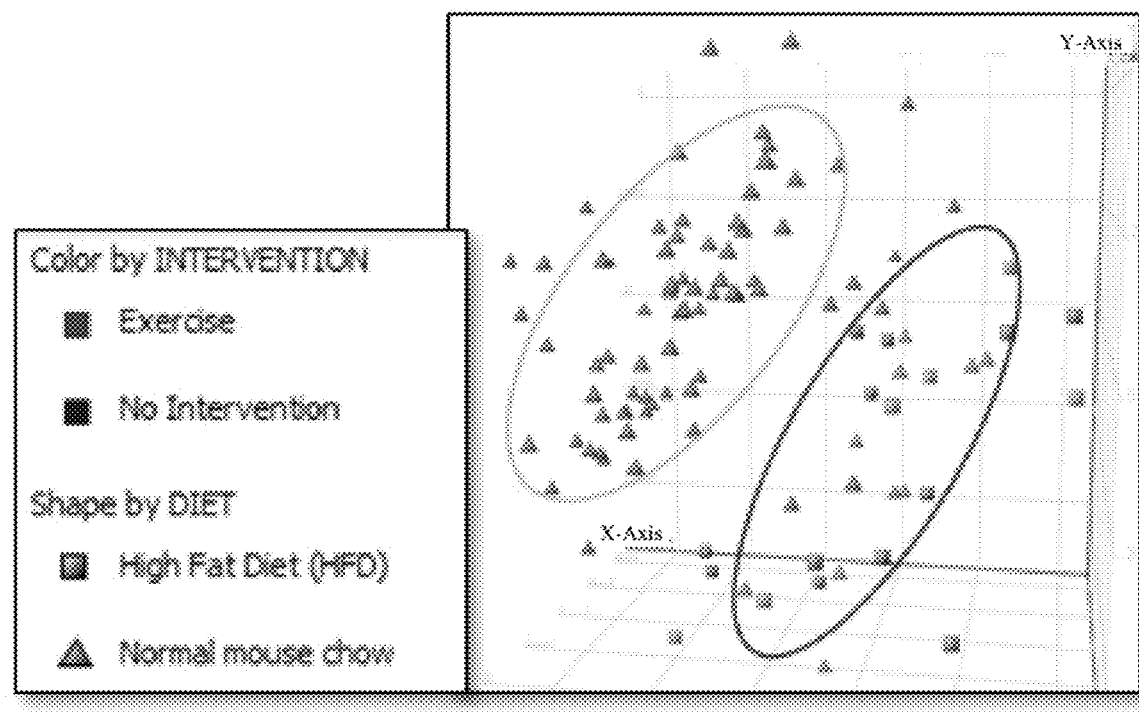
Figure 5C:
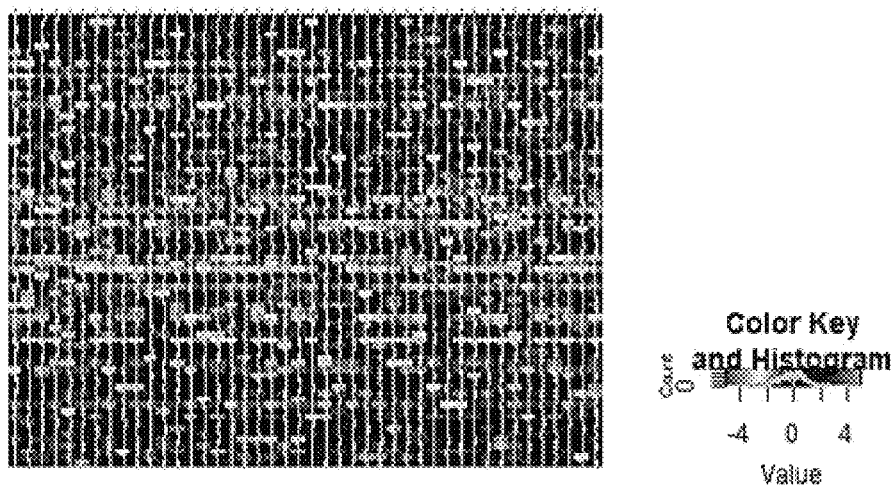
Figure 5D:
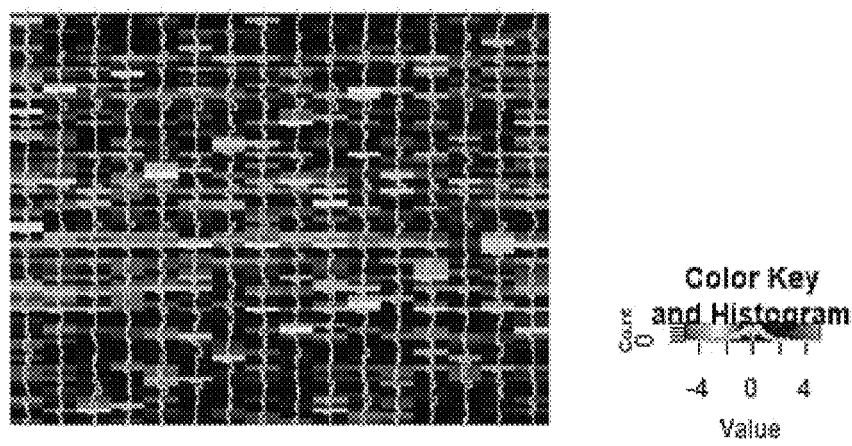
Figure 5E:
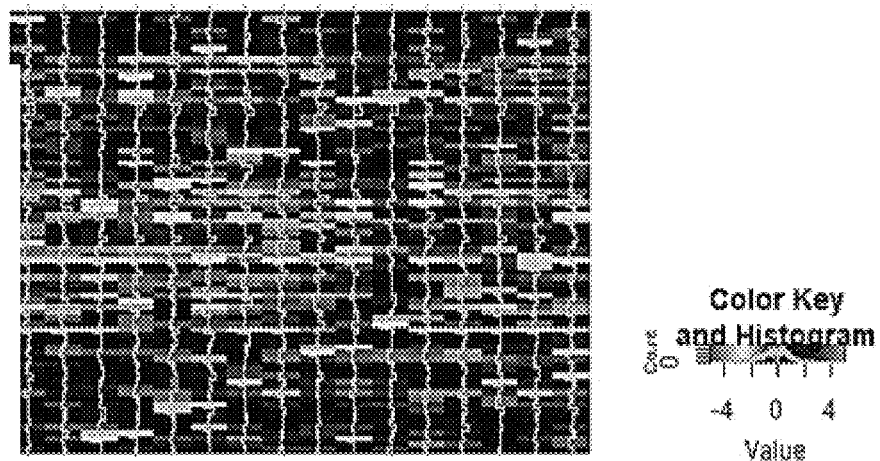

(FIGS. 5A-5B, p<0.05). Metabolite data were $Log^{10}$ transformed, and R-lab software was directed to display the data as visual arrays of NMC vs. HFD groups (FIG. 5C, Log 10_RatioHFD_CTL), NMC vs. pNaKtide groups (FIG. 5D, Log 10_RatioP_CTL), and Exercise vs. NMC groups (FIG. 5E, Log 10_RatioE_CTL). The displayed metabolic heat print from NMC vs. HFD (FIG. 5C) was significantly different from the metabolic print where the NMC group was compared to the pNaKtide or Exercise groups at 24 weeks (FIGS. 5B-5C, respectively, p<0.01, PCA). Due to the Log transformation, differences between groups are by a factor 1:100 to 1:1000.

Metabolites were categorized into amino/peptides, carbohydrates, and lipids (Tables 1 to 3). Some compounds differed among groups by diet (NMC vs. HFD), by the intervention (HFD NO intervention vs. HFD+Intervention (pNaKtide or exercise), or by both diet and the intervention. Each metabolite was listed alphabetically and its concentration was displayed as box plot among groups with its statistically significant variation. Differences in amino-acids were noted, among others on coumaric, hippuric and kynurenic acids, thymidines, uridines, and zeatins (Table 1, p<0.05). The majority of sugars with significant variation were substrates involved in Krebb's cycle (Table 2). Adipic acid, arachidonic acid, corticosterone, myristic, oleic, and palmitic acids were among other lipids that significantly changed in the HFD when compared to other groups (Table 3).

TABLE 1

List of amino-acids from the plasma of rodents exposed to normal mouse chow (NMC) or high fat diet (HFD). Animals exposed to HFD for 12W (established NASH) were provided in addition to HFD and intervention, pNaKtide or exercise.

| METABOLITE NAME (AA) | Kind | NMC 24 Week | HFD 24 Week | p-value* |
|---|---|---|---|---|
| 3-UREIDOPROPIONIC ACID | Peptide | 13633 ± 4566 | 15533 ± 10936 | NS |
| 4-COUMARIC ACID | Peptide | 31824 ± 19126 | 13121 ± 6363 | <.0.05 |
| 4-HYDROXYBENZOIC ACID | Peptide | 9132 ± 1185 | 5225 ± ND | *NP |
| 2-OXOPENTANOIC ACIDS | Peptide | 1713633 ± 334229 | 1278205 ± 320809 | <0.05 |
| GLUTAMINE | Peptide | 22951 ± 9624 | 20569 ± 9510 | NS |
| GLUTATHIONE (OXIDIZED) | Peptide | 21631 ± 9770 | 58391 ± 28237 | <0.05 |
| HIPPURIC ACID | Peptide | 22131742 ± 1988863 | 22456867 ± 2210184 | NS |
| ISOLEUCINE | Peptide | 212672 ± 45422 | 186668 ± 24327 | NS |
| KYNURENIC ACID | Peptide | 15956 ± 5823 | 9186 ± 4342 | NS |
| L-HISTIDINE | Peptide | 8280 ± 3336 | 7551 ± 3216 | NS |
| L-TRYPTOPHAN | Peptide | 526582 ± 58182 | 511388 ± 52165 | NS |
| LYSINE | Peptide | 8474 ± 2194 | 10975 ± 922 | <0.05 |
| N-ACETYL-GLYCINE | Peptide | 19086 ± 16253 | 6539 ± ND | NP |
| N-ACETYL-L-ALANINE | Peptide | 2428 ± ND | 20516 ± 10736 | NP |
| N-ACETYL-L-LEUCINE | Peptide | 130301 ± 44499 | 105017 ± 29922 | <0.05 |
| N-ACETYL-L-PHENYLALANINE | Peptide | 61046 ± 11829 | 38194 ± 6372 | <0.05 |
| PHENYLALANINE | Peptide | 341328 ± 50115 | 364373 ± 46304 | NS |
| PIMELIC ACID | Peptide | 7642 ± 1255 | 8244 ± 360 | NS |
| THYMIDINE | Peptide | 147065 ± 30243 | 136643 ± 23843 | NS |
| THYMINE | Peptide | 263379 ± 10027 | 245320 ± 22888 | NS |
| TYROSINE | Peptide | 223150 ± 20045 | 184140 ± 63255 | NS |
| URIC ACID | Peptide | 226627 ± 245663 | 597501 ± 781901 | NS |
| URIDINE | Peptide | 172167 ± 85947 | 398329 ± 251138 | <0.05 |
| ZEATIN | Peptide | 167655 ± 24268 | 150091 ± 10944 | <0.05 |

| METABOLITE NAME (AA) | Kind | HFD 24 Week | pNaKtide 24 Week | Exercise 24 Week | p-value* |
|---|---|---|---|---|---|
| 3-UREIDOPROPIONIC ACID | Peptide | 15533 ± 10936 | 36844 ± 15500 | 25387 ± 6649 | <0.05 |
| 4-COUMARIC ACID | Peptide | 13121 ± 6363 | 10785 ± 9725 | 12726 ± 5232 | NS |
| 4-HYDROXYBENZOIC ACID | Peptide | 5225 ± ND | ND | 8483 ± ND | NP |
| 2-OXOPENTANOIC ACIDS | Peptide | 1278205 ± 320809 | 1283838 ± 347822 | 1541819 ± 389056 | NS |
| GLUTAMINE | Peptide | 20569 ± 9510 | 28264 ± 1254 | 31441 ± 7436 | NS |
| GLUTATHIONE (OXIDIZED) | Peptide | 58391 ± 28237 | 32876 ± 7608 | 24511 ± 6561 | <0.05 |
| HIPPURIC ACID | Peptide | 22456867 ± 2210184 | 16549282 ± 9429530 | 18779494 ± 2949507 | NS |
| ISOLEUCINE | Peptide | 186668 ± 24327 | 199393 ± 71768 | 228445 ± 86743 | NS |
| KYNURENIC ACID | Peptide | 9186 ± 4342 | 7900 ± 1479 | 7803 ± 1002 | NS |
| L-HISTIDINE | Peptide | 7551 ± 3216 | 10549 ± 2406 | 15440 ± 5078 | NS |
| L-TRYPTOPHAN | Peptide | 511388 ± 52165 | 455774 ± 98196 | 470123 ± 181366 | NS |
| LYSINE | Peptide | 10975 ± 922 | 14163 ± 1867 | 19853 ± 4068 | <0.05 |
| N-ACETYL-GLYCINE | Peptide | 6539 ± ND | 11632 ± ND | 9306 ± ND | NP |
| N-ACETYL-L-ALANINE | Peptide | 20516 ± 10736 | 29284 ± ND | 21585 ± 10641 | NP |
| N-ACETYL-L-LEUCINE | Peptide | 105017 ± 29922 | 119675 ± 79799 | 109605 ± 39073 | NS |
| N-ACETYL-L-PHENYLALANINE | Peptide | 38194 ± 6372 | 30019 ± 14979 | 39666 ± 16066 | NS |
| PHENYLALANINE | Peptide | 364373 ± 46304 | 361671 ± 92631 | 347017 ± 73207 | NS |
| PIMELIC ACID | Peptide | 8244 ± 360 | 11154 ± 3274 | 7105 ± ND | NP |
| THYMIDINE | Peptide | 136643 ± 23843 | 157329 ± 28806 | 125731 ± 22723 | NS |
| THYMINE | Peptide | 245320 ± 22888 | 242683 ± 47507 | 237349 ± 53987 | NS |
| TYROSINE | Peptide | 184140 ± 63255 | 215290 ± 111067 | 302818 ± 70368 | <0.05 |

TABLE 1-continued

List of amino-acids from the plasma of rodents exposed to normal mouse chow (NMC) or high fat diet (HFD). Animals exposed to HFD for 12W (established NASH) were provided in addition to HFD and intervention, pNaKtide or exercise.

| | | | | | |
|---|---|---|---|---|---|
| URIC ACID | Peptide | 597501 ± 781901 | 346352 ± 446629 | 391535 ± 464285 | NS |
| URIDINE | Peptide | 398329 ± 251138 | 347011 ± 174990 | 239531 ± 95502 | NS |
| ZEATIN | Peptide | 150091 ± 10944 | 135863 ± 29654 | 135411 ± 18393 | <0.05 |

TABLE 2

List of carbohydrates from the plasma of rodents exposed to normal mouse chow (NMC) or high fat diet (HFD). Animals exposed to HFD for 12W (established NASH) were provided in addition to HFD and intervention, pNaKtide or exercise.

| | | Experimental Groups | | |
|---|---|---|---|---|
| METABOLITE NAME (CHO) | Kind | NMC 24 Week | HFD 24 Week | p-value* |
| BUTYRIC ACID | Carbohydrate | 136900 ± 13436 | 238877 ± 40419 | <0.05 |
| BENZOIC ACID | Carbohydrate | 52510 ± 18477 | 96710 ± 6365 | <0.05 |
| CITRAMALIC ACID | Carbohydrate | 1700753 ± 578074 | 1864369 ± 856907 | NS |
| CITRIC ACID | Carbohydrate | 2708109 ± 201367 | 3746763 ± 46031 | <0.05 |
| DEOXYURIDINE | Carbohydrate | 159485 ± 28692 | 113325 ± 57977 | NS |
| D-GLUCOSAMINE 6-SULFATE | Carbohydrate | 18374 ± 8325 | 17577 ± 1312 | *NP |
| GLUCOSE | Carbohydrate | 210782 ± 227566 | 345560 ± 150718 | <0.05 |
| GLUTARIC ACID | Carbohydrate | 55036 ± 20932 | 150603 ± 61610 | <0.05 |
| HOMOVANILLIC ACID | carbohydrate | 13689 ± 1028 | 10045 ± 3139 | <0.05 |
| INDOLE-3-PYRUVIC ACID | carbohydrate | 5357 ± 3622 | 4785 ± 2582 | NS |
| INOSINE's | Carbohydrate | 104312 ± 26218 | 163697 ± 66970 | <0.05 |
| ISOCITRIC ACID | carbohydrate | 3562142 ± 250803 | 4110980 ± 995231 | <0.05 |
| LACTIC ACID | carbohydrate | 233017 ± 53067 | 269941 ± 120642 | NS |
| MALEIC ACID | carbohydrate | 42927 ± 15026 | 73767 ± 24525 | <0.05 |
| MALIC ACID | carbohydrate | 46118 ± 11016 | 57993 ± 16328 | <0.05 |
| METHYL BETA-D-GALACTOSIDE | carbohydrate | 139948 ± 15875 | 15084 ± 9067 | <0.05 |
| METHYLMALONIC ACID | carbohydrate | 18467 ± 6095 | 21842 ± 1848 | NS |
| OXALOACETIC ACID | carbohydrate | 412772 ± 48365 | 388334 ± 39291 | NS |
| PHTHALIC ACID | carbohydrate | 22434 ± 0 | 11568 ± 2642 | NP |
| SUCCINIC ACID | carbohydrate | 209834 ± 153853 | 551798 ± 356372 | <0.05 |
| THYMIDINE | carbohydrate | 147065 ± 30243 | 136643 ± 23843 | NS |
| TRANS-ACONITIC ACID | carbohydrate | 234201 ± 210269 | 313096 ± 221031 | NS |
| XANTHINE | carbohydrate | 32567 ± 0 | 63862 ± 58166 | NP |
| XANTHOSINE | carbohydrate | 15451 ± 0 | 23618 ± 13508 | NP |

| | | Experimental Groups | | |
|---|---|---|---|---|
| METABOLITE NAME (CHO) | Kind | HFD 24 Week | pNaKtide 24 Week | Exercise 24 Week | p-value* |
| BUTYRIC ACID | Carbohydrate | 238877 ± 40419 | 342006 ± 144902 | 400409 ± 127502 | <0.05 |
| BENZOIC ACID | Carbohydrate | 96710 ± 6365 | 58182 ± 28555 | 70640 ± 17209 | <0.05 |
| CITRAMALIC ACID | Carbohydrate | 1864369 ± 856907 | 2465687 ± 1100861 | 2742937 ± 1038740 | <0.05 |
| CITRIC ACID | Carbohydrate | 3746763 ± 46031 | 3282571 ± 877303 | 2893585 ± 359716 | <0.05 |
| DEOXYURIDINE | Carbohydrate | 113325 ± 57977 | 118369 ± 63345 | 110416 ± 54091 | NS |
| D-GLUCOSAMINE 6-SULFATE | Carbohydrate | 17577 ± 1312 | 9953 ± 32 | 5867 ± 3090 | NP |
| GLUCOSE | Carbohydrate | 345560 ± 150718 | 180332 ± 210096 | 187387 ± 173998 | <0.05 |
| GLUTARIC ACID | Carbohydrate | 150603 ± 61610 | 219213 ± 213481 | 198069 ± 129484 | NS |
| HOMOVANILLIC ACID | carbohydrate | 10045 ± 3139 | 7951 ± 1041 | 7179 ± 939 | <0.05 |
| INDOLE-3-PYRUVIC ACID | carbohydrate | 4785 ± 2582 | 14389 ± 7618 | 12504 ± 11303 | <0.05 |
| INOSINE's | Carbohydrate | 163697 ± 66970 | 161328 ± 43310 | 131891 ± 46443 | NS |
| ISOCITRIC ACID | carbohydrate | 4110980 ± 995231 | 4003415 ± 820203 | 3761590 ± 403912 | NS |
| LACTIC ACID | carbohydrate | 269941 ± 120642 | 224862 ± 85464 | 281236 ± 73993 | NS |
| MALEIC ACID | carbohydrate | 73767 ± 24525 | 79419 ± 57489 | 81615 ± 32297 | NS |
| MALIC ACID | carbohydrate | 57993 ± 16328 | 112550 ± 121282 | 98393 ± 49210 | <0.05 |
| METHYL BETA-D-GALACTOSIDE | carbohydrate | 15084 ± 9067 | 21798 ± 6509 | 10411 ± 2838 | <0.05 |
| METHYLMALONIC ACID | carbohydrate | 21842 ± 1848 | 20232 ± 4480 | 18512 ± 3916 | NS |
| OXALOACETIC ACID | carbohydrate | 388334 ± 39291 | 399300 ± 75048 | 387790 ± 30313 | NS |
| PHTHALIC ACID | carbohydrate | 11568 ± 2642 | 11294 ± 1624 | 8818 ± 0 | NP |
| SUCCINIC ACID | carbohydrate | 551798 ± 356372 | 644551 ± 876855 | 279416 ± 130807 | NS |
| THYMIDINE | carbohydrate | 136643 ± 23843 | 136260 ± 48226 | 125731 ± 22723 | NS |
| TRANS-ACONITIC ACID | carbohydrate | 313096 ± 221031 | 302900 ± 193617 | 238550 ± 114493 | NS |
| XANTHINE | carbohydrate | 63862 ± 58166 | 63862 ± 58166 | 152911 ± 113380 | NS |
| XANTHOSINE | carbohydrate | 23618 ± 13508 | 64524 ± 0 | 0 ± 0 | NP |

TABLE 3

List of lipids from the plasma of rodents exposed to normal mouse chow (NMC) or high fat diet (HFD).
Animals exposed to HFD for 12W (established NASH) were provided in addition to HFD and intervention, pNaKtide or exercise.

| METABOLITE NAME (Lipid) | Kind | NMC 24 Week | HFD 24 Week | p-value* | HFD 24 Week | pNaKtide 24 Week | Exercise 24 Week | p-value* |
|---|---|---|---|---|---|---|---|---|
| ADIPIC ACID | Lipid | 9023 ± 2135 | 14024 ± 5700 | <0.05 | 14024 ± 5700 | 17227 ± 4781 | 13639 ± 5015 | NS |
| ARACHIDIC ACID | Lipid | 17808 ± 7593 | 16941 ± 10347 | NS | 16941 ± 10347 | 18081 ± 12009 | 18229 ± 9083 | NS |
| ARACHIDONIC ACID | Lipid | 56224 ± 20232 | 187550 ± 89136 | <0.05 | 187550 ± 89136 | 96568 ± 63643 | 88434 ± 46903 | <0.05 |
| BEHENIC ACID | Lipid | 17921 ± 2014 | 14981 ± 3108 | NS | 14981 ± 3108 | 18276 ± 7055 | 16349 ± 3991 | NS |
| CAPRYLIC ACID | Lipid | 8235 ± 0 | 14695 ± 5273 | NP | 14695 ± 5273 | 51796 ± 23068 | 87502 ± 50693 | <0.05 |
| CIS-11-EICOSENOIC ACID | Lipid | 6653 ± 1896 | 7079 ± 2194 | NS | 7079 ± 2194 | 16156 ± 12193 | 7895 ± 1027 | NS |
| CORTICOSTERONE | Lipid | 51373 ± 5709 | 85029 ± 11330 | <0.05 | 85029 ± 11330 | 77224 ± 20347 | 57310 ± 18100 | <0.05 |
| DOCOSAHEXAENOIC ACID | Lipid | 140460 ± 91921 | 125748 ± 111514 | NS | 125748 ± 111514 | 55801 ± 60722 | 47702 ± 31259 | NS |
| EPIBRASSINOLIDE | Lipid | 430639 ± 36260 | 392399 ± 39397 | NS | 392399 ± 39397 | 379010 ± 53178 | 378321 ± 74660 | NS |
| ERUCIC ACID | Lipid | 6393 ± 3349 | 7132 ± 3663 | NS | 7132 ± 3663 | 6543 ± 4767 | 6600 ± 3463 | NS |
| HEPTADECANOIC ACID | Lipid | 3545 ± 722 | 4146 ± 1220 | NS | 4146 ± 1220 | 7261 ± 2387 | 4673 ± 976 | <0.05 |
| LIGNOCERIC ACID | Lipid | 2016 ± 669 | 1951 ± 750 | NS | 1951 ± 750 | 3226 ± 876 | 2165 ± 723 | <0.05 |
| LINOLEIC ACID | Lipid | 102817 ± 66692 | 114235 ± 34869 | NS | 114235 ± 34869 | 166039 ± 49043 | 92415 ± 36615 | <0.05 |
| MYRISTIC ACID | Lipid | 4038 ± 1518 | 3553 ± 995 | NS | 3553 ± 995 | 5750 ± 3056 | 3231 ± 1067 | NS |
| MYRISTOLEIC ACID | Lipid | 8435 ± 4072 | 10032 ± 2060 | NS | 10032 ± 2060 | 12153 ± 6768 | 7023 ± 2555 | NS |
| NERVONIC ACID | Lipid | 1959 ± 482 | 1798 ± 334 | NS | 1798 ± 334 | 2468 ± 1169 | 1362 ± 419 | <0.05 |
| OLEIC ACID | Lipid | 177669 ± 100039 | 236903 ± 51510 | NS | 236903 ± 51510 | 380254 ± 138107 | 215827 ± 33938 | <0.05 |
| PALMITIC ACID | Lipid | 56987 ± 32515 | 63557 ± 8874 | NS | 63557 ± 8874 | 130281 ± 83954 | 68882 ± 19078 | <0.05 |
| PALMITOLEIC ACID | Lipid | 20565 ± 16069 | 27060 ± 7841 | NS | 27060 ± 7841 | 39032 ± 10464 | 24501 ± 10357 | <0.05 |
| SEBACIC ACID | Lipid | 28480 ± 8595 | 75404 ± 0 | NP | 0 ± 0 | 4752 ± 0 | 4618 ± 0 | NP |
| STEARIC ACID | Lipid | 57709 ± 20613 | 75404 ± 15206 | NS | 75404 ± 15206 | 122990 ± 68209 | 83680 ± 24176 | NS |

Example 4—Morphological Assessment

Figure 6A:
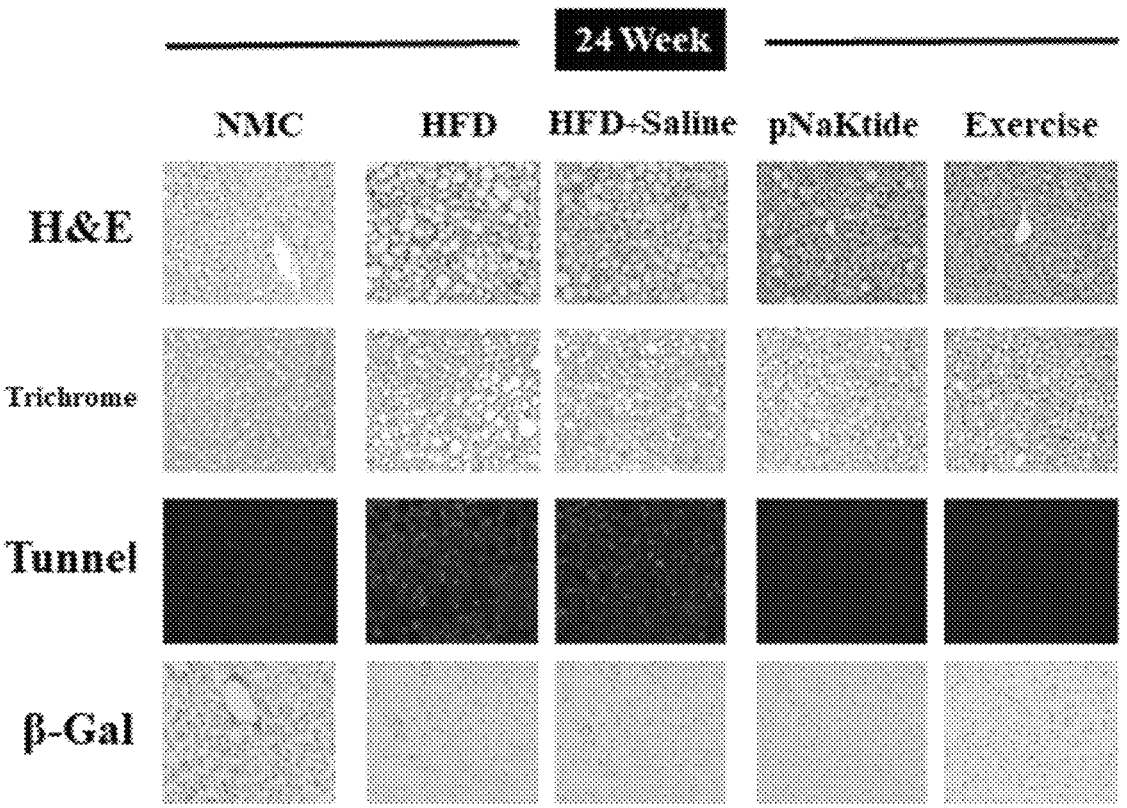
FIGS. 6A-6E include images and graphs showing the histological assessment of Murine Livers with NASH at week 24, where there was a significant increase in the NAS score (on H&E) of all HFD and intervention groups when compared to the NMC group (displayed in FIG. 6A and quantitated in FIG. 6B, as plots of M±SD, p<0.05, by $\chi^2$), where (FIG. 6C) there was a significant increase in the fibrosis score (on Trichrome, in FIG. 6A) among the HFD groups and where a significant regression of the fibrotic patterns was noted in the pNaKtide and Exercise groups (p<0.05), where, in addition, a dramatic difference was observed in the number of apoptotic (TUNEL) and cell senescence activity (in FIG. 6D-6E, respectively, p<0.05). A significant increase in apoptosis and senescence was observed in the HFD groups by week 24.
Figure 6B:
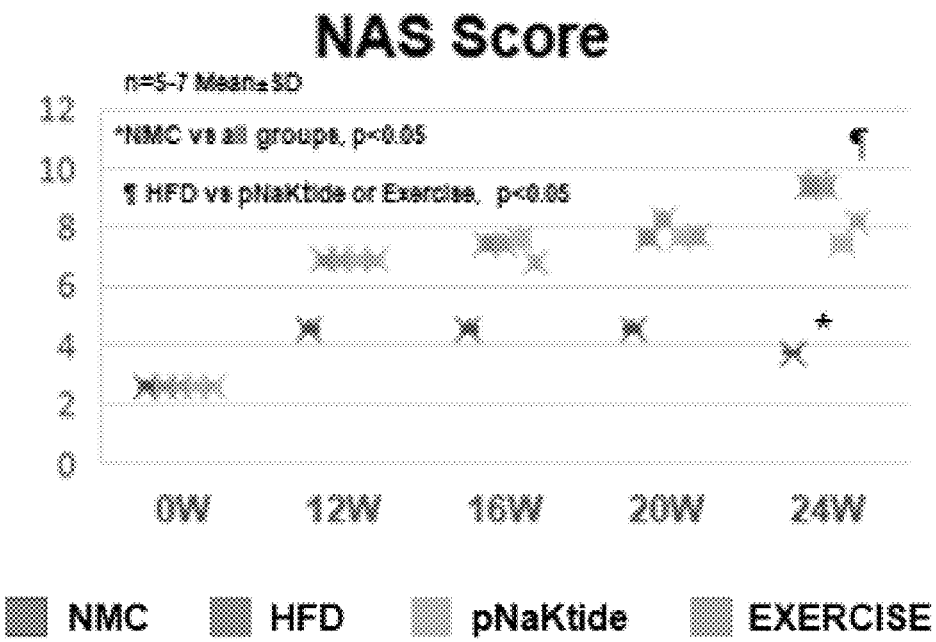
Figure 6C:
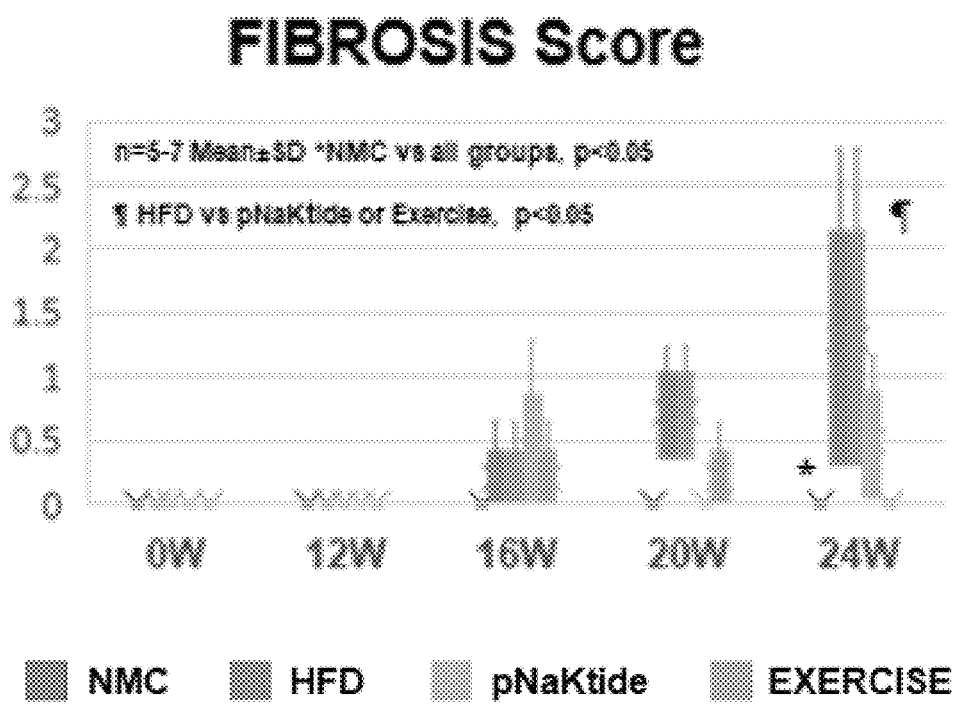
Figure 6D:
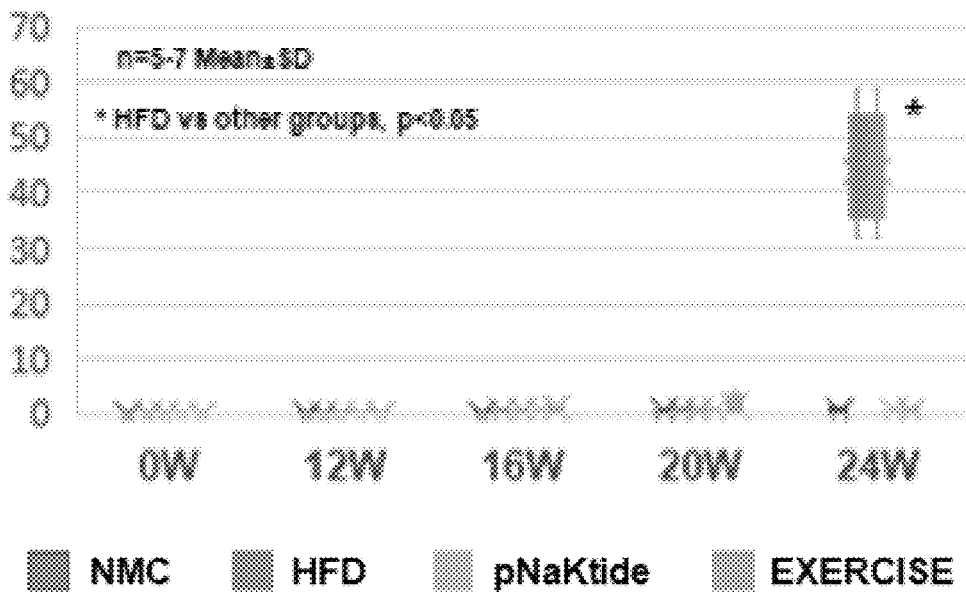
Figure 6E:
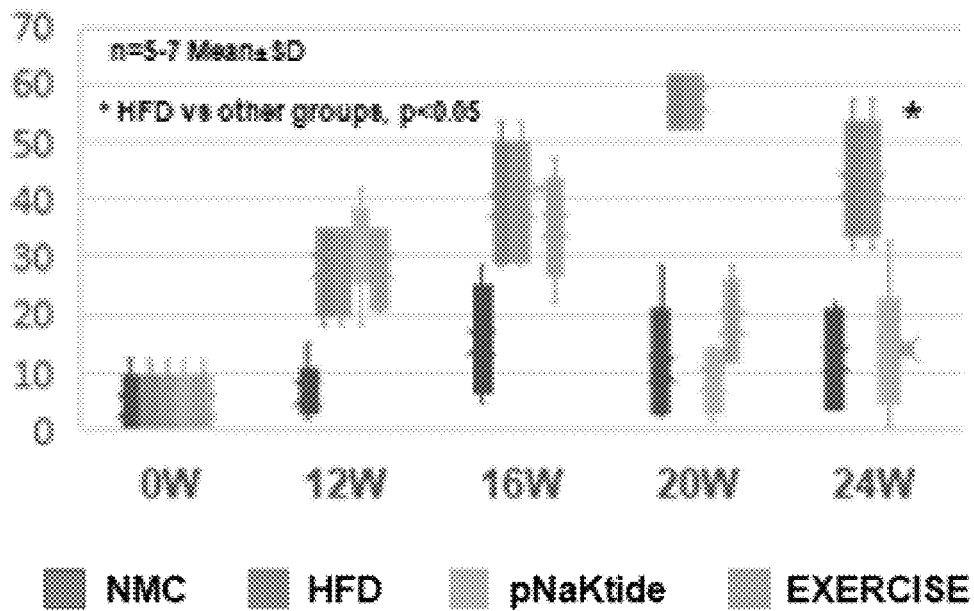
Figure 6F:
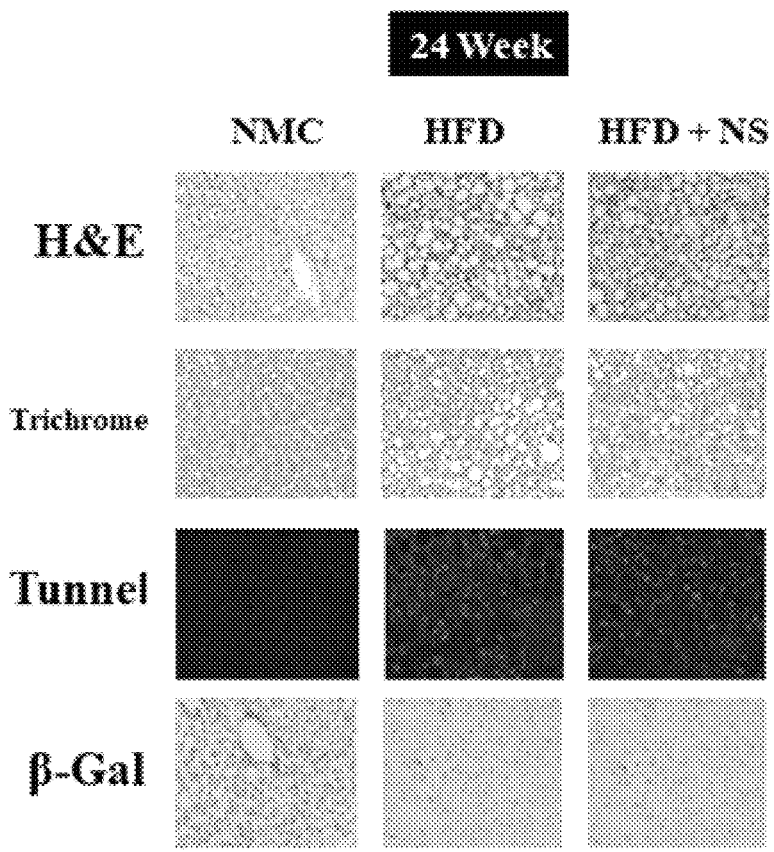
FIG. 6F includes images and graphs showing histological assessment of murine livers in NASH without pNaKtide intervention, where there was a significant increase in the NAS score of all HFD when compared to the NMC group (p<0.01, by $\chi^2$), where, in addition, there was a significant increase in the fibrosis score among the HFD groups (p<0.01), where a dramatic difference was observed in the number of apoptotic and cell senescence activity, where, while there was a significant increase in apoptosis in the HFD groups by week 24 when compared to the NMC group (p<0.01), the senescence activity was different at weeks 16 ad 20, and where there was no difference between the HFD and HFD+NS groups in any of the parameters (data not displayed, p<0.05).
Figure 6F:
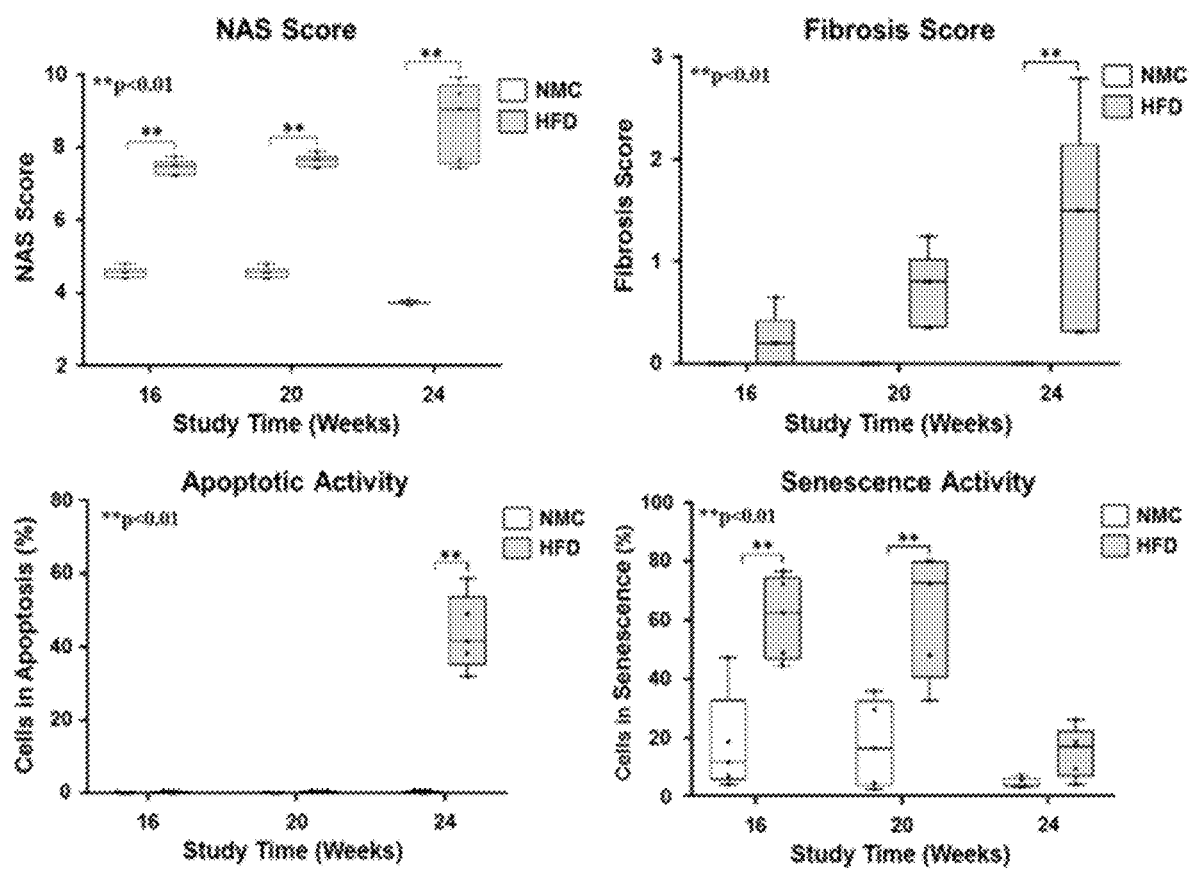
Figure 6G:
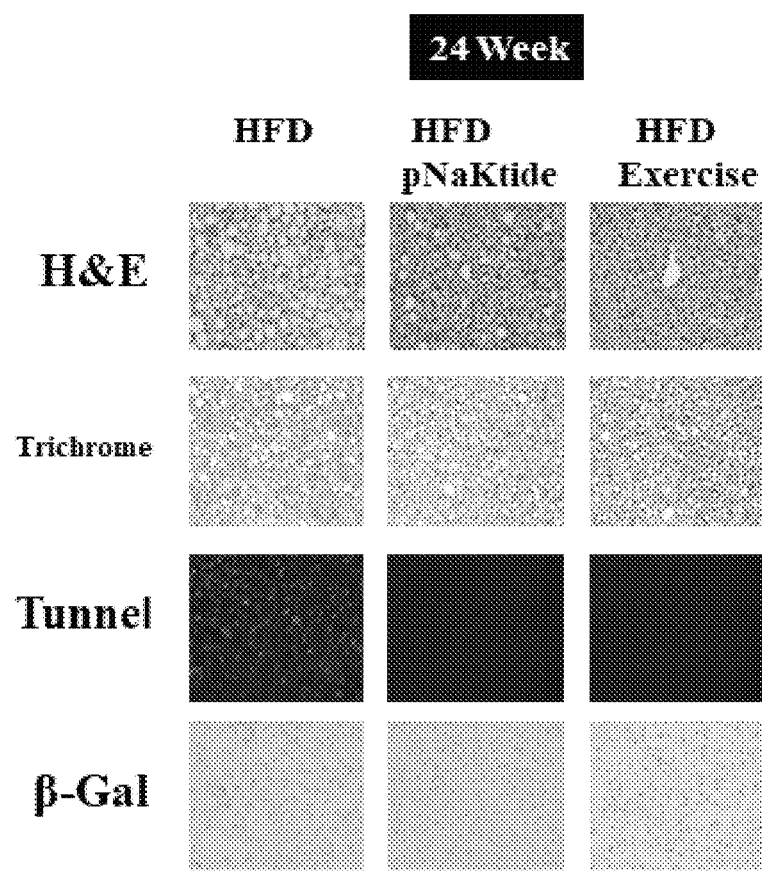
FIG. 6G includes images and graphs showing histological assessment of murine livers in NASH with pNaKtide intervention, where there was a significant increase in the NAS score in the HFD group when compared to the pNaKtide or Exercise groups (p<0.05, by $\chi^2$), where, in addition, there was a significant decrease in the fibrosis score among the pNaKtide and exercise groups (p<0.05), where a dramatic difference was observed in the number of apoptotic and cell senescence activities, where a significant decrease in apoptosis was observed in the HFD group when compared to the pNaKtide or Exercise groups by week 24 (p<0.01), and where, in contrast, the cell senescence activity was significantly increased in the exercise group compared to the HFD or pNaKtide groups (p<0.05).
Figure 6G:
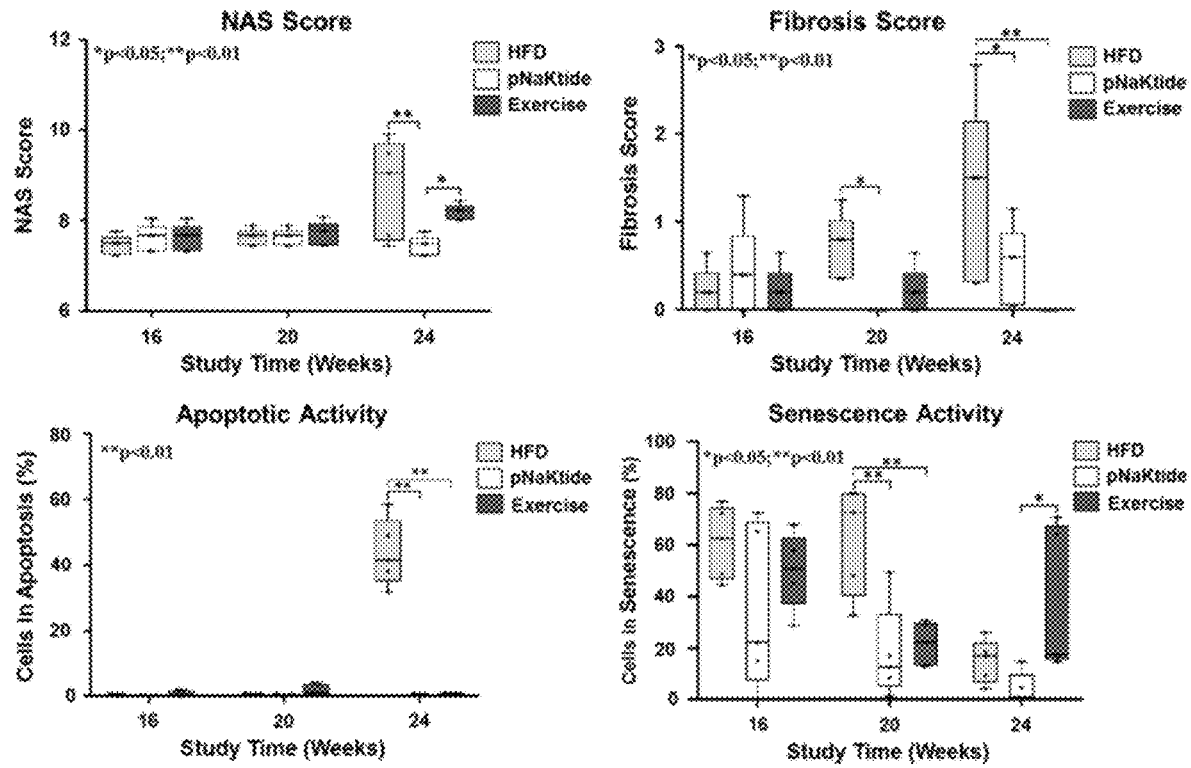

A dramatic difference was observed in apoptotic and cell senescent activity among groups by week 24 (FIG. 6A, D&E, p<0.05 by $\chi^2$). There was a significant decrease in cell senescence activity with the abrogation of apoptosis by week 24 in the intervention groups when compared to the HFD group. Concomitantly, there was a significant difference in the fibrosis score among groups, where progression to bridging fibrosis was noted in the HFD, and regression of the fibrotic pattern was observed in the intervention groups by week 24 (FIG. 6C, p<0.05 by $\chi^2$). There was a significant increase in the NAS score of HFD and intervention groups when compared to the NMC group from week 16 to week 24 (FIG. 6B, p<0.05, by $\chi^2$). As shown in FIG. 6F, there was a significant increase in the NAS score of all HFD when compared to the NMC group (p<0.01, by $\chi^2$), and, in addition, there was a significant increase in the fibrosis score among the HFD groups (p<0.01). A dramatic difference was observed in the number of apoptotic and cell senescence activity, and, while there was a significant increase in apoptosis in the HFD groups by week 24 when compared to the NMC group (p<0.01), the senescence activity was different at weeks 16 ad 20, and there was no difference between the HFD and HFD+NS groups in any of the parameters (data not displayed, p<0.05). As shown in FIG. 6G, there was a significant increase in the NAS score in the HFD group when compared to the pNaKtide or Exercise groups (p<0.05, by $\chi^2$), and, in addition, there was a significant decrease in the fibrosis score among the pNaKtide and exercise groups (p<0.05). A dramatic difference was observed in the number of apoptotic and cell senescence activities, and a significant decrease in apoptosis was observed in the HFD group when compared to the pNaKtide or Exercise groups by week 24 (p<0.01). In contrast, the cell senescence activity was significantly increased in the exercise group compared to the HFD or pNaKtide groups (p<0.05).

Each component of the NAS score (macro-vesicular steatosis, micro-vesicular steatosis, cell hypertrophy, and inflammatory foci) was evaluated separately (FIGS. 10A-10E). There was a significant increase in the macro-vesicular content in liver cells in the HFD groups with a peak at week 24 when compared to the NMC and the intervention groups (p<0.05, by $\chi^2$). Also, the inflammatory component was more significant in the HFD with its peak at week 24, when compared to the NMC and the intervention groups (p<0.05 by $\chi^2$). Interestingly, in the pNaKtide group, a reduced inflammatory process was seen at week 16, and it came down by week 24 to similar levels when compared to the NMC. Similar levels of inflammation were observed between the NMC and intervention groups.

Figure 7A:
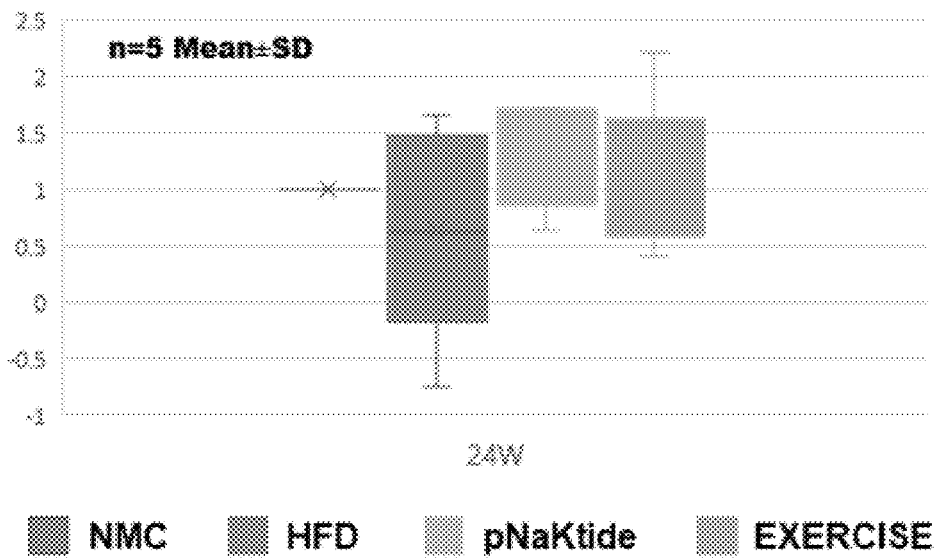
FIGS. 7A-7D include graphs showing the assessment of the α1-Na/K-ATPase expression, glutathionylation, and activity in the liver from rodent with NASH at 24 weeks, where there was not a significant difference in the expression of the α1 subunit of the Na/K-ATPase at week 24 (in FIG. 7A and FIG. 7B, p>0.05, t-test), where the degree of α1-Na/K-ATPase glutathionylation was similar between the NMC and the HFD groups (FIG. 7C, with or without interventions, p<0.05 by ANOVA), where, in contrast, there was a significant difference in the activity of the α1-Na/K-ATPase at week 24 among groups (in FIG. 7D, p<0.05, ANOVA), and where protein activity from the livers of animals in the pNaKtide group had a significantly higher activity when compared to the HFD or Exercise groups, and a similar activity when compared to the NMC group.
Figure 7B:
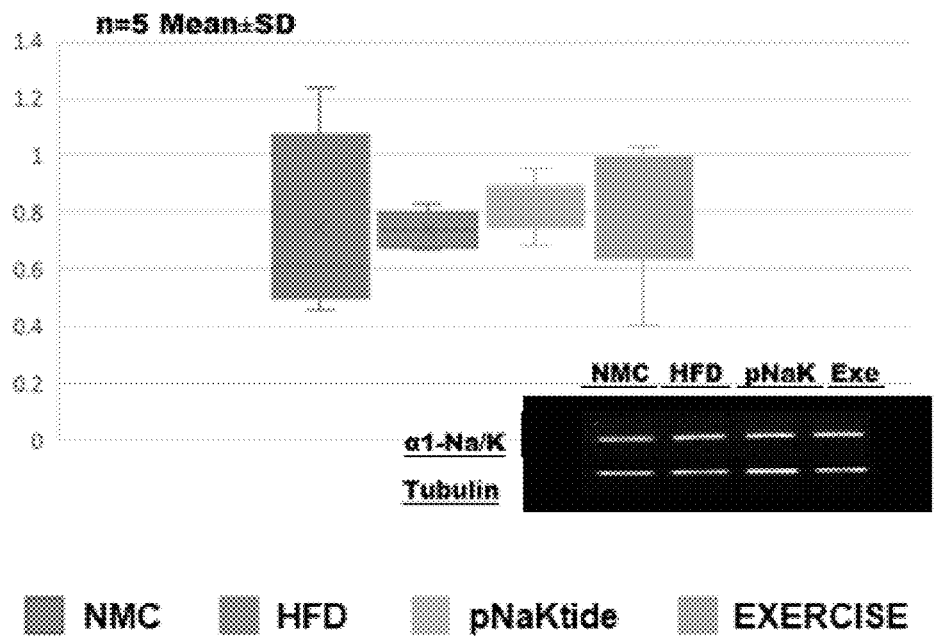
Figure 7C:
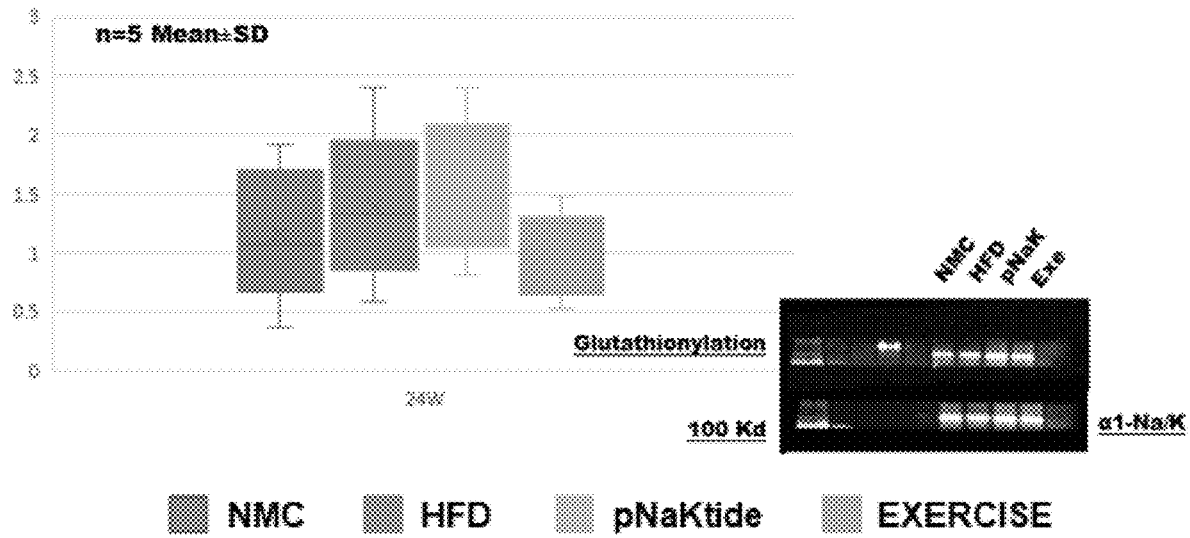
Figure 7D:
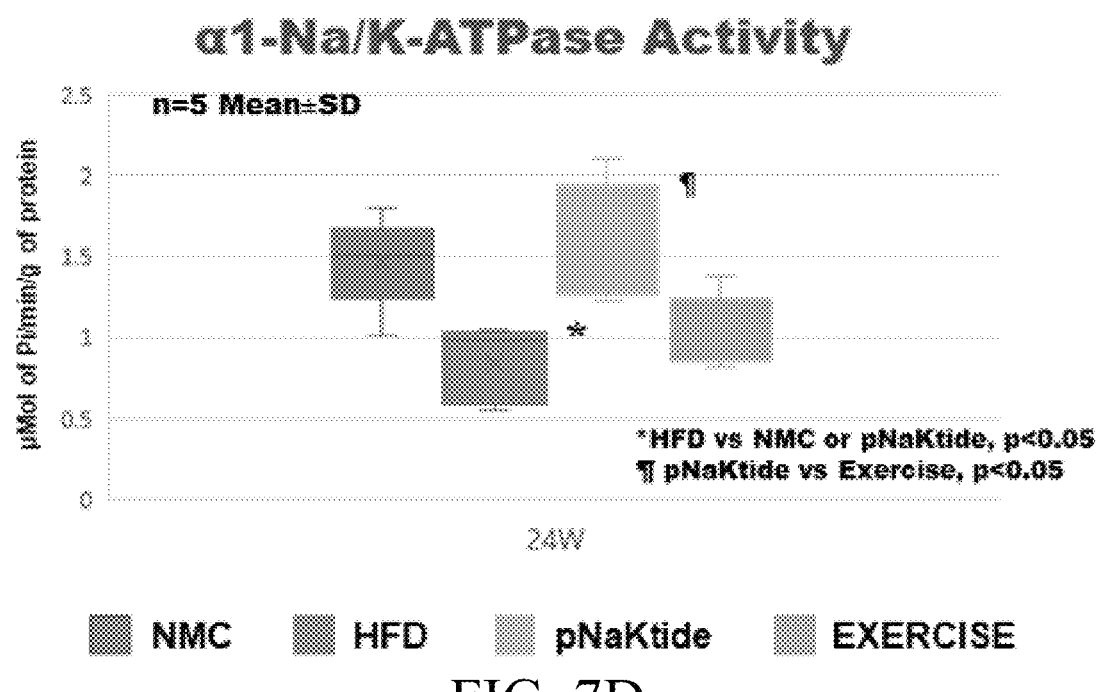

Example 5—Expression & Glutathionylation of the α1-Subunit and Activity of the Liver Na/K-ATPase There was not a significant difference in the expression of the α1-subunit of the Na/K-ATPase among groups at week 24 (FIGS. 7A-7B, p>0.05). In contrast, there was a significant difference in the activity of the Na/K-ATPase at week 24 among groups (FIG. 7D, p<0.05, ANOVA). Protein activity was significantly higher from livers of animals in the pNaKtide group when compared to the HFD or Exercise groups (p<0.05, t-test), and it showed similar activity when compared to the NMC group. Moreover, α1-NKA glutathionylation was similar in α1-subunits from the HFD group when compared to the NMC and intervention groups at all times periods as measured by immunoprecipitation (FIG. 7C, showed at 24 weeks, p>0.05, ANOVA followed by t-test).

Discussion of Examples 1-5

The global incidence and prevalence of chronic liver disease and its sequela ESLD and HCC are increasing as a consequence of viral hepatitis (B/C), and a continuous spread of the metabolic disturbances related to the obesity epidemic. Sustained oral intake enriched in lipids promotes liver fat accumulation, that in tandem with disturbed glucose degradation cycle, may further aggravate ATP production. This cell energy reduction originates from decreased mitochondrial β-lipid oxidation, thereby promoting the uncoupling of respiratory chain reactions that in turn further increase, ROI production. Increased radical intermediates enhances the evolution of cell senescence phenotypes and its progression to apoptosis favoring an inflammatory milieu with increased collagen deposition and progression to the end-organ stage. The present study demonstrated high concordance between the murine HFD induced NASH model, and the clinical manifestation of NASH observed in the human. There was a reduced cell oxi-redox status associated with metabolic and morphological progressive disturbances. Metabolic changes included dysregulated lipid and carbohydrate metabolisms with disarrayed gene expression; changes that in some instances preceded morphological alterations such as accelerated senescence/apoptotic activities, progressive inflammatory cell infiltration, and liver fibrosis. Uncouple respiratory chain reactions may explain the observed, reduced octanoate degradation rate followed by glucose intolerance with the associated glutathione sp. disturbances. Related liver changes induced by HFD were restored by blockage of the signaling cascade that follows the phosphorylation of Src at the α1-Na/K-ATPase. The inhibition of the pSrc phosphorylation mechanism in the liver, although different from the one induced by exercise, restores protein-pump activity without changes in protein expression or degree of glutathionylation at protein cysteine residues.

Rodents exposed for 12 weeks to a diet emulating the western HFD gained weight and developed fatty livers with NASH and progressive fibrosis. In the presented studies, animals gained their weight from an expansion on their body fat compartment with concomitant development of NAFLD and its progression to NASH, with dyslipidemia and hyperglycemia preceding the appearance of inflammatory foci and advanced fibrosis; morphological and metabolic disturbances that resemble the human clinical metabolic environment. Although animals in the NMC undergo senescence, they did not undergo apoptosis during the study period. Effects of decreased cell oxi-redox status may vary among physiological liver cell portfolios. Parenchymal cells primarily undergo fat storage in a macro and micro-vesicular pattern with increasing cell cycle arrest. When HepG2 cells were induced to senescence by $H_2O_2$ exposure, increased expression of SA-ß-GAL phenotype and SAF's accumulation were noted in addition to the upregulation of the Tp53 pathway. Additionally, stellate cell cycle arrest induces synthesis and deposition of collagen and further activates an inflammatory secretory phenotype. Sinusoidal endothelial cells express adhesion molecules promoting the roll-over and migration of systemic inflammatory cells into the liver microenvironment. Progressive metabolic changes along with an increasing number of cells in cycle-arrest may complete a loop of cell distress, surpassing at some point the cell survival threshold. pNaKtide and exercise disrupted the amplification of the ROI production loop promoted by HFD, affecting metabolic responses and phenotype in liver cells.

Figure 11A:
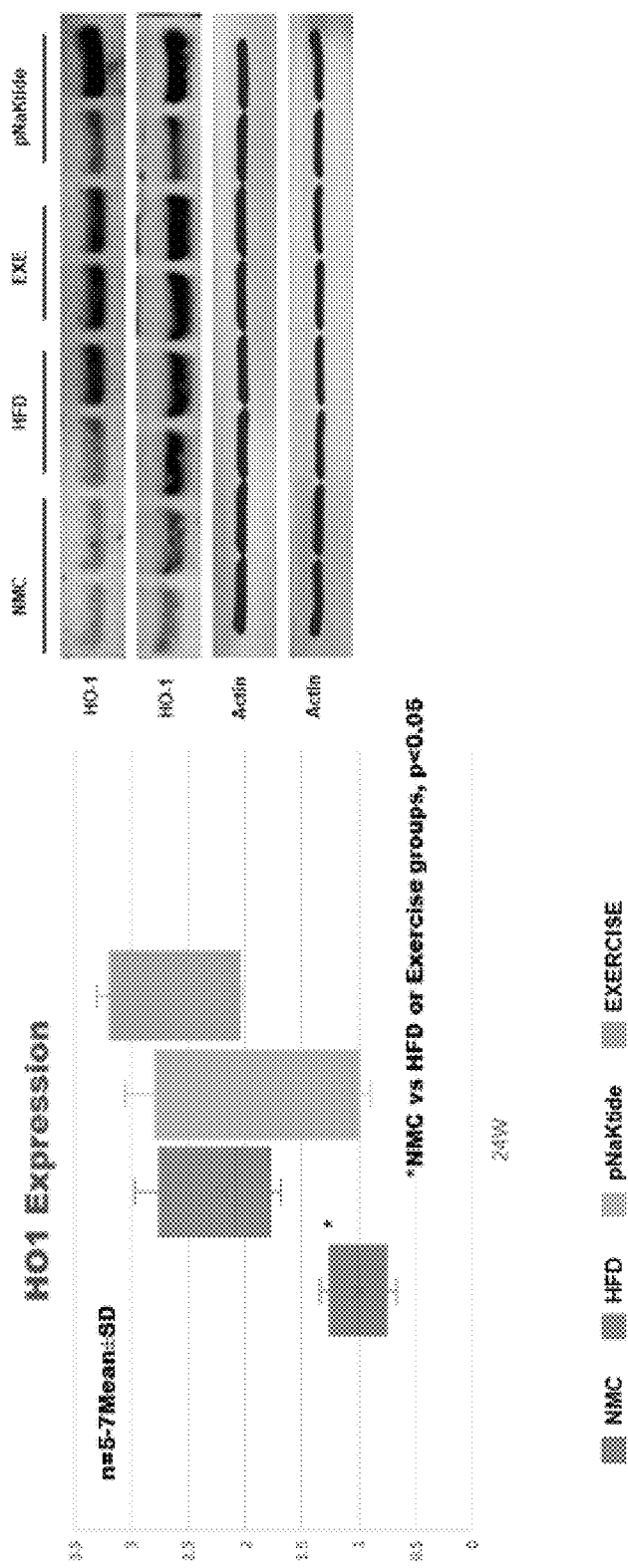
FIGS. 11A-11B include images and graphs showing homo-oxygenase-1 (HO-1) expression and assessment of pNaKtide presence on murine livers with NASH, where there was a significantly lower expression of HO-1 in the liver from animals exposed to NMC when compared to animals exposed to HFD (p<0.05 by ANOVA), where HO-1 expression among HFD groups (no intervention vs intervention) was similar (p>0.05), and where pNaKtide was present in all livers from animals exposed to IP pNaKtide in the intervention group.
Figure 11B:
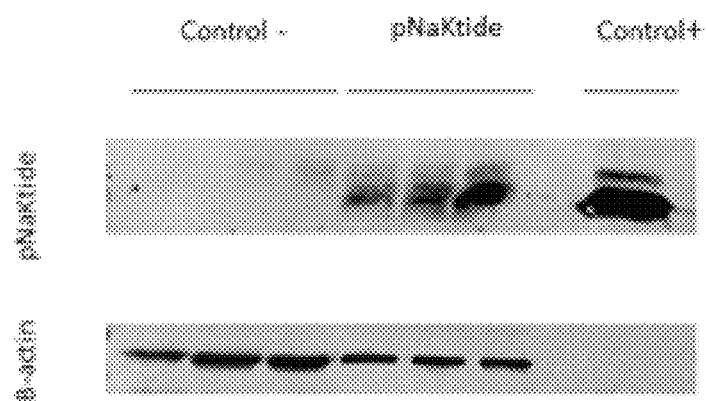
Figure 12:
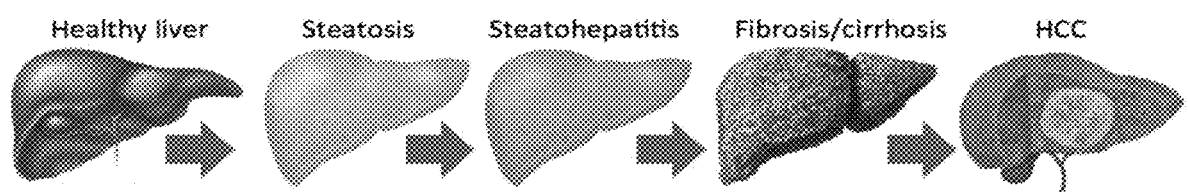
FIG. 12 includes images showing the progression of fatty liver to HCC.
Figure 13A:
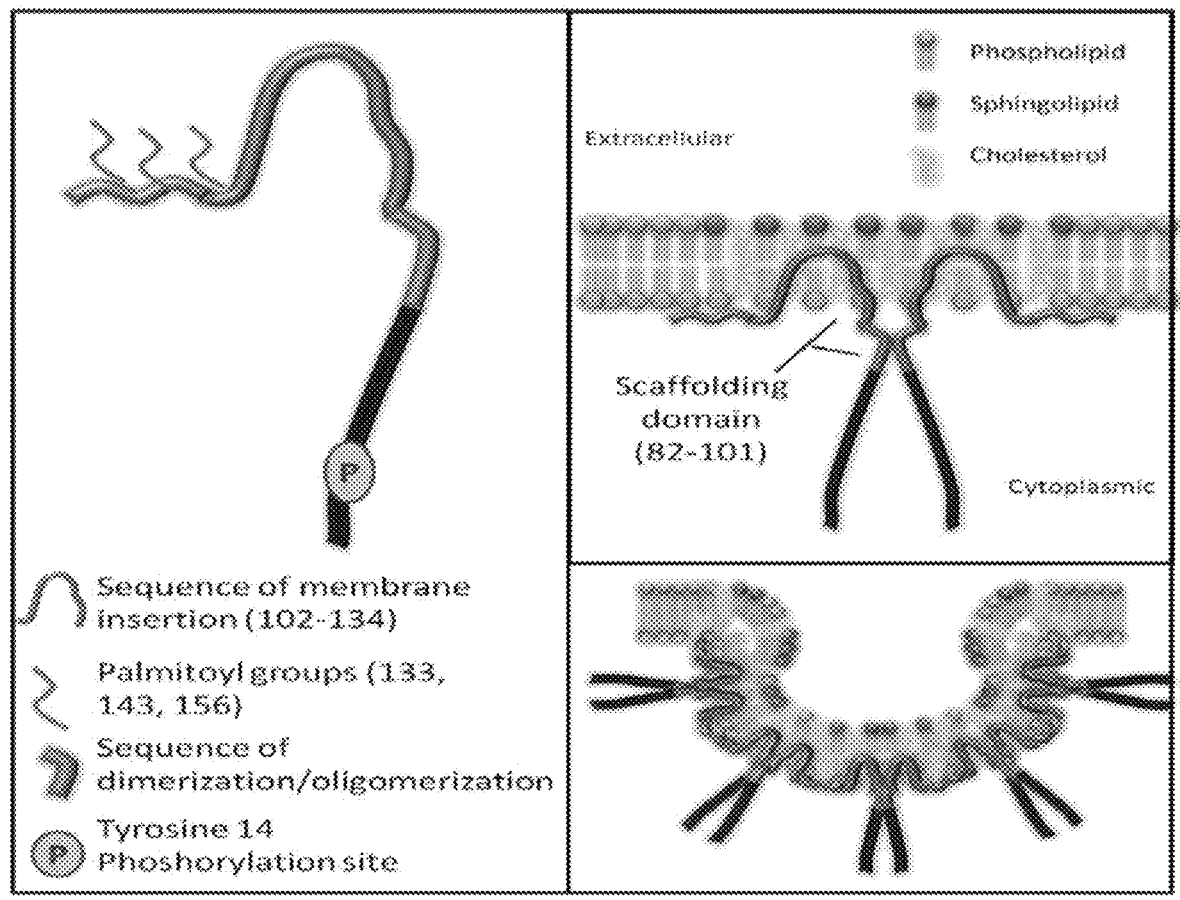
FIGS. 13A-13B include schematic diagrams showing caveolin-1 structure and caveolae morphology (FIG. 13A) and a model of Na/K-ATPase Signaling (FIG. 13B).
Figure 13B:
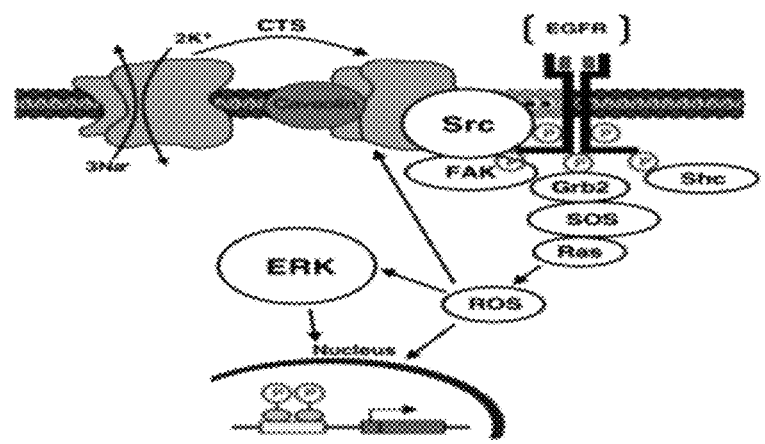
Figure 14:
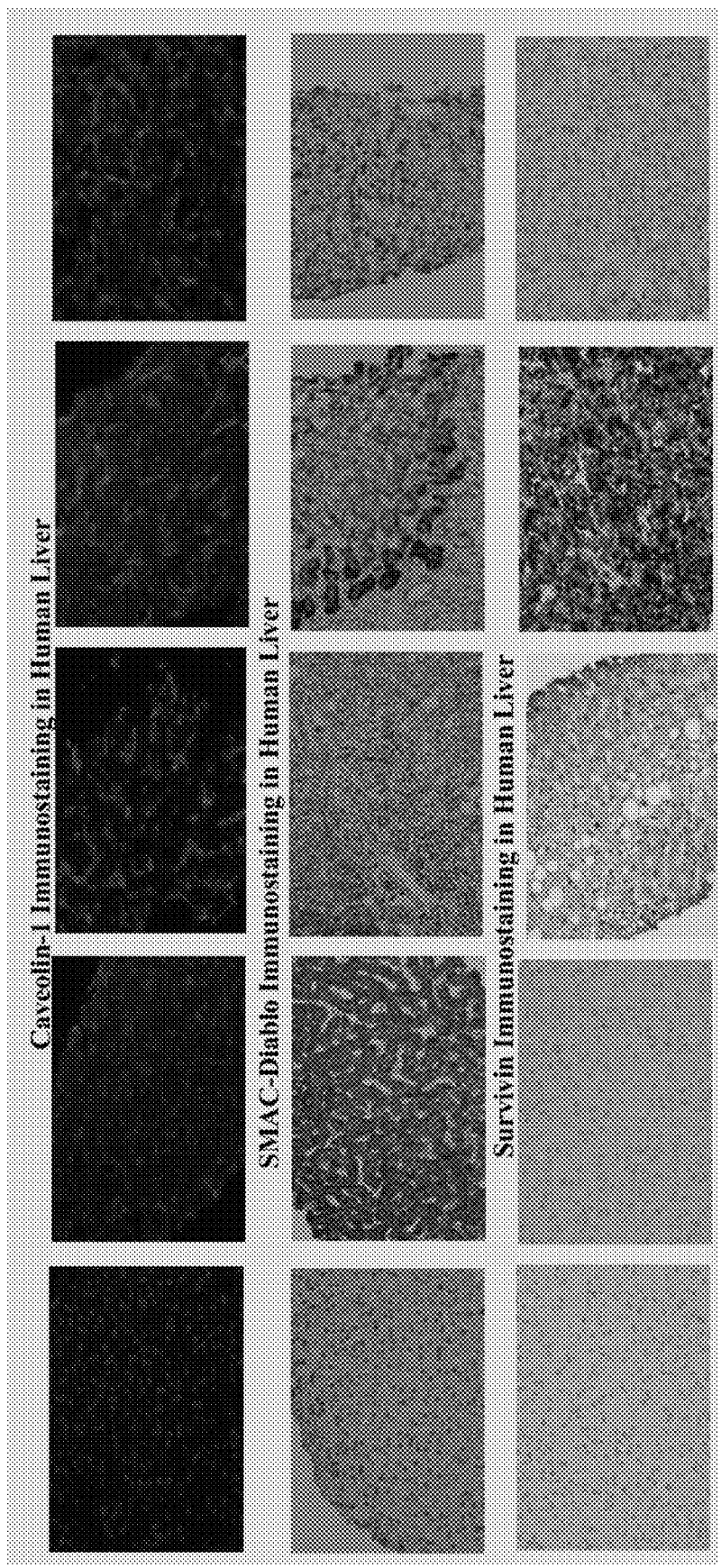
FIG. 14 includes images showing the results of immunohistochemistry of caveolin-1, SMAC and Survivin in Normal Human livers, Human livers with NASH, HCC and Metastatic cancer.
Figure 15:
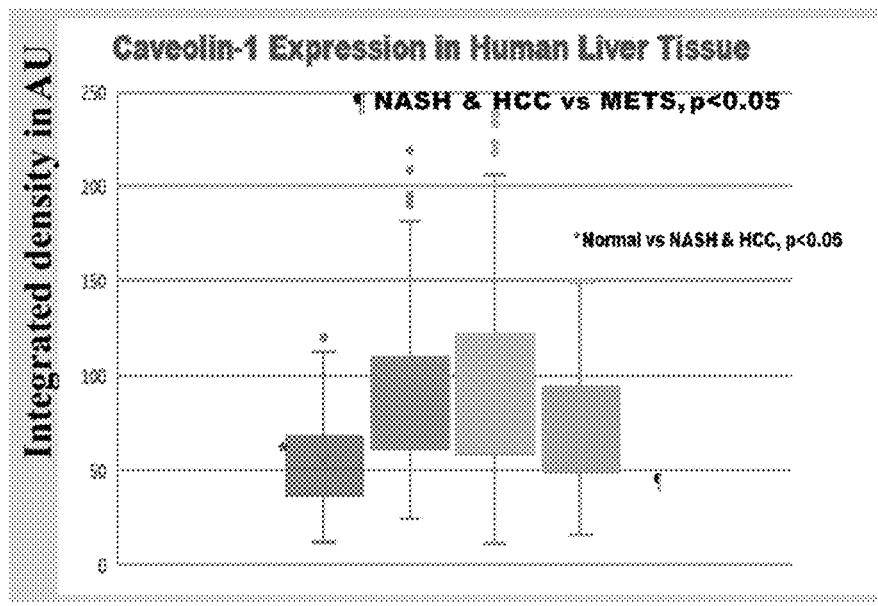
FIG. 15 is a graph showing the results of caveolin-1 expression in Normal Human livers, Human livers with NASH, HCC and Metastatic cancer. * P<0.05, when expression in normal livers are compared to NASH & HCC livers, ¶ p<0.05, when expression in Livers with NASH and HCC are compared to metastatic livers.
Figure 16:
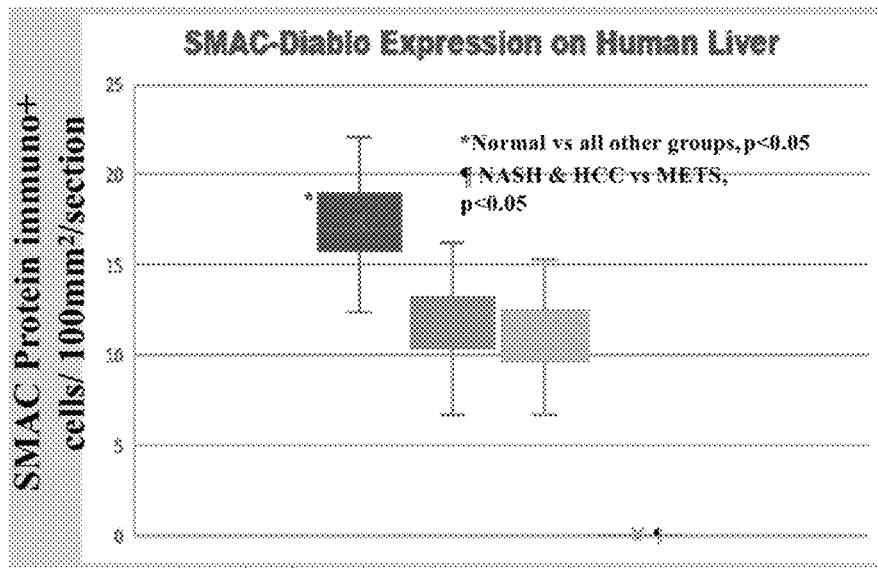
FIG. 16 is a graph showing the results of SMAC protein expression in Normal Human livers, Human livers with NASH, HCC and Metastatic cancer. * P<0.05, when expression in normal livers are compared to NASH & HCC livers, ¶ p<0.05, when expression in Livers with NASH and HCC are compared to metastatic livers.
Figure 17:
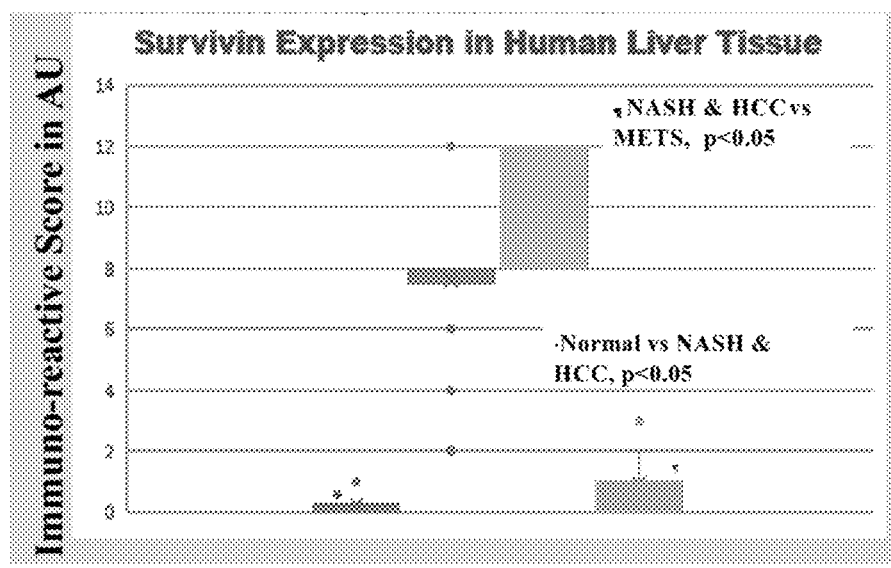
FIG. 17 is a graph showing the results of Survivin expression in Normal Human livers, Human livers with NASH, HCC and Metastatic cancer. * P<0.05, when expression in normal livers are compared to NASH & HCC livers, ¶ p<0.05, when expression in Livers with NASH and HCC are compared to metastatic livers.
Figure 18:
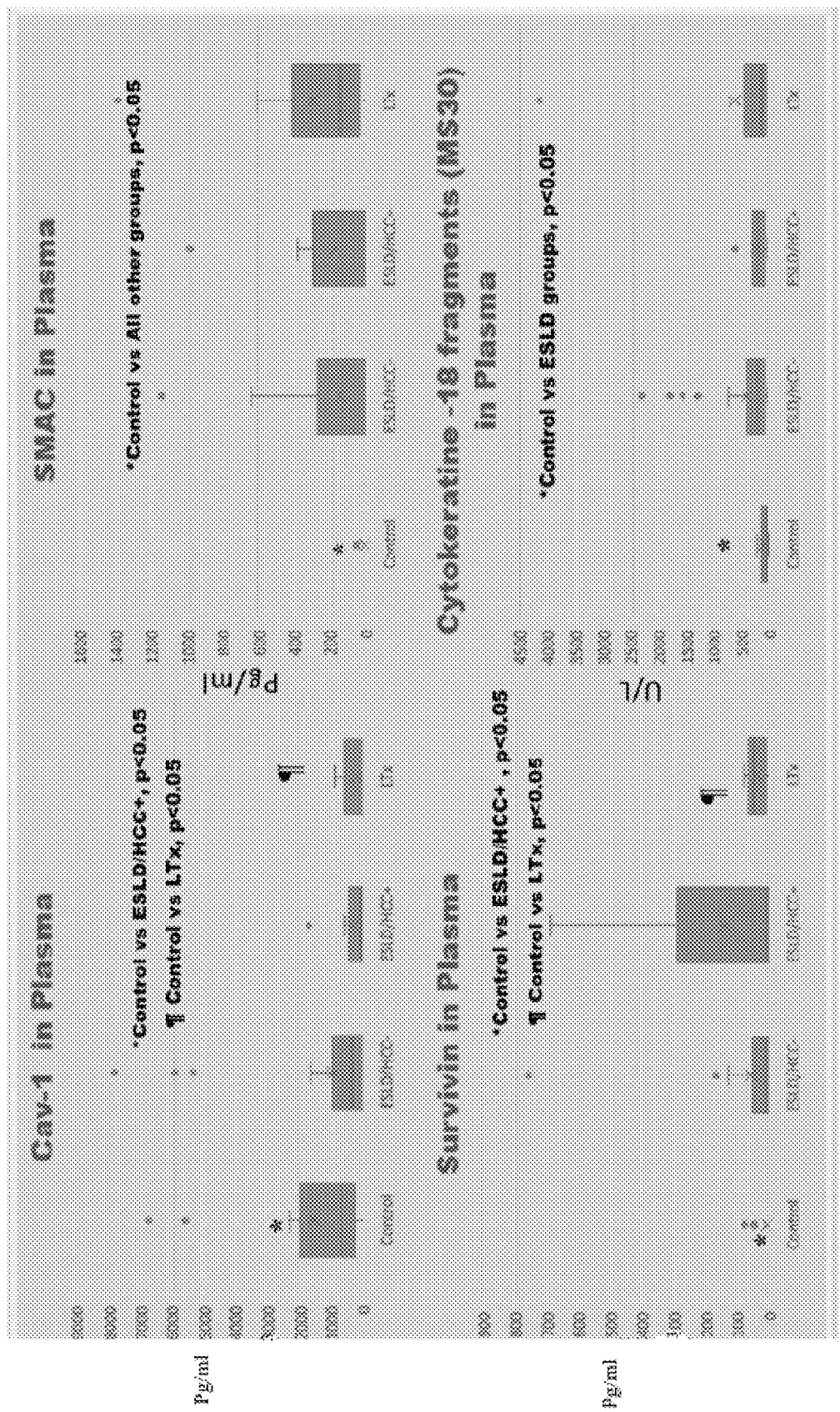
FIG. 18 includes graphs showing the results of ELISA analysis of Caveolin-1, SMAC, Survivin and cytokerain-18 fragments plasma levels in Normal Humans, Humans with NASH and HCC. * P<0.05, when plasma level of proteins in normal subjects are compared to those with NASH & HCC, ¶ p<0.05, when plasma levels of protein in NASH and HCC subjects are compared to patients with liver transplant.
Figure 19A:
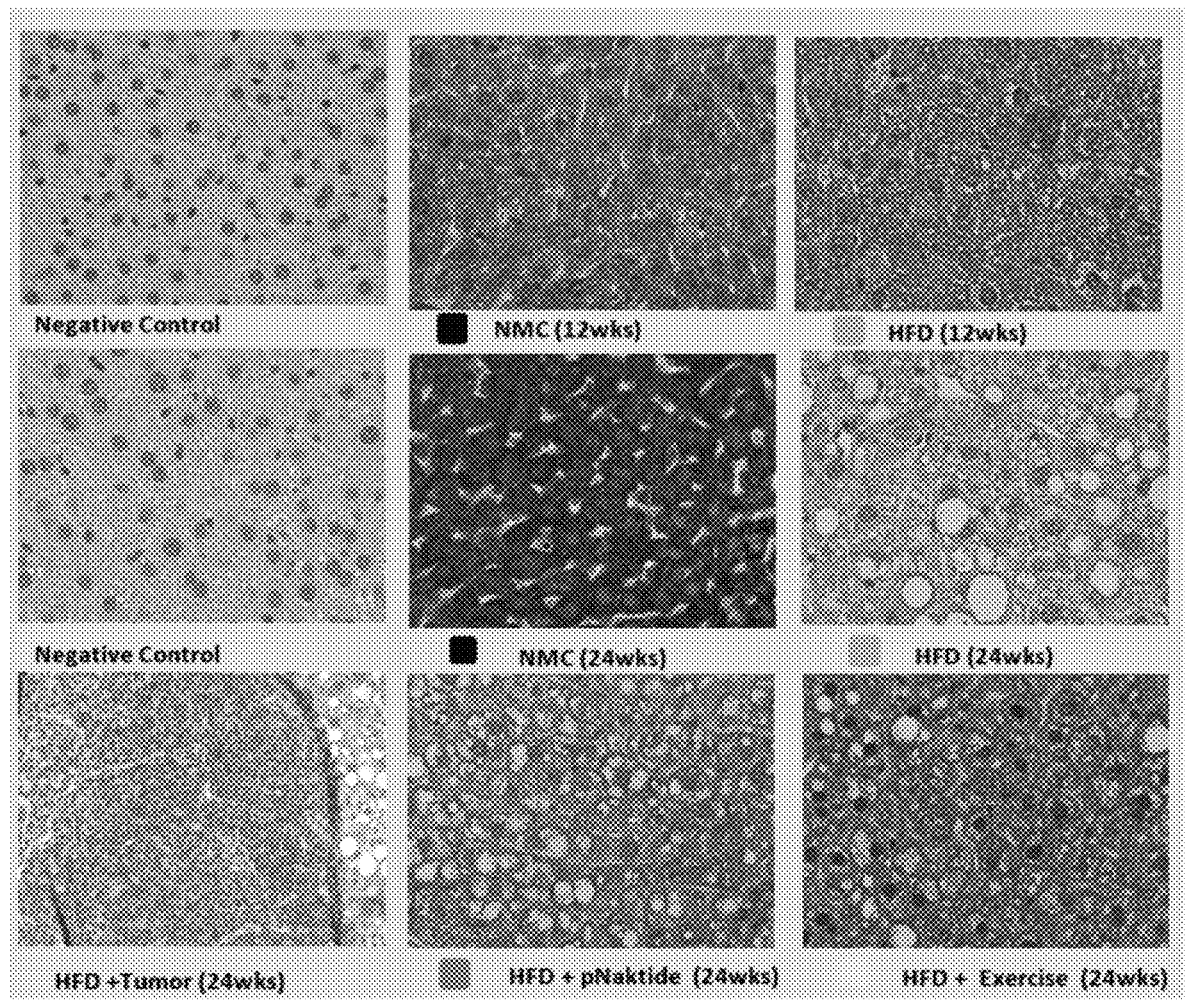
FIGS. 19A-19B include images and graphs showing the results of SMAC protein expression in liver tissues of Murine Model of Non-alcoholic steatohepatitis (NASH) (12&24 wks exposure to high fat diet), where NMC=Mice fed on normal mouse chow for 12& 24 wks, HFD=Mice fed on high fat diet for 12& 24 wks, HFD+pNaktide=mice fed with high fat diet for 24 wks with pNaktide intervention after 12 wks, and HFD+Exercise=Mice fed with high fat diet for 24 wks with Exercise intervention after 12 wks (n=5/group; C57bl6, females. * HFD vs all other groups (P<0.05)).
Figure 19B:
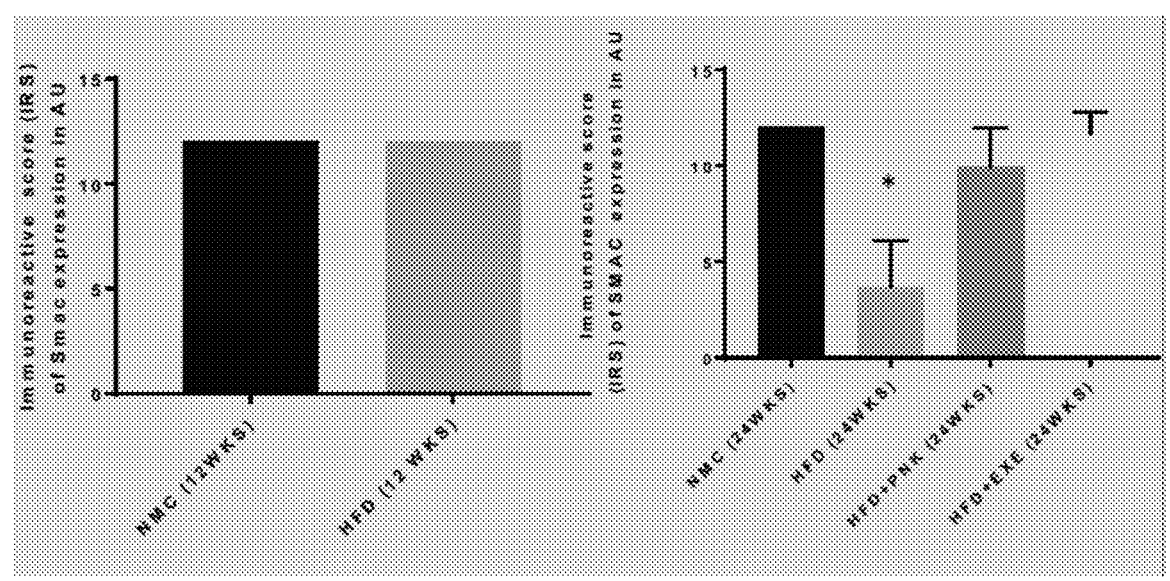
Figure 20A:
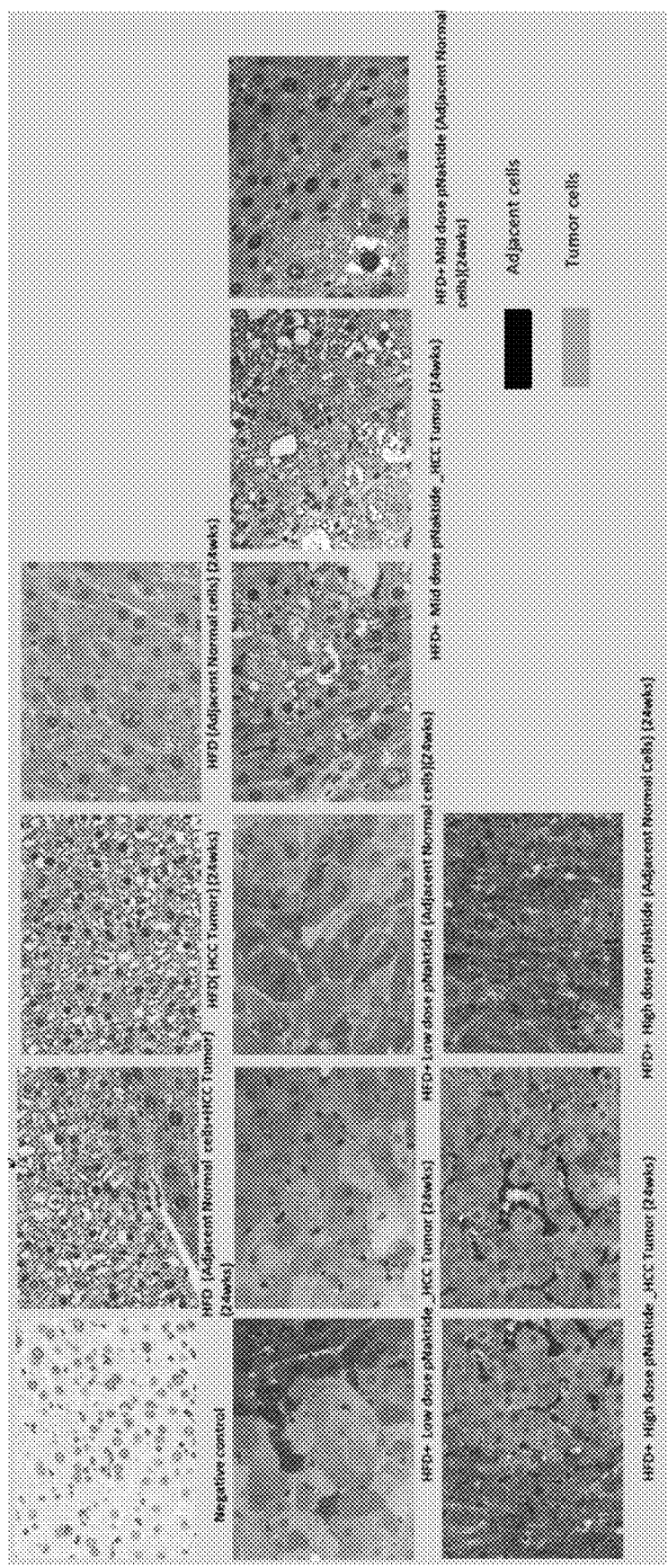
FIGS. 20A-20B include images and graphs showing the results of SMAC protein expression in liver tissues of Murine Model of Hepatocellular carcinoma (HCC) (24 wks exposure to high fat diet, where HFD=Mice fed on high fat diet for 24 wks, HFD+low dose pNaktide=mice fed with high fat diet for 24 wks with low dose of pNaktide intervention after 12 wks, HFD+mid dose of pNaktide=Mice fed with high fat diet for 24 wks with mid dose of pNaktide intervention after 12 wks, HFD+high dose of pNaktide=Mice fed with high fat diet for 24 wks with High dose of pNaktide intervention after 12 wks (n=5 for each group; C57 bl6, males, * HFD vs all other groups (P<0.05)).
Figure 20B:
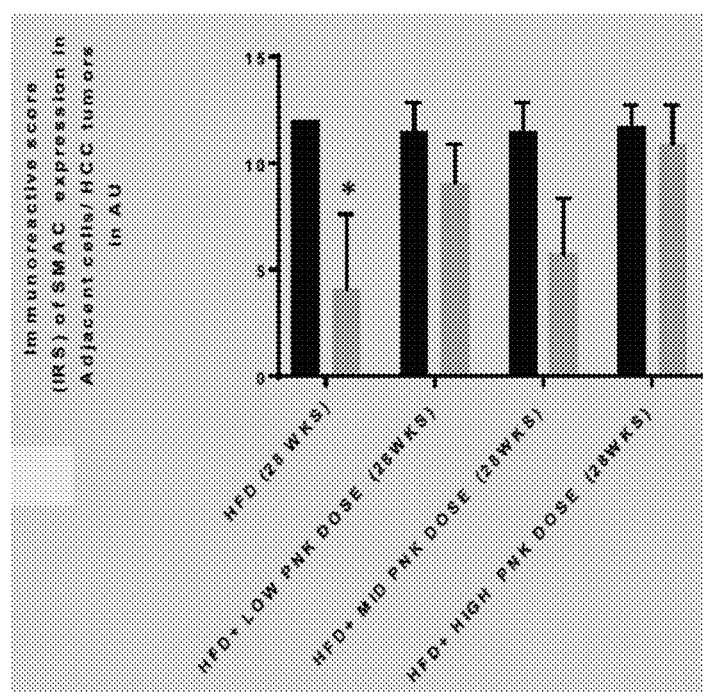
Figure 21A:
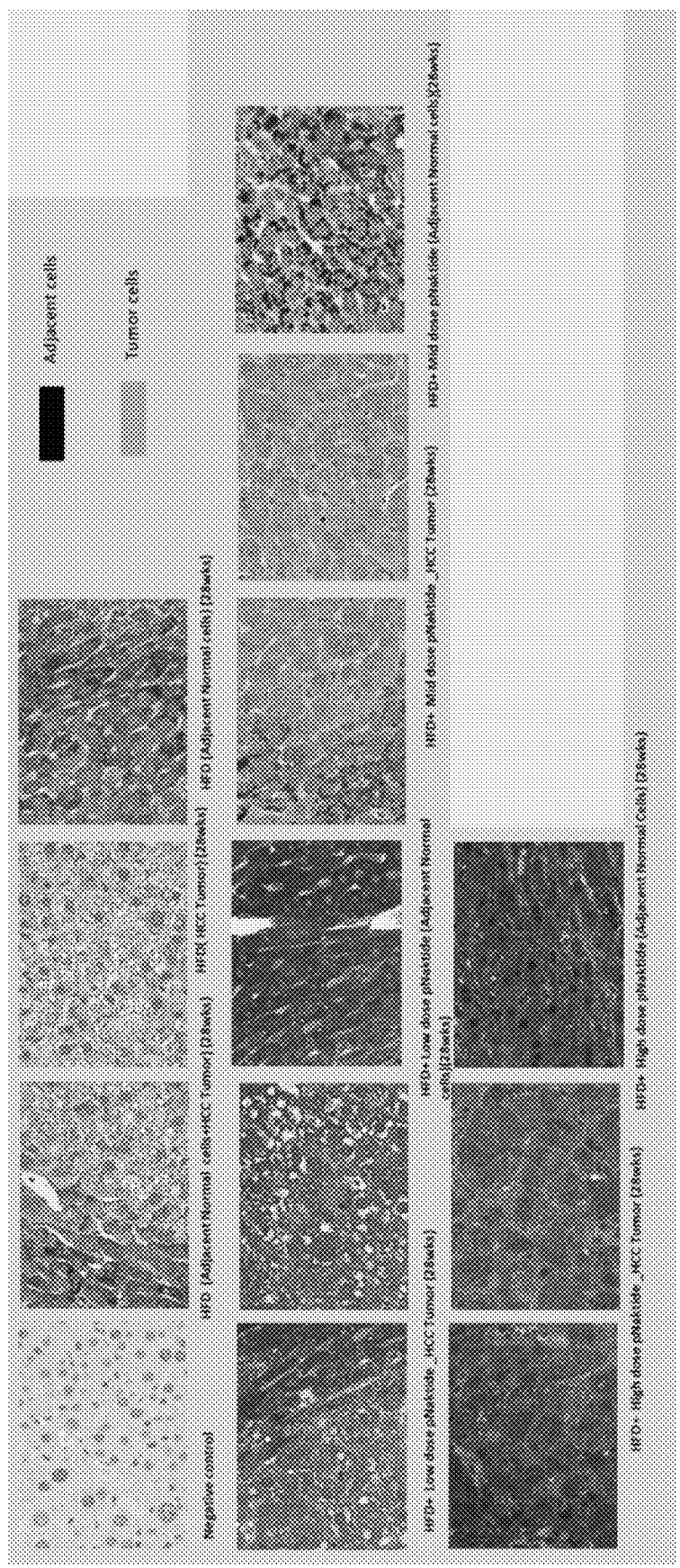
FIGS. 21A-21B include images and graphs showing the results of SMAC protein expression in liver tissues of Murine Model of Hepatocellular carcinoma (HCC) (28 wks exposure to high fat diet, where HFD=Mice fed on high fat diet for 24 wks, HFD+low dose pNaktide=mice fed with high fat diet for 28 wks with low dose of pNaktide intervention after 12 wks, HFD+mid dose of pNaktide=Mice fed with high fat diet for 28 wks with mid dose of pNaktide intervention after 12 wks, HFD+high dose of pNaktide=Mice fed with high fat diet for 28 wks with High dose of pNaktide intervention after 12 wks (n=5 for each group; C57 bl6, males, * HFD vs all other groups (P<0.05))
Figure 21B:
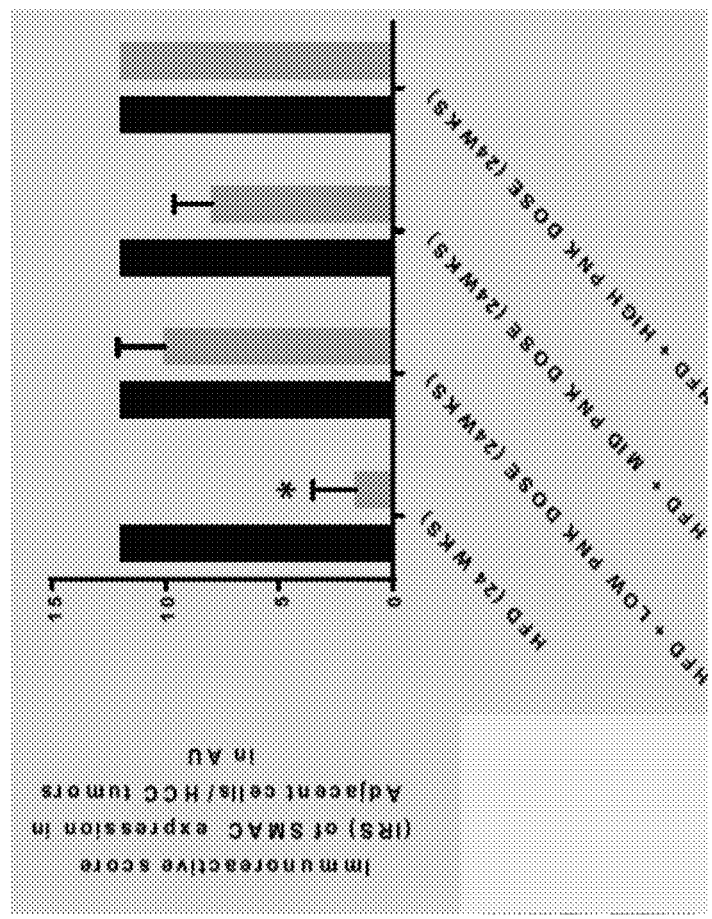
Figure 22A:
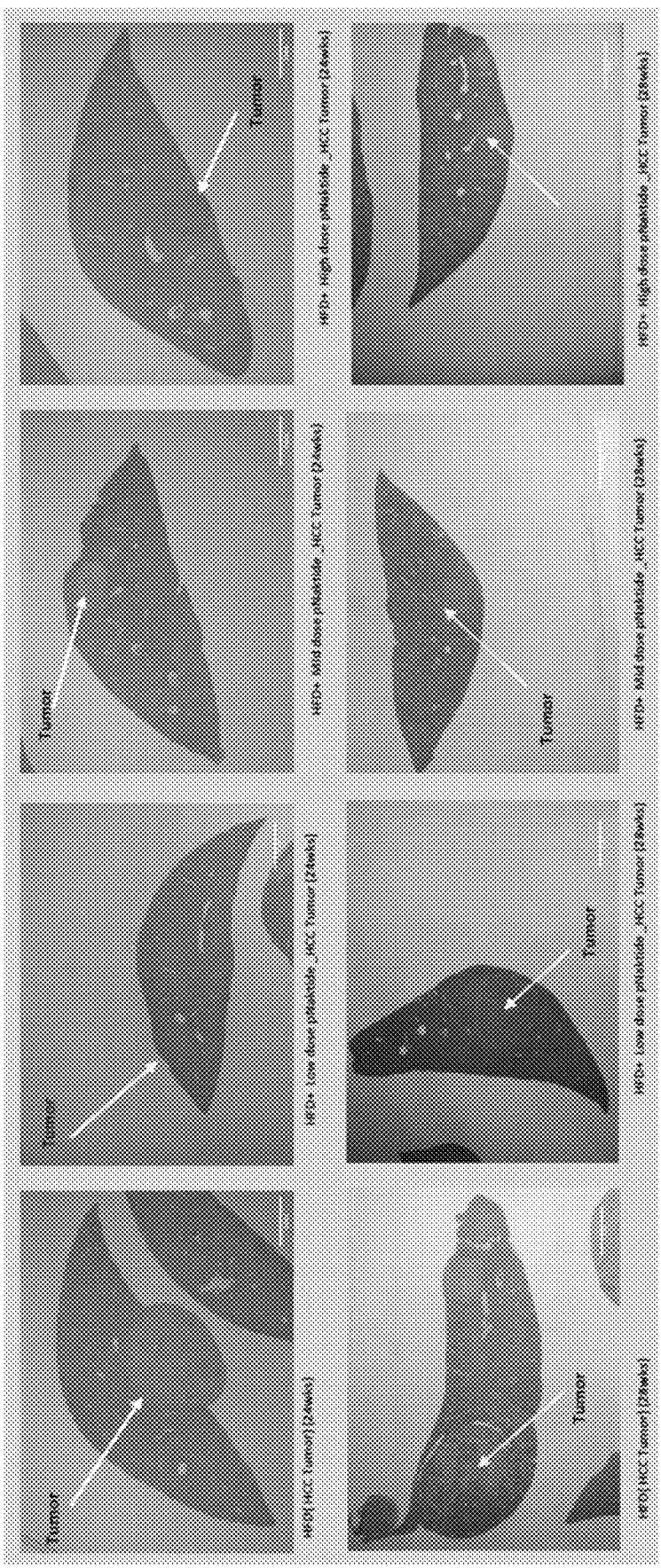
FIGS. 22A-22B include images and graphs showing the results of Tumor Burden in liver tissues of Murine Model of Hepatocellular carcinoma (HCC) (24&28 wks exposure to high fat diet, where HFD=Mice fed on high fat diet for 24 wks & 28 wks, HFD+low dose pNaktide=mice fed with high fat diet for 24 wks&28 wks respectively with low dose of pNaktide intervention after 12 wks, HFD+mid dose of pNaktide=Mice fed with high fat diet for 24 wks&28 wks respective with mid dose of pNaktide intervention after 12 wks, HFD+high dose of pNaktide=Mice fed with high fat diet for 24 wks&28 wks respectively with High dose of pNaktide intervention after 12 wks (n=5 for each group; C57bl6, males. * HFD+High dose pNaktide vs all groups (p<0.001)).
Figure 22B:
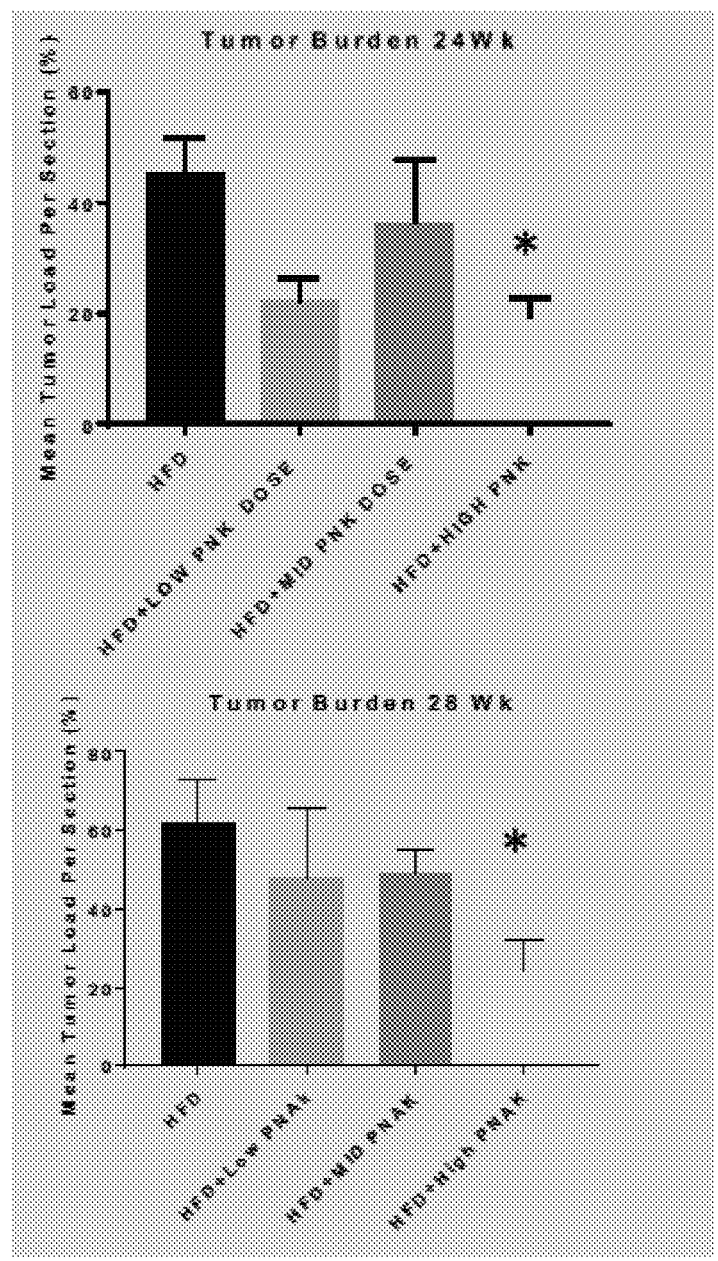

Glutathione sp. varied significantly in the HDF groups compared to the NMC and the intervention groups. Glutathione reduced, glutathione oxidized, and ophthalmic acid significantly increased in the HFD groups when compared to other groups, more so at weeks 20 and 24, when peaks in cell arrest and apoptosis were noted. Glutathione sp. is a surrogate for cell stress, and glutathione in plasma reflects the liver oxi-redox status since the rodent liver secretes >90% of glutathione present in plasma. A reduced oxi-redox is mainly caused by increased production of ROI from inefficient/uncoupled respiratory chain reactions. HFD groups expressed a progressive reduction in their cell oxi-redox status originated from a decrease of the liver mitochondrion to synthesize ketones from octanoate, a reaction that serves as a marker of 0-lipid oxidation. Further evidence was observed in the pNaKtide group, where an increase in the transcription of the PPRγ-PCG1α complex correlated with an increase in β-lipid oxidation. Non-efficient lipid oxidation increases succinate, and increased levels of mitochondrial succinate may disturb the citric acid cycle, as has been shown in skeletal muscle. ROI production is enhanced by an insulin-resistance status, indicated by glucose intolerance, which further promotes cell senescence phenotype expression and inflammation. pNaKtide and exercise reversed insulin-resistant status through common (PCG1a/FOX01) and different pathways (GrB2/Src). Moreover, pSrc may play different roles at the cell membrane and mitochondrial level. Inhibition of the active site of the α1-subunit of the Na/K-ATPase by pNaKtide, avoided the peak of phosphorylated Src (pSrc) observed in HFD at week 16, a reaction that involves the GrB2 protein. Similar inhibition was noted through the HO1-SirT1 pathway; however, other paths are likely involved, including the c-Jun-N terminal kinase (JNK) circuit. Yet and although HO1 expression was significantly higher in the HFD groups when compared to the NMC group at week 24, all HFD groups (no intervention vs interventions) had similar HO1 expression (FIGS. 11A-11B). Furthermore, pSrc is required in the mitochondria to maintain electron transport since decreased pSrc inhibits the respiratory chain and enhances ROI production. In light of the present studies, where glutathione sp. was significantly increased in the HFD when compared to NMC and intervention groups, glutathione sp. may play an additional role on top of acting as a surrogate for liver cell oxi-redox status. In fact, at higher rates of oxidation, glutathione sp. may promote an additional force for the uncoupling of the respiratory chain by sustained HFD through an ASK1-JNK-Sab-pSrc mitochondrial pathway. Interestingly, pNaKtide normalized glutathione sp. of rodents on HFD, restored β-lipid oxidation, and resolved glucose intolerance.

Metabolomic signatures were different in HFD, pNaKtide, and Exercise groups when compared to NMC. The visual display of metabolic heat maps could potentially serve as a surrogate for the diagnosis of a patient with liver disease, for their progression or response to treatment, and the early detection in the development of ESLD and HCC. Indeed, metabolic prints were able to discriminate patients with healthy livers from patients at different stages of ESLD, as judged by the MELD score. Furthermore, metabolic prints may help to discriminate patients with ESLD by tumor status. OH-butyrate was found to be an early biomarker of insulin resistance and glucose intolerance in non-diabetic subjects. Since non-targeted metabolic heat maps can be reproduced with a simple blood sample, this method may be translated to be a reliable tool for the screening of HCC in high-risk populations and perhaps replace the need for a liver biopsy when correlated with imaging modalities.

Increased permeability of mitochondrial membrane pores amplified the leakage of intermembrane cytochromes and activation of caspase processes, which may explain the morphological peak of apoptosis at week 24. pNaKtide normalized liver oxi-redox status by decreasing ROI, through a circuit that restored physiological mitochondrial β-lipid oxidation and insulin-sensitive state; paths included the upregulation of both PPRγ-PGC-1α complex and FOX01. Both proteins enhance insulin effects, and PPRγ-PGC-1α complex is involved in mitochondrial β-lipid oxidation. In culture, HepG2 cell lines showed a signaling defect downstream of the Akt pathway with an impact upon insulin-mediated FOX01 on cytosol sequestration and AS160 phosphorylation; a cascade that translated into insulin resistance of older cells when compared to younger cells. As pNaKtide normalized the glucose degradation path, the need for cell ATP assembly decreased with a lower peak of lipid oxidation at week 16, lowering levels of ROI production and normalizing the glutathione sp./cell oxi-redox status. The former mechanism may explain, at least in part, the prevention of parenchymal liver cell apoptosis, terminating cell arrest with the absorption of collagen deposition and paucity of the inflammatory loop. The apoptotic activity has been correlated with the progression of liver disease to an end-organ stage. Exercise may drive metabolic changes through a sarcoplasmic-lipid burning mechanism associated with the mobilization of lipid droplets from the liver. This line of thought may explain, at least in part, the increasing concentration of fatty acids, i.e., arachidonic, linoleic, palmitic acids in liver cells in the pNaKtide group when compared to the HFD and exercise groups.

Morphological assessment of livers from experimental groups showed striking differences. A dramatic and significant increase in cellular apoptotic and senescent activity was observed in the HFD groups when compared to the NMC and intervention groups. The proportion of aging cells expressing the senescence phenotype was progressively increased from weeks 12 to 24 in the HFD groups with a dramatic increase in the apoptotic activity at week 24 when compared to the NMC group. pNaKtide and Exercise were able to prevent the peak on apoptosis observed at week 24 with a progressive decrease in the proportion of cells expressing the senescent phenotype, a change associated with a decrease in the inflammatory score. Therefore, HFD promoted a progressive increase in the proportion of cells expressing the senescence phenotype, a marker of cell arrest associated with pro-inflammatory behavior, and activation of the collagen deposition pathway.

Figure 9A:
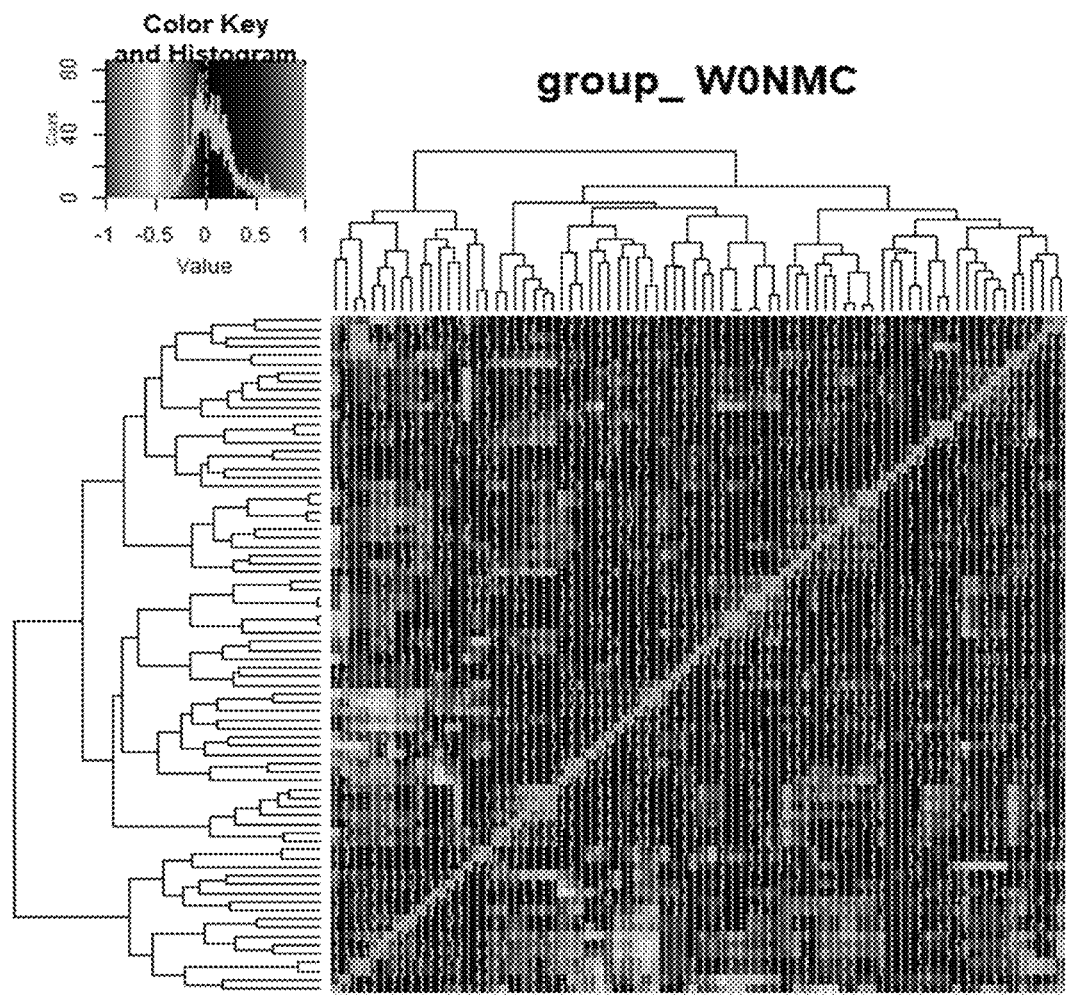
FIGS. 9A-9C include comparative metabolomic heat map signatures on treated plasma from diet-induced NASH in the rodent from week 0 to week 24, where R-lab software was programmed to display, as visual arrays, group comparisons of $log^{10}$ transformed metabolite data, where (FIG. 9A) the NMC group array was displayed at week 0 (WONMC) and then the NMC from each week was compared to the HFD group by week and labeled W12HFD, W16HFD, W20HFD, and W24HFD, to pNaKtide group and labeled W 12HFD, W 16HFDP, W20HFDP, and W24HFDP, and exercise group from each week and labeled W 12HFD, W 16HFDE, W20HFDE, and W24HFDE, respectively, where, in the Y-axis, the metabolite variable was entered while in the X-axis animal/group was recorded, where because of the Log transformation, differences are by a 100 to a 1000 factor between groups, and where there was a significant difference in both the metabolic print among groups at weeks 16, 20, and 24 and the progression of the metabolic print for each group (p<0.05 by PCA).
Figure 9A:
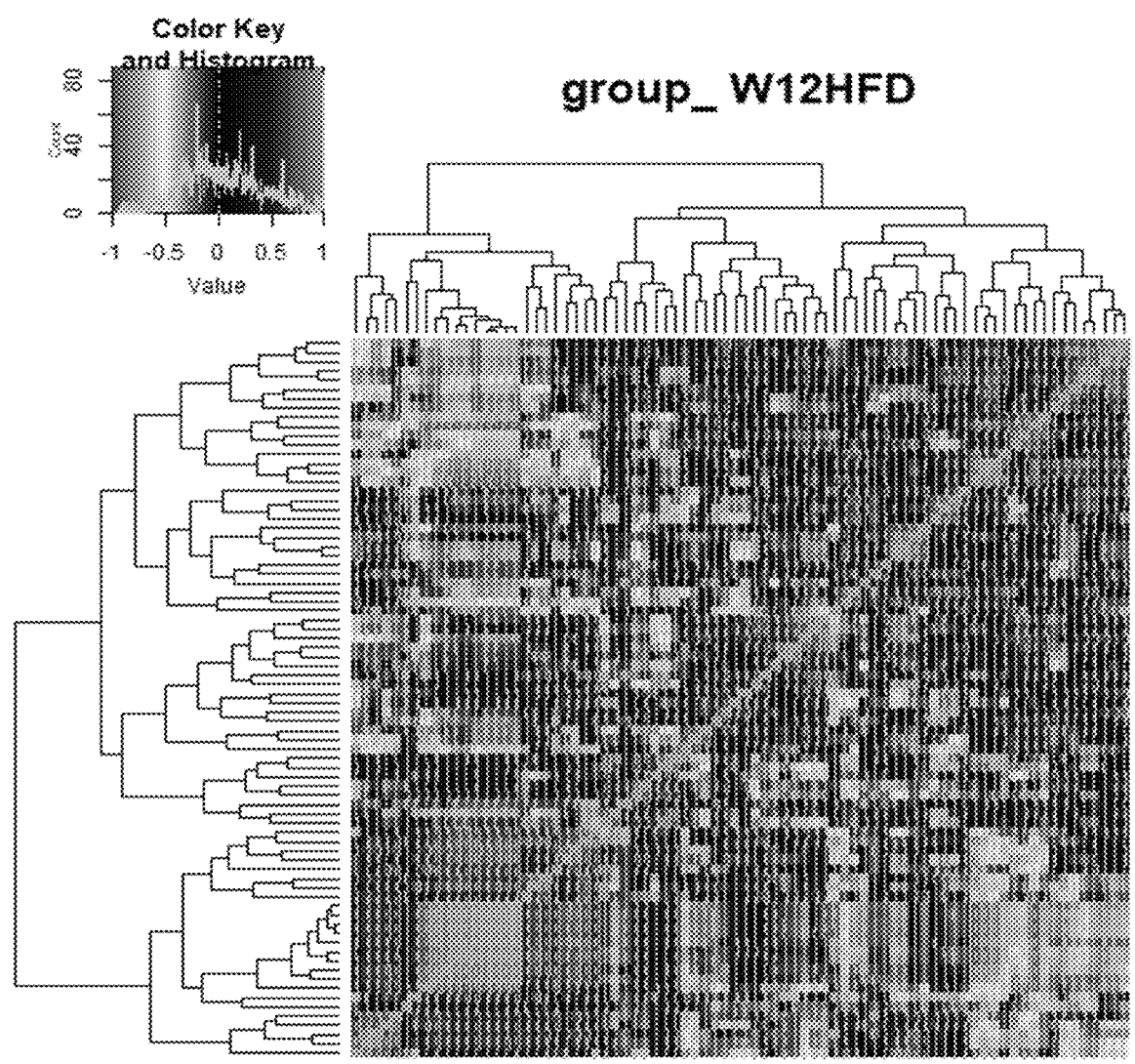
Figure 9A:
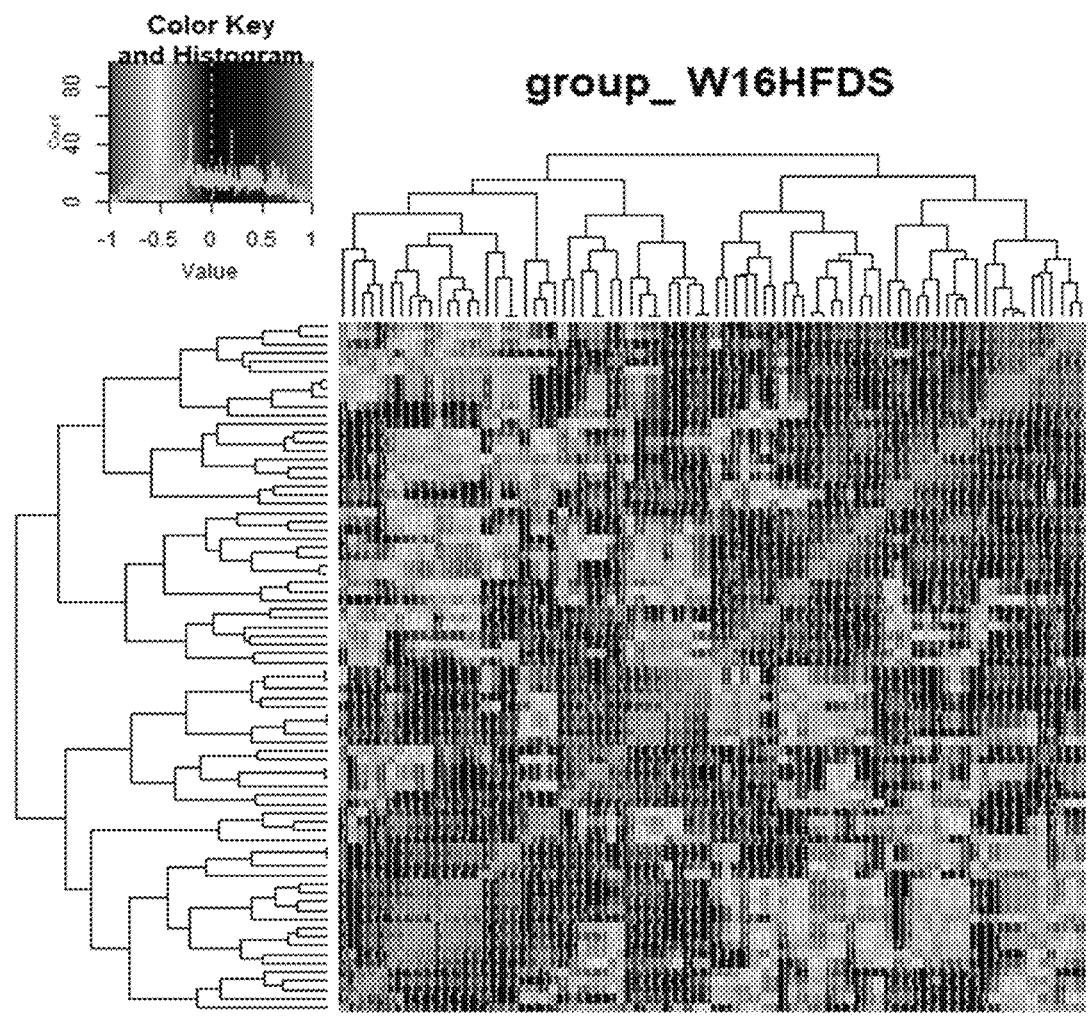
Figure 9A:
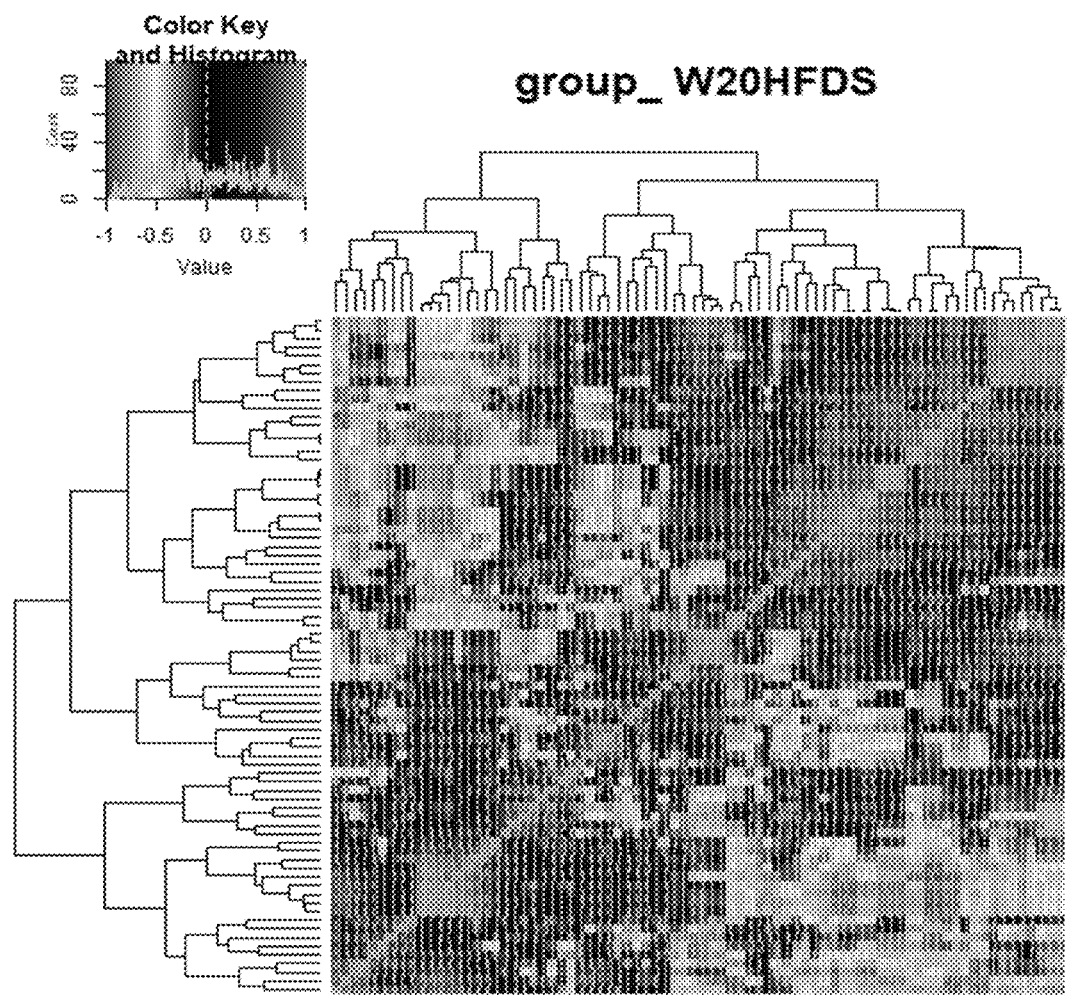
Figure 9A:
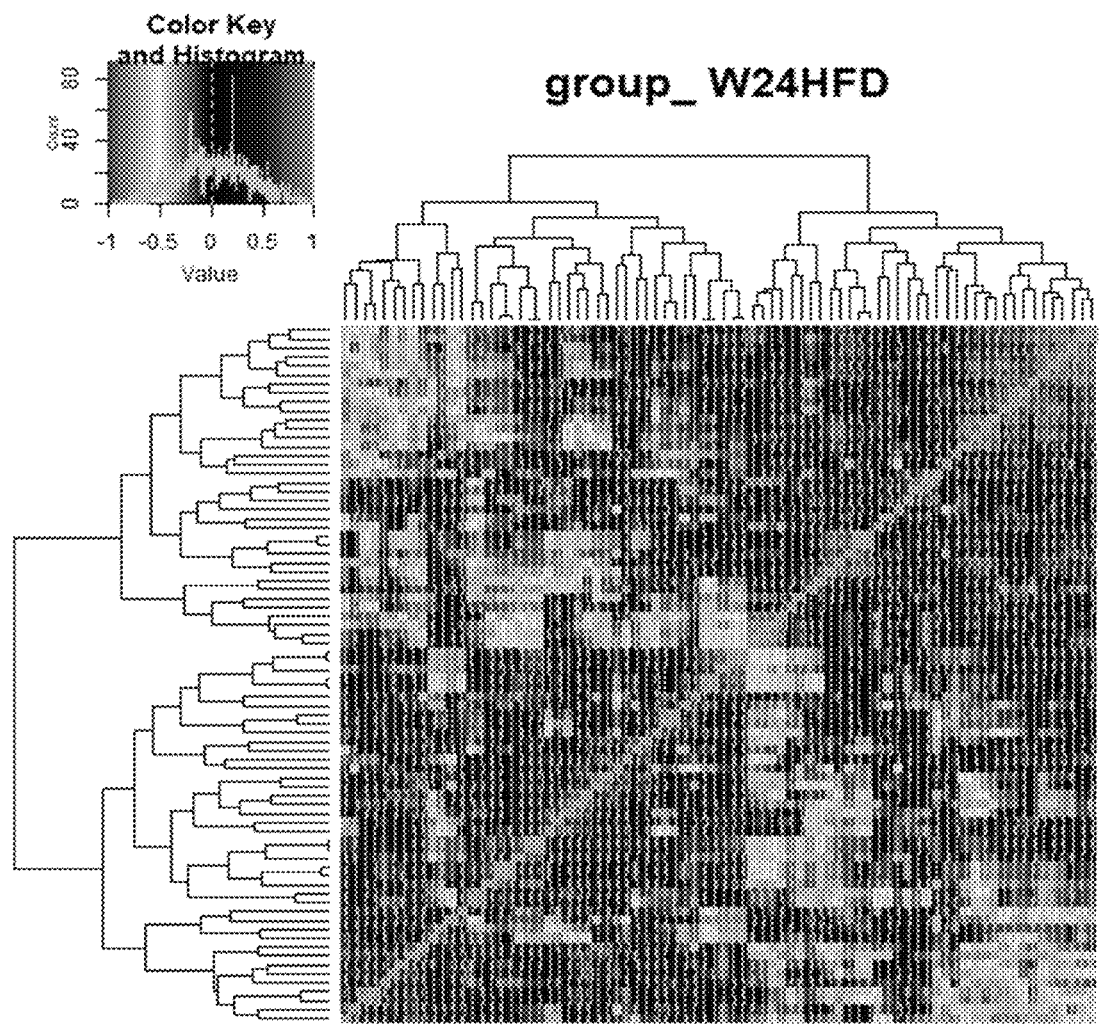
Figure 9B:
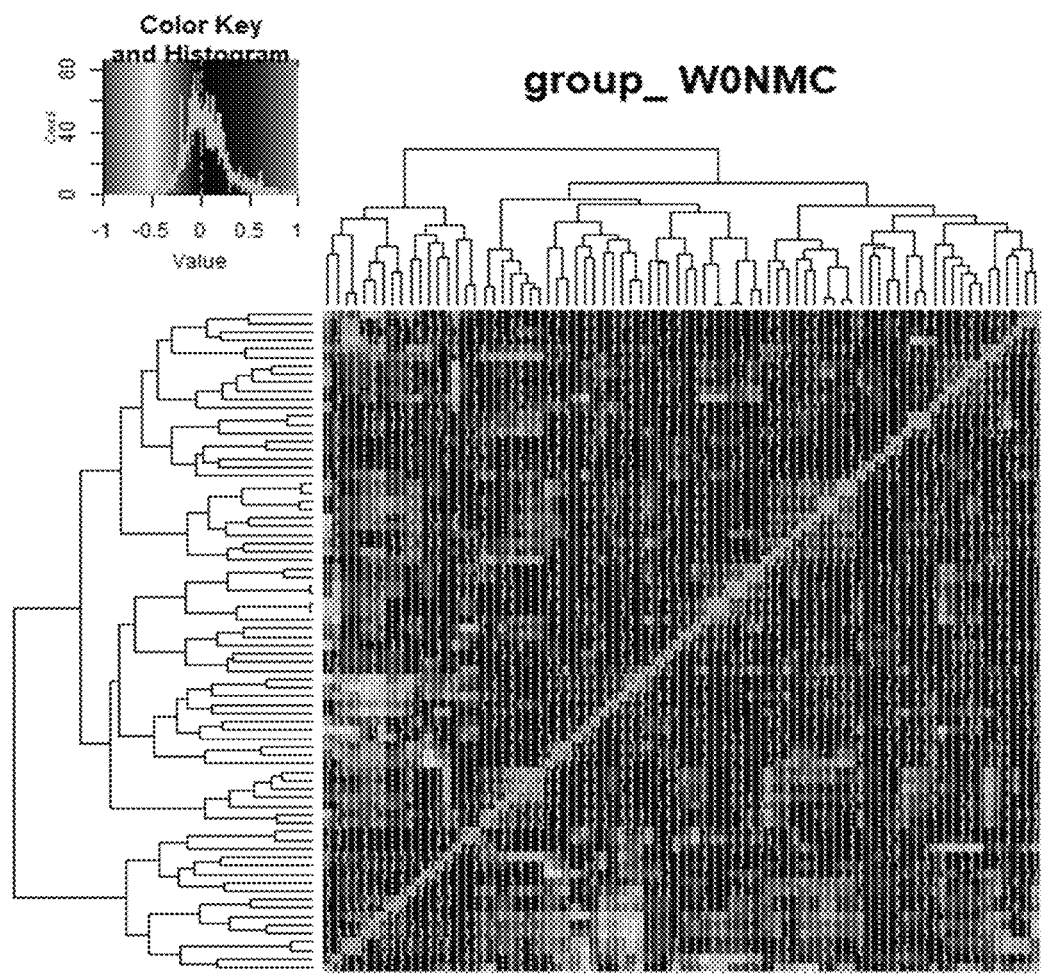
Figure 9B:
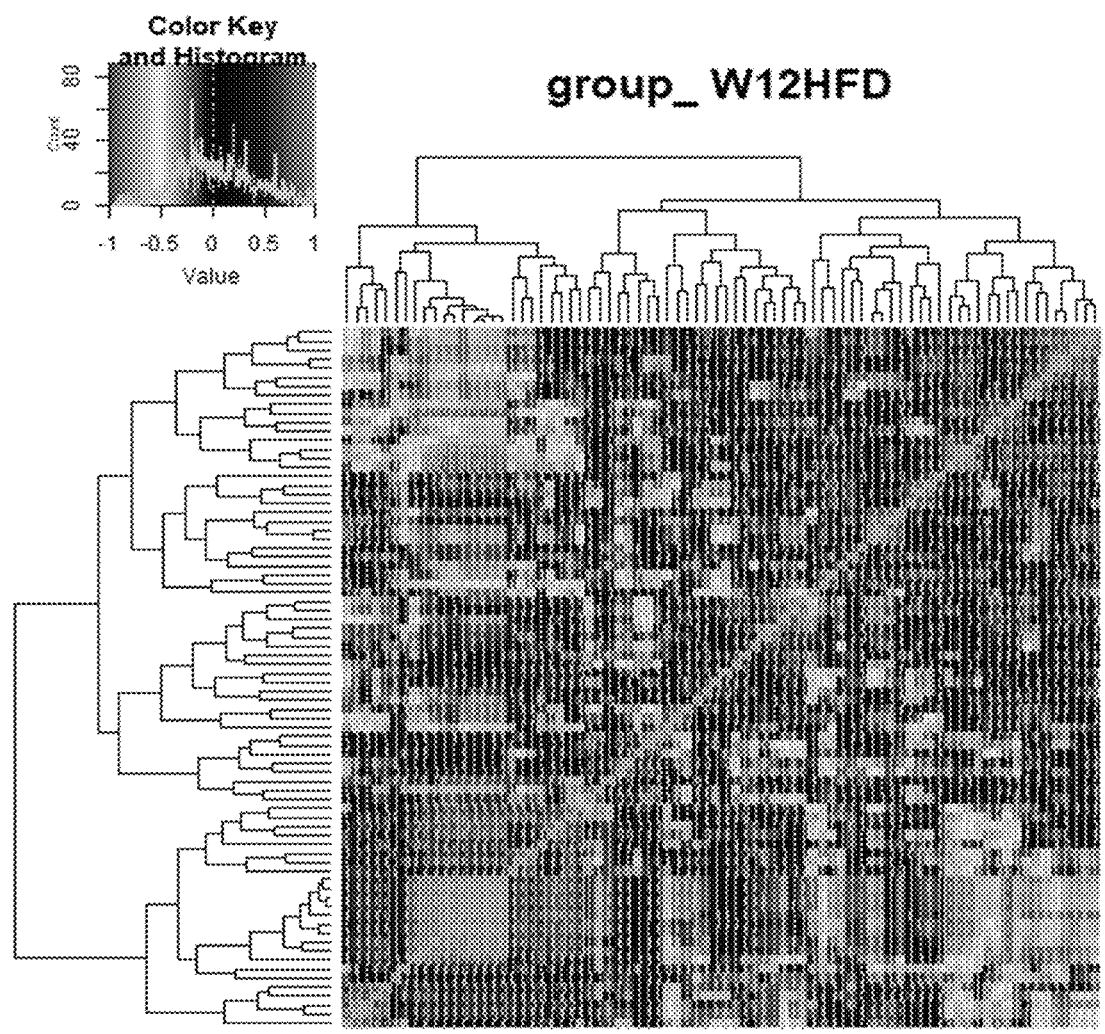
Figure 9B:
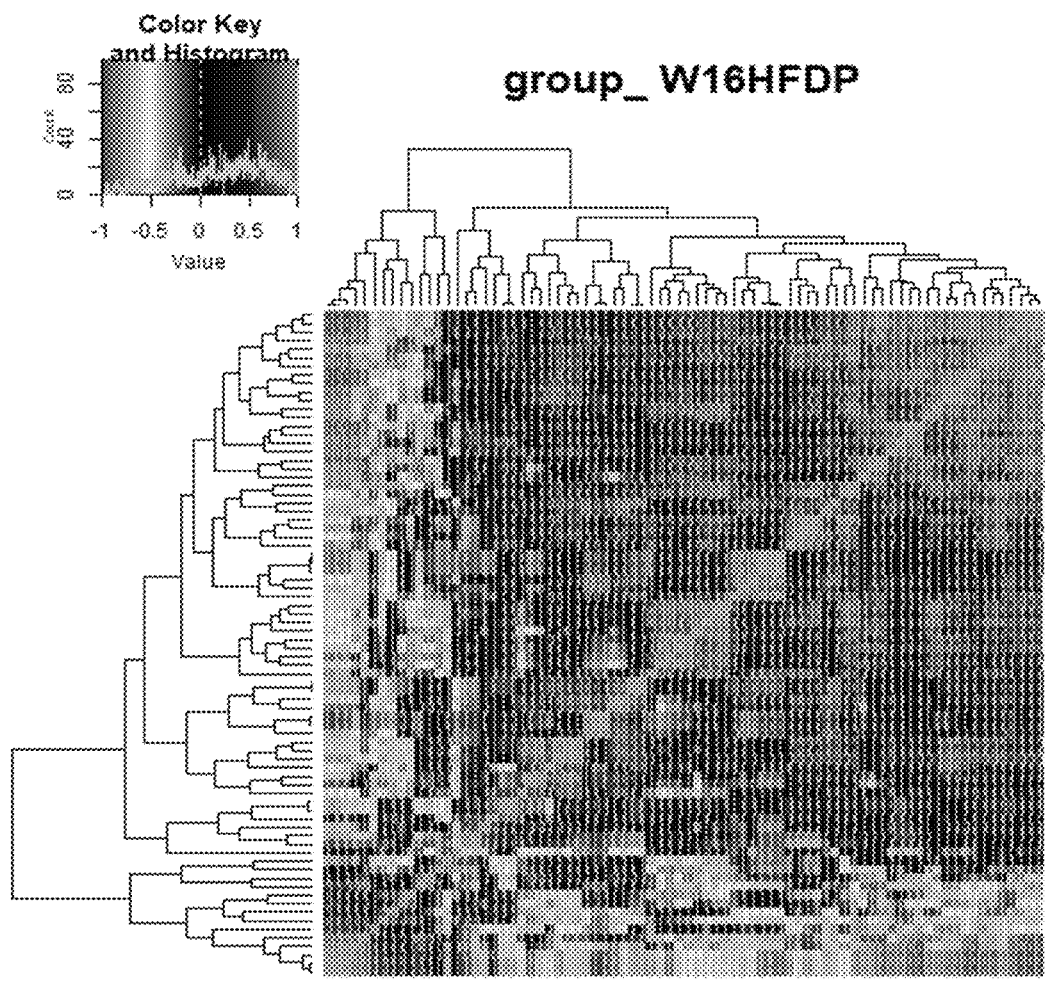
Figure 9B:
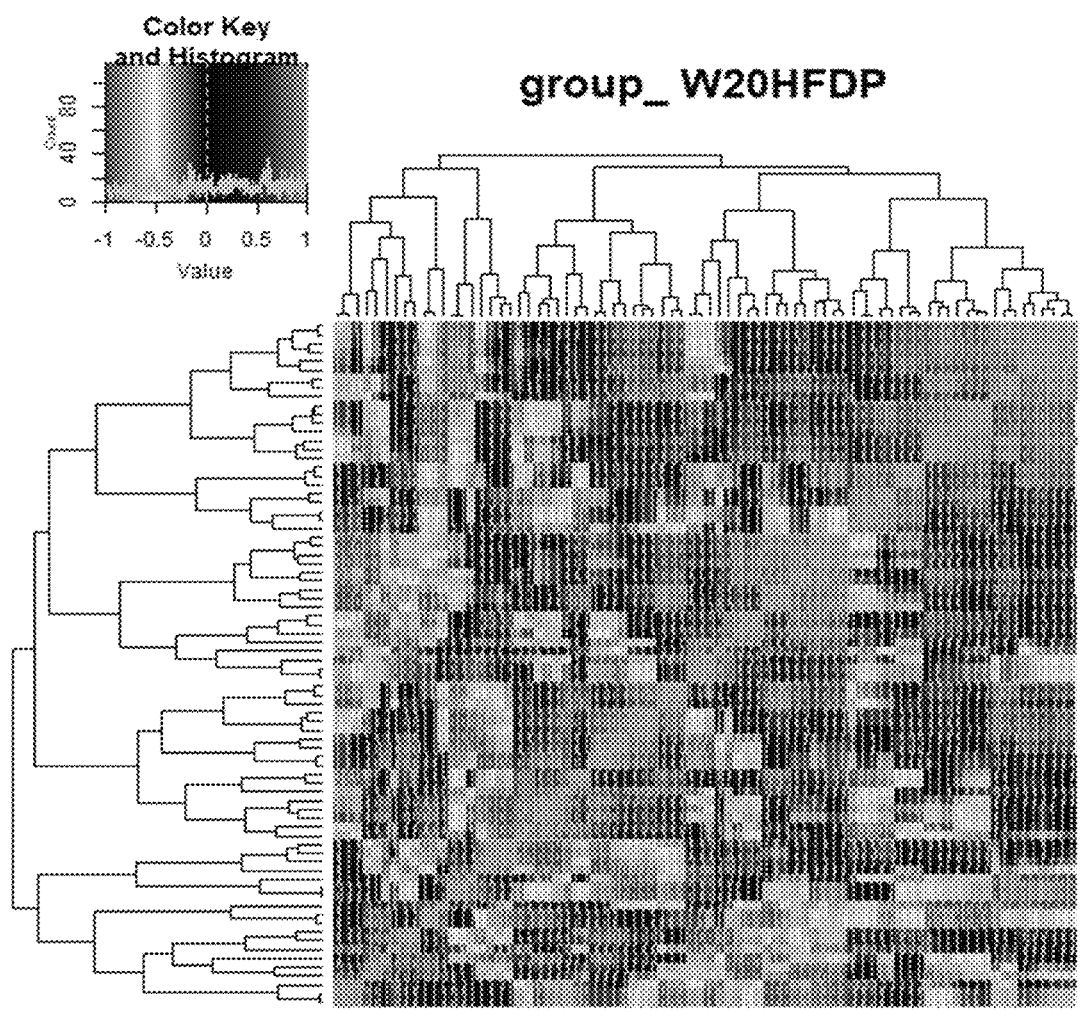
Figure 9B:
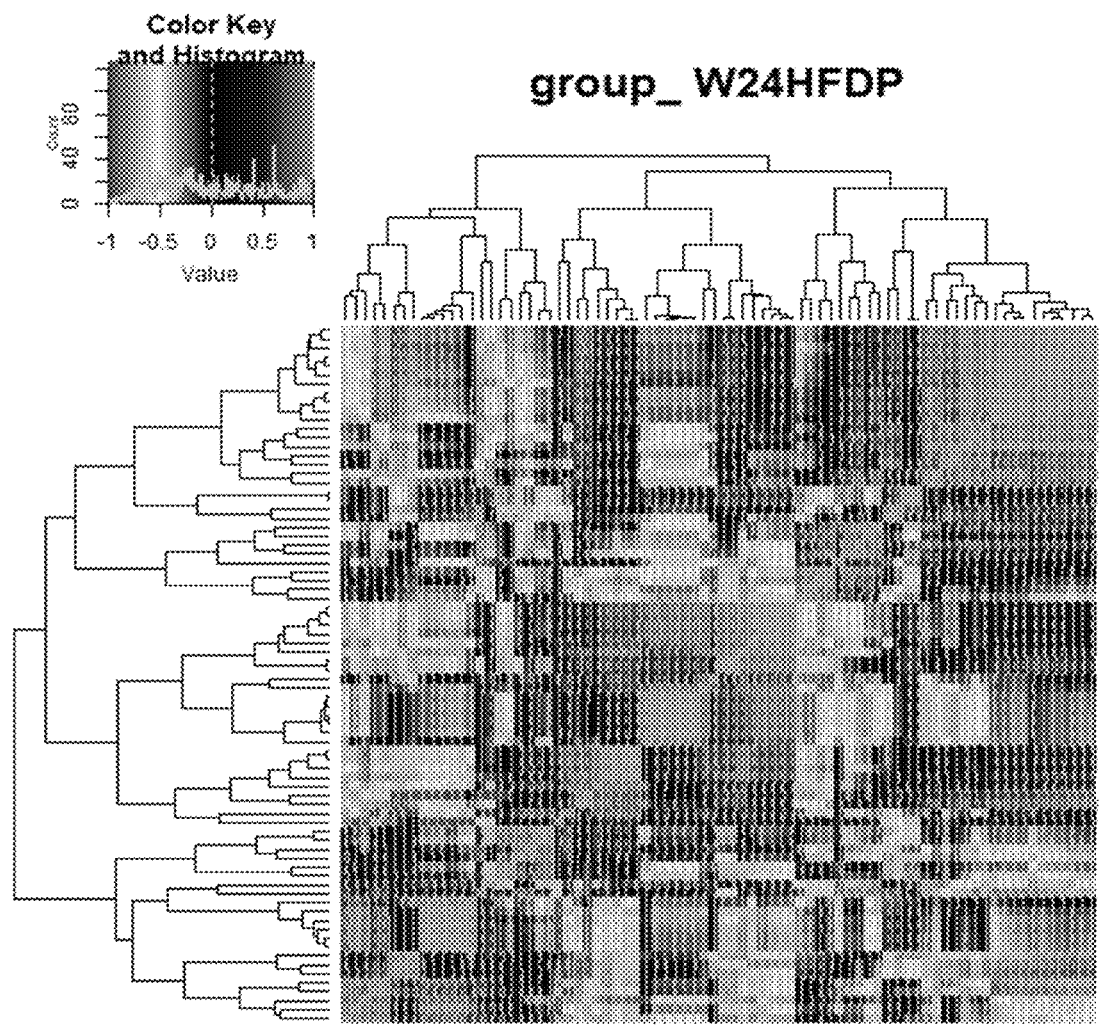
Figure 9C:
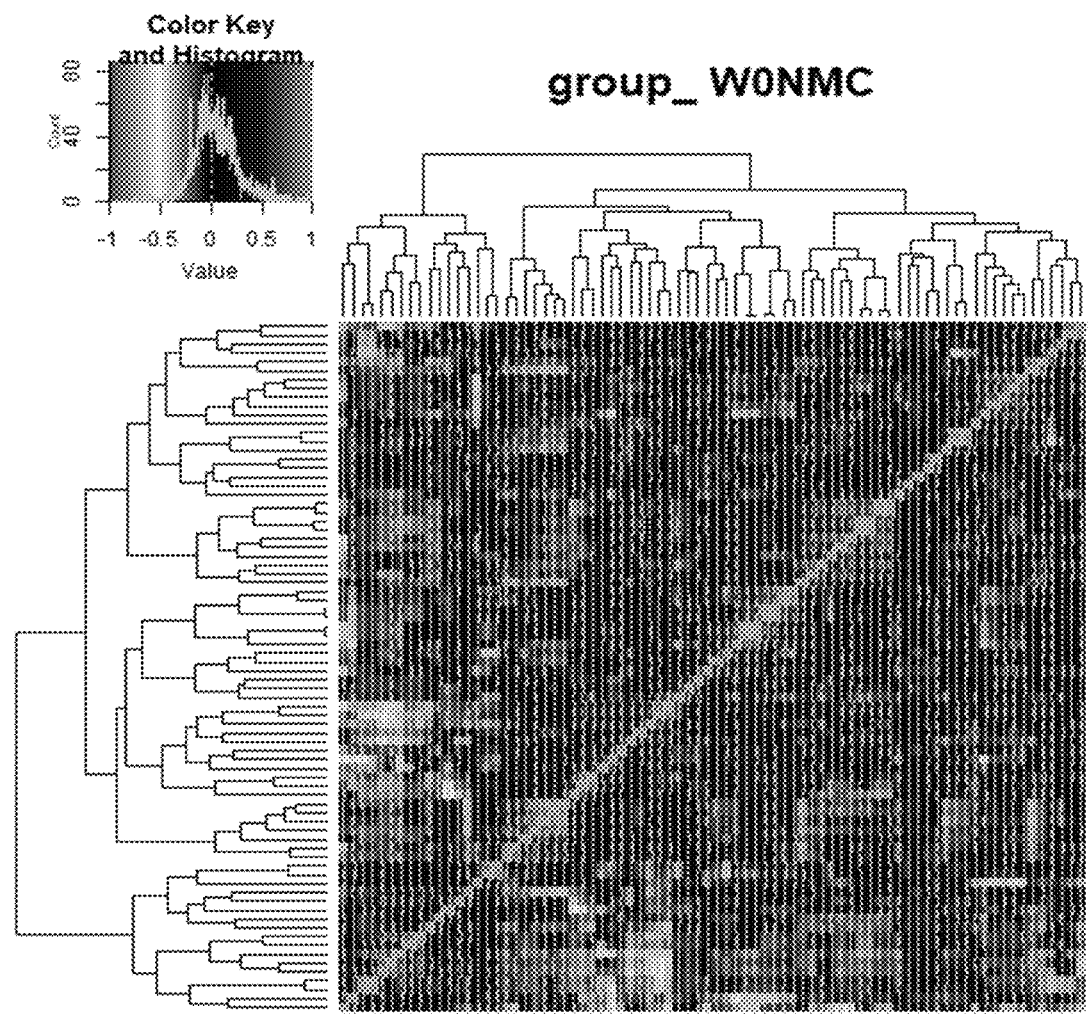
Figure 9C:
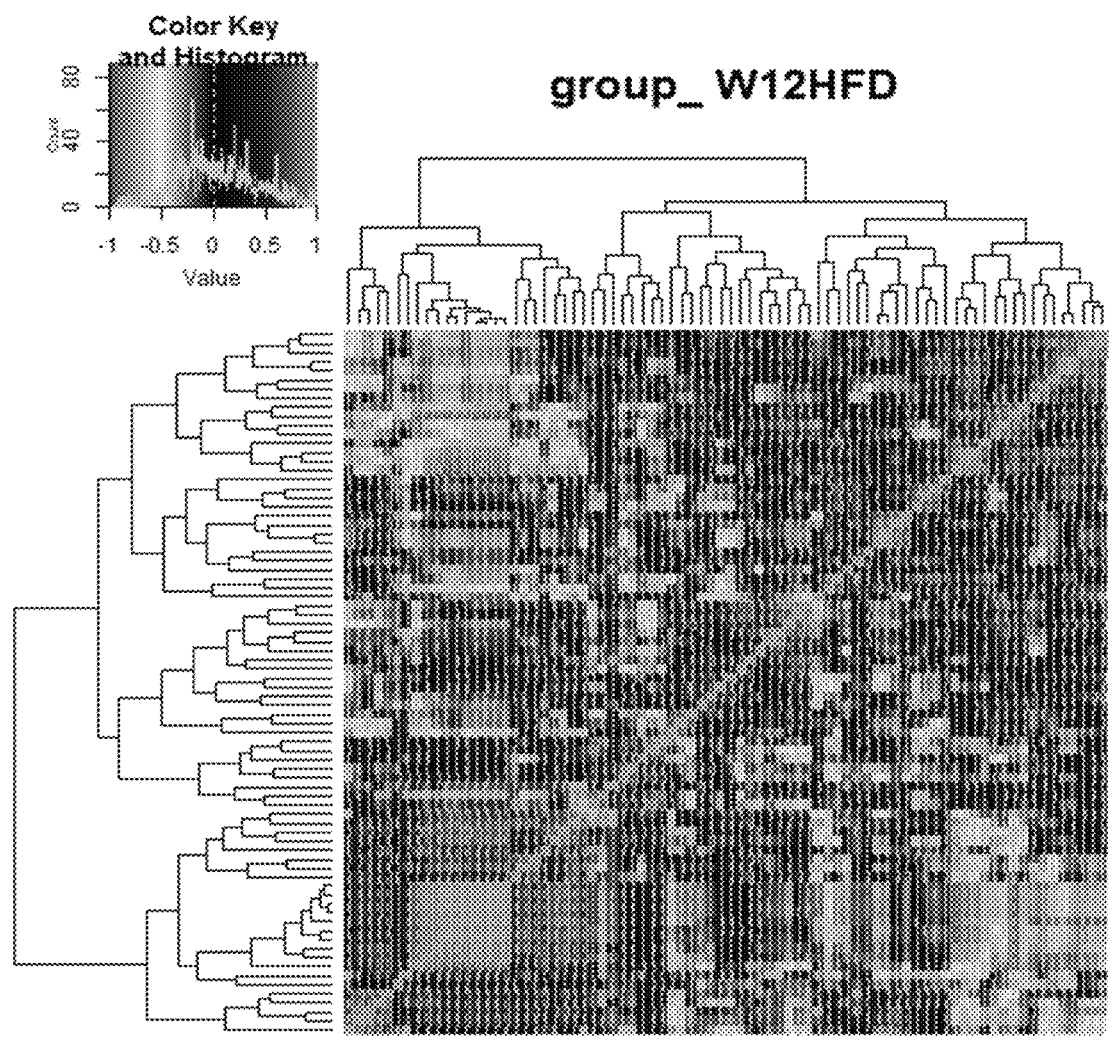
Figure 9C:
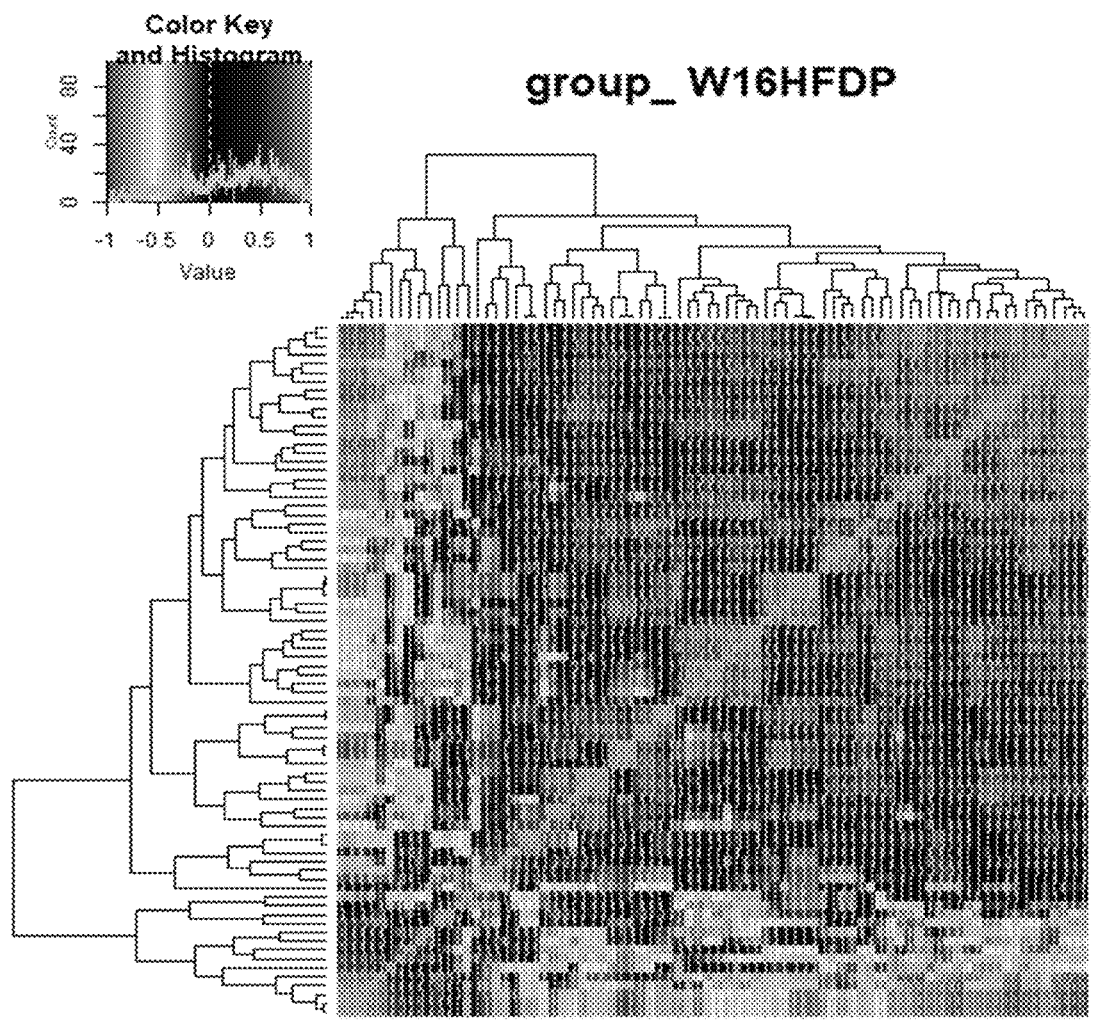
Figure 9C:
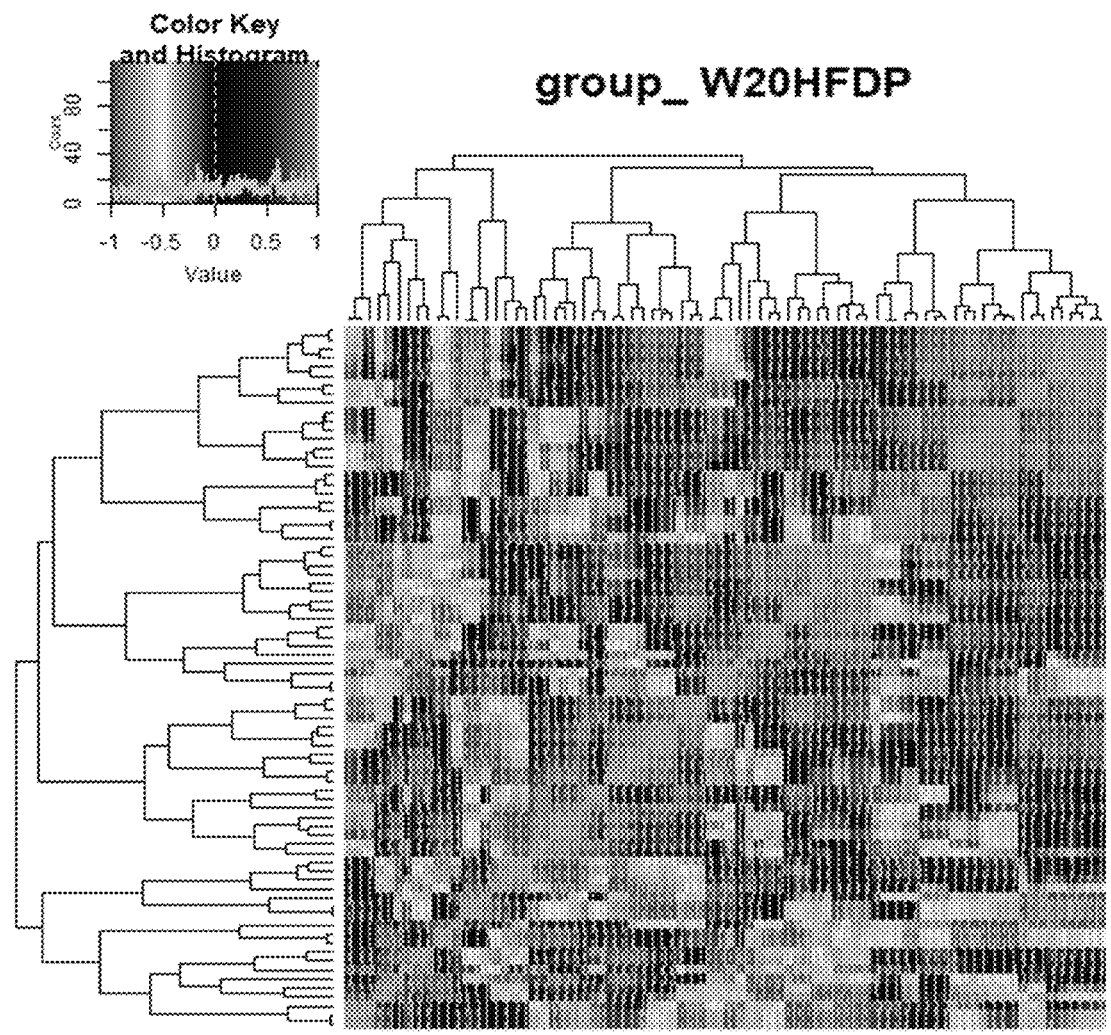
Figure 9C:
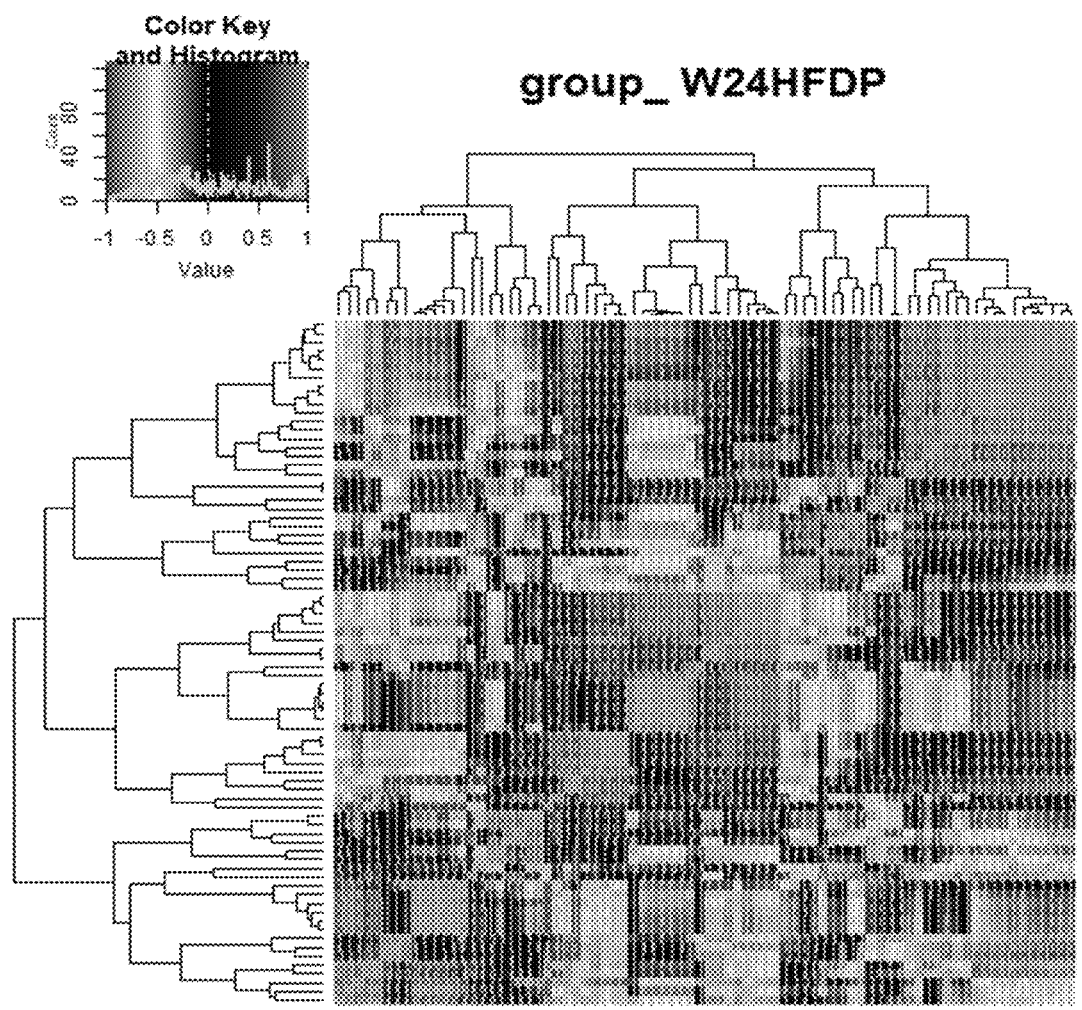
Figure 10A:
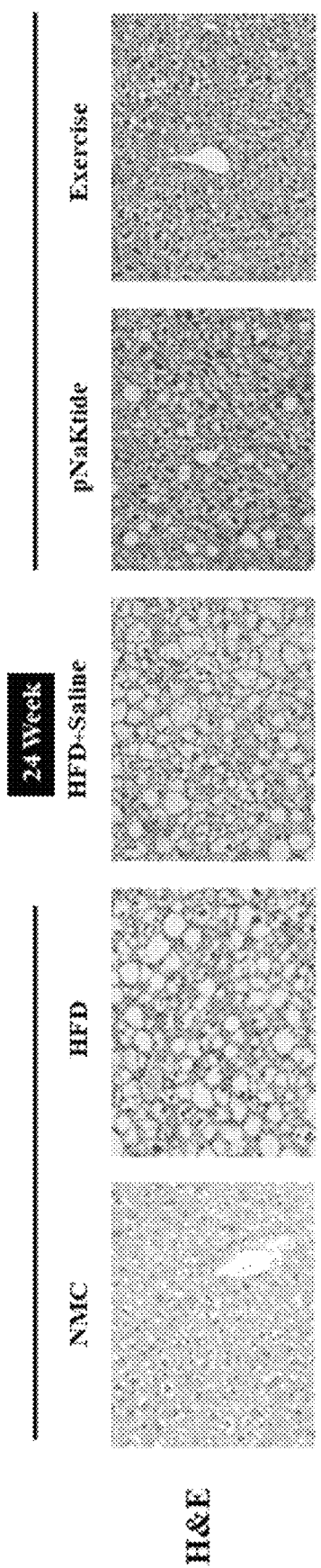
FIGS. 10A-10E include images and graphs showing the NASH Activity Score in the Murine Liver exposed to HFD plus interventions at 24 weeks, where (FIG. 10A) Non-Alcoholic Fatty Liver Disease Activity was evaluated by the NAS Score on hematoxylin/eosin slides (×40 magnification) at 24 W, where (FIG. 10B) there was a significant increase in the macro-vesicular content on liver cells in the HFD groups with a peak at week 24 when compared with NMC and the interventions groups (p<0.05 by $\chi^2$), where (FIG. 10C) nevertheless, and although NMC differed significantly from other groups (p<0.05), the storage of fat in liver cells as micro-vesicles did not have a significant variation when HFD was compared to the intervention groups (p>0.05), where similar results were observed for cell hypertrophy where cell size was significantly higher in animals exposed to HFD vs NMC, bur similar among all HFD exposed groups (in FIG. 10D, p>0.05), where (FIG. 10E) in contrast, the inflammatory component was significantly larger in the HFD groups, where it peaked at week 24 when compared to NMC and intervention groups (p<0.05 by $\chi^2$), and where, interestingly, inflammation in the intervention groups was reduced by week 16 and resolved by week 24 when the inflammatory score was similar to the NMC group.
Figure 10B:
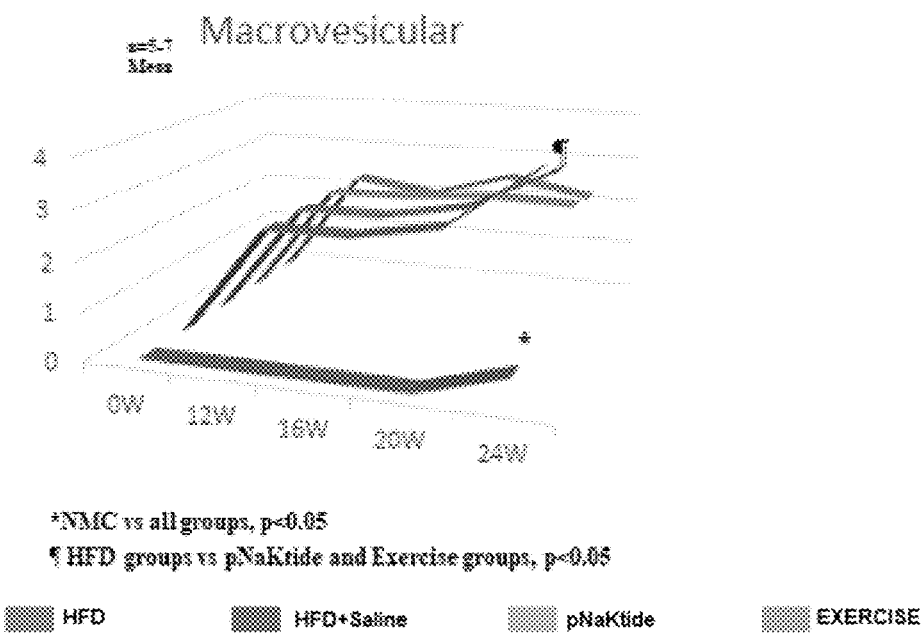
Figure 10C:
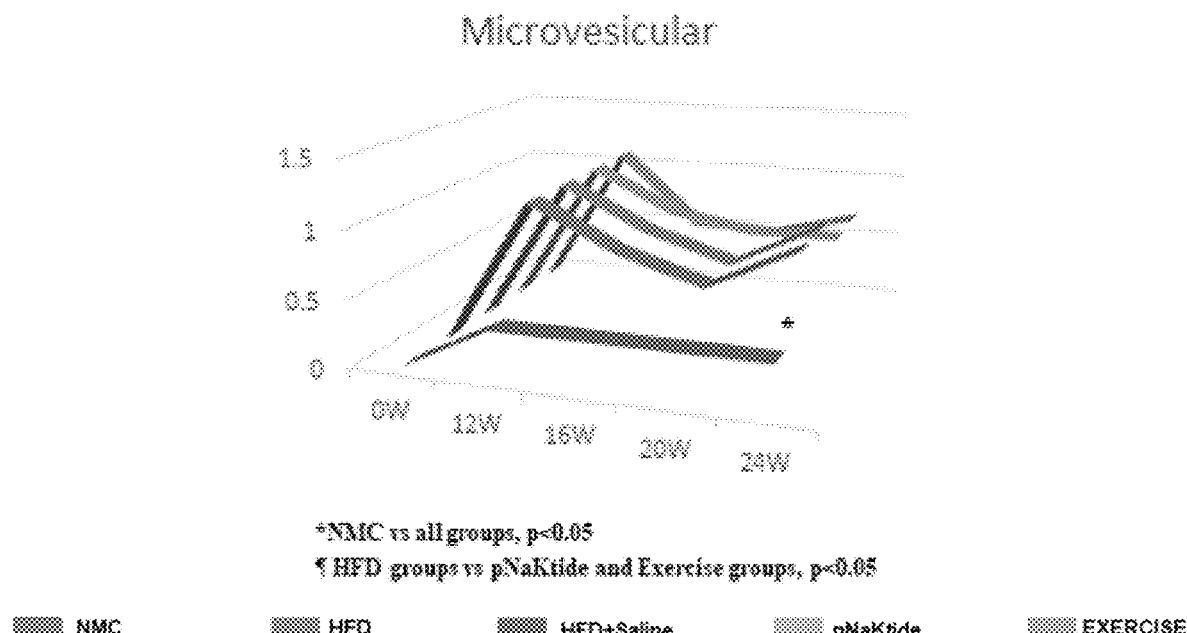
Figure 10D:
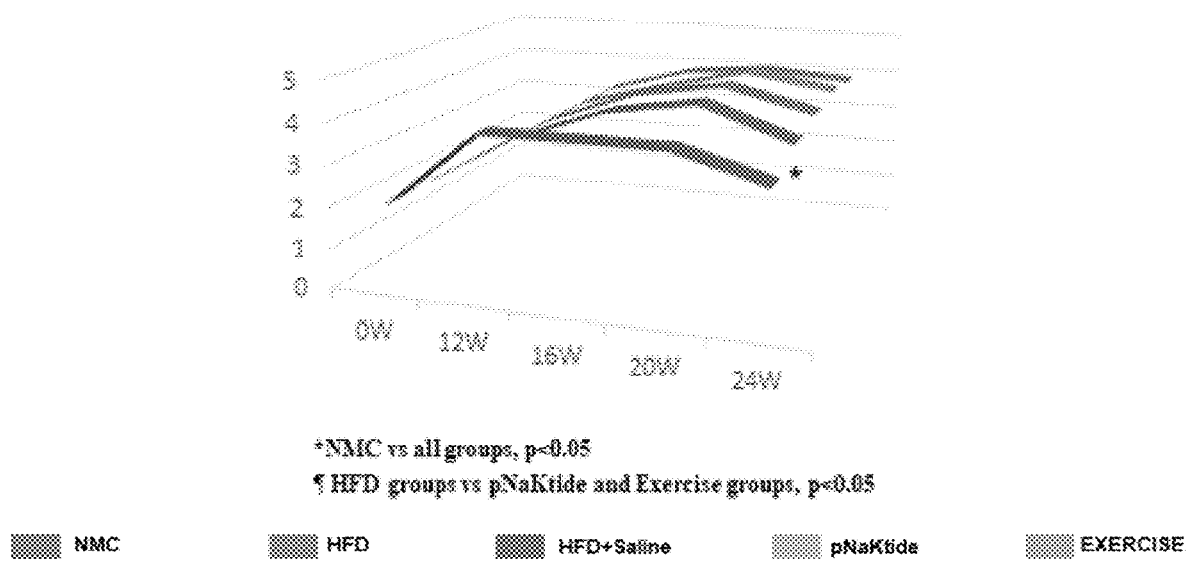
Figure 10E:
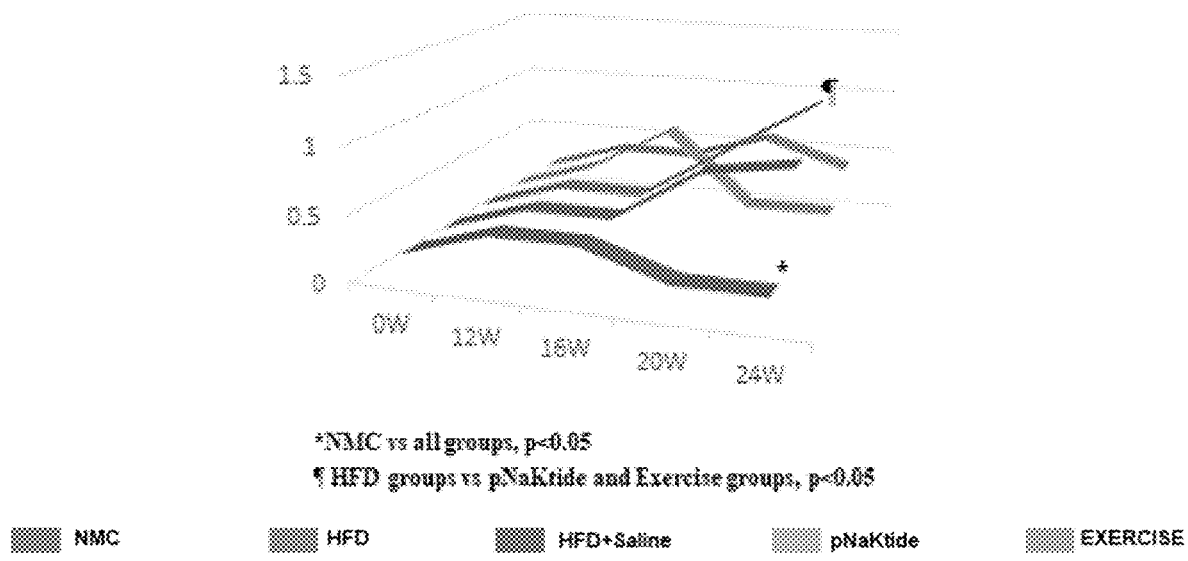

Further cellular stress may induce cell arrest to apoptosis, leading to an amplified local inflammatory response with increasing migration of immune responders. This action, in turn, further enhances the cell aging process, increasing both cell death and the progression to liver fibrosis, completing the loop of a process that results in end-stage liver disease. pNaKtide and exercise were able to influence the metabolism of liver cells with an abrogation of apoptotic activity and paucity of further liver disease progression. SirT7 expression was significantly lower in all HFD groups when compared to NMC at week 16. However, pNaKtide and exercise had no effect on SirT7 expression when compared to HFD, even though home-oxygenase 1 (HO1) was higher in all HFD groups when compared to NMC, and that pNaKtide was present in all treated livers (FIGS. 9A-9B, respectively).

Protein function may be affected by increased ROI through the glutathionylation of their subunits. The causes and consequences of protein glutathionylation at cysteine residues have been enunciated. Although not all proteins are prone or affected by glutathionylation, ATP-ases are affected in its function by 2-7 fold, as we have observed in our studies. In skeletal muscle, it has been shown that basal glutathionylation of the α/β subunits is present, but glutathionylation may affect protein function and is involved in muscle fatigue. Furthermore, cysteine residues 244 and 458-459 control the NKA hydrolytic and signaling functions under hypoxic conditions, and its α-subunit is very sensitive to cell oxi-redox status. It was found that HFD did not affect α1-NKA expression or associated glutathionylation, solely its function. Furthermore, blockage of the α1-NKA active site by pNaKtide normalized both hydrolytic and signaling protein function.

The HFD-induced NASH model in the rodent resembles the clinical manifestations of NASH and the metabolic syndrome observed in humans. Nonetheless, the response to interventions and its pathways may differ significantly. Although the present studies controlled animal variability by gender, age, circadian rhythm, and strict adherence to laboratory protocols, biological variability was unavoidable. The presence of metabolic syndrome has multiple organs as a target, and although plasma metabolites were associated with liver morphology and liver protein expression, the metabolic changes that occurred as a consequence of changes in other organs remain to be determined. The present study was performed under a relatively short time period (24 weeks), and during this time interval, the development of adverse events to pNaKtide were not observed. Nevertheless, the study aimed to evaluate the metabolic disturbances of NASH, correlate them with known morphological changes and assess the effects and mechanism of blocking Src phosphorylation signaling at the α1-subunit of the Na/K-ATPase.

In summary, the diet-induced murine model of NASH develops fatty livers with macro and micro-vesicular steatosis, inflammation, collagen deposition, and liver fibrosis, emulating liver changes of NASH in the human. Related morphological changes were associated with accelerated senescence/apoptotic cell activity induced by a decreased cellular oxi-redox status. Disturbances of the glutathione sp. occurred concomitantly with metabolic prints and gene expression from both uncoupled mitochondrial β-lipid oxidation process and insulin resistance status. Liver cell changes were reestablished through blockage of Src phosphorylation at the α1-subunit of the Na/K-ATPase, implying mechanisms that differ from exercise. Rather than an increase in NKA expression, restitution occurred through the protein-pump activity without changes of protein glutathionylation at the active sequence of the NKA/α1-subunit. Further metabolic changes may promote a switch from cell death to uncontrolled division, paving the introduction of both biological markers of early malignant development and potential preventive/therapeutic strategies.

Example 6—the Role of the Na/K-ATPase-α1-Caveolin-1/SMAC/Survivin Pathway in NASH-Related Hepatocellular Carcinoma (HCC) Genesis It is appreciated that in addition to the regulatory signaling for cell metabolism, the α1-subunit of the Na/K-ATPase (NKA) interacts with the anchoring protein caveolin-1 to provide a pathway for organogenesis during cell development. In addition, it may promote suppression of tumor development through the second mitochondria-derived activator of caspases (SMAC)/Survivin involvement. Furthermore, blockage of such a pathway, by pNaKtide (a newly synthetized 33 aa-peptide that exercises its effects on the α1-subunit of the Na/K-ATPase), inhibited cell replication of tumor cell lines. Without wishing to be bound by any particular theory or mechanism, it was thus believed that uncoupled metabolism (as it occurs in NASH) acts in tandem with an unbalanced NKA α1-caveolin-1/SMAC/Survivin circuit enhancing cell immortality genesis.

Accordingly, experiments were undertaken to investigate the expression and plasma concentration of Caveolin-1, SMAC-Diablo and Survivin proteins in patients with NASH related cirrhosis with/or without HCC in comparison to normal livers or livers with metastases. Experiments were also undertaken to assess the tissue expression and plasma level concentration of Caveolin-1, SMAC-Diablo and Survivin proteins in Murine modals of NASH and HCC; to elucidate if the inhibition of Na/K-ATPase-α1-caveolin-1/SMAC/Survivin pathway by pNaKtide could lead to disease (HCC) prevention or even disease regression; and, to find out if detected proteins may serve as biomarkers for early tumor detection in high risk populations.

Briefly, in these experiments, quantitation of the expression of caveolin-1, SMAC-Diablo and Survivin proteins was performed by confocal microscopy on immuno-stained livers from subjects with normal livers (n=10), patients with NASH (n=20), patients with cirrhosis and HCC from NASH (n=11) and patients with liver metastases (n=12). Additionally, in murine models of both NASH and HCC, quantitation of the expression of SMAC-Diablo protein was performed by confocal microscopy on immunostained livers from diseased mice and mice treated with varying doses of pNaKtide. Plasma levels of referred proteins were also measured by ELISA and significant differences among the various experimental groups were established at $p<0.05$ using ANOVA/t-test.

As shown in FIGS. 14-22B, upon the analysis of the results from these experiments, it was observed that Caveolin-1, SMAC and Survivin proteins expression differed significantly in patients with HCC+ vs NASH+HCC−, when compared to normal livers or livers with metastases. Specifically, the expression of Caveolin-1 was significantly higher in liver tissue from patients with NASH±HCC when compared to normal livers or livers with metastases. Survivin expression was significantly higher in patients with NASH/HCC+ vs NASH/HCC−, normal livers, and liver with metastases. In contrast, SMAC protein expression was significantly lower in liver tissue with NASH or HCC when compared to controls and livers with metastases.

It was also found that Survivin plasma levels had a direct correlation with protein expression on liver tissue. A significant decrease in the expression of SMAC (a proapoptotic protein) was also observed in the murine models of both NASH and HCC, but this effect was reversed by the administration of pNaktide, with the most potent effect obtained at a high dose of pNaktide. Moreover in HCC Murine Models, blockade of NKA α1-caveolin-1/SMAC/Survivin pathway via pNaktide administration significantly reduced tumor burden in treated animals.

Example 7—Tumor-Suppressor Role of the α1-Na/K-ATPase Signalosome at Caveola in NASH Related Hepatocellular Carcinoma Hepatocellular carcinoma is a highly lethal cancer and the most common type of primary malignancy, constituting 90-95% of all hepatic cancers. Non-alcoholic fatty liver disease including its inflammatory form, steatohepatitis (NASH) is one of the manifestations of the metabolic syndrome which has become an overly prevalent condition in the western world, affecting up to 45% of its overweight population. Even though NASH can progress to HCC with or without cirrhosis, the molecular mechanisms that underlie such progression is still unclear. The signaling function of the Na/K-ATPase (NKA), which resides in the liver on its α1-subunit, has previously been reported, including reports on organogenesis during cell development. In exploring further the α1-NA/K-ATPase-Caveolin-1-Src signalosome on its active (pathological) state, Src becomes phosphorylated (Src-p) and activates its downstream kinases including the PI3K-Akt-mTOR and STAT3 pathways, promoting the expression of proteins, such as survivin that drives abnormal cell growth, survival, proliferation, angiogenesis, and metabolism. Survivin, an anti-apoptotic protein regulates cell cycle during the G2/M phase, being essential during embryonic and fetal development but absent in normal adult tissues. In cancer, survivin is highly deregulated being present in all cell cycle phases, mainly at the cytoplasm but shuttling between the cytoplasm and the nucleus via a CRM1/exportin-dependent pathway. Its cytoplasmic pool inhibits apoptosis, while its nuclear pool control mitosis. A third survivin cell pool is mitochondrial, critical in cancer development and progression due to a higher anti-apoptotic effect when compared to the cytosolic pool. Survivin localizes in the mitochondria of malignant cells and its mitochondrial residence represents a gain of function over it physiological roles, driving cancer development and progression by reducing oxidative phosphorylation with greater dependency on glycolysis, changes that evokes the 'Warburg effect'. Additionally, survivin has been shown not only to delay the release of the pro-apoptotic protein Smac/DIABLO (second mitochondria-derived activator of caspases/direct inhibitor of apoptosis-binding protein with low pI, or SMAC) from the mitochondria but to directly block SMAC cytosolic apoptotic activity. Without wishing to be bound by any theory or mechanism, it was believed that in NASH related hepato-carcinogenesis, Src-p at the α1-NKA upregulates survivin with concomitant downregulation of SMAC expressions through the PI3K-Akt-S6K1 signaling pathway favoring a 'switch' of cell faith from programmed death to cell uncontrolled division. It was further believed that blocking the activation of the α1-NKA signalosome could be a target for the treatment of HCC.

Materials and Methods.

In-vitro studies: cell lines and cell culture. Human HCC cell lines (HEP3B and SNU475 from ATCC, Cambridge, Mass.) were checked regularly for *Mycoplasma* contamination using RT-PCR kit while growing in culture with high glucose DMEM media supplemented with 10% FBS and 1% Penicillin/Streptomycin (HEP3), or with RPMI 1640 media supplemented with 10% heat inactivated FBS and 1% Penicillin/Streptomycin (SNU475) in 37° C. humidified incubator in presence of $CO_2$ at 5%. Cells were transiently transfected with siRNA α1-specific polypeptide as previously described, to generate α1-NKA knock down (KND) HCC cell lines and cultured as described.

MTT Cell proliferation assay was performed by plating 5000 cells/well in 6 wells (per condition) of 96 well plates and allowed to adhere for 24 hours, when media was replaced with media±treatment agent for another 24 hours to finally assess cell proliferation according to the manufacturer's instructions (MTT assay, from #ATCC® 30-1010K, Cambridge, Mass.). Digoxin was dissolved in serum free media before addition to cells at designated concentrations.

In-vivo studies: NASH and NASH related HCC rodent models. Seven-week-old female C57BL/6J mice (Jackson Laboratory, Farmington, Conn.) were housed following a 12 h:12 h light-dark cycle under a temperature and humidity-controlled environment. Following acclimation, mice were fed with a standard mouse chow (NMC, Bio-Serv, NJ) or a Western diet consisting of a high-fat diet (HFD, Bio-Serv, NJ, 60% of calories from fat) complemented with 55% fructose-in-water ad libitum for 12 weeks. Mice developed NASH after 12 weeks with no visible tumors. NASH-HCC mouse model (STAM™ mice, Tokyo, Japan) was generated by injecting Streptozotocin (200 µg STZ, Sigma, MO, USA) to neonatal male C57BL/6J mice 2 days after birth, and after 4 weeks of age injected animals were exposed to a high-fat diet (HFD32, CLEA Japan) ad libitum. These mice developed NASH at 12 weeks with the presence of HCC consistently by 16-20 weeks of age.

Experimental Design. After 12 weeks, mice were randomized into control and treatment groups (n=5-6 per group) and the study continued for an additional 12 to 16 weeks as follows: 1) HFD with no treatment, 2) HFD treated with pNaKtide. While the NASH animals were treated at a fixed dose of pNaKtide (25 mg/kg TBW dissolved in 100 µl 0.9% NS, IP once a week), the NASH-HCC rodents were provided with pNaKtide at a low (2 mg/kg TBW×3 a week), or high dose (10 mg/Kg BW×3 a week). All mice continued HFD ad libitum throughout the experiment period that lasted 24 weeks for the NASH and early-stage HCC arm (12 weeks of treatment), or 28 weeks for the for late-stage NASH-HCC (16 weeks of treatment). Animals were sacrificed at the end of the study period for liver and blood procurement. Livers were washed with 0.9% NS at room temperature and sharply divided before being snap-frozen in liquid nitrogen to be stored at −80° C. or fixed at 4° C. (10% formaldehyde). Animal care followed the guidelines of the University IACUC approved protocols.

Human Liver Tissues. Liver tissue samples were obtained during surgical procedures from subjects with normal livers (n=7), patients with NASH (n=17), with NASH related HCC (n=11), and patients with liver metastases (n=10) during a period of 3 years under IRB approved protocols. Routine processing and evaluation of liver tissues was performed by experienced pathologists at our Institution.

Treatment agents. i) pNaKtide. The sequence at the N domain of the α1-subunit of the NKA that interfaces with Src kinase domain was identified to be subsequently synthetized (NaKtide=20 amino acids; SEQ ID NO: 1) and merged with a TAT leader sequence (13 amino acids) establishing cell permeability (pNaKtide; SEQ ID NO: 5). Consistently, pNaKtide blocked the formation of the receptor NKA-Src/GrB2 complex preventing Src phosphorylation but not affecting Src activity regulated by IGF1. The Na/K-ATPase interacts with Src through two binding motifs, namely the CD2 of the al subunit-with-the Src 5E12 domain, and the third cytosolic domain (CD3) of the al subunit-with-the Src $NH_2$ domain. These peptides did not directly affect the ionic pumping function of the NKA or appear to directly interact with the NKA in any way. In fact, NaKtide and pNaKtide appears to function as Src antagonists, mimicking the normal scaffolding function of the NKA. It has been established that the CD3-Src kinase binding keeps Src in its wild type (physiological conditions or inactive) whereas in pathological states as when ouabain binds to the Na/K-ATPase, this binding is broken activating different signaling pathways including ERK cascades, PLC/PKC pathway and mitochondrial production of reactive oxygen intermediates (ROI). ii) Sorafenib is an oral multi-kinase inhibitor approved by the FDA for clinical use in advanced HCC stage. It has been recognized since 2007 as the standard of care for patients with advanced unresectable HCC. Doxorubicin is anthracycline and one of the most commonly used agents in trans-arterial chemo-embolization (TACE) procedure for HCC patients at the intermediate stage. iv) Digoxin is a specific inhibitor of Na/K-ATPase through the al subunit, and it is the only FDA-approved cardiac glycoside for the treatment of mild or moderate heart failure patients with reduced ejection fraction. iv) PP2 is a selective potent inhibitor of Src family kinases. It inhibits Lck and FynT but only weakly inhibit ZAP-70 and JZK2. v) AG490 is a selective inhibitor of the Janus kinase 2 (JAK2) which is a signal transducer and activator of transcription 3 (STAT3) signaling pathway. vi) Wortmannin is a potent and selective inhibitor of PI3K protein with anti-inflammatory and immunosuppressant effects in vivo.

Liver apoptotic activity assessment. Apoptotic activity was assessed by the TUNEL (terminal deoxynucleotidyl transferase (TdT)-mediated dUTP nick end labeling) method for liver tissue and Cell lines (Click-iT #C10617, Thermo Fisher Scientific, MA) following the manufacturer's instructions. While cell line images were taken at 10× magnification, animal liver tissue images were taken at 40× magnification on label-blinded slides (random 5 regions per slide/liver) using a confocal microscope (Leica TCS SP5 II) to count positive cells/total cells and expressed as % of apoptotic cells to be processed using ImageJ software (NIH, Bethesda, Md.) and GraphPad prism 9.0.1 (licensed to the University).

Liver Collagen Deposition (Fibrosis). Liver fibrosis was assessed by Masson's Trichrome staining using a standard protocol. Five images of stained liver slides taken at ×40 magnification with Leica confocal fixed stage microscope (LEICA DM6000 CFS) for each animal/group were graded for fibrosis as follows: grade 0, normal liver (no fibrosis), grade 1, an increase in collagen matrix accumulation without the formation of septa; grade 2, formation of incomplete septa from the portal tract to the central vein (septa that do not interconnect with each other); grade 3, complete but thin septa interconnecting with each other to divide the parenchyma into separate fragments; grade 4, presence of thick interconnecting septa (complete cirrhosis). The fibrotic scores were recorded into excel spreadsheet for data quantitation and analyzed using GraphPad prism 9.0.1.

Tumor Burden in Mouse Liver. H&E-stained liver slides per each animal/group were taken and stitched at low magnification to obtain the whole cut liver slide view, and pixel intensities assigned to specific channel for tumor vs. non-tumor areas (AUC) assessment using ImageJ 1.53c Fiji software (http://imagej.nih.gov.ij). Pixel-color attributes on intensity-area was transferred into an excel sheet to be analyzed by GraphPad prism 9.0.1 methodology.

Confocal microscopy assessment on Immuno-stained cells/liver tissue. For in vitro studies, immunocytochemistry was performed on both human HCC cell lines as previously described. Briefly, the treated for 4 hours cells and the untreated cells were plated on glass coverslips and allowed to reach 70% confluency. For α1-subunit and pSrc staining, cells were fixed (adding ice-cold methanol-10 min), permeabilized (0.05% Triton X-100) and then incubated with a monoclonal (α1-NKA, Millipore Cat #05-369) or polyclonal antibody (to Tyr419 of Src kinase, Invitrogen Cat #44-660G) overnight. Next day, slides were incubated with secondary antibodies (Alexa Fluor 488 or 549) and mounted with Vectashield mounting media on slides containing DAPI (Vector Laboratories, Inc., H-1800). For Survivin/SMAC staining, cells were permeabilized and fixed using 4% Paraformaldehyde/0.05% Triton X-100, stained with polyclonal Survivin/SMAC antibodies (ab 469/ab 8115, Abcam, Cambridge, Mass., respectively), and then processed at 63× mag. as described.

For in vivo and human studies, immunohistochemical staining was performed on formalin-fixed and paraffin-embedded liver tissue sections after deparaffinization and rehydration using xylene and graded ethanol exposure. In brief, the tissues were subjected to antigen retrieval with 0.01M citrate buffer (pH 6.0) and permeabilized with 0.1% Triton-X100 in PBS (PBS-T, Sigma, MI). Endogenous peroxidase activity and non-specific binding was blocked with $H_2O_2$ and protein blocks respectively (kit-ab236469, Abcam, Cambridge, Mass.). Sections were incubated overnight at 4° C. with specific primary antibodies for survivin/SMAC (ab 469/ab 8115, Abcam, Cambridge, Mass., respectively). After overnight incubation, sections were washed, incubated at RT° in the HRP-Conjugate (kit-ab236469, Abcam, Cambridge, Mass.) and visualized with DAB (3, 3'-diaminobenzidine tetrahydrochloride, Sigma, MI). Sections were then washed, counterstained with hematoxylin, and dehydrated to be cover-slipped using VectaMount Permanent Mounting Medium (H-5000 Vector Laboratories, Inc. Burlingame, Calif.). For caveolin-1, sections were washed (PBS, pH 7.4), blocked at RT° for 2 h (10% normal goat serum plus 1% BSA in PBS), and incubated overnight at 4° C. with primary antibody (ab 2910, Abcam, Cambridge, Mass.). Sections were then washed with PBS-T and incubated in a fluorophore-conjugated secondary antibody (ab150080-Alexa fluor594, Abcam, Cambridge, Mass.) diluted in 1% BSA-PBS for 1 hour. The sections were then rinsed to be cover-slipped with Vectashield Vibrance Antifade Mounting Medium with DAPI (H-1800, Vector Laboratories, Inc., Cambridge, Mass.). Images were taken at 40× mag. under similar light intensity and exposure time conditions.

Evaluation of Tissue expression of Survivin, SMAC and Cav-1. Survivin expression in the cytoplasm and SMAC staining were quantified by two independent researchers via the use of a described semi-quantitative technique which takes into consideration the intensity of positive staining and percentage of positive cells. The color intensity of survivin and SMAC immunostaining was scored as follows: cell-free coloring (no staining)=0; light yellow (weak staining)=1; buffer (moderate staining)=2 and brown (strong staining)=3. The percentage of positive cells was rated as follows: 0=<5%; 1=5-25%; 2=25-50%; 3=50-75% and 4>75%. Scores for percentage of positive cells and scores for immunostaining intensities were multiplied to give an immunoreactive score (IRS). Caveolin-1 expression in tissue sections was analyzed using ImageJ software (NIH, Bethesda, Md.). The integrated density of the immunostaining of caveolin-1 in the tissues was evaluated after subtraction of background fluorescence for each reading.

Western Blotting. After indicated treatment, cells lysates from ice-cold PBS washed cells exposed to RIPA buffer (pH=7.4) were cleared by centrifugation (14,000 rpm/15 min./4° C.), and supernatants were separated by SDS-PAGE gel to be transferred to Protran nitrocellulose membranes (Thermo Fisher Scientific, Waltham, Mass.). Blocked membranes were incubated with the specific primary/secondary antibodies for protein signals to be detected by the Pierce ECL kit (Thermo Fisher Scientific, Waltham, Mass.), and quantified using ImageJ software.

TUNEL assay. Liver tissue sections were processed for the TUNEL assay using the terminal deoxynucleotidyl transferase (TdT)-mediated dUTP nick end labeling Apoptotic kit (Click-iT #C10617, Thermo Fisher Scientific, MA) according to the manufacturer's instruction. Sections were deparaffinized, fixed in 4% paraformaldehyde at 37° C., equilibrated in PBS, permeabilized with proteinase K solution, post-fixed in 4% paraformaldehyde at 37° C. and incubated in TdT reaction mixture for 60 minutes at 37° C. Slides were then washed with 3% BSA and 0.1% Triton™ X-100 in PBS for 5 minutes and incubated in the TUNEL reaction cocktail for 30 minutes at 37° C. in the dark, and cover slipped with Vectashield mounting medium with DAPI. Images of apoptotic cells (green) and cell nuclei (blue) were taken using a confocal microscope (Leica TCS SP5 II). For the cells, the same procedure was followed after fixation with 4% paraformaldehyde and permeabilization with 0.25% Triton™ X-100 in PBS.

Immunohistochemistry. Formalin-fixed and paraffin-embedded liver tissue sections (4 µm thick) from each group of patients, normal subjects and mice were deparaffinized using xylene and rehydrated by transfer through graded ethanol concentrations. Thereafter antigen retrieval was performed in 0.01 M citrate buffer (pH 6.0) at 96-97° C. for 20 minutes. Sections were then washed with PBS containing 0.1% Triton-X100 (pH 7.4) (PBST) and endogenous peroxidase activity was blocked by incubating the sections in the Hydrogen Peroxide Block (from abcam kit-ab236469) for 10 min. After washing the sections in PBST, blocking of non-specific antibody binding was achieved by incubating the sections in the Protein Block (from abcam kit-ab236469) for 10 mins at room temperature. The sections were then washed and incubated overnight at 4° C. with primary antibodies (Rabbit polyclonal anti-SMAC/Diablo Abcam, ab8115, 1:200 and Rabbit polyclonal anti-Survivin, Abcam, ab 469, 1:500) diluted in PBS-T+10% (NGS)+1% BSA. Negative control slides were incubated without the primary antibody. After overnight incubation, sections were washed in PBST and incubated in the HRP-Conjugate (from abcam kit-ab236469) for 15 mins at room temperature. After washing with PBST, peroxidase reaction was visualized by incubating with DAB (3, 3'-diaminobenzidine tetrahydrochloride) (from abcam kit-ab2364690). Sections were then washed 4 times in PBST, rinsed in tap water, counterstained with hematoxylin (Hematoxylin QS, Vector Laboratories, Inc., H-3404), dehydrated through graded series of ethanol and xylene and coverslipped using VectaMount Permanent Mounting Medium (Vector Laboratories, Inc., H-5000). Finally, the sections were observed under Leica confocal fixed stage microscope (LEICA DM6000 CFS) and images taken at 20× and 40× magnification with the same light intensity and exposure time. 40× magnification images were used for analysis. For Caveolin-1, immunofluorescent staining was carried out on the liver tissue sections after deparaffinization, rehydration and antigen retrieval as earlier described. Thereafter sections were washed with PBS (pH 7.4) and blocked with 10% normal goat serum plus 1% BSA in PBS for 2 h at room temperature and incubated overnight at 4° C. with primary antibody (Anti-Caveolin-1 antibody, Abcam, ab2910, 1:200). After overnight incubation, sections were washed with PBS-T and incubated in a fluorophore-conjugated secondary antibody (Alexa fluor594, Abcam, ab150080, 1:500) diluted in PBS with 1% BSA for 1 hour. The sections were then rinsed and coverslipped with Vectashield Vibrance Antifade Mounting Medium with DAPI (Vector Laboratories, Inc., H-1800). Finally, sections were examined under Leica confocal laser scanning microscope (Leica TCS SP5 II), and images taken at 40× magnification with the same light intensity and exposure time were used for analysis.

Statistical Analysis Results are shown as box-whisker plots. Data are presented as median (central line), first and third quartiles (bottom and top of boxes, respectively), and whiskers (extreme values) from independent biological experiments. Differences among groups were determined by analyses of variance (ANOVA), Turkey's Post hoc test and t-test using GraphPad Prism version 9.0.1 (GraphPad, San Diego, Calif.). The likelihood of less than 1/20 chance was considered statistically significant. Statistical tests, sample size and p-value are provided in the figure's legends.

Results.

Figure 23A:
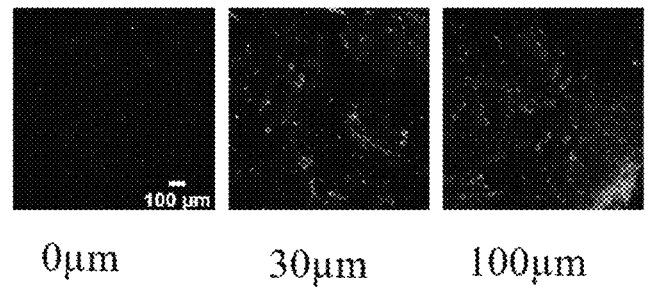
FIGS. 23A-23F include images and graphs showing the effect of Src-p inhibition at the α1-NKA on apoptosis and proteins expression in two human HCC cell lines, where (FIG. 23A) apoptotic activity was significantly increased on treated with pNaKtide Human HCC cell lines in a dose dependent manner (positive cells by TUNEL and quantitated as box-whisker plots, n=4 for each group. p<0.01, by ANOVA and Turkey's Post hoc test), where (FIG. 23B) mitotic catastrophe on human HCC cell lines from Src-p inhibition. (notice the presence of multiple micronuclei and aneuploidy in the treated cells (arrows) compared to the untreated group, (FIG. 23C) cell proliferation effect of pNaKtide (IC50 for Hep3=62.5 μM and for SNU475 cells=6 μM) on Human HCC cell lines as compared to sorafenib and doxorubicin (n=5), (FIG. 23D) time course α1-subunit expression (0 to 24 hours) of two human HCC cell lines exposed to IC50 pNaKtide (n=5 for each group, p<0.01, by ANOVA and Turkey's Post hoc test), (FIG. 23E) confocal microscopy images on the effect of pNaKtide on Src-p expression quantitated on a 24 hour time course by western blotting in two human HCC cell lines (results are shown as box-whisker plots (central line, median; box limits, $25^{th}$ and $75^{th}$ percentiles, whiskers, minimum and maximum values; actual values superimposed in black) showing a fold change in each protein relative to 0 hour (n=5 for each group, p<0.01 by ANOVA and Turkey's Post hoc test)), (FIG. 23F) in survivin and SMAC proteins expression in two treated vs non-treated with IC50 pNaKtide human HCC cell lines on a 24 hour time course, there was a significantly progressive decrease in survivin with concomitant significantly increase in SMAC over time (n=5 for each group, p<0.01 by ANOVA and Turkey's Post hoc test), and where effects were faster in case of Survivin (significantly decreased for Hep3 at 2 h and for SNU475 cells at 30 min) when compared to SMAC expression (significantly increased for Hep3 at 20 h and for SNU475 cells at 16 h).
Figure 23A:
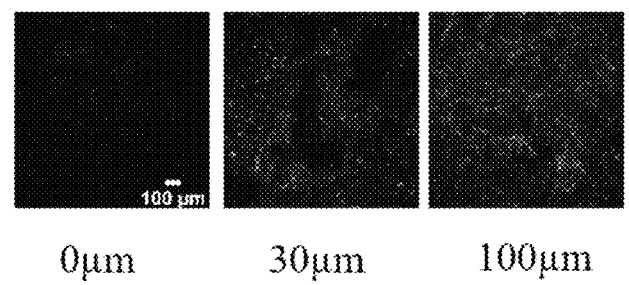
Figure 23A:
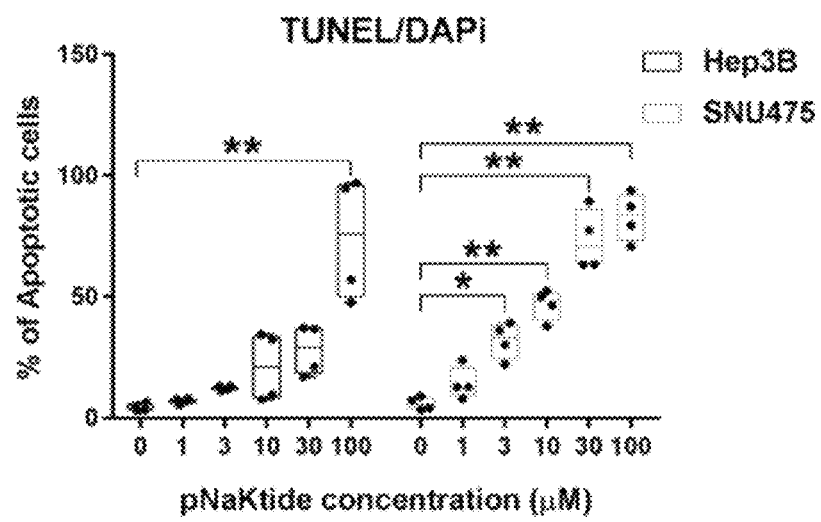
Figure 23B:
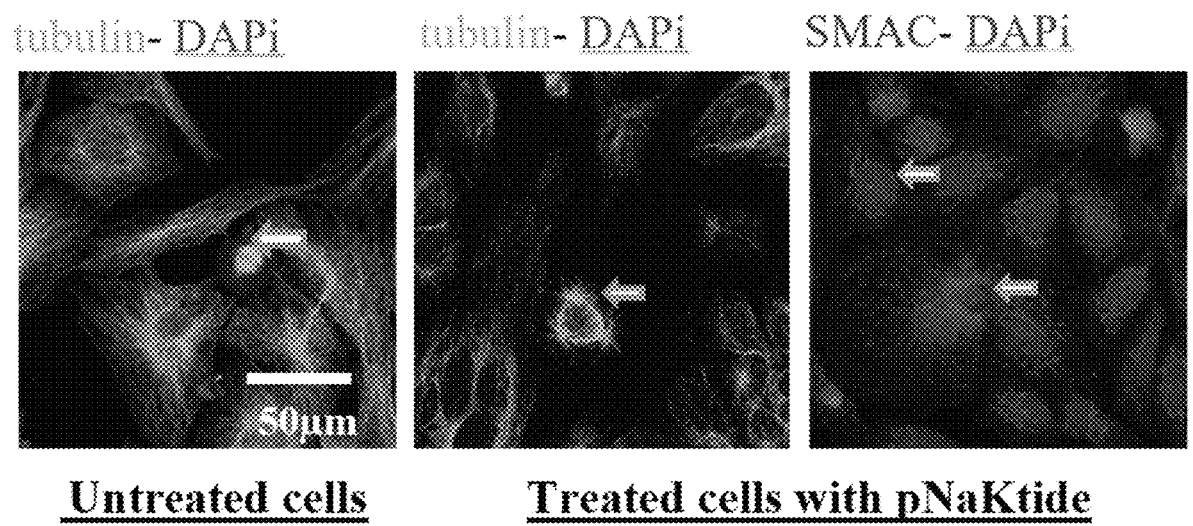
Figure 23C:
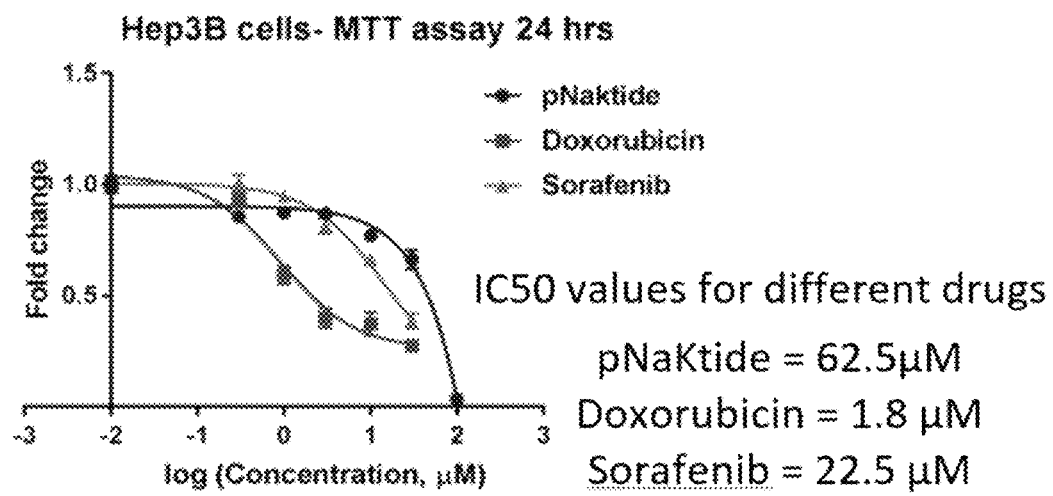
Figure 23C:
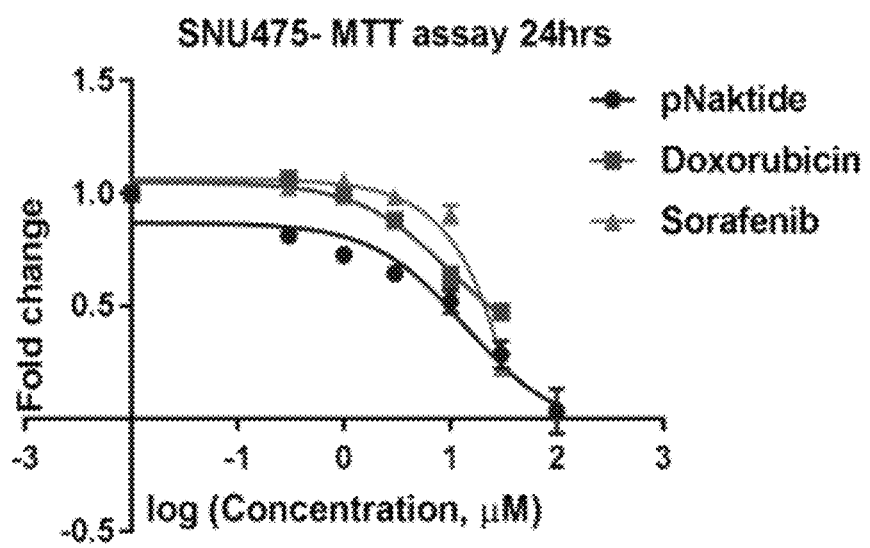

Effect of Src-phosphorylation (Src-p) inhibition at the α1-NA/K-ATPase (α1-NKA) on apoptosis in two human HCC cell lines. In vitro, Src-p inhibition by pNaKtide significantly induced a dose dependent increase on apoptotic activity in two human HCC cell lines when compared to the untreated cells by TUNEL assay (FIG. 23A). In addition to the intrinsic apoptotic pathway in the treated cells, pNaKtide also drove cell death via the process of mitotic catastrophe (FIG. 23B). Mitotic catastrophe is a type of cell death that might be induced by substances that cause deregulation of mitosis disturbing mitotic spindle formation and cell division. Morphologically, as seen in FIG. 23B, it results in the formation of large cells with multiple micronuclei and decondensed chromatin. These findings confirmed that malignant cell growth was arrested when exposed to pNaKtide. Furthermore, cell proliferation (MTT assay) on two human HCC cell lines exposed to IC50 pNaKtide were comparable to known HCC chemo-active FDA approved for clinical use agents (sorafenib and doxorubicin, FIG. 23C).

Figure 23D:
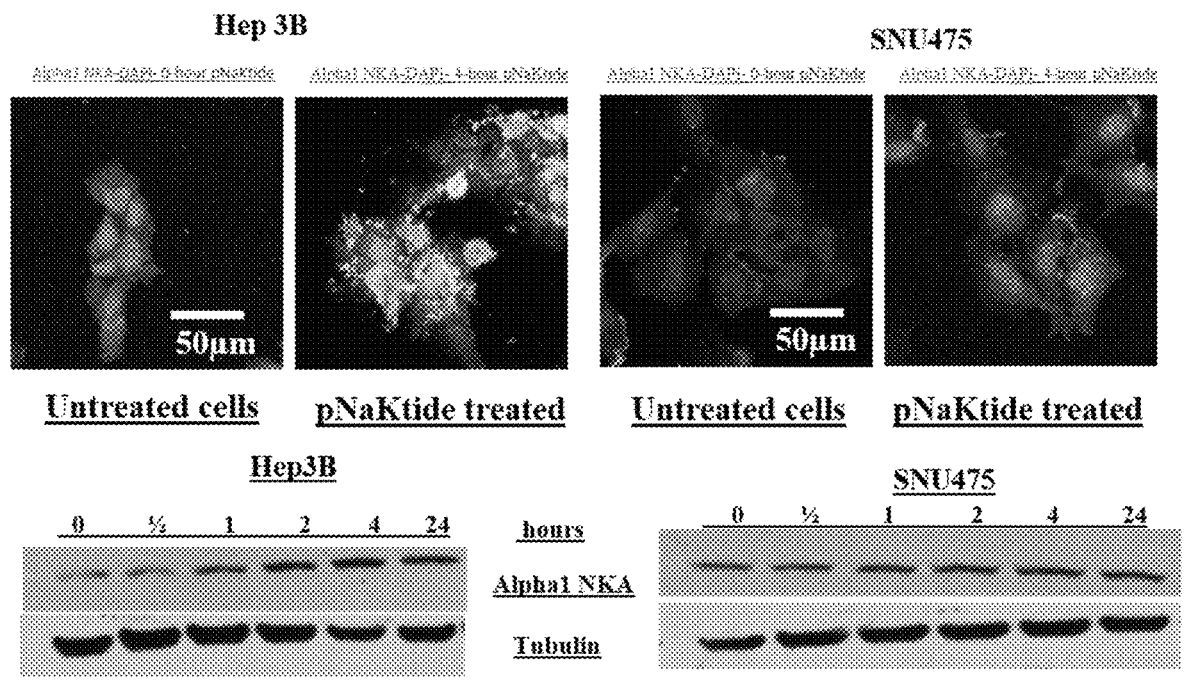
Figure 23D:
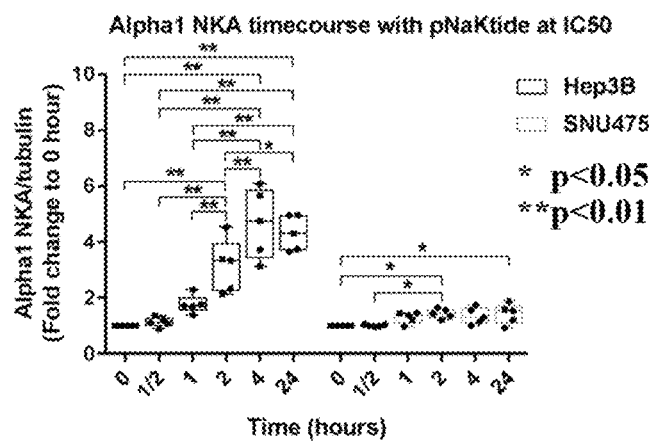
Figure 23E:
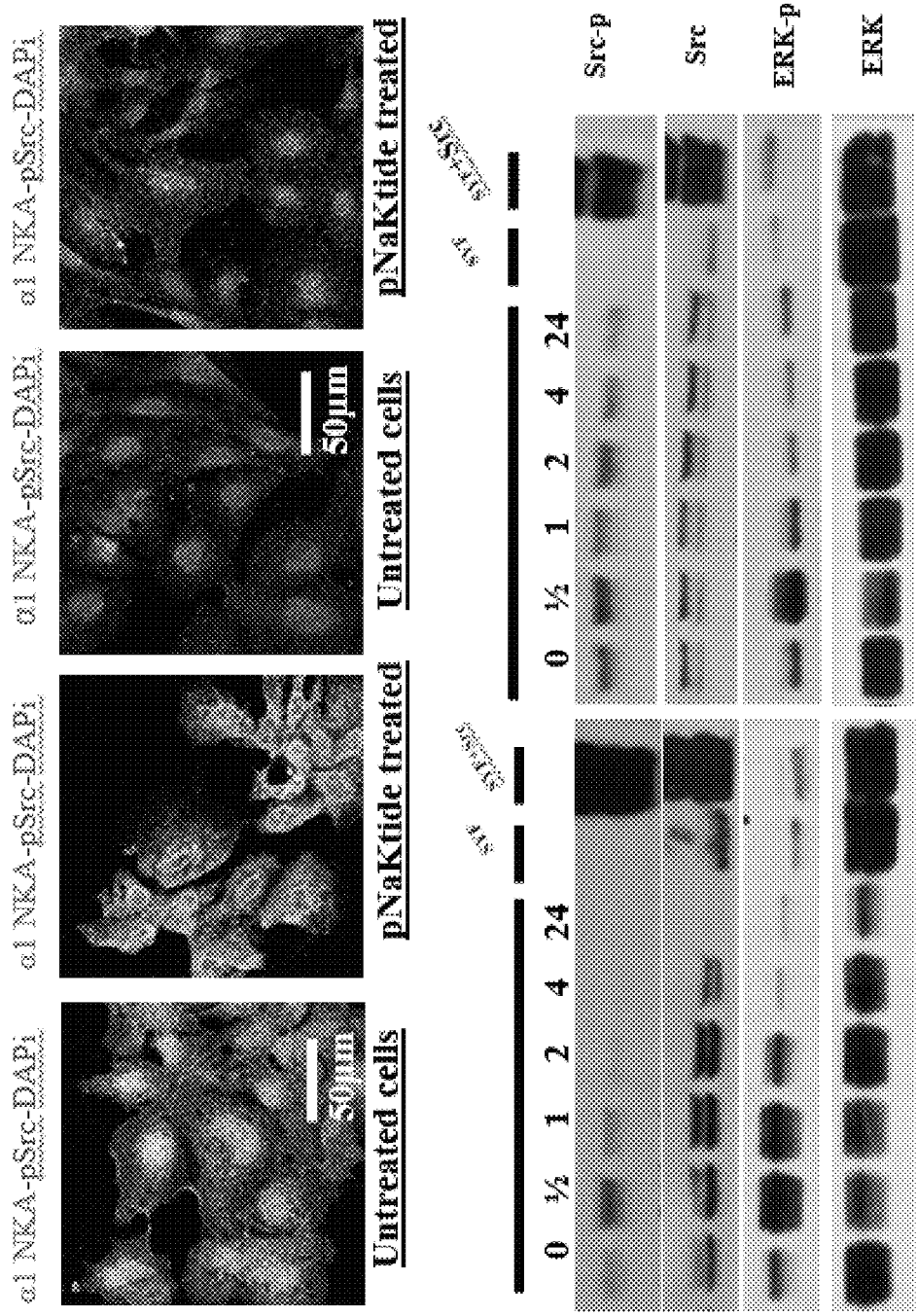
Figure 23E:
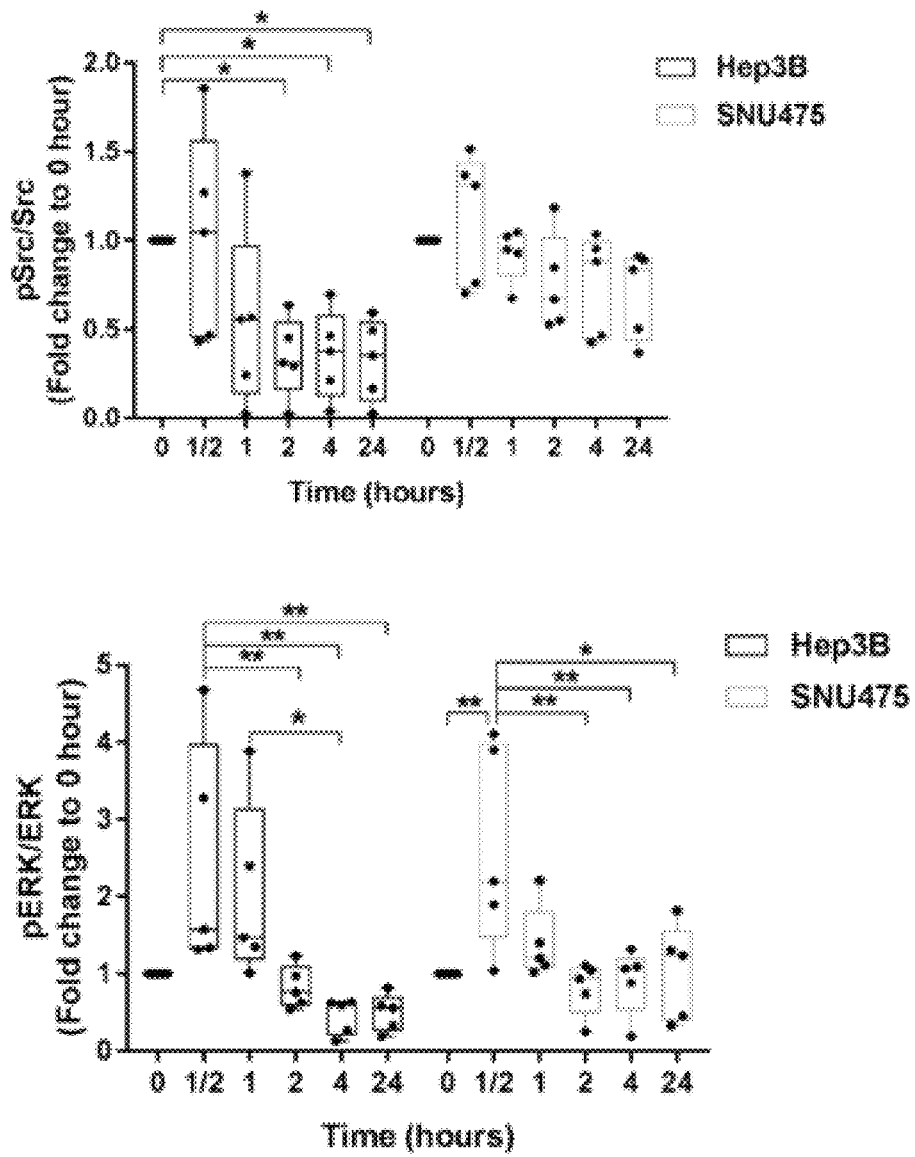
Figure 23F:
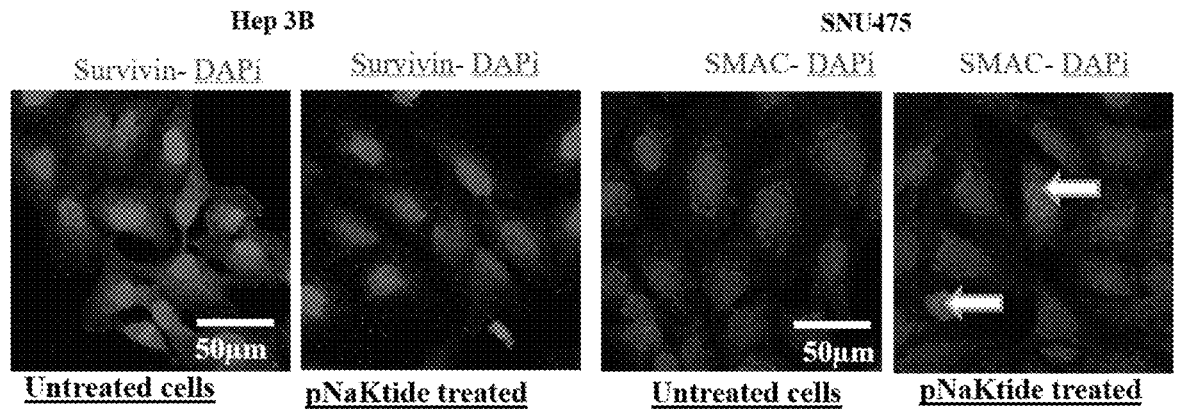
Figure 23F:
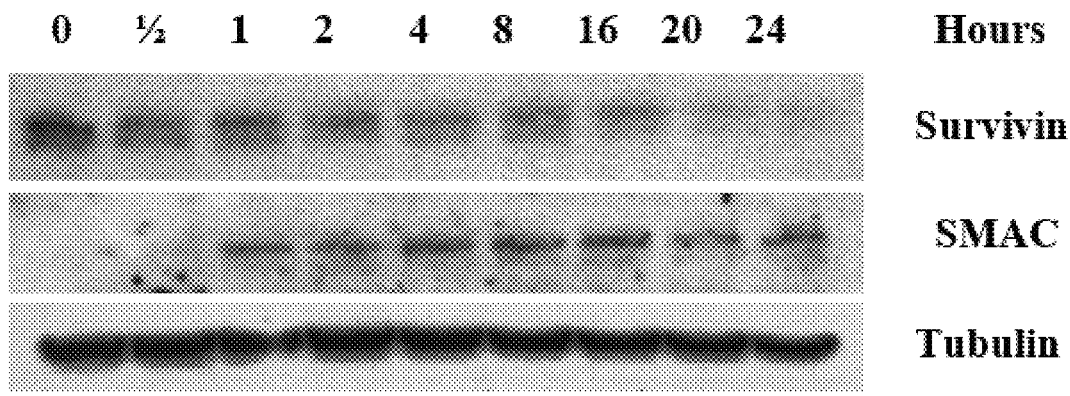
Figure 23F:
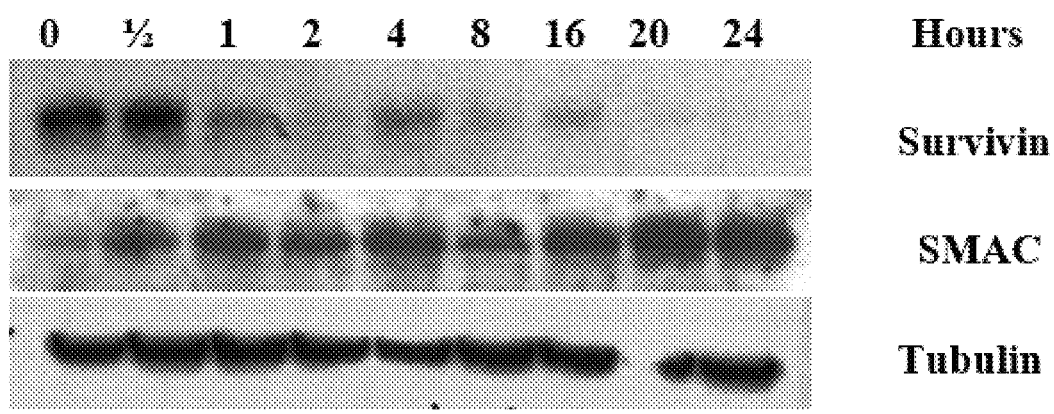
Figure 23F:
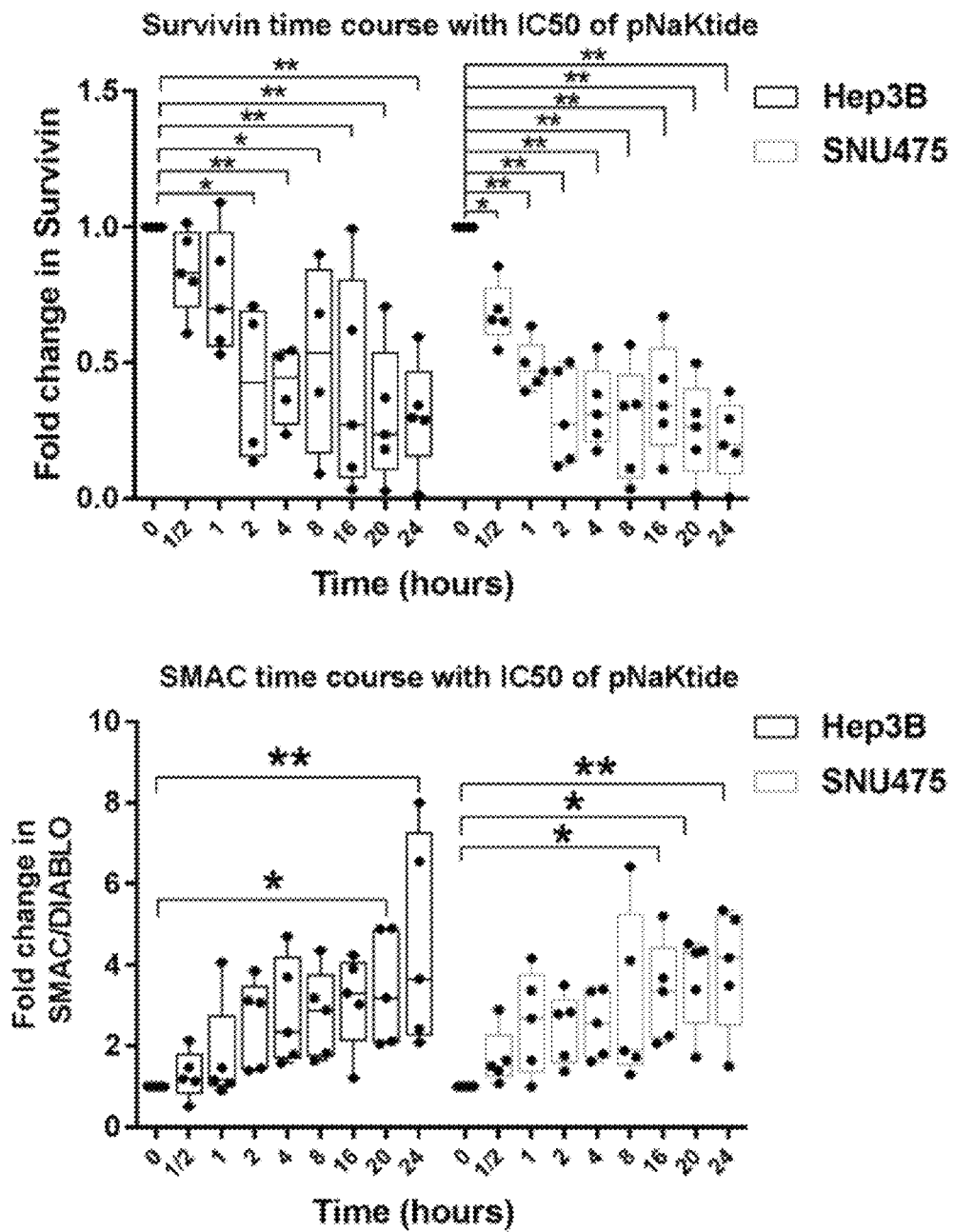

Effect of Src-p Inhibition on α1-Subunit, Src/Akt Kinases, Survivin/SMAC Protein Expressions In-Vitro. The effect of Src-p on Human HCC cell lines protein expressions was visualized by confocal microscopy on immuno-staining slides and quantitated by proteins western blotting. The baseline α1-subunit expression of the NKA was decreased in both cell lines, and it was significantly upregulated after IC50-pNaKtide treatment (as early as 2 hours) with subunit increments stabilization over time (up to 24 hours, FIG. 23D). On the contrary, significant downregulation of Src-p was observed in the Hep3 cell line and only a trend on the SNU475 cell line (FIG. 23E). The observed difference in Src-p may be due to Caveolin-1 (Cav-1) expression, where wild type Hep3 cell line is Cav-1$^{neg}$ while wild type SNU475 cell line is Cav-1$^{pos}$. Nevertheless, Akt-p was significantly downregulated in both cell lines (as early as 2 hours), effect that lasted for up to 24 hours (FIG. 23E). There was a significant upregulation of Survivin with concomitant downregulation SMAC proteins in both Human HCC cell lines (FIG. 23F). Cell lines Src-p inhibition reversed protein expressions with attenuation of survivin and heightening of SMAC (FIG. 23F) in a dose dependent manner.

The first set of results in vitro show that in HCC, there is an increase Src-p state associated with concomitant downregulation of the α1-NKA subunit, upregulation of the anti-apoptotic protein survivin and downregulation of the proapoptotic SMAC protein expression, promoting a cell 'switch' from apoptosis to mitosis. Restoring a decreased Src-p state by blockage of its phosphorylation at α1-NKA reversed proteins expression to a physiological level. Our results are in agreement with earlier reports of associated upregulated Src-p to decreased α1-NKA expression in many cancer types such as prostate, pancreatic, and renal.

Figure 24A:
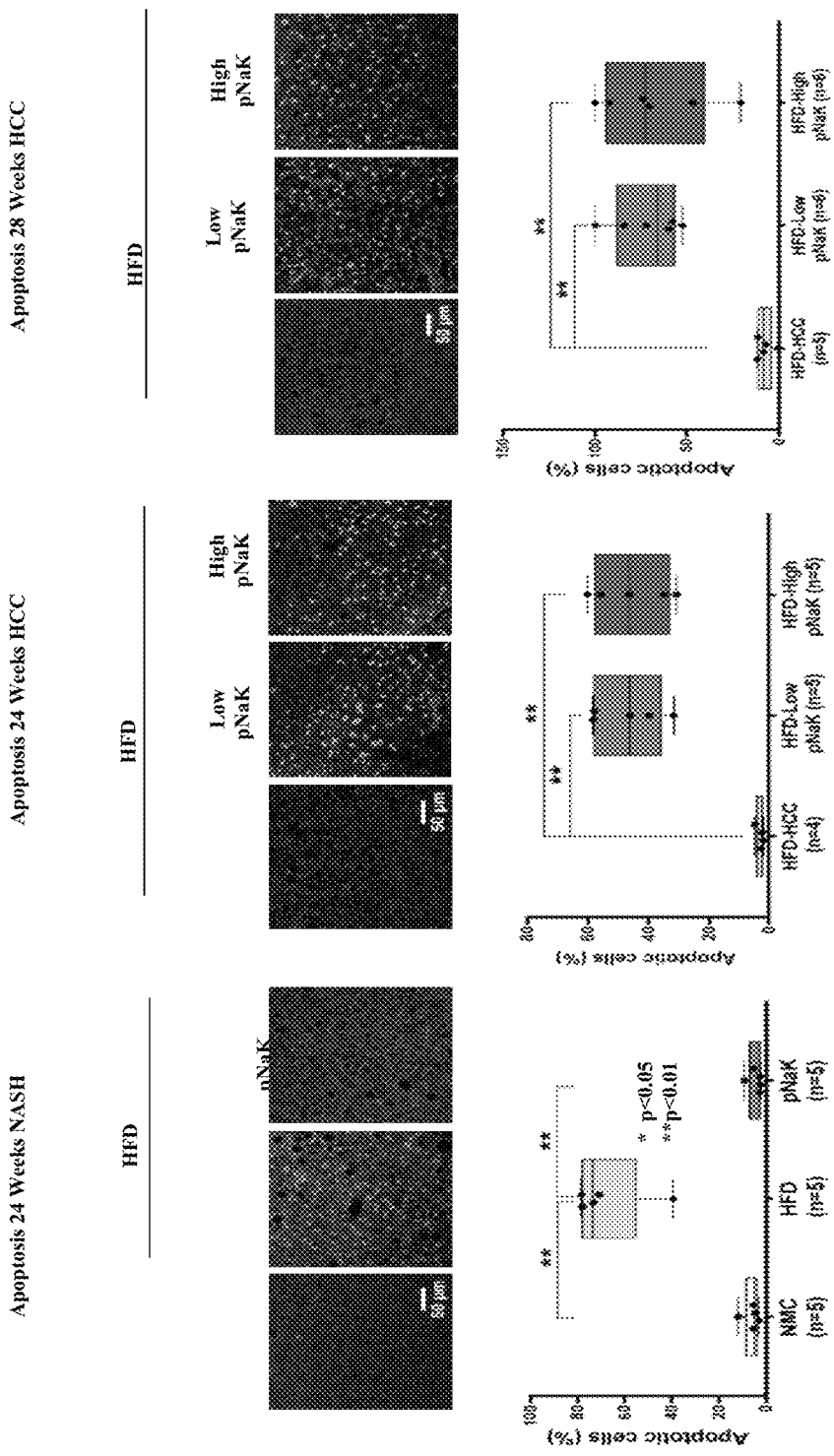
FIGS. 24A-24C include images and graphs showing the effect of Src-p inhibition on apoptosis, tumor burden and fibrosis in livers with NASH & NASH-HCC from rodent models, where (FIG. 24A) the apoptotic activity of livers from animals with NASH was increased when compared to controls (NMC) and pNaKtide abrogate such activity on treated animals, and in contrast in the NASH-HCC model, the decreased apoptotic activity showed in HCC from NASH livers was significantly increase by an apoptotic 'switch' promoted by the treatment with pNaKtide (**p<0.01 by ANOVA and Turkey's Post hoc test, on TUNEL stained liver slides), (FIG. 23B) there was a significant decrease in the tumor burden of livers treated with pNaKtide from NASH related HCC at 24 and 28 weeks when compared livers from untreated animals. compared to those of the untreated HFD mice (results are shown as box- and whisker plots (*p<0.05, p<0.01, by ANOVA and Turkey's Post hoc test, n=5-6 mice for each group)) and the effect of Src-p inhibition followed a dose dependent effect at 24 weeks, and (FIG. 24C) in addition, there was a significant increase in collagen deposition in the untreated HFD groups when compared to the pNaKtide treated groups and NMC group (p<0.01, by ANOVA and Turkey's Post hoc test, on Trichrome stained liver slides).
Figure 24B:
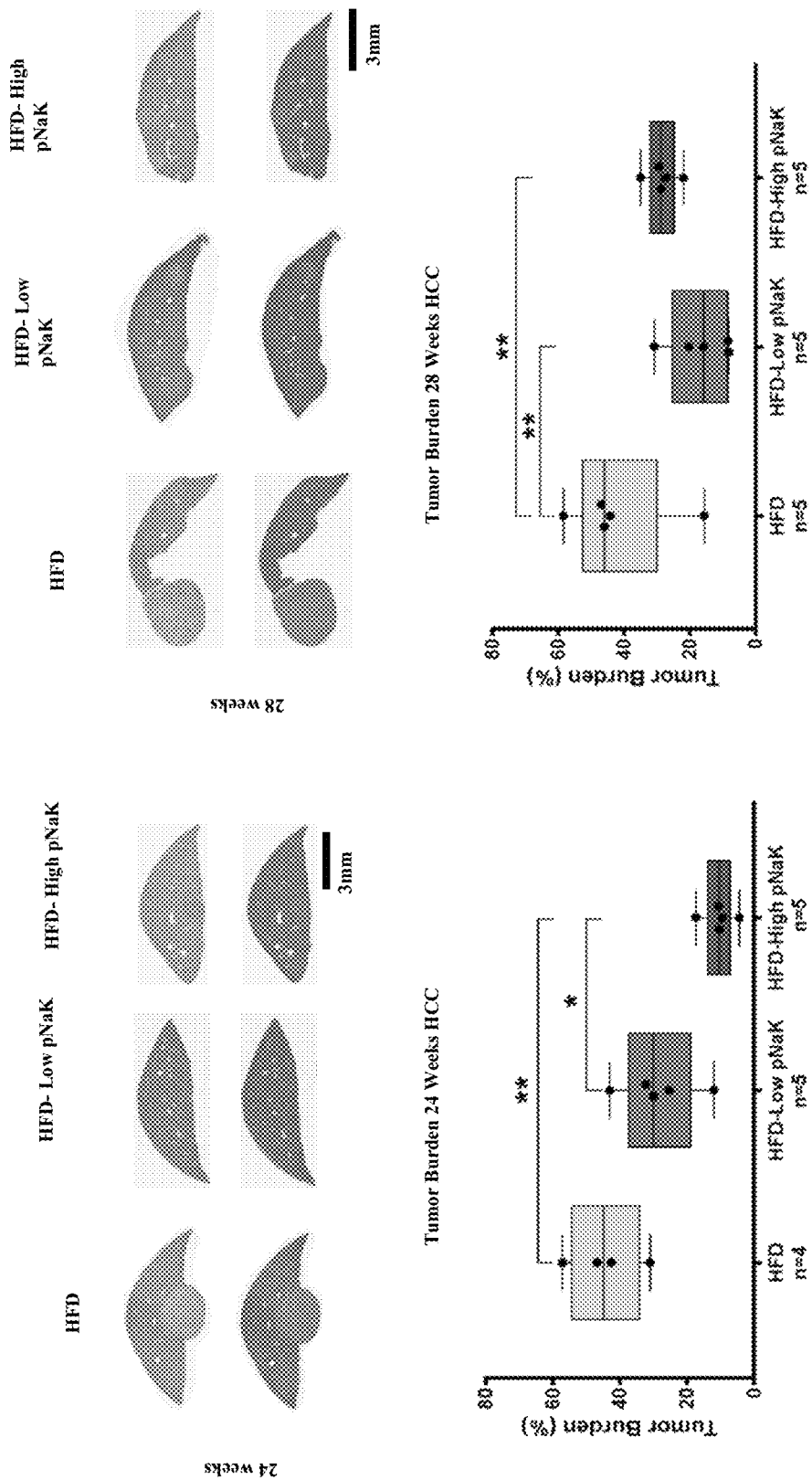
Figure 24C:
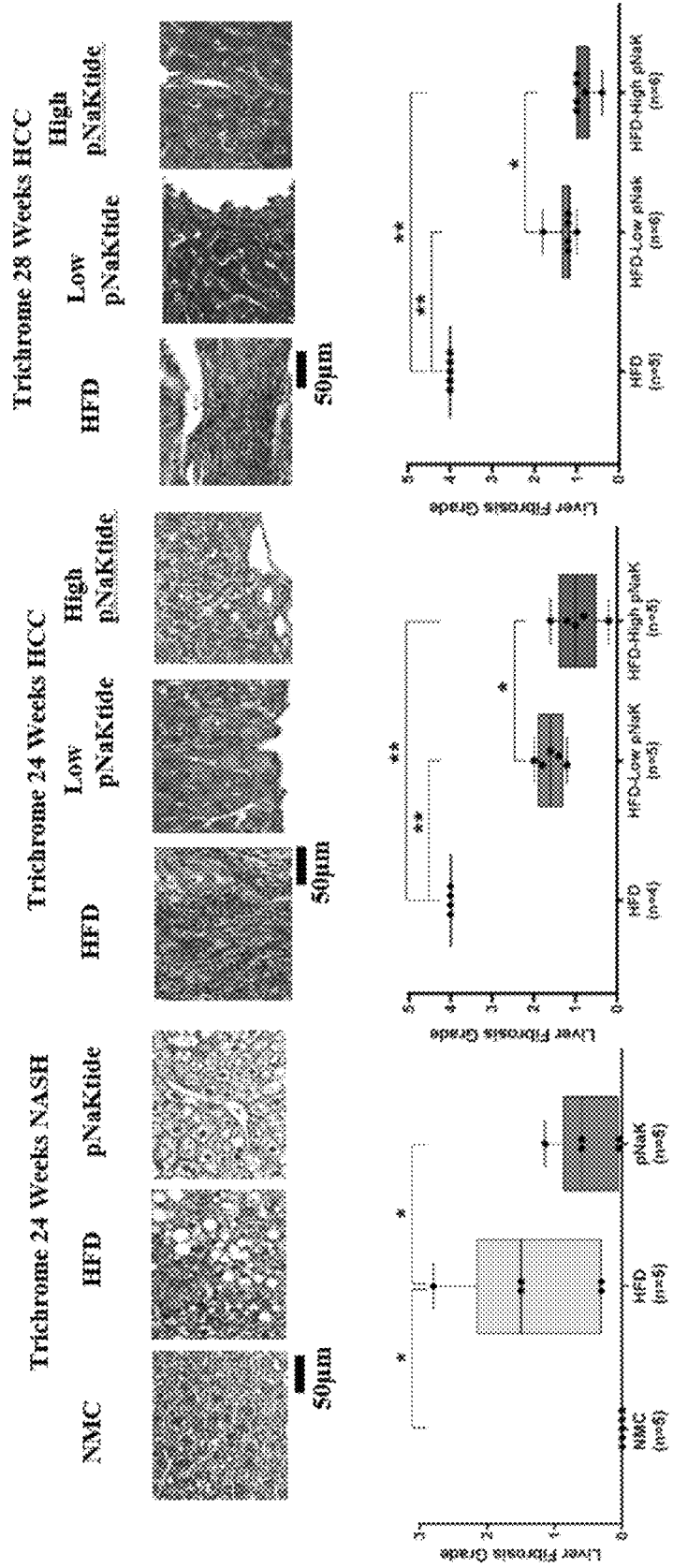

Effect of Src-p inhibition on apoptosis in liver tumor cells from rodent models of NASH & NASH-HCC. Experiments were performed to elucidate the effect of pNaKtide in vivo by using murine models. In the NASH model, a paucity of apoptosis was observed in the treated animals when compared to untreated animals at 24 weeks by TUNEL assay (FIG. 24A). Preclinical and clinical studies had correlated apoptotic activity with NASH progression, findings that confirmed earlier studies. In contrast, in the NASH-HCC model Src-p inhibition remarkably increased tumor apoptotic activity in treated animals when compared to non-treated animals at both 24 and 28 weeks (FIG. 24A). In addition, tumor burden was evaluate in treated/untreated animals on H&E slides where malignant vs. normal parenchymal cells masked by color-pixel attributed channels to determine tumor AUC. A significant lower tumor load was noted on treated animals at 24 and 28 weeks in a dose dependent fashion (FIG. 24B) and associated with a decreased collagen activity deposition and therefore liver fibrosis of treated vs. non-treated animals by trichrome staining (p<0.05, FIG. 24C). Liver fibrosis is the pathological process of diffuse and excessive deposition of extracellular matrix (ECM) in the liver from abnormal connective tissue proliferation. It is caused by several pathogenic factors and is a common phase in the progression of many chronic liver diseases to end stage liver disease or cirrhosis. Specific signaling pathways implicated in the formation and progression of fibrosis include TGF-β1/Smad, NF-κB, and PI3K/Akt pathways on activated hepatic stellate cells (HSCs). Active HSCs transform into α-SMA-positive cells that synthetized collagen-I and collagen-III leading to the deposition of large amount of ECM and progressive liver fibrosis.

Figure 25A:
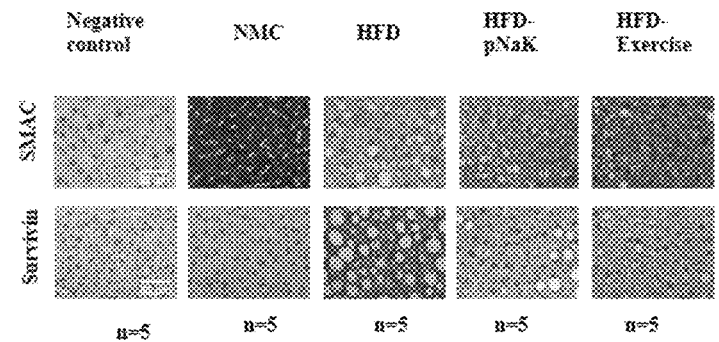
FIGS. 25A-25C include images and graphs showing the effect of Src-p inhibition on Survivin/SMAC and Cav-1 proteins expression in NASH & NASH-HCC rodent models and Human Liver tissues, where (FIG. 25A) there was a significant down-regulation of Survivin and upregulation of SMAC expression in tumor cells from treated vs non treated animals at 24 and 28 weeks (p<0.01, by ANOVA and Turkey's Post hoc test) and there were not significant changes in protein expressions in the peritumor cells of mice in the HFD groups vs High pNaKtide treated groups in the NASH-HCC mice model (24 &28 weeks), where in human tissues, the findings were consistent with the in-vitro and in-vivo findings for survivin and SMAC proteins, where there was a significant upregulation of survivin expression in livers form patients with NASH and NASH related HCC when compared to livers from normal subjects and patient with liver metastases (p<0.01, by ANOVA and Turkey's Post hoc test), where, on the contrary, SMAC expression decreased significantly in livers form patients with NASH, NASH related HCC and liver metastases when compared to livers from the Normal subjects (**p<0.01, by ANOVA and Turkey's Post hoc test), where (FIG. 25B) the expression of Cav-1 was not similar from in vitro to in vivo studies and for the in vitro studies HCC cell lines were chosen that differed on Cav-1 expression to determine if Cav-1 expression would change Src-p downstream effects, where, although Cav-1 expression on cell lines exposed to pNaKtide may influenced Src-p with a higher effect on Hep3$^{Cav-1/neg}$ than on SNU475$^{Cav-1/pos}$, pNaKtide did not exercised any changes on baseline cell Cav-1 expression, where nevertheless, Cav-1 was upregulated in patients with NASH or NASH-HCC when compared to control subjects or patients with liver metastases (*p<0.05, **p<0.01, by ANOVA and Turkey's Post hoc test), and where (FIG. 25C) in addition, treated vs. non-treated animals with pNaKtide showed a dose response downregulation of Cav-1 expression on tumor tissue.
Figure 25A:
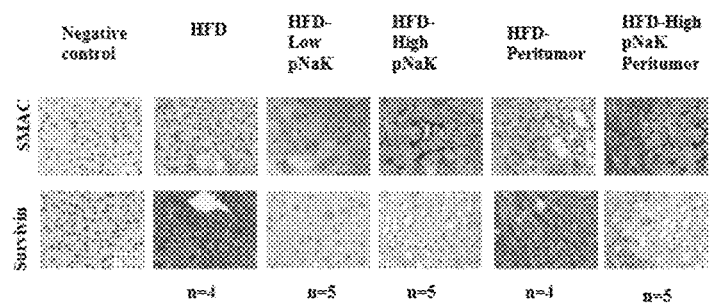
Figure 25A:
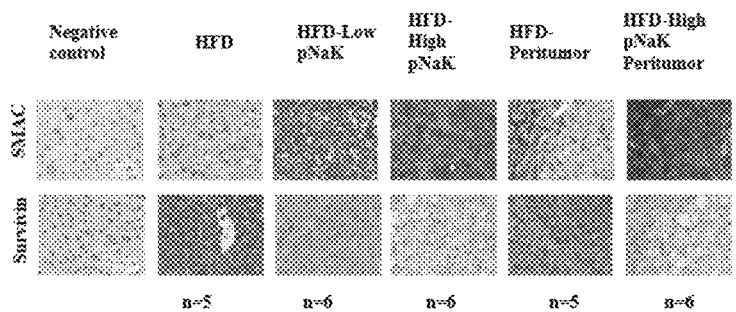
Figure 25A:
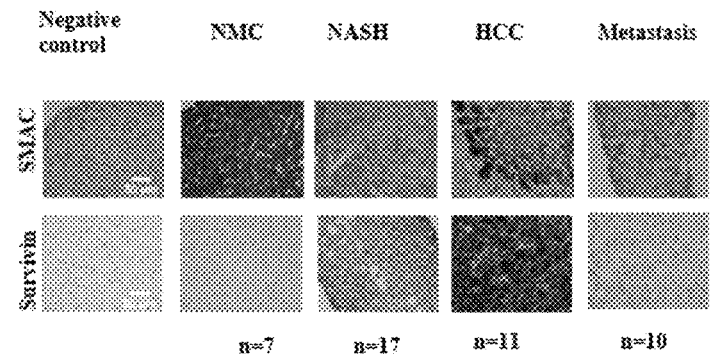
Figure 25A:
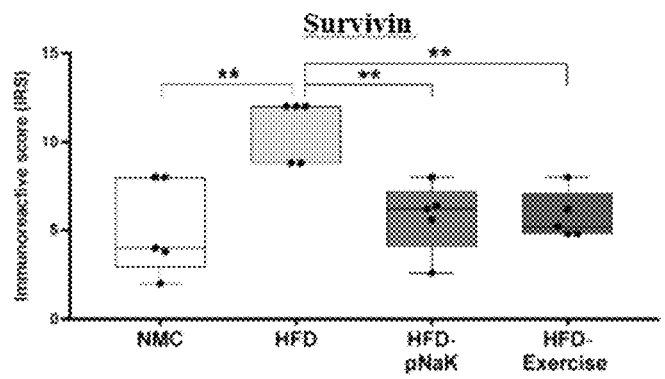
Figure 25A:
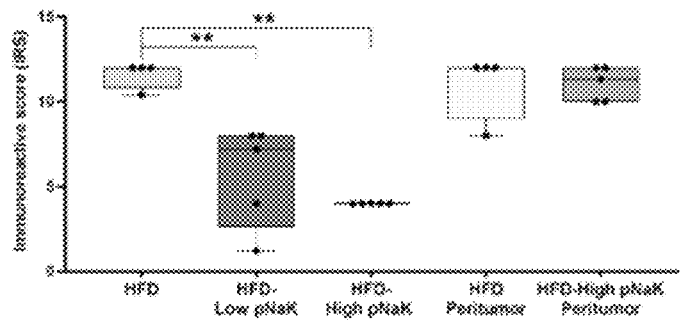
Figure 25A:
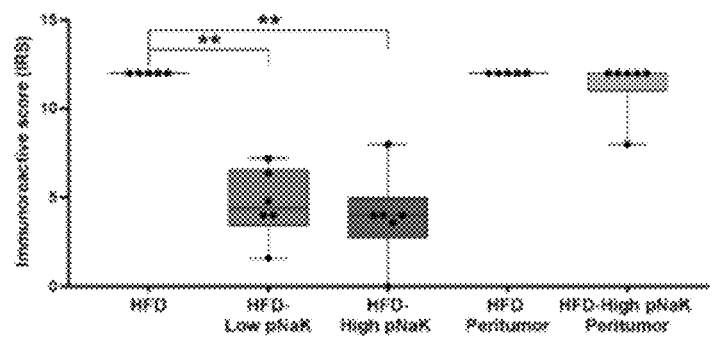
Figure 25A:
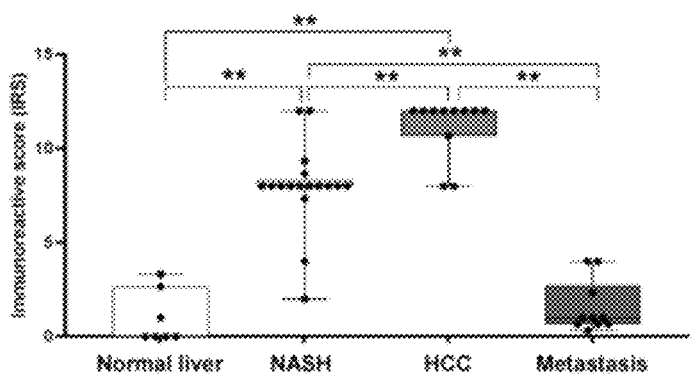
Figure 25A:
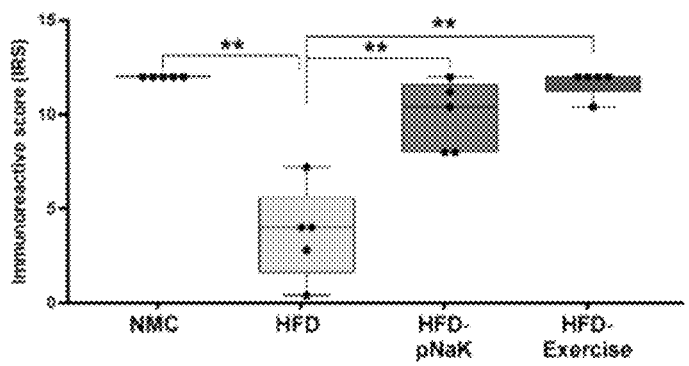
Figure 25A:
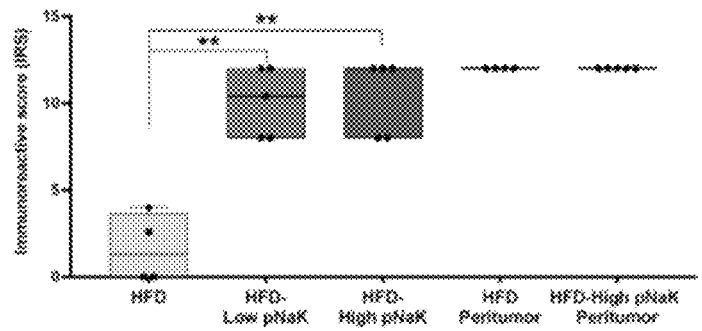
Figure 25A:
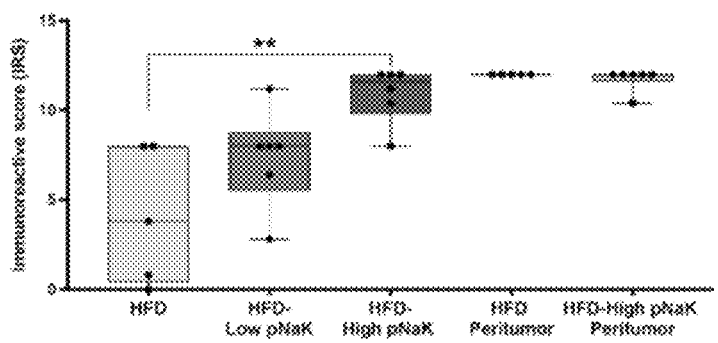
Figure 25A:
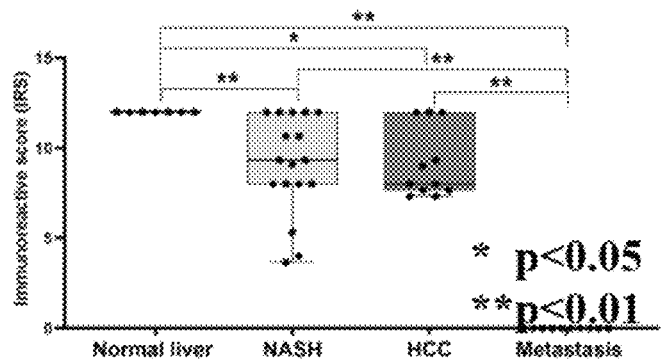
Figure 25B:
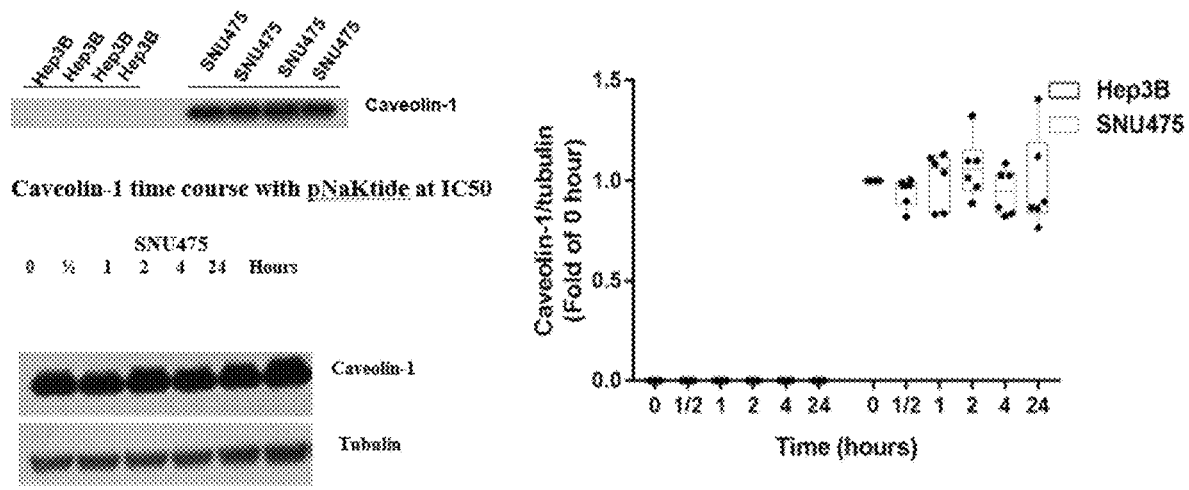
Figure 25B:
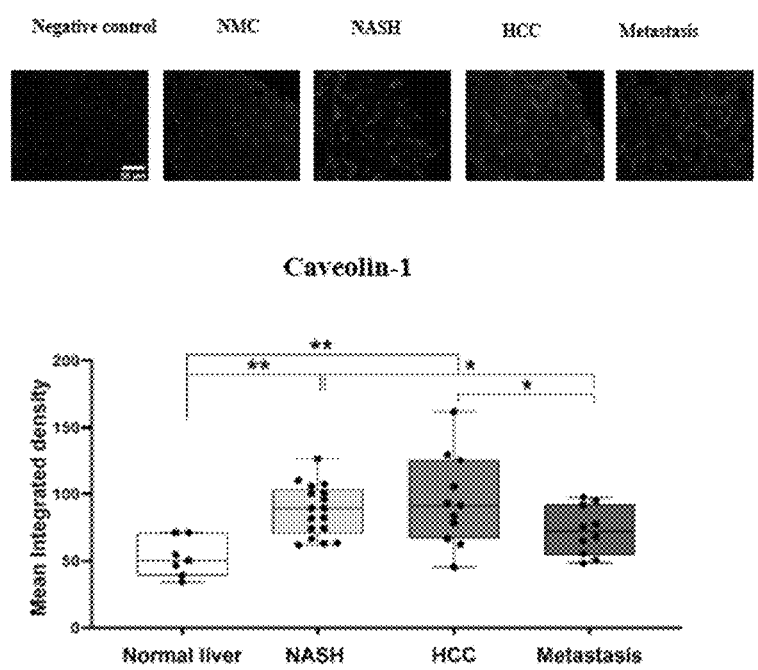
Figure 25C:
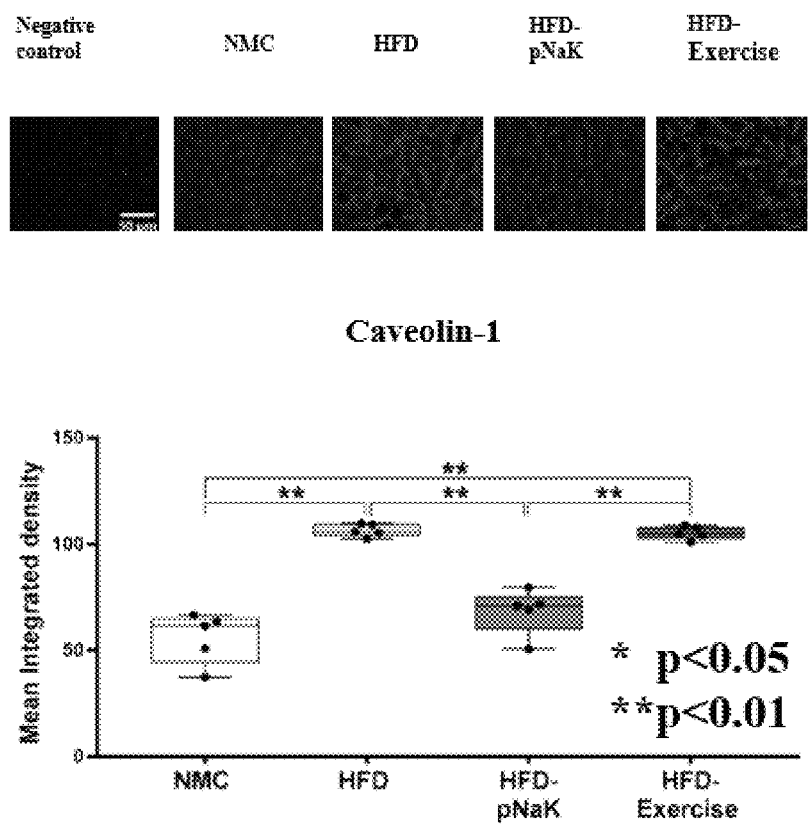
Figure 25C:
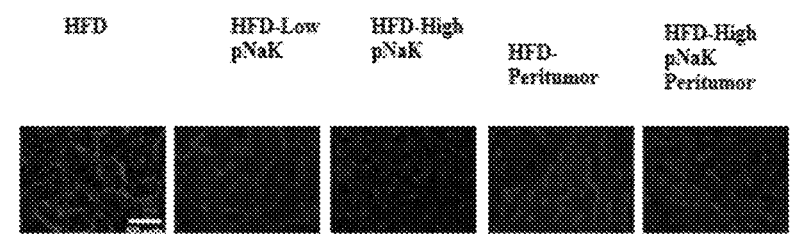
Figure 25C:
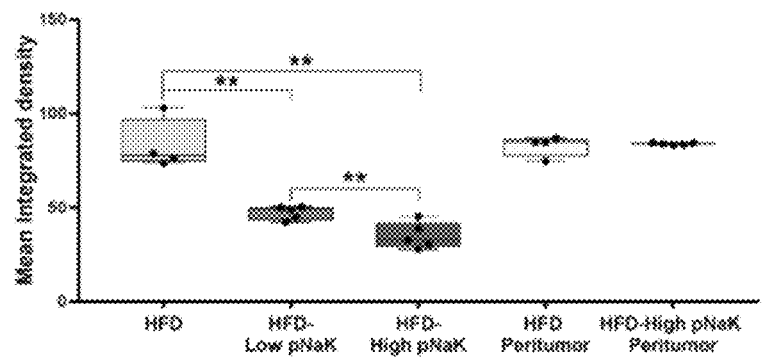
Figure 25C:
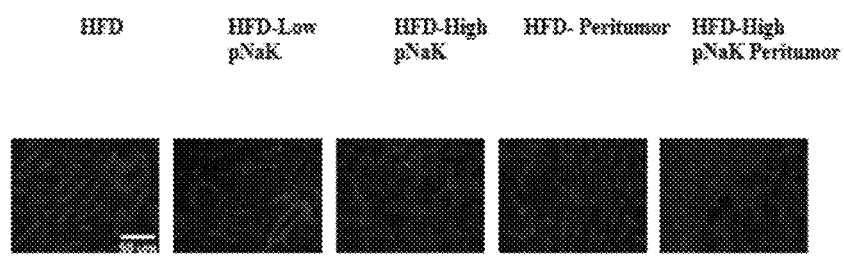
Figure 25C:
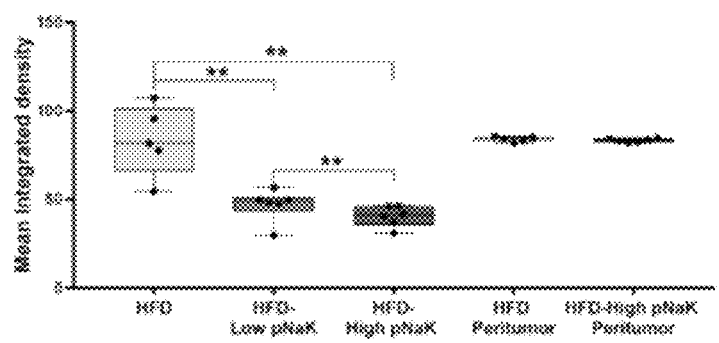

Effect of Src-p inhibition on Survivin, SMAC, and Cav-1 proteins expression in rodent models of NASH & NASH-HCC, and Human Subjects. Immunostaining of each protein followed by quantitation using ImageJ software (NIH, Bethesda, Md.) was carried out. Non-treated livers had an increase in survivin expression in liver tissues from both the NASH and NASH-HCC mice, protein expression that was significantly attenuated in treated livers (FIG. 25A). In contrast, a significantly lower expression of SMAC was observed in non-treated vs. treated livers form both NASH and NASH-HCC animals (FIG. 25A). Survivin has been shown to play a critical role in the release of SMAC from the mitochondria and the activation of downstream caspases following apoptotic stimuli. Upregulation of survivin, as it occurs in HCC tumor cells causes a delay in the release of SMAC from the mitochondria mediated by a direct binding of mitochondrial survivin with SMAC, thus by a simple size-exclusion mechanism. In addition, survivin also regulates the activity of cytosolic SMAC neutralizing its effect on inhibitors of apoptotic proteins like XIAP. To translate our findings to the clinical setting, Survivin/SMAC protein expression analyses were performed on human liver tissues from normal subjects, patients with NASH related HCC, NASH, and liver metastasis. Survivin is highly expressed in liver from patients with NASH related HCC as compared to normal subjects, patients with NASH, or patients with liver metastasis. In contrast, a significant reduced expression of SMAC was observed in the liver tissue from patients with NASH related HCC, NASH, and liver metastasis when compared to normal subjects (FIG. 25A). The expression of Cav-1 was not similar from in vitro to in vivo studies. For the in vitro studies HCC cell lines were chosen that differed on Cav-1 expression to determine if Cav-1 expression would change Src-p downstream effects. Although Cav-1 expression on cell lines exposed to pNaKtide may influenced Src-p with a higher effect on Hep3$^{Cav-1/neg}$ than on SNU475$^{Cav-1/pos}$ (FIG. 23E), pNaKtide did not exercised any changes on baseline cell Cav-1 expression (FIG. 25B). Nevertheless, Cav-1 was upregulated in patients with NASH or NASH-HCC when compared to control subjects or patients with liver metastases (FIG. 25B). In addition, pNaKtide treated vs. non-treated animals showed a dose response downregulation of Cav-1 expression on tumor tissue (FIG. 25C). Our group had determined α1-NKA regulates trafficking of Cav-1 from the cytoplasm to caveola.

The set of in vivo studies showed Src-p inhibition induces apoptosis in tumor cells, decreasing tumor burden with concomitant amelioration of liver fibrosis. Tumor regression on liver tissue exposed to pNaKtide is attributed to concomitant downregulation of survivin and upregulation of SMAC proteins. Protein print observed from NASH-HCC rodent models was reproduced in livers from patients with NASH related HCC. The inhibition of apoptosis by survivin is mediated via its interaction with SMAC and the release of inhibitor of apoptosis proteins (IAPs) that in turns inhibit caspases activity ending in abrogation of apoptosis. Another important function of survivin is the promotion of cell proliferation. During the G2/M phase of cell cycle, survivin is highly expressed and binds to microtubules that make up the mitotic spindles. Such binding stabilizes the structure of the microtubules and prevents the hydrolysis of the spindles, securing the integrity of mitotic organelles, with evasion of checkpoints growth arrest and assuring a continuous cell division. Additionally, survivin plays a key role in tumor angiogenesis motivating the proliferation and migration of endothelial cells promoting cancer cells survival. Inhibition of survivin as it occurs following the administration pNaKtide, has been shown to increased spontaneous apoptosis, mitotic catastrophe, and cell cycle arrest in cells.

Figure 26A:
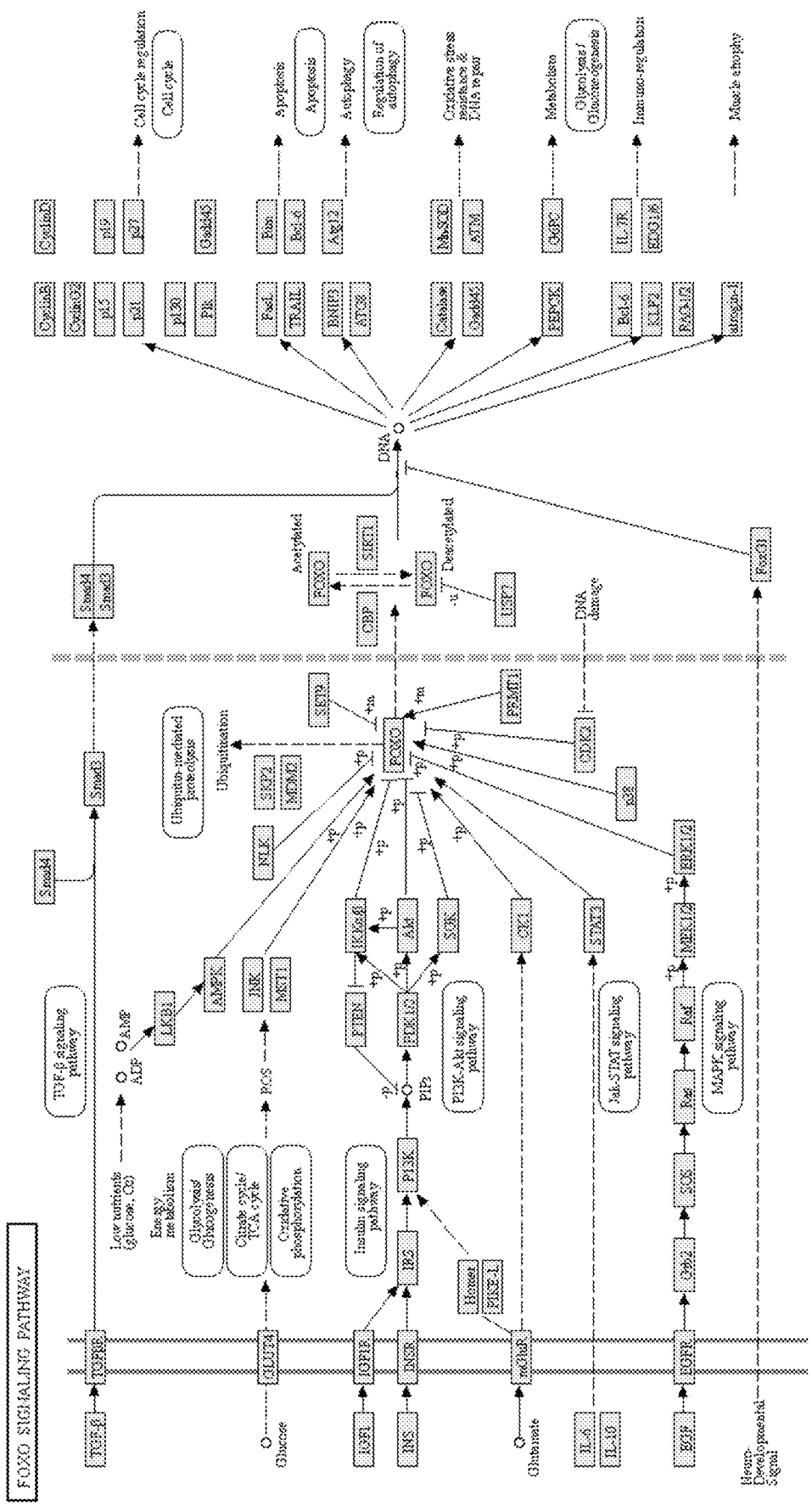
FIGS. 26A-26E include schematic diagrams, images, and graphs showing the α1-NKA Signalosome, including (FIG. 26A) an RNA sequencing KEGG diagram showing the activation of PI3K-Akt signaling pathway leading to inhibition of FoxO in two human HCC cell lines, (FIG. 26B) images and graphs showing there was a significant increase in the activation of phosphor-Akt and phosphor-S6k1 in human HCC cell lines when compared with pNaKtide treated cells (*p<0.05, **p<0.01, by ANOVA and Turkey's Post hoc test), (FIG. 26C) a graph showing MTT assay results of PI3K/Akt pathway inhibitors—wortmannin, PP2 and AG490 on two human HCC cell lines, where the inhibition of cell proliferation in these cell lines following the administration of these agents was noted, (FIG. 26D) images and graphs showing, in addition, survivin was noted to be over-expressed in α1-NKA Knockdown (siRNA) cells from two human HCC Cell Lines. Significance was determine using ANOVA and Turkey's Post hoc test. *p<0.05, **p<0.01, (FIG. 26E) a graph and images showing, furthermore, digoxin increased the expression of survivin in the two Human HCC cells, and administration of pNaKtide reversed the phenomena (*p<0.05, **p<0.01, by ANOVA and Turkey's Post hoc test).
Figure 26B:
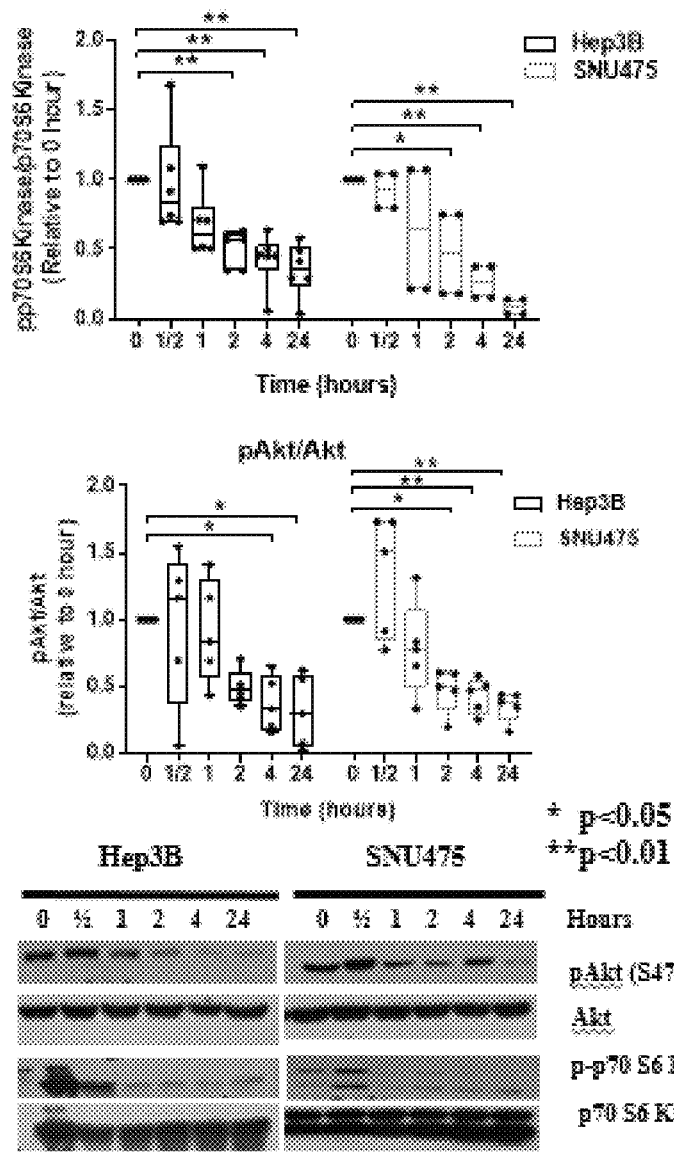
Figure 26C:
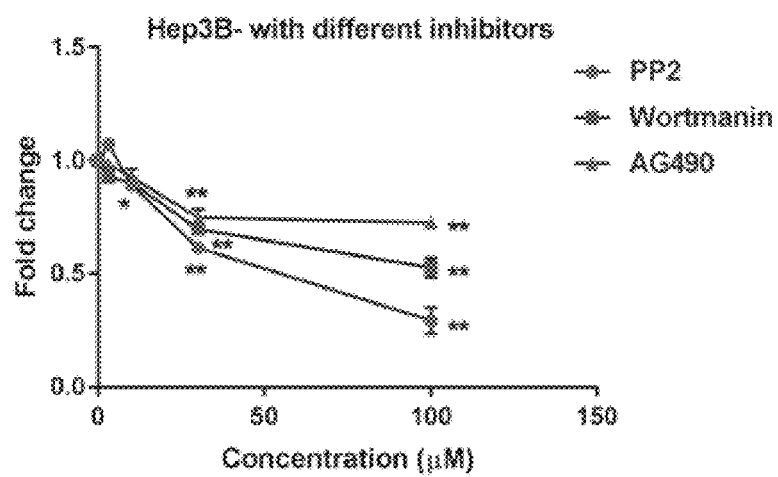

Signalosome of the α1-NKA. To determine the pathway from Src-p at the α1-cell membrane to the nucleus for gene rearrangement concluding in survivin upregulation and cell division, RNA sequencing was performed on two untreated human HCC cell lines (Novogene, CA). The RNA sequencing results revealed activation of the PI3K-mTOR-AKT-S6K1 pathway associated with inhibition of the pro-apoptotic FoxO signaling trail (FIG. 26A). Immunoblotting techniques confirmed an increase in Akt-p and S6k1-p, depicting the activation of PI3K-Akt pathway in HCC cell lines (FIG. 26B). Cell lines exposed to pNaKtide showed a progressive reduction in kinases phosphorylation, connoting the inhibition of this pathway (FIG. 26B). The PI3K-Akt-mTOR-SK61 pathway has been reported to be constitutively activated in many types of malignancy. Factors that activate this pathway include loss of the tumor suppressor PTEN function, activation/amplification of PI3K/Akt, activation of growth factor receptors including EGFR, and exposure to carcinogenic agents. PI3K/Akt signaling induces survivin transcription through the phosphorylation of p70S6K1 protein driving cell proliferation, survival, and angiogenesis. Additionally, PI3K/Akt inhibition downregulates survivin expression, the most potent anti-apoptotic protein that has been discovered till date, and PI3K/Akt pathway inhibitors-wortmannin, PP2 and AG490 inhibited cell proliferation on two human HCC cell lines (FIG. 26C).

The forkhead box O (FoxO) family of transcription factors, recognized as tumor suppressors play key roles in cell cycle arrest, senescence, apoptosis, differentiation, DNA damage repair and scavenging of reactive oxygen intermediates. FoxO proteins are phosphorylated during activation of the PI3K-Akt pathway. Upon phosphorylation, the FoxO proteins are extruded from the nucleus to the cytoplasm, resulting in a negative regulation of their activities and decrease expression of FoxO target genes which drive apoptosis, thereby favoring cancer initiation and progression. Specifically, FoxO3 downregulates the transcription and expression of the anti-apoptotic protein survivin. Studies have showed that the inhibition of the PI3K/Akt pathway resulted in translocation of FoxO3 to the nucleus, leading to the repression of the survivin. Similarly, FoxO3-induced apoptosis was accelerated upon survivin knockdown in cells. Furthermore, insulin resistant status is recognized as one of the "hits" that induces NASH progression, and FoxO1 is a key regulator of intracellular insulin effects, confirming our prior findings on FoxO1 upregulation prior glucose normalization in treated animals with pNaKtide.

Figure 26D:
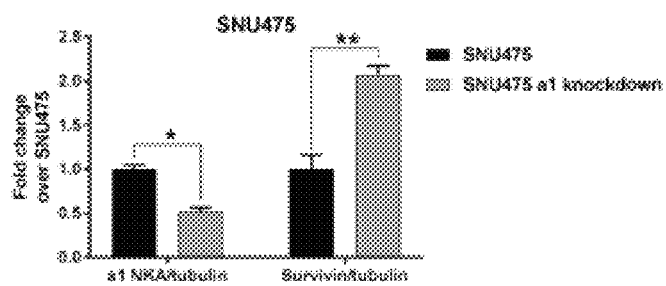
Figure 26D:
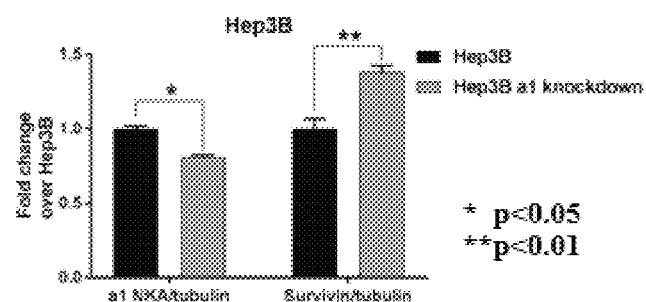
Figure 26D:
Figure 26E:
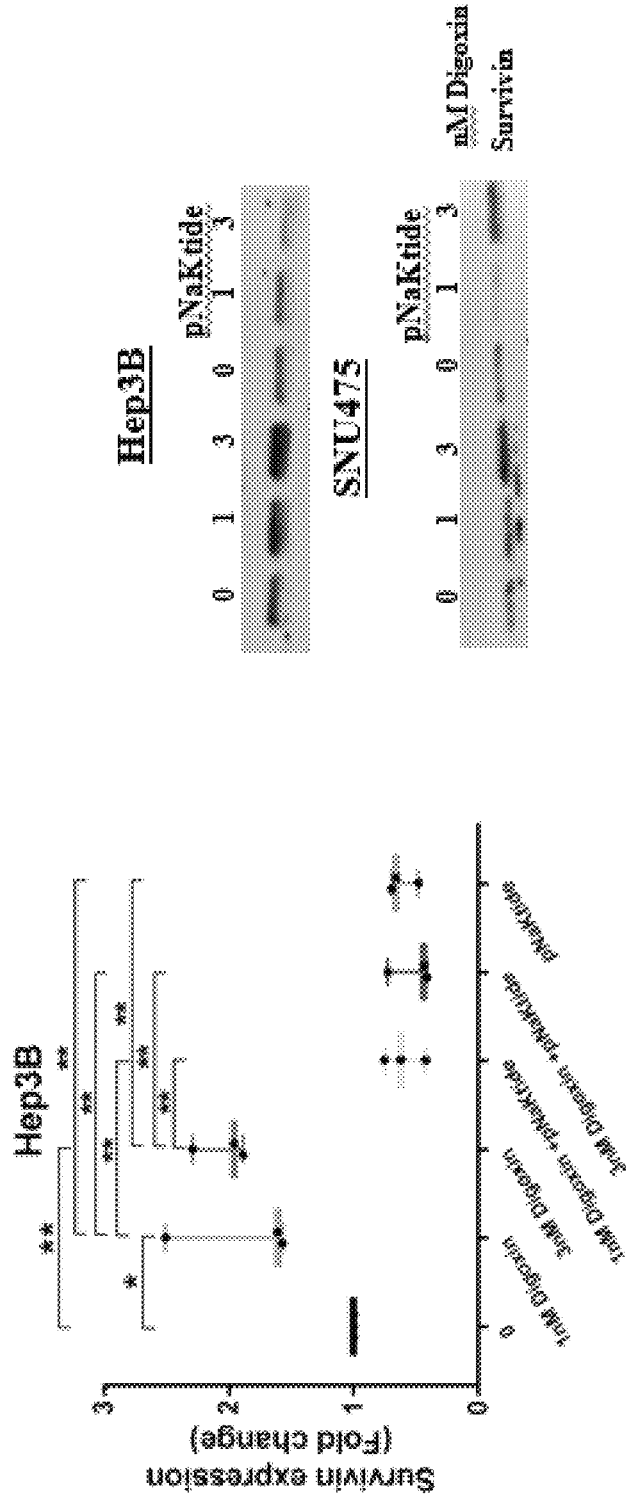
Figure 27:
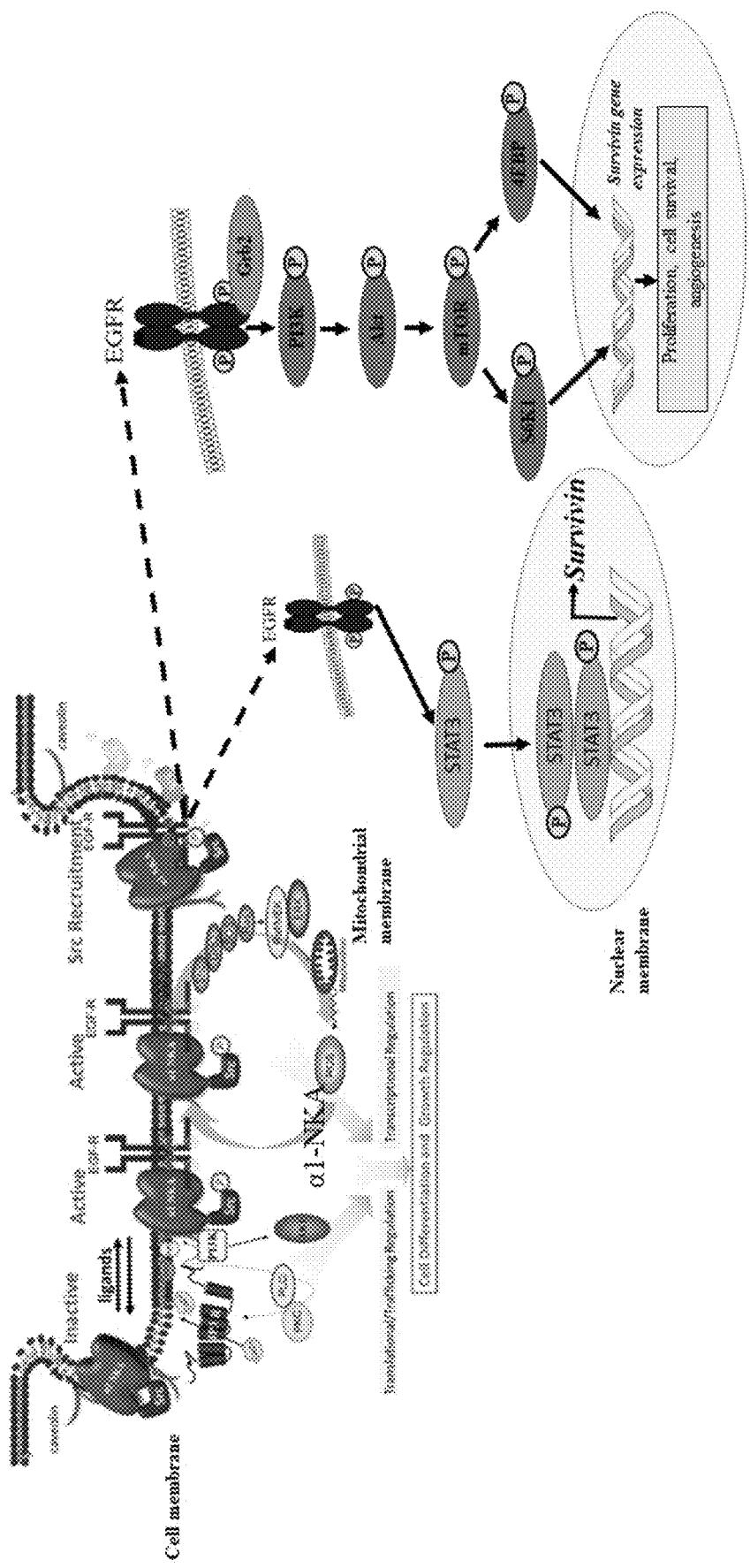
FIG. 27 is a schematic diagram showing an α1-NKA Signalosome in accordance with the presently-disclosed subject matter.

To further determine if the circuit that increase survivin expression observed in the HCC cell lines was mediated at the α1-NKA through Src-p$^+$ and PI3K-Akt axis activation, α1-subunit heterozygote knockdown (KND) at the NKA cells were fabricated from the two human HCC cell lines using small interfering RNA (siRNA). α1-NKA-KND cell lines expressed survivin (FIG. 26D), observing an increased effect when HCC cell lines were exposed to cardiotonic steroids (digoxin), and the effect of digoxin on survivin was reverted by pNaKtide treatment (FIG. 26E). Digoxin, a partial inhibitor of the NKA mediates its action by binding to the α-subunit. It is the only FDA-approved cardiac glycoside indicated in the treatment of patients with mild or moderate heart failure and reduced ejection fraction. Understanding the molecular mechanisms that underlie the development and evolution of NASH related HCC could bring light on checkpoint therapies for tumor regression. Our findings point Src-p at α1-NKA as the initiator of a circuit that renders upregulation of survivin, down-regulation of SMAC, and inhibition of pro-apoptotic FoxO pathway motivating a "switch" of cell faith from programmed death to uncontrolled cell division. This 'switch' is reversed by inhibition of phosphorylation of the Src kinase at α1-NKA. The proposed signaling cascade (FIG. 27) includes activation of the PI3K-Akt-mTOR-S6K1 pathway from the cell membrane in caveola to the cell nucleus.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Collaborators GBDO, Afshin A, Forouzanfar M H, Reitsma M B, Sur P, Estep K, et al. Health Effects of Overweight and Obesity in 195 Countries over 25 Years. N Engl J Med. 2017; 377(1):13-27.
2. Stanaway J D, Flaxman A D, Naghavi M, Fitzmaurice C, Vos T, Abubakar I, et al. The global burden of viral hepatitis from 1990 to 2013: findings from the Global Burden of Disease Study 2013. Lancet. 2016; 388 (10049):1081-8.
3. Younossi Z, Anstee Q M, Marietti M, Hardy T, Henry L, Eslam M, et al. Global burden of NAFLD and NASH: trends, predictions, risk factors and prevention. Nat Rev Gastroenterol Hepatol. 2018; 15(1):11-20.
4. Estes C, Razavi H, Loomba R, Younossi Z, Sanyal A J. Modeling the epidemic of nonalcoholic fatty liver disease demonstrates an exponential increase in burden of disease. Hepatology. 2018; 67(1):123-33.
5. Dongiovanni P, Romeo S, Valenti L. Hepatocellular carcinoma in nonalcoholic fatty liver: role of environmental and genetic factors. World J Gastroenterol. 2014; 20(36):12945-55.
6. Global Burden of Disease Cancer C, Fitzmaurice C, Akinyemiju T F, Al Lami F H, Alam T, Alizadeh-Navaei R, et al. Global, Regional, and National Cancer Incidence, Mortality, Years of Life Lost, Years Lived With Disability, and Disability-Adjusted Life-Years for 29 Cancer Groups, 1990 to 2016: A Systematic Analysis for the Global Burden of Disease Study. JAMA Oncol. 2018; 4(11):1553-68.
7. Karagozian R, Derdak Z, Baffy G. Obesity-associated mechanisms of hepatocarcinogenesis. Metabolism. 2014; 63(5):607-17.
8. Li Z, Zhang Z, Xie J X, Li X, Tian J, Cai T, et al. Na/K-ATPase mimetic pNaKtide peptide inhibits the growth of human cancer cells. J Biol Chem. 2011; 286 (37):32394-403.
9. Sodhi K, Maxwell K, Yan Y, Liu J, Chaudhry M A, Getty M, et al. pNaKtide inhibits Na/K-ATPase reactive oxygen species amplification and attenuates adipogenesis. Sci Adv. 2015; 1(9):e1500781.
10. Sodhi K, Srikanthan K, Goguet-Rubio P, Nichols A, Mallick A, Nawab A, et al. pNaKtide Attenuates Steatohepatitis and Atherosclerosis by Blocking Na/K-ATPase/ROS Amplification in C57Bl6 and ApoE Knockout Mice Fed a Western Diet. Sci Rep. 2017; 7(1):193.
11. Aravinthan A, Shannon N, Heaney J, Hoare M, Marshall A, Alexander G J. The senescent hepatocyte gene signature in chronic liver disease. Exp Gerontol. 2014; 60:37-45.
12. Aini W, Miyagawa-Hayashino A, Ozeki M, Adeeb S, Hirata M, Tamaki K, et al. Accelerated telomere reduction and hepatocyte senescence in tolerated human liver allografts. Transpl Immunol. 2014; 31(2):55-9.
13. Aravinthan A, Mells G, Allison M, Leathart J, Kotronen A, Yki-Jarvinen H, et al. Gene polymorphisms of cellular senescence marker p21 and disease progression in non-alcohol-related fatty liver disease. Cell Cycle. 2014; 13(9):1489-94.
14. Irvine K M, Skoien R, Bokil N J, Melino M, Thomas G P, Loo D, et al. Senescent human hepatocytes express a unique secretory phenotype and promote macrophage migration. World J Gastroenterol. 2014; 20(47):17851-62.
15. Lade A, Noon L A, Friedman S L. Contributions of metabolic dysregulation and inflammation to nonalcoholic steatohepatitis, hepatic fibrosis, and cancer. Curr Opin Oncol. 2014; 26(1):100-7.
16. Bagrov A Y, Shapiro J I, Fedorova O V. Endogenous cardiotonic steroids: physiology, pharmacology, and novel therapeutic targets. Pharmacol Rev. 2009; 61(1):9-38.
17. Kombu R S, Zhang G F, Abbas R, Mieyal J J, Anderson V E, Kelleher J K, et al. Dynamics of glutathione and ophthalmate traced with 2H-enriched body water in rats and humans. Am J Physiol Endocrinol Metab. 2009; 297(1):E260-9.
18. Abbas R, Kombu R S, Ibarra R A, Goyal K K, Brunengraber H, Sanabria J R. The dynamics of glutathione species and ophthalmate concentrations in plasma from the VX2 rabbit model of secondary liver tumors. HPB Surg. 2011; 2011:709052.
19. Andres Ibarra R, Abbas R, Kombu R S, Zhang G F, Jacobs G, Lee Z, et al. Disturbances in the glutathione/ophthalmate redox buffer system in the woodchuck model of hepatitis virus-induced hepatocellular carcinoma. HPB Surg. 2011; 2011:789323.
20. Sanabria J R, Kombu R S, Zhang G F, Sandlers Y, Ai J, Ibarra R A, et al. Glutathione species and metabolomic prints in subjects with liver disease as biological markers for the detection of hepatocellular carcinoma. HPB (Oxford). 2016; 18(12):979-90.
21. Luo P, Yin P, Hua R, Tan Y, Li Z, Qiu G, et al. A Large-Scale, Multicenter Serum Metabolite Biomarker Identification Study for the Early Detection of Hepatocellular Carcinoma. Hepatology. 2018; 67(2):662-75.
22. Charlton M, Krishnan A, Viker K, Sanderson S, Cazanave S, McConico A, et al. Fast food diet mouse: novel small animal model of NASH with ballooning, progressive fibrosis, and high physiological fidelity to the human condition. Am J Physiol Gastrointest Liver Physiol. 2011; 301(5):G825-34.
23. Hirsova P, Ibrahim S H, Bronk S F, Yagita H, Gores G J. Vismodegib suppresses TRAIL-mediated liver injury in a mouse model of nonalcoholic steatohepatitis. PLoS One. 2013; 8(7):e70599.
24. Ibrahim S H, Hirsova P, Tomita K, Bronk S F, Werneburg N W, Harrison S A, et al. Mixed lineage kinase 3 mediates release of C-X-C motif ligand 10-bearing chemotactic extracellular vesicles from lipotoxic hepatocytes. Hepatology. 2016; 63(3):731-44.
25. Krishnan A, Abdullah T S, Mounajjed T, Hartono S, McConico A, White T, et al. A longitudinal study of whole body, tissue, and cellular physiology in a mouse model of fibrosing NASH with high fidelity to the human condition. Am J Physiol Gastrointest Liver Physiol. 2017; 312(6):G666-G80.
26. Deng S, Zhang G F, Kasumov T, Roe C R, Brunengraber H. Interrelations between C4 ketogenesis, C5 ketogenesis, and anaplerosis in the perfused rat liver. J Biol Chem. 2009; 284(41):27799-807.
27. Kasumov T, Adams J E, Bian F, David F, Thomas K R, Jobbins K A, et al. Probing peroxisomal beta-oxidation and the labelling of acetyl-CoA proxies with [1-(13C)] octanoate and [3-(13C)]octanoate in the perfused rat liver. Biochem J. 2005; 389(Pt 2):397-401.
28. Li Q, Deng S, Ibarra R A, Anderson V E, Brunengraber H, Zhang G F. Multiple mass isotopomer tracing of acetyl-CoA metabolism in Langendorff-perfused rat hearts: channeling of acetyl-CoA from pyruvate dehydrogenase to carnitine acetyltransferase. J Biol Chem. 2015; 290(13):8121-32.
29. Aon M A, Bhatt N, Cortassa S C. Mitochondrial and cellular mechanisms for managing lipid excess. Front Physiol. 2014; 5:282.
30. Aravinthan A, Challis B, Shannon N, Hoare M, Heaney J, Alexander G J. Selective insulin resistance in hepatocyte senescence. Exp Cell Res. 2015; 331(1):38-45.
31. Neuman M G, Voiculescu M, Nanau R M, Maor Y, Melzer E, Cohen L B, et al. Non-Alcoholic Steatohepatitis: Clinical and Translational Research. J Pharm Sci. 2016; 19(1):8-24.
32. Arriazu E, Ruiz de Galarreta M, Cubero F J, Varela-Rey M, Perez de Obanos M P, Leung T M, et al. Extracellular matrix and liver disease. Antioxid Redox Signal. 2014; 21(7):1078-97.
33. Hayashi T, Kotani H, Yamaguchi T, Taguchi K, Lida M, Ina K, et al. Endothelial cellular senescence is inhibited by liver X receptor activation with an additional mechanism for its atheroprotection in diabetes. Proc Natl Acad Sci USA. 2014; 111(3):1168-73.
34. Sczelecki S, Besse-Patin A, Abboud A, Kleiner S, Laznik-Bogoslayski D, Wrann C D, et al. Loss of Pgc-1alpha expression in aging mouse muscle potentiates glucose intolerance and systemic inflammation. Am J Physiol Endocrinol Metab. 2014; 306(2):E157-67.
35. Zhang D M, Jiao R Q, Kong L D. High Dietary Fructose: Direct or Indirect Dangerous Factors Disturbing Tissue and Organ Functions. Nutrients. 2017; 9(4).
36. Sodhi K, Ouri N, Favero G, Stevens S, Meadows C, Abraham N G, et al. Fructose mediated Non-alcoholic Fatty Liver Disease is attenuated by H O-1-SIRT1 module in murine hepatocytes and mice fed a high fructose diet. PLOS one. 2015; DOI: 10.1371.
37. Win S, Than T A, Zhang J, Oo C, Min R W M, Kaplowitz N. New insights into the role and mechanism of c-Jun-N terminal kinase signaling in the pathobiology of liver diseases. Hepatology. 2018; 67(2):2103-014.
38. Barreyro F J, Holod S, Finocchietto P V, Camino A M, Aquino J B, Avagnina A, et al. The pan-caspase inhibitor Emricasan (IDN-6556) decreases liver injury and fibrosis in a murine model of non-alcoholic steatohepatitis. Liver Int. 2015; 35(3):953-66.
39. Walheim E, Wisniewski J R, Jastroch M. Respiromics—An integrative analysis linking mitochondrial bioenergetics to molecular signatures. Mol Metab. 2018; 9:4-14.
40. Luo P, Yin P, Hua R, Tan Y, Li Z, Qiu G, et al. A Large-scale, multicenter serum metabolite biomarker identification study for the early detection of hepatocellular carcinoma. Hepatology. 2017.
41. Gall W E, Beebe K, Lawton K A, Adam K P, Mitchell M W, Nakhle P J, et al. alpha-hydroxybutyrate is an early biomarker of insulin resistance and glucose intolerance in a nondiabetic population. PLoS One. 2010; 5(5):e10883.
42. Feldstein A E, Canbay A, Angulo P, Taniai M, Burgart L J, Lindor K D, et al. Hepatocyte apoptosis and fas expression are prominent features of human nonalcoholic steatohepatitis. Gastroenterology. 2003; 125(2):437-43.
43. Feldstein A E, Wieckowska A, Lopez A R, Liu Y C, Zein N N, McCullough A J. Cytokeratin-18 fragment levels as noninvasive biomarkers for nonalcoholic steatohepatitis: a multicenter validation study. Hepatology. 2009; 50(4): 1072-8.
44. Grek C L, Zhang J, Manevich Y, Townsend D M, Tew K D. Causes and consequences of cysteine S-glutathionylation. J Biol Chem. 2013; 288(37):26497-504.
45. Carsten J. Oxidative Stress (Glutathionylation) and Na,K-ATPase Activity in Rat Skeketal Muscle PLOS one. 2014; 9(10):e110514.
46. Juel C, Hostrup M, Bangsbo J. The effect of exercise and beta2-adrenergic stimulation on glutathionylation and function of the Na,K-ATPase in human skeletal muscle. Physiol Rep. 2015; 3(8).
47. Petrushanko I Y, Mitkevich V A, Lakunina V A, Anashkina A A, Spirin P V, Rubtsov P M, et al. Cysteine residues 244 and 458-459 within the catalytic subunit of Na,K-ATPase control the enzyme's hydrolytic and signaling function under hypoxic conditions. Redox Biol. 2017; 13:310-9.
48. Andres Ibarra R, Abbas R, Kombu R S, Zhang G F, Jacobs G, Lee Z, et al. Disturbances in the glutathione/ophthalmate redox buffer system in the woodchuck model of hepatitis virus-induced hepatocellular carcinoma. HPB Surg. 2011; 2011:789323.
49. Ibarra R, Dazard J E, Sandlers Y, Rehman F, Abbas R, Kombu R, et al. Metabolomic Analysis of Liver Tissue from the VX2 Rabbit Model of Secondary Liver Tumors. HPB Surg. 2014; 2014:310372.
50. Kombu R S, Zhang G F, Abbas R, Mieyal J J, Anderson V E, Kelleher J K, et al. Dynamics of glutathione and ophthalmate traced with 2H-enriched body water in rats and humans. Am J Physiol Endocrinol Metab. 2009; 297(1):E260-9.
51. Sanabria J R, Kombu R S, Zhang G F, Sandlers Y, Ai J, Ibarra R A, et al. Glutathione species and metabolic prints in subjects with liver disease as biological markers for the detection of hepatocellular carcinoma. HPB (Oxford). 2016; 18(12):979-90.
52. Dazard J E, Sunil Rao J. Joint adaptive mean variance regularization and variance stabilization of high dimensional data. Computational Statistics and Data Analysis. 2012; 56(7):2317-33.
53. Dazard J E, Xu H, Santana A. MVR R package: mean variance regularization. Comprehensive R Archive Network. 2011.
54. Efron B. Robbins, Empirical Bayes analysis of microarrays. The Annals of Statistics. 2003; 31(2):366-78.
55. Efron B, Tibschirani J D, Storey D, Tusher V. Empirical bayes analysis of a microarray experiment. Journal of the American Statistical Association 2001; 96(456):1151-60.
56. Lonnstedt I, Rimini R, Nilsson P. Empirical bayes microarray a ANOVA and grouping cell lines by equal expression levels. Statistical Application in Genetics and Molecular Biology 2005; 4(7).
57. Newton Mass., Noueiry A, Sarkar D, Alhquist P. Detecting differential gene expression with a semiparametric hierarchical mixture method. Biostatistics. 2004; 5(2): 155-76.
58. Ismail-Beigi F, Edelman I S. The mechanism of the calorigenic action of thyroid hormone. Stimulation of Na plus+K plus-activated adenosinetriphosphatase activity. J Gen Physiol. 1971; 57(6):710-22.
59. Juel C, Hostrup M, Bangsbo J. The effect of exercise and beta2-adrenergic stimulation on glutathionylation and function of the Na,K-ATPase in human skeletal muscle. Physiol Rep. 2015; 3(8).
60. Liu C C, Karimi Galougahi K, Weisbrod R M, Hansen T, Ravaie R, Nunez A, et al. Oxidative inhibition of the vascular Na+-K+ pump via NADPH oxidase-dependent beta$\alpha$1-subunit glutathionylation: implications for angiotensin I I-induced vascular dysfunction. Free Radic Biol Med. 2013; 65:563-72.
61. Petrushanko I Y, Mitkevich V A, Lakunina V A, Anashkina A A, Spirin P V, Rubtsov P M, et al. Cysteine residues 244 and 458-459 within the catalytic subunit of Na,K-ATPase control the enzyme's hydrolytic and signaling function under hypoxic conditions. Redox Biol. 2017; 13:310-9.
62. Petrushanko I Y, Yakushev S, Mitkevich V A, Kamanina Y V, Ziganshin R H, Meng X, et al. S-glutathionylation of the Na,K-ATPase catalytic alpha subunit is a determinant of the enzyme redox sensitivity. J Biol Chem. 2012; 287(38):32195-205.
63. Abdel-Razik A, Mousa N, Shabana W, Refaey M, ElMandy Y, Elhelaly R, et al. A novel model using mean platelet volume and neutrophil to lymphocyte ratio as a marker of nonalcoholic steatohepatitis in NAFLD patients: multicentric study. Eur J Gastroenterol Hepatol. 2016; 28(1):e1-9.
64. Ballestri S, Nascimbeni F, Romagnoli D, Lonardo A. The independent predictors of non-alcoholic steatohepatitis and its individual histological features: Insulin resistance, serum uric acid, metabolic syndrome, alanine aminotransferase and serum total cholesterol are a clue to pathogenesis and candidate targets for treatment. Hepatol Res. 2016; 46(11):1074-87.
65. Cao Y, Pan Q, Cai W, Shen F, Chen G Y, Xu L M, et al. Modulation of Gut Microbiota by Berberine Improves Steatohepatitis in High-Fat Diet-Fed BALB/C Mice. Arch Iran Med. 2016; 19(3):197-203.
66. Hannah W N, Jr., Harrison S A. Lifestyle and Dietary Interventions in the Management of Nonalcoholic Fatty Liver Disease. Dig Dis Sci. 2016; 61(5):1365-74.
67. Linden M A, Sheldon R D, Meers G M, Ortinau L C, Morris E M, Booth F W, et al. Aerobic exercise training in the treatment of non-alcoholic fatty liver disease related fibrosis. J Physiol. 2016; 594(18):5271-84.
68. Bird B, Rowlette J. A protocol for rapid, label-free histochemical imaging of fibrotic liver. Analyst. 2017; 142(8):1179-84.
69. Cheung J S, Fan S J, Gao D S, Chow A M, Man K, Wu E X. Diffusion tensor imaging of liver fibrosis in an experimental model. J Magn Reson Imaging. 2010; 32(5): 1141-8.
70. Kimm S Y, Tarin T V, Monette S, Srimathveeravalli G, Gerber D, Durack J C, et al. Nonthermal Ablation by Using Intravascular Oxygen Radical Generation with WST11: Dynamic Tissue Effects and Implications for Focal Therapy. Radiology. 2016; 281(1):109-18.
71. Hayes C N, Zhang P, Chayama K. The Role of Lipids in Hepatocellular Carcinoma. In: Tirnitz-Parker J E E, editor. Hepatocellular Carcinoma. Brisbane (AU) 2019.
72. Liebig M, Dannenberger D, Vollmar B, Abshagen K. n-3 PUFAs reduce tumor load and improve survival in a NASH-tumor mouse model. Ther Adv Chronic Dis. 2019; 10:2040622319872118.
73. Bray F, Ferlay J, Soerjomataram I, Siegel R L, Torre L A, Jemal A. Global cancer statistics 2018: GLOBOCAN estimates of incidence and mortality worldwide for 36 cancers in 185 countries. C A Cancer J Clin. 2018; 68(6):394-424.
74. Rawla P, Sunkara T, Muralidharan P, Raj J P. Update in global trends and aetiology of hepatocellular carcinoma. Contemp Oncol (Pozn). 2018; 22(3):141-50.
75. Takeda M, Sakaguchi T, Hiraide T, Shibasaki Y, Morita Y, Kikuchi H, et al. Role of caveolin-1 in hepatocellular carcinoma arising from non-alcoholic fatty liver disease. Cancer Sci. 2018; 109(8):2401-11.
76. El-Serag H B. Epidemiology of viral hepatitis and hepatocellular carcinoma. Gastroenterology. 2012; 142 (6):1264-73 e1.
77. Beyoglu D, Idle J R. The metabolomic window into hepatobiliary disease. J Hepatol. 2013; 59(4):842-58.
78. Younossi Z M, Otgonsuren M, Henry L, Venkatesan C, Mishra A, Erario M, et al. Association of nonalcoholic fatty liver disease (NAFLD) with hepatocellular carcinoma (HCC) in the United States from 2004 to 2009. Hepatology. 2015; 62(6):1723-30.
79. Michelotti G A, Machado M V, Diehl A M. NAFLD, NASH and liver cancer. Nat Rev Gastroenterol Hepatol. 2013; 10(11):656-65.
80. Cholankeril G, Patel R, Khurana S, Satapathy S K. Hepatocellular carcinoma in non-alcoholic steatohepatitis: Current knowledge and implications for management. World J Hepatol. 2017; 9(11):533-43.
81. Younossi Z, Stepanova M, Ong J P, Jacobson I M, Bugianesi E, Duseja A, et al. Nonalcoholic Steatohepatitis Is the Fastest Growing Cause of Hepatocellular Carcinoma in Liver Transplant Candidates. Clin Gastroenterol Hepatol. 2019; 17(4):748-55 e3.
82. Cui X, Xie Z. Protein Interaction and Na/K-ATPase-Mediated Signal Transduction. Molecules. 2017; 22(6).
83. Cai T, Wang H, Chen Y, Liu L, Gunning W T, Quintas L E, et al. Regulation of caveolin-1 membrane trafficking by the Na/K-ATPase. J Cell Biol. 2008; 182(6):1153-69.
84. Liang M, Cai T, Tian J, Qu W, Xie Z J. Functional characterization of Src-interacting Na/K-ATPase using RNA interference assay. J Biol Chem. 2006; 281(28): 19709-19.
85. Xie Z, Cai T. Na+-K+—ATPase-mediated signal transduction: from protein interaction to cellular function. Mol Interv. 2003; 3(3):157-68.
86. Wang X, Cai L, Xie J X, Cui X, Zhang J, Wang J, et al. A caveolin binding motif in Na/K-ATPase is required for stem cell differentiation and organogenesis in mammals and C. elegans. Sci Adv. 2020; 6(22):eaaw5851.
87. Li Z, Zhang Z, Xie J X, Li X, Tian J, Cai T, et al. Na/K-ATPase mimetic pNaKtide peptide inhibits the growth of human cancer cells. J Biol Chem. 2011; 286 (37):32394-403.
88. Holmes D. PI3K pathway inhibitors approach junction. Nat Rev Drug Discov. 2011; 10(8):563-4.
89. LoPiccolo J, Blumenthal G M, Bernstein W B, Dennis P A. Targeting the PI3K/Akt/mTOR pathway: effective combinations and clinical considerations. Drug Resist Updat. 2008; 11(1-2):32-50.
90. Yamashita N, Kondo M, Zhao S, Li W, Koike K, Nemoto K, et al. Picrasidine G decreases viability of MDA-M B 468 EGFR-overexpressing triple-negative breast cancer cells through inhibition of EGFR/STAT3 signaling pathway. Bioorg Med Chem Lett. 2017; 27(11):2608-12.
91. Iskandar Z A, Al-Joudi F S. Expression of survivin in fetal and adult normal tissues of rat. Malays J Pathol. 2006; 28(2):101-5.
92. Mita A C, Mita M M, Nawrocki S T, Giles F J. Survivin: key regulator of mitosis and apoptosis and novel target for cancer therapeutics. Clin Cancer Res. 2008; 14(16):5000-5.
93. Barrett R M, Osborne T P, Wheatley S P. Phosphorylation of survivin at threonine 34 inhibits its mitotic function and enhances its cytoprotective activity. Cell Cycle. 2009; 8(2):278-83.
94. Townley A R, Wheatley S P. Mitochondrial survivin reduces oxidative phosphorylation in cancer cells by inhibiting mitophagy. J Cell Sci. 2020; 133(21).
95. Colnaghi R, Connell C M, Barrett R M, Wheatley S P. Separating the anti-apoptotic and mitotic roles of survivin. J Biol Chem. 2006; 281(44):33450-6.
96. Dohi T, Beltrami E, Wall N R, Plescia J, Altieri D C. Mitochondrial survivin inhibits apoptosis and promotes tumorigenesis. J Clin Invest. 2004; 114(8):1117-27.
97. Dohi T, Xia F, Altieri D C. Compartmentalized phosphorylation of IAP by protein kinase A regulates cytoprotection. Mol Cell. 2007; 27(1):17-28.
98. McKenzie J A, Grossman D. Role of the apoptotic and mitotic regulator survivin in melanoma. Anticancer Res. 2012; 32(2):397-404.
99. Ceballos-Cancino G, Espinosa M, Maldonado V, Melendez-Zajgla J. Regulation of mitochondrial Smac/DIABLO-selective release by survivin. Oncogene. 2007; 26(54):7569-75.
100. McNeish I A, Lopes R, Bell S J, McKay T R, Fernandez M, Lockley M, et al. Survivin interacts with Smac/DIABLO in ovarian carcinoma cells but is redundant in Smac-mediated apoptosis. Exp Cell Res. 2005; 302(1): 69-82.
101. Song Z, Yao X, Wu M. Direct interaction between survivin and Smac/DIABLO is essential for the anti-apoptotic activity of survivin during taxol-induced apoptosis. J Biol Chem. 2003; 278(25):23130-40.
102. Vakifahmetoglu H, Olsson M, Zhivotovsky B. Death through a tragedy: mitotic catastrophe. Cell Death Differ. 2008; 15(7):1153-62.
103. Castedo M, Perfettini J L, Roumier T, Andreau K, Medema R, Kroemer G. Cell death by mitotic catastrophe: a molecular definition. Oncogene. 2004; 23(16): 2825-37.
104. Yamanaka Y, Onda M, Uchida E, Yokomuro S, Hayashi T, Kobayashi T, et al. Immunohistochemical localization 104. [continued] of Na+, K+-ATPase in human normal and malignant pancreatic tissues. Nihon Ika Daigaku Zasshi. 1989; 56(6):579-83.

105. Seligson D B, Rajasekaran S A, Yu H, Liu X, Eeva M, Tze S, et al. Na,K-adenosine triphosphatase alpha1-subunit predicts survival of renal clear cell carcinoma. J Urol. 2008; 179(1):338-45.

106. Hirsova P, Bohm F, Dohnalkova E, Nozickova B, Heikenwalder M, Gores G J, et al. Hepatocyte apoptosis is tumor promoting in murine nonalcoholic steatohepatitis. Cell Death Dis. 2020; 11(2):80.

107. Cao S, Zheng B, Chen T, Chang X, Yin B, Huang Z, et al. Semen *Brassicae* ameliorates hepatic fibrosis by regulating transforming growth factor-beta1/Smad, nuclear factor-kappaB, and AKT signaling pathways in rats. Drug Des Devel Ther. 2018; 12:1205-13.

108. Yang J H, Kim S C, Kim K M, Jang C H, Cho S S, Kim S J, et al. Isorhamnetin attenuates liver fibrosis by inhibiting TGF-beta/Smad signaling and relieving oxidative stress. Eur J Pharmacol. 2016; 783:92-102.

109. Suzuki A, Ito T, Kawano H, Hayashida M, Hayasaki Y, Tsutomi Y, et al. Survivin initiates procaspase 3/p21 complex formation as a result of interaction with Cdk4 to resist Fas-mediated cell death. Oncogene. 2000; 19(10): 1346-53.

110. Su C. Survivin in survival of hepatocellular carcinoma. Cancer Lett. 2016; 379(2):184-90.

111. Giodini A, Kallio M J, Wall N R, Gorbsky G J, Tognin S, Marchisio P C, et al. Regulation of microtubule stability and mitotic progression by survivin. Cancer Res. 2002; 62(9):2462-7.

112. Zaffaroni N, Pennati M, Daidone M G. Survivin as a target for new anticancer interventions. J Cell Mol Med. 2005; 9(2):360-72.

113. O'Connor D S, Schechner J S, Adida C, Mesri M, Rothermel A L, Li F, et al. Control of apoptosis during angiogenesis by survivin expression in endothelial cells. Am J Pathol. 2000; 156(2):393-8.

114. Dan H C, Jiang K, Coppola D, Hamilton A, Nicosia S V, Sebti S M, et al. Phosphatidylinositol-3-O H kinase/AKT and survivin pathways as critical targets for geranylgeranyltransferase I inhibitor-induced apoptosis. Oncogene. 2004; 23(3):706-15.

115. Zhao P, Meng Q, Liu L Z, You Y P, Liu N, Jiang B H. Regulation of survivin by PI3K/Akt/p70S6K1 pathway. Biochem Biophys Res Commun. 2010; 395(2):219-24.

116. Boidot R, Vegran F, Lizard-Nacol S. Transcriptional regulation of the survivin gene. Mol Biol Rep. 2014; 41(1):233-40.

117. Lam E W, Brosens J J, Gomes A R, Koo C Y. Forkhead box proteins: tuning forks for transcriptional harmony. Nat Rev Cancer. 2013; 13(7):482-95.

118. Jiramongkol Y, Lam E W. FOXO transcription factor family in cancer and metastasis. Cancer Metastasis Rev. 2020; 39(3):681-709.

119. Beretta G L, Corno C, Zaffaroni N, Perego P. Role of FoxO Proteins in Cellular Response to Antitumor Agents. Cancers (Basel). 2019; 11(1).

120. Obexer P, Hagenbuchner J, Unterkircher T, Sachsenmaier N, Seifarth C, Bock G, et al. Repression of BIRC5/survivin by FOXO3/FKHRL1 sensitizes human neuroblastoma cells to DNA damage-induced apoptosis. Mol Biol Cell. 2009; 20(7):2041-8.

121. Liu L, Wu J, Kennedy D J. Regulation of Cardiac Remodeling by Cardiac Na(+)/K(+)-ATPase Isoforms. Front Physiol. 2016; 7:382.

122. Xie J X, Li X, Xie Z. Regulation of renal function and structure by the signaling Na/K-ATPase. IUBMB Life. 2013; 65(12):991-8.

123. Kroh A, Ivanova V, Drescher H, Andruszkow J, Longerich T, Nolting J, et al. Mouse Models of Nonalcoholic Steatohepatitis: Head-to-Head Comparison of Dietary Models and Impact on Inflammation and Animal Welfare. Gastroenterol Res Pract. 2020; 2020:7347068.

124. Takakura K, Oikawa T, Tomita Y, Mizuno Y, Nakano M, Saeki C, et al. Mouse models for investigating the underlying mechanisms of nonalcoholic steatohepatitis-derived hepatocellular carcinoma. World J Gastroenterol. 2018; 24(18):1989-94.

125. Fujii M, Shibazaki Y, Wakamatsu K, Honda Y, Kawauchi Y, Suzuki K, et al. A murine model for nonalcoholic steatohepatitis showing evidence of association between diabetes and hepatocellular carcinoma. Med Mol Morphol. 2013; 46(3):141-52.

126. Li Z, Cai T, Tian J, Xie J X, Zhao X, Liu L, et al. NaKtide, a Na/K-ATPase-derived peptide Src inhibitor, antagonizes ouabain-activated signal transduction in cultured cells. J Biol Chem. 2009; 284(31):21066-76.

127. Tian J, Cai T, Yuan Z, Wang H, Liu L, Haas M, et al. Binding of Src to Na+/K+-ATPase forms a functional signaling complex. Mol Biol Cell. 2006; 17(1):317-26.

128. Chen Y, Cai T, Wang H, Li Z, Loreaux E, Lingrel J B, et al. Regulation of intracellular cholesterol distribution by Na/K-ATPase. J Biol Chem. 2009; 284(22):14881-90.

129. Marisi G, Cucchetti A, Ulivi P, Canale M, Cabibbo G, Solaini L, et al. Ten years of sorafenib in hepatocellular carcinoma: Are there any predictive and/or prognostic markers? World J Gastroenterol. 2018; 24(36):4152-63.

130. Cervello M, Bachvarov D, Lampiasi N, Cusimano A, Azzolina A, McCubrey J A, et al. Molecular mechanisms of sorafenib action in liver cancer cells. Cell Cycle. 2012; 11(15):2843-55.

131. Buschauer S, Koch A, Wiggermann P, Muller M, Hellerbrand C. Hepatocellular carcinoma cells surviving doxorubicin treatment exhibit increased migratory potential and resistance to doxorubicin re-treatment in vitro. Oncol Lett. 2018; 15(4):4635-40.

132. Heldsinger A, Grabauskas G, Song I, Owyang C. Synergistic interaction between leptin and cholecystokinin in the rat nodose ganglia is mediated by PI3K and STAT3 signaling pathways: implications for leptin as a regulator of short term satiety. J Biol Chem. 2011; 286(13):11707-15.

133. Cheung J S, Fan S J, Gao D S, Chow A M, Man K, Wu E X. Diffusion tensor imaging of liver fibrosis in an experimental model. J Magn Reson Imaging. 2010; 32(5): 1141-8.

134. Jiang Y, Wang C, Li Y Y, Wang X C, An J D, Wang Y J, et al. Mistletoe alkaloid fractions alleviates carbon tetrachloride-induced liver fibrosis through inhibition of hepatic stellate cell activation via TGF-beta/Smad interference. J Ethnopharmacol. 2014; 158 Pt A:230-8.

135. Taubert H, Heidenreich C, Holzhausen H J, Schulz A, Bache M, Kappler M, et al. Expression of survivin detected by immunohistochemistry in the cytoplasm and in the nucleus is associated with prognosis of leiomyosarcoma and synovial sarcoma patients. BMC Cancer. 2010; 10:65.

136. Kawasaki H, Altieri D C, Lu C D, Toyoda M, Tenjo T, Tanigawa N. Inhibition of apoptosis by survivin predicts shorter survival rates in colorectal cancer. Cancer Res. 1998; 58(22):5071-4.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method for treating hepatocellular carcinoma, comprising administering a polypeptide antagonist of a Na/K ATPase/Src receptor complex to a subject in need thereof, wherein the polypeptide antagonist comprises the sequence of SEQ ID NO: 1 or a functional fragment thereof.

2. The method of claim 1, wherein the polypeptide antagonist further includes a cell penetrating polypeptide having an amino acid sequence selected from the group consisting of SEQ ID NOS: 2-4.

3. The method of claim 1, wherein the polypeptide antagonist comprises the sequence of SEQ ID NO: 5, or a functional fragment thereof.

4. The method of claim 1, wherein the administering step includes oral administration, transdermal administration, administration by inhalation, nasal administration, topical administration, intraaural administration, rectal administration, intravenous administration, intramuscular administration, subcutaneous administration, intravitreous administration, subconjunctival administration, intracameral administration, intraocular administration or combinations thereof.

5. The method of claim 1, wherein the subject is human.

6. The method of claim 1, wherein administering the polypeptide antagonist increases a level of expression or activity of SMAC in the subject.

7. The method of claim 1, wherein administering the polypeptide antagonist reduces a level of expression or activity of Caveolin-1 or Survivin in the subject.

* * * * *